(12) United States Patent
Chen et al.

(10) Patent No.: US 6,342,351 B1
(45) Date of Patent: Jan. 29, 2002

(54) METHODS AND COMPOSITIONS FOR DIAGNOSING AND TREATING CHROMOSOME-18P RELATED DISORDERS

(75) Inventors: Hong Chen, Brookline, MA (US); Nelson B. Freimer, San Francisco, CA (US)

(73) Assignees: Millennium Pharmaceuticals, Inc., Cambridge, MA (US); Regents of the University of California, Oakland, CA (US)

(*) Notice: Subject to any disclaimer, the term of this patent is extended or adjusted under 35 U.S.C. 154(b) by 0 days.

(21) Appl. No.: 09/268,992

(22) Filed: Mar. 16, 1999

Related U.S. Application Data

(63) Continuation-in-part of application No. 09/236,134, filed on Jan. 22, 1999.
(60) Provisional application No. 60/106,056, filed on Oct. 28, 1998, provisional application No. 60/088,312, filed on Jun. 5, 1998, and provisional application No. 60/078,044, filed on Mar. 16, 1998.

(51) Int. Cl.⁷ .......................... C12Q 1/68; C12Q 1/00; C07K 1/00; A16K 38/00; C07H 21/02

(52) U.S. Cl. ............................. 435/6; 435/4; 530/350; 530/300; 514/12; 514/44; 536/23.1

(58) Field of Search .................. 435/6, 4; 536/23.1; 530/350, 300; 514/12, 44

(56) References Cited

U.S. PATENT DOCUMENTS

| | | | |
|---|---|---|---|
| 4,190,496 A | 2/1980 | Rubenstein et al. | 435/7 |
| 4,376,110 A | 3/1983 | David et al. | 436/513 |
| 4,656,127 A | 4/1987 | Mundy | 435/6 |
| 4,683,202 A | 7/1987 | Mullis | 435/91 |
| 4,745,051 A | 5/1988 | Smith et al. | 435/68 |
| 4,816,397 A | 3/1989 | Boss et al. | 435/68 |
| 4,816,567 A | 3/1989 | Cabilly et al. | 530/387 |
| 4,851,331 A | 7/1989 | Vary et al. | 435/6 |
| 4,873,191 A | 10/1989 | Wagner et al. | 435/172.3 |
| 4,946,778 A | 8/1990 | Ladner et al. | 435/69.6 |
| 5,075,217 A | 12/1991 | Weber | 435/6 |
| 5,364,759 A | 11/1994 | Caskey et al. | 435/6 |
| 5,585,089 A | 12/1996 | Queen et al. | 424/133.1 |

FOREIGN PATENT DOCUMENTS

| | | |
|---|---|---|
| WO | WO88/04300 | 6/1988 |
| WO | WO88/09810 | 12/1988 |
| WO | WO89/10134 | 11/1989 |
| WO | WO90/11364 | 10/1990 |
| WO | WO91/02087 | 2/1991 |
| WO | WO92/15712 | 9/1992 |
| WO | WO95/00669 | 1/1995 |
| WO | WO95/11995 | 5/1995 |

OTHER PUBLICATIONS

Adams et al. Initial assessment of human gene diversity and expression patterns based upon 83 milion nucleotides of cDNA sequence. Nature, vol. 377 (6547 suppl), pp. 3–17, Sep. 1995.*
D.F. MacKinnon et al., *Annu. Rev. Neurosci.*, 20, 355–373 (1997).
H. Ewald et al., *Psychiatric Genetics*, 7, 1–12 (1997).
M. Baron, *Molecular Psychiatry*, 2, 200–210 (1997).
D18S1140 Chromosomal MNW (Database ID: AFM287WE1).
D18S59 Chromosomal MNW (Database ID: AFM178XC3).
Altschul, et al., 1990, J. Molec. Biol., 215:403–410.
Altschul et al. (1997)*Nucleic Acids Res.* 25:3389–3402.
Ausubel F.M. et al., eds., 1989, Current Protocols in Molecular Biology, vol. 1, Green Publishing Associates, Inc., and John Wiley & sons, Inc., New York, at pp. 6.3.1–6.3.6 and 2.10.3.
Baron, et al., 1987, Nature 326, 289–292.
Baron, et al., 1993, Nature Genet. 3, 49–55.
Been and Cech, 1986, Cell, 47:207–216.
Benoist and Chambon, 1981, Nature 290:304–310.
Bertelsen, et al., 1977, Br. J. Psychiat. 130, 330–351.
Bird, 1988, Science 242:423–426.
Bitter, et al., 1987, Methods in Enzymol. 153:516–544.
Brinster, et al., 1982, Nature 296:39–42.
Butler, J.E., 1981, Meth. in Enzymol. 73:482–523.
Campbell, et al., 1996, Nature 380:64–66.
Chien, et al., 1991, Proc. Natl. Acad. Sci. USA, 88:9578–9582.
Cohen et al., 1993, C.R. Acad. Sci. 316:1484–1488 (Abstract).
Colbère–Garapin, et al., 1981, J. Mol. Biol. 150:1–14.
Cote et al., 1983, Proc. Natl. Acad. Sci. USA 80:2026–2030.
Cole et al., 1985, Monoclonal Antibodies And Cancer Therapy, Alan R. Liss, Inc., pp. 77–96.
Creighton, 1983, "Proteins: Structures and Molecular Principles," W.H. Freeman & Co., N.Y., pp. 34–49.
Cronin, et al., 1996, Human Mutation 7:244–255.
Egeland, et al., 1987, Nature 325, 783–787.
Freimer and Reus, 1993, in *The Molecular and Genetic Basis of Neurological Disease*, Rosenberg, et al., eds., Butterworths, New York, pp. 951–965.
Freimer et al., 1996, Nature Genetics 12:436–441.

(List continued on next page.)

Primary Examiner—Stephanie Zitomer
Assistant Examiner—Cynthia Wilder
(74) Attorney, Agent, or Firm—Pennie & Edmond, LLP

(57) ABSTRACT

The present invention relates of the mammalian HKNG1 gene, a gene associated with bipolar affective disorder (BAD) in humans. The invention relates, in particular, to methods for the diagnostic evaluation, genetic testing and prognosis of HKNG1 neuropsychiatric disorders including schizophrenia, attention deficit disorder, a schizoaffective disorder, a bipolar affective disorder or a unipolar affective disorder.

17 Claims, 89 Drawing Sheets

OTHER PUBLICATIONS

Freimer et al., 1996, Neuropsychiat. Genet. 67:254–263.
Gautier, et al., 1987, Nucl. Acids. Res. 15:6625–6641.
GenBank Accession No. D63813.
Goodwin, et al., 1990, *Manic Depressive Illness*, Oxford University Press, New York.
Gordon, 1989, Transgenic Animals, Intl. Rev. Cytol. 115, 171–229.
Grompe, 1993, *Nature Genetics* 5:111–117.
Gu, et al., 1994, Science 265, 103–106.
Harlow and Lane 1988, "Antibodies: A Laboratory Manual", Cold Spring Harbor Laboratory Press, Cold Spring Harbor, New York.
Haseloff and Gerlach, 1988, Nature, 334:585–591.
Helene, 1991, Anticancer Drug Des., 6(6):569–584.
Helene, et al., 1992, Ann. N.Y. Acad. Sci., 660:27–36.
Houghten,et al., 1991, Nature 354:84–86.
Huse, et al., 1989, Science 246:1275–1281.
Huston, et al., 1988, Proc. Natl. Acad. Sci. USA 85:5879–5883.
Innis, et al., PCR Protocols: A Guide to Methods and Applications, eds. Academic Press, Inc., New York, 1990.
Inouye and Inouye, 1985, Nucleic Acids Res. 13:3101–3109.
Inoue, et al., 1987, Nucl. Acids Res. 15:6131–6148.
Inoue, et al., 1987, FEBS Lett. 215:327–330.
Ishikawa, E. et al., (eds.), 1981, Enzyme Immunoassay, Kgaku Shoin, Tokyo.
Jalanko et al., 1992, *Clin. Chem.* 38:39–43.
Janknecht, et al., 1991, Proc. Natl. Acad. Sci. USA 88:8972–8976.
Karlin and Altschul (1990) *Proc. Natl. Acad. Sci. USA* 87:2264–2268.
Karlin and Altschul (1993) *Proc. Natl. Acad. Sci. USA* 90:5873–5877.
Kelsoe, et al., 1989, Nature 342, 238–243.
Kohler and Milstein, (1975) Nature 256:495–497.
Kozbor et al., 1983, Immunology Today 4:72–79.
Krol et al., 1988, BioTechniques(6:958–976) or intercalating agents (see, e.g., Zon, 1988, Pharm. Res. 5:539–549.
Lasko, et al., 1992, Proc. Natl. Acad. Sci. USA 89:6232–6236.
Lam, et al., 1991, Nature 354:82–84.
Landegren et al., 1988, *Science* 241:1077–1080.
Lavitrano et al., 1989, Cell 57:717–723.
Lemaitre, et al., 1987, Proc. Natl. Acad. Sci. U.S.A. 84:648–652.
Letsinger, et al., 1989, Proc. Natl. Acad. Sci. U.S.A. 86:6553–6556.
Levinson and Levitt, 1987, Am. J. Psychiat. 144, 415–426.
Lo, 1983, Mol. Cell. Biol. 3:1803–1814.
Logan and Shenk, 1984, Proc. Natl. Acad. Sci. USA 81:3655–3659.
Lowy, et al., 1980, Cell 22:817–823.
Maggio, E. (ed.), 1980, Enzyme Immunoassay, CRC Press, Boca Raton, FL.
Maher, 1992, Bioassays 14(12):807–815.
Maier, et al., 1995, Psych. Res. 59, 7–15.
McInnes and Freimer, 1995, Curr. Opin. Genet. Develop., 5, 376–381.
McInnes et al., Proc. Natl. Acad. Scie. U.S.A. 93:13060–13065.
Morrison, et al., 1984, Proc. Natl. Acad. Sci., 81:6851–6855.
Murray, et al., 1994, Science 265, 2049–2054.
Myers and Miller, (1988) *CABIOS* 4:11–17.
Neuberger, et al., 1984, Nature 312:604–608.
Nickerson et al., 1990, Proc. Natl. Acad. Sci. U.S.A. 87:8923–8927.
Nuovo, G.J., 1992, "PCR In Situ Hybridization: Protocols and Applications", Raven Press, NY.
Orita et al., 1989, *Proc. Natl. Acad. Sci. USA* 86:2766–2770.
Pastinen et al., 1996, *Clin. Chem.* 42:1391–1397.
Pastinen et al., 1997, *Genome Res.* 7:606–614.
Pauls, et al., 1992, Arch. Gen. Psychiat. 49, 703–708.
Pauls, et al., 1995, Am. J. Hum. Genet. 57, 636–643.
Platt, 1994, J. Biol. Chem. 269, 28558–28562.
Rosenthal, et al., 1980, Arch. General Psychiat. 37, 804–810.
Rossi, 1994, Current Biology 4:469–471.
Santerre, et al., 1984, Gene 30:147–156.
Sarin, et al., 1988, Proc. Natl. Acad. Sci. U.S.A. 85:7448–7451.
Sarver, et al., 1990, Science 247, 1222–1225.
Shimizu–Matsumoto, A. et al., 1997, Invest. Ophthalmol. Vis. Sci. 38:2576–2585.
Shumaker et al., 1996, *Hum. Mutation* 7:346–354.
Smith, et al., 1983, J. Virol. 46:584–593.
Smithies, et al., 1985, Nature 317:230–234.
Songyang, et al., 1993, Cell 72:767–778.
Stein, et al., 1988, Nucl. Acids Res. 16:3209–3221.
Straub, et al., 1994, Nature Genet. 8, 291–296.
Szybalska and Szybalski, 1962, Proc. Natl. Acad. Sci. USA 48:2026–2039.
Thomas and Capecchi, 1987, Cell 51:503–512.
Thompson, et al., 1989, Cell 56:313–321.
Van Heeke and Schuster, 1989, J. Biol. Chem. 264:5503–5509.
Van der Putten, et al., 1985, Proc. Natl. Acad. Sci., USA 82:6148–6152.
Voller, A. et al., 1978, J. Clin. Pathol. 31:507–520.
Voller, A., "The Enzyme Linked Immunosorbent Assay (ELISA)", 1978, Diagnostic Horizons 2:1–7, Microbiological Associates Quarterly Publication, Walkersville, MD.
Weintraub, H. Trends In Genetics 1:22–25 (1985).
Wigler, et al., 1977, Cell 11:223–232.
Wigler, et al., 1980, Proc. Natl. Acad. Sci. USA 77:3567–3570.
Wilmut, et al., Nature 385:810–813.
Yamamoto, et al., 1980, Cell 22:787–797.
Young et al., 1998, *American Journal of Human Genetics* 63:109–119.
Zaug, et al., 1984, Science, 224:574–578.
Zaug and Cech, 1986, Science, 231:470–475.
Zaug, et al., 1986, Nature, 324:429–433.
Zon, 1988, Pharm. Res. 5:539–549.
Roberts et al. (1989) Proc. Natl. Acad. Sci. USA 86:32–36.
A. Shimizu–Matsumoto et al., Isolation and Chromosomal Localization of the Human Conge cGMP Phosphodiesterase Gamma cDNA (PDE6H), Genomics, 121–124 (1996).

* cited by examiner

TGCGTCACCTGCAGGCCCGGGGCCGCGGGGTTGGTTCCACCCTGGAGGTTGCTGACACCCTGTGCCCTCGGCTGACTTC

CAGCCGGTGGCACAGAGCCTCCAGGGGGCACACTCAAGGCGCATCTTAGGAATGACAGAGTTGCGTCCCTCTCTGTTG

CCAGGCTGGAGTTCAGTGGCATGTTCTTAGCTCACTGAAGCCTCAAATTCCTGGGTTCAAGTGACCCTCCCACCTCAGC

```
                       M   K   I   K   A   E   K   N                        8
CCCATGAGGACCTGGGACTACAGGACACAGCTAAATCCCTGACACGG ATG AAA ATT AAA GCA GAG AAA AAC   24

E   G   P   S   R   S   W   W   Q   L   H   G   D   I   A   N   N   S   G       28
GAA GGT CCT TCC AGA AGC TGG TGG CAA CTT CAC GGA GAT ATT GCA AAT AAC AGC GGG       84

N   M   K   P   P   L   V   F   I   V   C   L   L   W   L   K   D   S   H       48
AAC ATG AAG CCG CCA CTC GTG TTT ATT GTG TGT CTG CTG TGG TTG AAA GAC AGT CAC       144

C   A   P   T   W   K   D   K   T   A   I   S   E   N   L   K   S   F   E       68
TGC GCA CCC ACT TGG AAG GAC AAA ACT GCT ATC AGT GAA AAC CTG AAG AGT TTT TCT GAG   204

V   G   E   I   D   A   D   E   E   K   E   H   T   N   L   M   S   Q   M       88
GTG GGG GAG ATA GAT GCA GAT GAA GAG AAA GAG CAC ACC AAT CTA ATG AGC CAA ATG       264

K   I   M   M   E   R   K   E   A   L   L   N   E   V   Q   E   H   L   K       108
AAA ATC ATG ATG GAA AGA AAA GAG GCC CTG AAA CTT CTG AAT GAA GTT CAA GAA CAT CTG AAG   324

C   R   E   E   K   Q   E   R   E   S   L   A   D   S   W   G   E   H   E       128
TGC AGA GAA GAA AAG CAG GAG AGG GAG TCT TTG GCA GAT TCC TGG GGT GAA CAT GAG       384

E   E   R   L   C   R   L                                        S   C         148
GAA GAA GAA AGG CTA TGC CGG GAG TCT CGG GAG TGC AGG TCT TGC                       444
```

FIG.1A

| | | | | | | | | | | | | | | | | | | | |
|---|---|---|---|---|---|---|---|---|---|---|---|---|---|---|---|---|---|---|---|
| L | E | N | N | C | M | R | I | Y | T | C | Q | P | S | W | S | S | V | K | 168 |
| CTG | GAA | AAT | AAC | TGC | ATG | AGA | ATT | TAT | ACA | ACC | TGC | CAA | CCT | AGC | TGG | TCC | TCT | GTG | AAA | 504 |
| N | K | I | E | R | F | F | R | K | I | Y | Q | F | P | F | H | E | D | 188 |
| AAT | AAG | ATT | GAA | CGG | TTT | TTC | AGG | AAG | ATA | TAT | CAA | TTT | CCT | TTC | CAT | GAA | GAT | 564 |
| N | E | K | D | L | P | I | S | E | K | L | I | E | D | A | Q | L | T | Q | 208 |
| AAT | GAA | AAA | GAT | CTC | CCC | ATC | AGT | GAA | AAG | CTC | ATT | GAG | GAT | GCA | CAA | TTG | ACC | CAA | 624 |
| M | E | D | V | F | S | Q | L | T | V | D | Q | E | D | V | N | S | L | F | N | R | S | F | 228 |
| ATG | GAG | GAT | GTG | TTC | AGC | CAG | TTG | ACT | GTG | GAT | CAG | GAA | GAT | GTG | AAT | TCT | CTC | TTT | AAC | AGG | AGT | TTT | 684 |
| N | V | F | R | Q | M | Q | E | F | D | Q | T | F | Q | S | H | F | I | S | 248 |
| AAC | GTC | TTC | AGA | CAG | ATG | CAG | GAG | TTT | GAC | CAG | ACT | TTT | CAA | TCA | CAT | TTC | ATA | TCA | 744 |
| D | T | D | L | T | E | P | Y | F | F | P | A | F | S | K | E | P | M | T | K | 268 |
| GAT | ACA | GAC | CTA | ACT | GAG | CCT | TAC | TTT | TTT | CCA | GCT | TTC | TCT | AAA | GAG | CCG | ATG | ACA | AAA | 804 |
| A | D | L | E | Q | C | W | D | I | P | N | F | F | Q | L | F | C | N | F | S | 288 |
| GCA | GAT | CTT | GAG | CAA | TGT | TGG | GAC | ATT | CCC | AAC | TTC | TTC | CAG | CTG | TTT | TGT | AAT | TTC | AGT | 864 |
| V | S | I | Y | E | S | V | S | E | T | I | T | K | M | L | K | A | I | E | D | 308 |
| GTC | TCT | ATT | TAT | GAA | AGT | GTC | AGT | GAA | ACA | ATT | ACT | AAG | ATG | CTG | AAG | GCA | ATA | GAA | GAT | 924 |
| L | P | K | Q | D | K | A | P | D | H | G | G | L | S | K | M | L | P | G | 328 |
| TTA | CCA | AAA | CAA | GAC | AAA | GCT | CCT | GAC | CAC | GGA | GGC | CTG | ATT | TCA | AAG | ATG | TTA | CCT | GGG | 984 |
| Q | D | R | G | L | C | G | E | L | D | Q | N | L | S | R | C | F | K | F | H | 348 |
| CAG | GAC | AGA | GGA | CTG | TGT | GGG | GAA | CTT | GAC | CAG | AAT | TTG | TCA | AGA | TGT | TTC | AAA | TTT | CAT | 1044 |

FIG. 1B

```
E   K   C   Q   K   C   Q   A   H   L   S   E   D   C   P   D   V   P   A   L      368
GAA AAA TGC CAA AAA TGT CAG GCT CAC CTA TCT GAA GAC TGT CCT GAT GTA CCT GCT CTG     1104

H   T   E   L   D   E   A   I   R   L   V   N   V   S   N   Q   Q   Y   G   Q      388
CAC ACA GAA TTA GAC GAG GCG ATC AGG TTG GTC AAT GTA TCC AAT CAG CAG TAT GGC CAG     1164

I   L   Q   M   T   R   K   H   H   L   E   D   T   A   Y   L   V   E   K   M   R  408
ATT CTC CAG ATG ACC CGG AAG CAC CAC TTG GAG GAC ACC GCC TAT CTG GTG GAG AAG ATG AGA 1224

G   Q   F   G   W   V   S   E   L   A   N   Q   A   P   E   T   E   I   I   F      428
GGG CAA TTT GGC TGG GTG TCT GAA CTG GCA AAC CAG GCC CCA GAA ACA GAG ATC ATC TTT     1284

N   S   I   Q   V   V   P   R   I   H   E   G   N   I   S   K   Q   D   E   T      448
AAT TCA ATA CAG GTA GTT CCA AGG ATT CAT GAA GGA AAT ATT TCC AAA CAA GAT GAA ACA     1344

M   M   T   D   L   S   I   L   P   S   S   N   F   T   L   K   I   P   L   E      468
ATG ATG ACA GAC TTA AGC ATT CTG CCT TCC TCT AAT TTC ACA CTC AAG ATC CCT CTT GAA     1404

E   S   A   E   S   S   N   F   I   G   Y   V   V   A   K   A   L   Q   H   F      488
GAA AGT GCT GAG AGT TCT AAC TTC ATT GGC TAC GTA GTG GCA AAA GCT CTA CAG CAT TTT     1464

K   E   H   F   K   T   W   *                                                       496
AAG GAA CAT TTT AAA ACC TGG TAA                                                     1468

GAAGATCTAATGCATCCTATATCCAGTAAGTAGAATTATCTCTTCATCTGGGACCTGGAAATCCTGAAATAAAAAGGA
TAATGCAATAAACACAGTTGCAGGAAAGTATGTTAGCTATATACTGAAGTACTCTTAGTTTACTTATGTTGAATGGC
TTAGCTATTAATACTCAAATTGAGTTAAAATGAAAATTCCTCCTTAAAAAATCAAAGTAATATGTATTACATTTCATG
GTACATTAGTAGTTCTTTGTATATTGAATAAATACTAAATCACCTA
```

FIG.1C

TGCGTCACCTGCAGGCCCGGGCCCGGGCGGGGTTGGTTTCCACCCTGGAGGTTGCTGACACCCTGTGCCCTCGGCTGACTTC
CAGCCGGTGGCACAGACGCCTCCAGGGGCAGCACTCAAGGCACTCTTAGGAATGACAGAGTTGCGTCCCTCTCGGTTG
CCAGGCTGGAGTTCAGTGGCATGTTCATAGCTCACTGAAGCCTCAAATTCCTGGGTTCAAGTGACCCTCCTACCTCAGC

| | | | | | | | | | | | | | | | | | | |
|---|---|---|---|---|---|---|---|---|---|---|---|---|---|---|---|---|---|---|
|M|R|T|W|D|Y|S|N|S|G|N|M|K|P|P|L|L|V|F| 19
|CCC|ATG|AGG|ACC|TGG|GAC|TAC|AGT|AAC|AGC|GGG|AAC|ATG|AAG|CCG|CCA|CTC|TTG|GTG|TTT| 57

|I|V|C|L|L|W|L|K|D|S|H|C|A|P|T|W|K|D|K|T| 39
|ATT|GTG|TGT|CTG|CTG|TGG|TTG|AAA|GAC|AGT|CAC|TGC|GCA|CCC|ACT|TGG|AAG|GAC|AAA|ACT| 117

|A|I|S|E|N|L|K|S|F|S|E|V|G|E|I|D|A|D|E|E| 59
|GCT|ATC|AGT|GAA|AAC|CTG|AAG|AGT|TTT|TCT|GAG|GTG|GGG|GAG|ATA|GAT|GCA|GAT|GAA|GAG| 177

|V|K|K|A|L|T|G|I|K|Q|M|K|I|M|E|R|K|E|K| 79
|GTG|AAG|AAG|GCT|TTG|ACT|GGT|ATT|AAG|CAA|ATG|AAA|ATC|ATG|GAA|AGA|AAA|GAG|AAG| 237

|E|H|T|N|L|M|S|T|L|K|K|C|R|E|E|K|Q|E|A|L| 99
|GAA|CAC|ACC|AAT|CTA|ATG|AGC|ACC|CTG|AAG|AAA|TGC|AGA|GAA|GAA|AAG|CAG|GAG|GCC|CTG| 297

|K|L|L|N|E|V|Q|E|H|L|R|S|C|L|E|N|C|R|E|S| 119
|AAA|CTT|CTG|AAT|GAA|GTT|CAA|GAA|CAT|CTG|AGG|TCT|TGC|CTA|GAG|AAT|TGC|CGG|GAG|TCT| 357

|L|A|D|S|W|G|E|C|R|S|V|K|N|I|E|R|F|F|R|K| 139
|TTG|GCA|GAT|TCC|TGG|GGT|GAA|TGC|AGG|TCT|GTG|AAA|AAT|ATT|GAA|AGG|TTT|TTC|AGG|AAG| 417

| | | | | | | | | | | | | | | | | | | |
|T|T|C|Q|P|S|W|S|S|V|K|N|I|E|R|F|F|R|K| 159
|ACA|ACC|TGC|CAA|CCT|AGC|TGG|TCC|TCT|GTG|AAA|AAT|AAG|ATT|GAA|CGG|TTT|TTC|AGG|AAG| 477

FIG.2A

FIG. 2B

```
I    Y    Q    F    L    F    P    F    H    E    D    N    E    K    D    L    P    I    S    E     179
ATA  TAT  CAA  TTT  CTA  TTT  CCT  TTC  CAT  GAA  GAT  AAT  GAA  AAA  GAT  CTC  CCC  ATC  AGT  GAA    537

K    L    I    E    E    D    A    Q    L    T    Q    M    E    D    V    F    S    Q    L    T     199
AAG  CTC  ATT  GAG  GAA  GAT  GCA  CAA  TTG  ACC  CAA  ATG  GAG  GAT  GTG  TTC  AGC  CAG  TTG  ACT    597

V    D    V    N    S    L    F    N    R    S    F    N    V    F    R    Q    M    Q    E          219
GTG  GAT  GTG  AAT  TCT  CTC  TTT  AAC  AGG  AGT  TTT  AAC  GTC  TTC  AGA  CAG  ATG  CAG  GAG         657

F    D    Q    T    F    Q    S    M    F    I    S    D    T    D    L    T    E    P    Y    F     239
TTT  GAC  CAG  ACT  TTT  CAA  TCA  CAT  TTC  ATA  TCA  GAT  ACA  GAC  CTA  ACT  GAG  CCT  TAC  TTT    717

F    P    A    F    S    K    E    P    M    T    K    A    K    A    D    L    E    Q    C    W    D    I    259
TTT  CCA  GCT  TTC  TCT  AAA  GAG  CCG  ATG  ACA  AAA  GCA  AAA  GCA  GAT  CTT  GAG  CAA  TGT  TGG  GAC  ATT  777

P    N    F    F    Q    L    F    C    N    F    I    E    D    L    P    K    Q    D    K    A    P    279
CCC  AAC  TTC  TTC  CAG  CTG  TTT  TGT  AAT  TTC  ATT  GAA  GAT  TTA  CCA  AAA  CAA  GAC  AAA  GCT  CCT  837

T    I    T    K    M    I    S    K    L    M    L    P    G    Q    Q    D    R    G    L    C    G    E    299
ACA  ATT  ACT  AAG  ATG  ATT  TCA  AAG  ATG  TTA  CCT  GGG  CAG  CAG  GAC  AGA  GGA  CTG  TGT  GGG  GAA  CTT  897

H    G    G    L    M    S    I    K    A    L    P    F    K    F    H    E    K    C    Q    K    Q    A    H    319
CAC  GGA  GGC  CTG  ATG  TCA  ATT  AAG  GCA  TTA  CCT  TTC  AAA  TTT  CAT  GAA  AAA  TGC  CAA  AAA  CAG  GCT  CAC  957

D    Q    N    L    S    R    C    F    K    F    H    T    E    K    E    L    D    A    I    R          339
GAC  CAG  AAT  TTG  TCA  AGA  TGT  TTC  AAA  TTT  CAT  ACA  GAA  AAA  GAA  TTA  GAC  GCT  ATC  CAC        1017

L    S    E    D    C    P    D    V    P    A    L    H    T    E    L    D    E    A    I    R           359
CTA  TCT  GAA  GAC  TGT  CCT  GAT  GTA  CCT  GCT  CTG  CAC  ACA  GAA  TTA  GAC  GAG  GCG  ATC  AGG        1077
```

```
L   V   N   V   S   N   Q   Q   Y   G   Q   I   L   Q   M   T   R   K   H   L    379
TTG GTC AAT GTA TCC AAT CAG CAG TAT GGC CAG ATT CTC CAG ATG ACC CGG AAG CAC TTG  1137

E   D   T   A   Y   L   V   E   K   M   R   G   Q   F   G   W   V   S   E   L    399
GAG GAC ACC GCC TAT CTG GTG GAG AAG ATG AGA GGG CAA TTT GGC GTG TCT GAA CTG      1197

A   N   Q   A   P   E   T   E   I   I   F   N   S   I   Q   V   V   P   R   I    419
GCA AAC CAG GCC CCA GAA ACA GAG ATC ATC TTT AAT TCA ATA CAG GTA GTT CCA AGG ATT  1257

H   E   G   N   I   S   K   Q   D   E   T   M   M   T   D   L   S   I   L   P    439
CAT GAA GGA AAT ATT TCC AAA CAA GAT GAA ACA ATG ATG ACA GAC TTA AGC ATT CTG CCT  1317

S   S   N   F   T   L   K   I   P   L   E   E   S   A   E   S   S   N   F   I    459
TCC TCT AAT TTC ACA CTC AAG ATC CCT CTT GAA GAA AGT GCT GAG AGT TCT AAC TTC ATT  1377

G   Y   V   A   K   A   L   Q   H   F   K   E   H   F   K   T   W   *            478
GGC TAC GTA GTG GCA AAA GCT CTA CAG CAT TTT AAG GAA CAT TTT AAA ACC TGG TAA      1434

GAAGATCTAATGCATCCTATATCCAGTAAGTAGAATTATCTCTTCATCTGGGACCTGGAAATCCTGAAATAAAAAGGA

TAATGCAATAAACACAGTTGCAGGAAAGTATGTTAGCTATATACTGAAGTACTCTTAGTTACTTATGTTGAATGGC

TTAGCTATTAATACTCAAATTGAGTTAAAATGAAAATTCCTCCTTAAAAAATCAAACGTAATATGTATTACATTTCATG

GTACATTAGTAGTCTTTGTATATTGAATAAATACTAAATCACCTA
```

FIG.2C

```
ACATTTAAGCTACTTATAGTCCTTGGAAATAGCAACAAATATCTTAGTTATTGGACTATTATAACCTTAGTCATCTTATTACTGCTTG
ATTATGAGACACTCTCCCTGCTAATCCTTAGAACATCTTGGTTCTTGGTACTTGACTTTAGCCCCTCTGACATATAGTTGATGTCAGA
GTGTCTGGCATTTCAGTAGTGCTCTATTTTACAAATCCCAGTAAACTGCTCCACTGTGCTTGTTTATGTGTTAATACTGCTGTTTTC
TGTTATAAATTATTTTTGCTTGGAGTAAGATATCATCATTTGCATAGCTACAAATCTGAAGTTAAAGAAAAATTTAAAAATGTAAT
TGTGGAAAATAACAAATAGATCTGCTGAGATGGAGGCTTTGACTAATGTTTTAATAACAGGCAACAAAACAAAGAGGCAGGATATTT
GGTCACAACTAAACCTAAATTAAATCCTCATACAAAGCCCCATTAAGATAAATGTCAAATTCTGGGAACATTTCACTTGCTTTGCCAG
CAATTTTACCCTTCAGAGGGTGTGGATCTAATCAGGGGAACAAACTACCCTGGGCTTAATTCTCATTAACAGGGACTAATTTGTCAAAG
CGGCAGTACTAGCTGAAGTGATGGGTATGGAAGCATTCAGGTCTGTGAGGATTTTGCTGAGGTGCCTGGCACAGGGTAGGGAACTCACCCA
GGCTGCAAGATGCTAACAGTTCAGGTTCAGGTCTAAGGTGCAGTCAGGATGGAACAGGTGCAACTTGGGCCAACAT
CAGTATGAAGGGCCTGATCTGAAGGGCAGGGCAGGGAGGGGGCATTCTGGAAGCAAGAGTTCCTGGTATCCTGTTGACCAGAGTCTTGG
CCCAAGGATCAACGTATGAATTAAAGTAGAAATACCAGAAACAAGAAAGTTGGCAGAAACTAGGAGAGAAGCAGAGTCTCAGCCAACTGG
ACTGGGCTCAGCCTTGGCTACTGGCCGGCAGATGATAGAAGGGCATGTGGTCGCTGAAGCTGAAGCCCAGGCTGAAGCTGGTTGGGCTGGCCACA
CACCATGCATAGCCTTAAAGGGGGTGGCCTAAGGGGTCAATTCACTCAATAGTGCATTCTCCTGCTTCTCAATAGGCTAATACTCTAGAGAATATTTCTGAATCCCACTC
ACTGCCAAGAAGAACCTCTAGTGAACAGGTCTAAACTGGCTCTAAACTTCAATTGAATTCAGTGAATCATACATTGCAGATGAGGAAACACGGCTATGAAGATTGGGAA
GAGGAGGGTCTAGTGGAACAACAAAAAAATCAATGGAAATCTATTTGCAGATGAGGAAACACGGCTATGAAGATTGGGAA
TCTTTACAAAAGTAGAACAACTGGCCAGGTCTAAACTGGCTCTAAACTTCAATTGAATTCAGTGAATCATACATTGGTCTGGGTCAGCCATGTCTCTTAG
GATTGGAAGAACCTGGCCAGGTGTGGTGCTCACGCCTGTAACGAGCCCTGTGTTCTCACCAGCCTTGGGAGGCCGAGCCTGGTGGATCACTTGAGGTCAGGA
GTTGGAGACCAGCCTGGGCAACATAGTAAAAACCCTGTCTCTACTCAAATTACAAAAATCAGCCAGGGTGTGGTGAGCCAAAATCACGCCACTGTACTCCAG
CCAGCTATGCAGGAGGCTGAGGCAGGAGAATCACTTGAACCTGGTAGGCGAGGTTGCAGTGAGCCAAGATCACACCACTGCACTCCAG
CCTGGGTGACAGAGCAAGACTTTGTTTAAAAAAAAAAAGGGAAGAACTAAAAATGTAATTTCAAGGGGCTATCACAAATGGT
CCCAATAACAGAGAAAAGCAGGACTCATGTTTAAGAAACCCATGAGATGTGTATGACCTCATGGAAGAGCTCTTGCTTTCTAATGATCTA
CGTAACAGATGAAAAGCAGAGCATAGGGCTAAGGACTTTTTTCTTAAGGATATCTTAATGTTTAAATGAGAAGACATAGAAAGGGATAGGTCCAAC
ACATAAGCAGAGGACATTAAAGGGACTTTTTTCTTAAGGATATCTTAATGTTTAAATGAGAAGACATAGAAAGGGATAGGTCCAAC
TCTTGGGATTGTTGCAGGTTGGTTTCCATCGGAAGCACTCTGAGTCTGAGATTTGTATGCAGAAAATTAATTGAATGTGCTTTCAGA
TCACCCAGGTGGGGAGGTGGAGGAGAAACCAGGACTGGGCAGAGAGAGGCTGGGCTGTAACCAAGTCACAACAAAGGTGTCAGCTGGTCCCA
TGGTGAATTCTGGACCTAGGATGGCTGACTCCCAAGGCATTCCAAACTGGGGCAAGGAAGTTGTGCTTTAAAACTTCTCATTGACTGTCA
GTCACTGGGCATGAGCAGTCCCAGGAAGGGGGATGACCTTGAGCCAAGGTGATGTCTTCAGCCAAGGGCAAYCACTGGGAAGGAGAA
CCCAGCTATGAACTGTCAGCTGCCAACACTCCCAGCATCCCAGCATCCCAGCATCTCGAGAGGATGAGGGCTTCAATTCTAAGGGCAGGGCCAGGGCAGGGG
TACGGATGGTGGAATCTGGGCAGTACCTGTGGCTTCCACTACACAGTCCACCCTTGCCACCACTTAGTTCCACTGGCTTTTTTTTTTT
```

FIG. 3A

```
TTCTTTTCTGAGACAGTCTCACTCTGTCACCCAGGCTGGAGTGCGGTGGCAGCATCTCGGCTGCTGCAACCTCCGCCTCCCAGGTTCA
AGCAATTCTTGAACCTCCTGAGTAGCTGGGACTACAGATGTGCCACCACACCCAGCTAATTTTTGTATTTTTAGTAGAGACGGGGT
TTACCGTGTTAGCCAGGATTGGTCTCGATCTCCTGACCTCGCCTGCTTTGGCCTCCCAAAGTGCTGGGATTACAGGTGTGAG
CCACCGCACACAGCCAGATCCACTGGCTTCTATATAATTCTGGGTGAAGCTAATTCAGGATTCTGATGGACCTGTCTTCCGAGGGAA
ACTTGTAAAAGGAAAGTTAGAGGGACAAACTATAGCCCCTGCCACAGCAGCTGCTGTGCAGACAAAAATGGTGCTCCTCATTTCCCTT
AACCACCTGACCTAGATTCCCCTAAGCCCTTAGTGGGCACCTCTGTGGATGGAAGTGGTGGCTCACYKGKKGGRWKRWYCMRRWYYCWYM
YCCCTGAGTGGTCTGAGCTCCAGTTACCAGGCCCTTCCAGGCTGTGGCTGTTGCACTTACCTCCCCAGCCATCCCCACTTTTTTT
CTTGAGACTGGGTCTTGCTCTGTCACCCAGGCTGAAATGCAGTGGCATAACCTCAGCTCACTGCAGCCTTGATCTCCAAGCTCAAGCC
ATCTTCTCACCTCTGCCTGCCTCAAGTGGCTGGGACTACAGGCACATGCCACCATGCCCAGCTAATATTTTTATTTTTATTTTTGTA
GCAATGGGATTTTTGCCATGTTCCCAGGCTGGTCTTGAACTCCTGACCTCAAGTGATCCTCCCACCTCTGCTTCCCAAAGTGCTGGAT
TACAGGCTTGAGTCACTGCATCTGGCCACATTATTCCTTTAAAACGTTAAAATTGAATGCAGGATCACTGAGAGACAGGTGAGTGATT
ACCAGGGTGCCAAACATACCCTTCTCTCCTTCCGCAGCTCTACCTCCTCCTCCTGATGATCAGGACAATCATGTATGACTCCTTTC
CTTGACTGCGTCTCTCAGAAGGAACCCATTGTGTTGGGTGAGAACACATCATTTGAAATTTAGTAAGACTCTTGCTGTGCTATGGT
AGAAGCATTCCCTCTCTGGGGCCAAGATCTTAAATGCACAGATCGTGGGAACCAAAGCAGAAATTAAAAGGAGATGACT
GGGATTATGGTAAGAACTGTTTCCACCCTTGATTGCTGCACTGCATTCTCATGTCCTGTCATCTGGTCATCATGTGCCACCTGCTGCCACTCCTCAGAGCCTGCGCTGCAGAGGCTTTCCATTGC
TTGGATTACATGCTGCATCCCGGAGAATGGGCACTGCATTCTCATGTCCTGTCATCATGTCCACCTGCTGCCACCCACTGCGCTGCAGAGCTTTCCATTGC
TCTGTCAGTGTGTTATAGGGTCAGTGGATTCAATGAATAAATACTCAGATGTTCTGGCTGAAGCTTTACAAGCAGAAAAGGCCAACGATGAC
TGTGATGCCATGTGGATCTTGTGTCAATAGAATAAATACTCAGATGTTCTGGCTGAAGCTTTACAAGCAGAAAAGGCCAACGATGAC
TGAAATAAGCGTTGAGCCCAGTCAAGATGAGAGTTCCTGCTCTTTCCAGGATAGACGGAGTCTAGTGTAGATCACTTGACATCAAGAGACT
GGCTGGTCTCCTTGAGGGATGGTGCTGTTCTGCATTCATCATCCTTGATGAATGAGGGACCCTGCTATTGGGCTCATGTACAGCCCCA
TCTCTGCCAATGAGCGCTCCATTCATTGTGTTCCTGCTCTGCTGTGCCAAGGCTGGAGTGCAGTGCAGATCTCAGCTCACTGCAACCTCTGCCT
TATTATTTTTTTGAGACAGAGTCTCGCTCTGTCGCCAGCCTGGGCACGATCTCAGCTCACTGCAACCTCTGCCT
CCCGGCTTCAAGTGATTCTCCCGCCTCAGCCTCCAGAGTAGCTGGGATTATAGGCATGGCCACCACGCCTGGCTAATTTTTGTATTT
TAGTAGAGACAGTCTTTGCCATGTTGGCCAGGCTGGTCTGTCTGGCTCTCGAACTCGTGACCTCAGGTGATCTGCCCGCCTTGGCCTTCCGGAGTGCT
AGGATTATAGGCGTGAGCCACCGTGCCCAGCCATGTATTATTGTTAAGTAGATGAATGCAAAGACTGTTTCAATTACATACATCTTTTCTTACTCTTGAGAGGTTGTTGG
TGCCTTTATTCCTTCTGAGGCCCTCTAATGCTGCTACTGCTATCGTATACCCTTGACCAAAGACTGGTCCTTGCTCTATCAAGGATGGTGTCTTCTTCACCAAG
AGGTTCCAGCAGGGACCACGAGCGCCACCACCTGCTACTGCCACACATGAGGTGGTGGGAGAGGAGGACACCCGCCTAGCCAGCTAGATCAGCCAAGCAGAATAACC
CACACAGCTTCTGAGGGGACGGCAGCAGTGCAGAGTGGTGCAGCCAGATGCGCAGCAGTGGTCGCAGCAGGGAGATGCCCCTCCACATCCAACTCTTAGTGATCTTCTTAACATTCTTGCAAGGCAG
CTGGTAGTCAATGGGGTGACAGTGGTCGCAGCCAGATGCCCTCCACATCCAACTCTTAGTGATCTTCTTAACATTCTTGCAAGGCAG
```

FIG. 3B

```
GTCTACTGGTACAAATTCTCTAATTTTTGCTTGTTGTTTCTTCTTCACCTTTTTTTTTTTTTTGGAGACAGAG
TCTCCCTCTGTGTCCAGGCTGGAGTGCAGTGGCCTGATCTCTTGGCTCACTGCAAACTCTGCCTCCCAGGTTCAAGTGATCCTCATTCCT
CAGCCATCTGAGTAGCTGTGGTTACAGGCGTGGTGCCACCATGCCTAGCTAAATTTTGTATTTTAGTAGAGACGAGGTTTACCGTGTT
GGCCAGGATGGTCTTCAGCCTTCTTAACTTTCTTGCTTGTGTGGTTCTGAAGATAATGATATAATTCTTATTCTTGTTTCTCTGCAGGTAAGGTGGTTT
AATATTTCACTCACTCCACTTTCTTCTTGCTTGTGTGGTTCTGAAGATAATGATATAATTCTTATTCTTGTTTCTCTGCAGGTAAGGTGGTTT
CATACCTCTGGCTTCTTTGGAGAATTTCTCTTGTCTTGTGTGCTTCTTGATTCCTACAGTTGAATATGATATAATTATGTATAGACTGGGGCTAT
TTATCCTTTCTGGTGTAGTCTGAGCTCCCTAAGTCTGTGGTATGGTGTCTTGTAATTGATTGGGAAAATTCTCAGTCATTATTACTTC
AAATATTTCTCTGTTCCTTTGTGTTTTAACTTGTGCCAACTTTTAATTGATACATAGTATTTACATATTTATGGGTACATGT
GATACTTCATTACCTGCATAGAATGTGTAAATGATCTAGTGAAGGTGTTGGACTATTACCTGAGTATGTATCGTTCTATGTGTTGG
GAGCTTTTCAAGTCCCTCTCTTGTAACAATTTTGAAATATACAATGCCTGTTGTTAACTAGTCACCCTGCTCTGCTCTCAAACACTAGG
ATTTATCCTTCTGTCTAACTGGGTGTTTGTACCCATTAACCAACCTGTCTCATCCCCTCTACCCACACATGAGTGAGAACATGTAGTACTTGTTTGCCGTGTC
ATCTATCATTCTACTCTTACCTCCATGAGATCAGCCTTTTAACTCCCAGGTCACTGCAAATAACAAGATTTCATTGCTTTCTTTTATGGCCAA
TGGCTTATTCACTTAAGATAATGACCTTTATTCCATCCAGGTCACTGCAAATAACAAGATTTCATTGCTTTCTTTTATGGCCAA
ATAGTGTCCATTGTTTATATAGACCACATTTACTTTATCCTTAATTGTACATTGATGAACACTGAGGTTGATCCATATCTTGGCTATTG
TGAATAGTGCTGCAATAAACATGGGGTGCAGGTATCCCTTAATTGTACATTGATGAACACTGAGGTTGATCCATATCTTGGCTATTG
GCTGGATCATGTGGTAGATGTATTTAAGTTTTTGAGAAACCTCCATACTCTCTTCATCATGGCTGTATTAATTTACATTCTAACCAGGTAAGAT
AGTATATGAGTTCCCTTTTTTCTGCATCCTCCACCAGCATCATCTGTCTTTTTCATTCTTTTCTTCTTCTTGTATTCAGTTTGGAAGTTTCTATT
GATATCTCATTGTGGTTTGATTGCATCTCCCTGATGAGTAGTGATGTCAAGGCGTTTTCCATATGCCATTGGCCATTGTATGTCT
TCTTTTGATGAAGTCTGTTGTGTCCCACAATCTGCATTTCTTGGCCACTGTTTATGCTCCTTTTTCATTCTTTCTTCTTCTTCTTGTATTCAGTTTGGAAGTTTCTATT
GACCTTTTTAATTGTCCCACAATCTGCATTTCTTGGCTCTTCCTCGGCTCTTCTTCTTCCTCCTTCCTTCCTTCTTCCTTCTTCCTCTCT
GATATTCAAGCTCACTGATTCTCCTCGGCTCTTCCTCGGCTCTTCCTCGGCTCTTCCTCCTCCTTCCTTCCTTCTTCCTTCTTCCTCTCT
CTCTCTCTTCTCTCTTTCCTTCCTTCCTCCTCCTCCTTCCTTCCTTCCTTCCTTCCTTCCTTCCTTCCTTCCTTCTTCCTCTTCCTTCT
TTTCTTTTCTTCTTCTTCTTCTTCTTCTTCTTTTCTTTTTGACCAGTTCTCAGGCTAGCCTAGAACCCCTGGGCTCAAGTATCCTCAG
TCCTTTCCTTCCTTCCTTCCTTCCTTCCTTCCTTCTTCCTTCTTCCTTTCTTTCTTCT
CTCAGCCTTCAAGTAGGTGGGACAAATGCGCCATTCCATCTCCTGCTTACATACCAACATTCTGTCTCCTATATTCTGTTACAGTGGTTTTATTCTAGCA
TTTCTTTTGATTCTTTCCTAGAGTTATTTCAATTCAGCCTGATAATTCCAAATCTGGTATATTTGAGTCGTATCATGCTGGTTGCT
TCAGCATATTAATTAGTATTTCCTTTTAGGATGTCCCTTATCATTTTTTGTTGAAAACAAGACATGATGTATCAGATAAAGTAATTGAGGT
CCTCAGACTGCGTTTTTTCCTTTTAGGATGTCCCTTATCATTTTTTGTTGAAAACAAGACATGATGTATCAGATAAAGTAATTGAGGT
```

FIG. 3C

FIG. 3D

```
CTCTCTCTCTGGTCAGTCTTTCCAGAGGTTGTCAATTTGTTGACTTTTTCCCCCAAAGAATCAGCTCTTTGTTCATGGATTTCT
GCTTTTCTGTTTCAACTTCATTGATTTCTGCTGTTTATTATTCTCTCCTTCGTGGTTGTGAGTTGTTTGCTTTCTTTTCTA
CATATTCGATGTGAAATCTTACATTATTCACTCGGGACTTTTCTTCTTCTTTTTGATGTATGCATTTAGTATTCTAAATTTACTTCTKAGT
ACTGCATACTGCTTGAACTATGTCTGACAAATATAATATATATGTTTTAAATCTTTATTCAGTTCAGTGTATTTTAAAATTCCTTC
TCTGCCTCTTCTTGATTTGTATTTAGAATTGTGTTGTTTTCCGAGTATTTACATTTTCCTCTTATCTTTCTGCATTGATTCCAT
CGTAGTCAGAGTGCATGCTCTGTACAGTTCAGTTCTTCTTCAAATTTATTGAGCTTTGTTAATGGATCTGGATACAGTTATCTTGGCA
TATATATATATACACACATATGTATGTGGGCGCTGAAAAGAAAGCGTATCGTCTGTGTTGGTGGAATGTTGGAGTGTTCTATAA
GCGGTGATTAGATACTGTGGTGATGATGTCATTGAGGGTCCGATAACCCTACTGATTAAATTATTAGTCTGTCAATTATTCAGA
GAGAGAGGTGTTGAACTCTGCACATTATGCACCAAATTAGGATTGTCAATTTCTCCTTTCAGTTCTATTAGTTTTTCTTCACATATTTACAA
CTCTGTTGTTGGTGCATACACATTGTGGTTGCTCTGAAGTCTATGTTATCTCAATATAATATTATGTTGAAGTGAGCTTCTTGTAGACAGCATGTAGTAGG
CTTTTTCTGTCCCTGGTAATTGTGGTTGCTCTGAAGTCTATGTTATCTCAATATAATATTATGTTGAAGTGAGCTTCTTGTAGACAGCATGTAGTAGG
ACATGATACATCTTTTCTATTCTTTACTTCAACTTCTTATATATTTTTTGAGATGGTGTACTCTGTCACCCAGGCTGGAGTACAGGCACGCACCACATGCCACGCAGCTAGTGCTCACTGCAACCTCTG
TCATATATGTACATAGATATATATATTTTTTGAGATGGTGTACTCTGTCACCCAGGCTGGAGTACAGGCACGCACCACATGCCACGCAGCTAGTGCTCACTGCAACCTCTG
CCTCCTGGGTCAAGTGATCTCGTGCCKAGCCAGCCTCGTCGTCTCTCAGTAGCTGGATTACAGGCACGCACCACCGATTAGCCACCTTGGCCTCCCAAAGTGCT
TTAGTAGAGACGGGTTTAACCATGATGGAACAGGCTGGTCTCGAACTCCTGACCTCAGGTGATCAGTCTTGCTTCTCTATGTTTTTAGTGTGTCTCTTTGCATAGC
GGCATTACAGGTGTGAGCCACCGTGCCTGGCCTGGTTAATATTTACATTCTTTATGTTTATGTTTTGCTTTCTCATTTGATTACTACACAGTATATTGGTATTCTTGTACATACATTTAAACCGGATGA
GTAATGTAAATGTGATATGTAAGAGCTGAATGTAAGAACACTTTCATTATATATGAATCATTCCATTTGATTACTACACAGTATATTGGTATTCTTGTACATACATTTAAACCGGATGA
TTTTCTGCTTCATATTGGCTAATGAAGTATTTCATTATATATGTAAGAGCTGAATGTAAGAACACTTTCATTATATATGAATCATTCCATTTGATTACTACACAGTATATTGGTATTCTTGTACATACATTTAAACCGGATGA
TTTTTTAGGGGGTTACTTTAAGTATTCATTATATATGTAAGAGCTGAATGTAAGAACACTTTCATTATATATGAATCATTCCATTTGATTACTACACAGTATATTGGTATTCTTGTACATACATTTAAACCGGATGA
ATGGAAATGTTTCCTCTCTACATTCCTTACCTACTTAACTTTCCAAATAATTCCAAAACTCAAGAGAAAAAAGGAAAAGCTTACTATATTGACCCATATTTCATTCACCA
GTGTTATTTTGATTAGCTATCAAATAATTCCAAAACTCAAGAGAAAAAAGGAAAAGCTTACTATATTGACCCATATTTCATTCACCA
TGTTGTTCTCCCTCTTATGCCCATAGTTCCTTCTTTCTGTGAATGTCTTATGTTTCGTTTAGAGAACTTCCTAGCCATTCTATGGGGTAGATCT
CCTAGTGACAAATTTGGGTCTTTCTTTGGCACTTTGTAAGTGTGCAGCCTGCAGCTGTCAAAATAAAATTAAAATAAAATGAAT
ATTCTGGCTATGGGTCTTTCTTTGGCACTTTGTAAGTGTGCAGCCTGCAGCTGTCAAAATAAAATTAAAATAAAATGAAT
GTTTCCTTGCTACGTTCATGAAAGTATAATTCACTGAATGAATGAATCTGTTGAGACCAAGCATGTGGACCTCCAAAGAAACAGGACTTTTCT
AATAGTACATTGCAGAGAATAAGGCTGTTTCTCCTAAAAGAACTAAAGGAAATGAATGAAAAGGAGAGATTTCAGCTTAGTCTCAGGAAGACATGTGACCTCCAAGAAACAGGACTTTTCT
AGAGAAATGGTTAAAGGAACTAAGGCTGTTTCTCCTAAAAGAACTAAAGGAAATGAATGAAAAGGAGAGATTTCAGCTTAGTCTCAGGAAGACATGTGACCTCCAAGAAGGATACAAAACCATATCCAA
ATGGGGCTCCAAGGGGTTTCTATGAGAGAATGATAAAGGAAGATTTCAGCTTAGTCTCAGGAAGACTTTTCAACAACCAAACCTGCCC
AAAGATGGACTGCCCTGCCCTAAGGATTGTGTCTCGACATTGTGGAGGTATGGAGGTTAGATGAATATTTACCAAAATGCCATAG
```

FIG. 3E

```
ATATTTCAGGCTATTGATGTTGTAATATCATACTAGGCAACTCCACTTCAATATGAGTCTCTATGATGTAAAATGAAATAGGATGTGTT
TCGATAGAGAGTTGCAGATTTCATTTTGATGTTAGCGACCACACAAAATTACTTTCCCTACATAAGAACATGTTATTACTCTAGTTGAT
GATGACTGCTTATGGGAAATGTGTCTGCTTGTTAGGAATCTTGCCTAATATATGTATAATTCAAGATGGTATTATAAAGTGACATATA
TGATTTTAACATTGCACTTAAATAACACTTATTCTGTACCATGMASTGTCTAGGAGCTTCTACATATTCCATTATTATCTTTATTT
ACAAGACAGGGAACTAAGGCATGGAGAGATTGAGTAATTGTGCAATATTACCTACCTAGTAAGTGGTAAAGGAAAGATTGGAACCCAT
TCTGGCTCCAGGATCCAGGCTCAAAGCCAGGCCAATATACTATCCACCACCCCAACTCTTTAGTTGATCAATTTGTCAAATTATTTACAGTT
ATTTATCTGTAAATTAAGGGGATAATTGCCCAGTCAATAAATGTGTCCCCTTCAAAGGTTACATACTTAACCAATGGTGCTACTGGCT
CAGAACATTTTGGAACTACGATTTTGGTGGCAACCAAAAAAACCTCCAGTAGCCTGAAGTTGTTGAGGTCAAATCTGATGAAAAGAGCGGCTGGGGAAGCTGGATATTTT
ATGGAGACTGGGCTTCATTTTTGAATTAGCCTGAAGTTGTTTGAGGTCAAATCTGATGAAAAGAGCGGCTGGGGAAGCTGGATATTTT
CGTTCGTGATTTAAAACAGTAAATGCCACTTAAAATGAGAAGGCTACTTTCTTGAATGTTTGTAAACTGGCTTTGAAGGTACTTCTT
AAAAAGAAGCACAAGAAAGACGGTGACTGGCAACAGCCTCACTGGAATACGTCTCTAATCATCAAGGCAACCCACACTCATTTGGATG
TGTGCATCCGGTGATGTTATTATTTTAAAGTTATGTGCCACAAAGATGCATTCTTTGCTATACAAAAGAGCTGTTGTTAAATTTATAA
AGATATAAAAGGGAGAAGGGAAAGGGAGAAGGCACCAAATGGAAGATTCTTAGGAGTTCTTGAGACGCAGCATAGATCTTCATTAGATGACGT
CAGGGAGAAGAGACAGACTTTGCCATCTCAGGTAGAAGTATCAAAGTCAAGCCTCCTAGTAAGACAGACCTGGGTTTGAAGCTCT
GCACAGCCATTTCCTAGCTGGTCTGGGGAAAAATAATTTAAAGAGGTCCAGCGACGAGCAGGTCAATCAAGGGAAGATGTTAAAAATAACAACAGGT
TGTCAGGATGTGTCAGAATTAGAAATAAAGTTGGATACATAGAAGTGGAGGTAGCACTGMCTTCCTGCCCTCCTGTTCCAGCATCCAGAGTTGTGAACCTG
GAAATGTACTCCCAAAAGATAAAGTTGGATACATAGAAGTGGAGGTAGCACTGMCTTCCTGCCCTCCTGTTCCAGCATCCAGAGTTGTGAACCTG
TAAACATGCCTCCCAAGCCAACGTTCATCATCCAGGAATACGGAGAGGATGTTTGGGATATGGGGGCATGAAGATGAAATTTTACAATTGTAGG
GCCCTTTAACAAGGGTAGACTTGCAAGTTGCACTGMCTTCCTGCCCTCCTGTTCCAGCATCCAGAGTTGTGAACCTG
GGGMCCAAAGGACAGCACCCTGGCATGGGCAGGCCACATTAAGCCCAGTCAGGGCAGGGAGCAACTGCTCAGAGGACGCACCTTTGACCCACTACTTTTTT
CTGACATCCAGCCATGACCATGCCATTAAGCCCAGTCAGGGCAGGGAGCAACTGCTCAGAGGACGCACCTTTGACCCACTACTTTTT
CCCCTCCTGCTTTTATCTGCCCAGAGGCGAGGCTCTCTTTCTAATGTGTACAAGGCGTTCTACCTATGACTCGTGGTCCTGCCATAGAAAT
GCTTTTTTTTTTTAACTGAATTAAGTTGCCAAGTTGAAAAATCAGAATTTCACATAAGATCCCTATTTCTGTCTTCTTTTGAAAAA
CTGAATGTTCTTTCCACAGTGAGCCCACATTCCTTCCTGACGACATCACCGTTCAGCTGGAGTAGAGAGGGCTCTGCTGGCTTCAGAT
CCGGACGCGCAGGTCCTCTGCAGGCCCGCGTCGCAGGCCCCGCCACCCGGGTCTGCAGGCCCCGCCCACCCGG
CGTCACCTGCAGGCCCGGCGTCGCAGGCCCCGCCACCCGGGCGTCGCAGGCCCCGCCACCCGGTCGCAGGC
CCCGCCACCCGGCGTCGCAGGCCCCGCAGGCCCCTGGTGACACCCTGTGCCTGCGGCTGACTTGCAGGCCCAGGCGTCACTC
GGTTGGTTTCCACCMTGGAGGTTGCTGACAATGGAGARCATCCTCCGGGCCCCAGATTTCTCTCCTGCCGCTCTTGCCCATTCTTGCCCGTCTCGGAGAGCCAG
AAGGCGCATCTTAGGAATGACAGGTGAGARCATCCTCCGGGCCCCAGATTTCTCTCCTGCCGCTCTTGCCCATTCTTGCCCGTCTCGGAGAGCCAG
```

FIG. 3F

```
AGAAAGCCGCTCCCAAGTCCAAGGCCGAGCTCCGCAGAGAGCCCGGCCCTCCGGCGGCGGACAGAACAAAGCCATTGTTCTTGCCGGGGA
AGGTAGAAATACTGTGGGCTGCTTCAGAGGCTGCCGAGCTGCCGAGCAAAACTCAGGCAATCTCCTGGGCTGTCCAATACGTTTATTCTCTTTTC
AAAACAGGAGGAGGAGGTAGAGGCGGGAGAGACACACCATCCTGCAAAACTACTGGCAAAAACTAAGCGGAGCCGGGTGTGGTGGCTCA
CGCCTGTAATCTCAACACTTTGGGAGGCCGAGGGGCCGATCACTTGAGGTCAGGAGTTGGAGCGCAGAGGTTGGAGGCCAGCCTGGCCATGGTGAAAC
ACAAAATTAGTCGATTGTGGTGGTGCATGCTTGTAATCCCATCTACTTGGGAGGCTGAGGCAGGAGAATCGCTTGAACCCGGGAGGCG
GAGGTTGCAGTGAGCCGAGATTGCGCCACTGCACTCCAGCCTGGACAACACAAGTGAGATTCTGTCTCAAAATAAATAAATAAAAC
CCAAGCAGAAAAAGAATCACTCTGAAAACGATCACATCTAACTATCAATGCTCATACAGTTTATGGAATTATCAGCCCAACTTGATAAA
ATCAGTATTTGAGGAAAACTGTGGATAAGCCCCCTGATTTCAATCCCATTGTGCCAGGTCCTGGTTAACTGAGGTTAACGAAGTAAAGA
GCTGCAGACACTATTAACTGCTACCTTAAACGATTACTCTAGCTTAGCCTACTTTCCAGTACAGATTTACCAGTGGACAACATGAT
GCTTTATCTTGTTTTCTCTCCCTGGGACTTTTCTCCAGACATTGAAAAACAGAAATACTAATAAGGCCACTTTACCTGCCTGATGCAA
GAACAGAATTTTCAAACTCAACATTAATGCAACTCCTCAGTCCTGACAATGGCGGGTGGAAAAGTTTCTAAAAATATGCAGCAGCACA
ATTATCGGGAAGAGATGAGATACTGTTACCTAATCAATGCCATAAATAGAGAATGATGAACTACCATGGGAAATGAATGCATAGAAG
AGGACATGCTGGAATGTGGGACAGTCAGTAAAAATCACTTAAACTTTGCGTGACCTTGAAGAAAAGTCACGATGATCTGTTTTCCAGGTCCCT
CAAACAGTGAGATGTGGCTGTTTCCCAAGTCTTCCTCTCCAGTGTAAAGGGTCTGAATTTAGACGCTTTGTGAGTCTTCCTTCTTCGA
CAGCCTGAGTCTCTCTTGAGTCTCAAGGCTACCTCTCTGAGTTCCTCTCAACATCCTCTAGGCAGTATCAGCTAATGAGACAATGAATTCC
ATGGAGGCAGCAGTGGGAACAGAAGTACCTCTCTGGATAATTACAACACTGGTGAGCAGAGGGTCAGATCACCCTGGGTTTGTGTC
ACAACCAAAAAAGTGGCTGTGGCACTGAGTTCTGGCACTGAGTTCTGAGTTCTTCTACGCTGGTCCAGATTTCCATGGCTCACCTTTAAATTAAAA
GAATTTCTGCACTTGAAGAATTTGAAAAACAAAGCACCCCTCTTTCTTTTTTCAGAAGGCATATATGTAAAGATCCAAATTAATCTTTAGCAT
TCCTTTTTCCGGACTTAAAAAAAAGCACCCTCTTTAAAATATGTCCATTGTGTCTGTTAACAGCTTTGGCAACTTTTTCAGAGATTGAAA
GTGCCTATGTTGTTCTGATTAGAGAAATGAGTACAATTATTAGCCATATAAGGTTCTTATTACATGTCTTAAGTGTATGTTGTTTGTTGTTTAAGGATACAAATGAAATTACATAG
TATGTGAGCAAATTAGAGAAATGAGTACAATTATTAGCCATATAAGGTTCTTATTACATGTCTTAAGTGTATGTTGTTTGTTGTTTAAGGTAATATGTGATGT
AGGAATGATTATATAGTAGATTTTATAATGCCATATAAGGTATTTTACATGTCTTAAGTGTATGTTGTTTGTTTTAAGGTAATATGTGATGT
AAGCAAAGTAATAATAGTTACCAGAATAGTATTTAGATAAAATTCCGGTGTCTACCAGATTGTGATAGTGAGCAAATTACTTAACCTCTATGATCCT
TGTGGAAAGAACAGAGACCTGGGTTAGATAAACAGGATTGGTAATACTCATATCATAAGGTTGAAAGGATTAAATGAGGCACTATGGAAAATTTCTAACAT
TATCTTATTTATCTATGAAACAGTAGAAGATAGCTTAATAAGATAGCTTCATTATTATTATTAGCTTAATGATTAAGACTGCTTATTTAATCATTTATTTATCACCAGATTTATT
GGTGGTGCCTGGGACAGTAGAAGATGCTTAATAAGATAATTGATTTCAAATGATTAAGACTGCTTATTTAATCATTTATTTATCACCAGATTTATT
TAGGTAATTTTTAAACTTTAGAAATAATTGATTTCAAATGATTAAGACTGCTTATTTAATCATTTATTTATCACCAGATTTATT
TTTATTACCCAAAATGTCAACGACTGTCATAAAGATAAAAATAATAATAATTGGCCAGGTGCGGTGGCTCACGCCTGTAATCCCAGCA
CTTTGGGAGCTGAGGTGGGTAGATCACAAGGTCAGGAGATTGAGACCATCCTGGCTAACGCGGTGAAACCCCGTCTCTACTAAAATAC
```

FIG. 3G

```
AAAAAATTAGCTGGGGTGTGTTGGCGGGGCGCCTGTAGTCCCAGCTACTCATAGTCCCAGCTACTCAGGAGGCTGAGGCAGGAGAATGGTG
TGAACCCGGGAGGCGGAGCTTGCAGTGAGCCGAGATGCGCCACTGCACTCCAGCTGGGCTACACAGAGCCAGACTTCATCTCAAAAAAA
AAAAAAATTAATAATAATTAAACCCGAAGTAATGAACTGAATATTTCCCTTAGTAGCACATCACATAGGCTGATGATAGTTTTGGTG
ACTGGTTTATCTATTCTTCCTAAAAGCAAACTGTTGTTAGATGATGAATTCCTACCAAGATTGAACAATCCATTTGCCTTTTTTCCCTAAAATCTCTCAT
TTTTATTTTTATTTGCTTCAGTAGCATTADCCTTTCGTGCATGTTGTGACTGAACTCAGCAGTTGGGTTTAT
ACATTGTAAATACTACATATTGGCTAAATATTTCCTGGACAGACATGAAGGACACATAAATCAGTCTCTGTATGATGTTTCTCACTGTA
ATGGAGTTTATCTGGCTCAAGACCAGGACATTTATTGCATATCAGGTTTCTACAGTTCAGGCAAAAGTTTGAGGATAAGGACTTACTGC
AAAAGTCTTCTATTGTTCTCAACCATTTCTCGCTTAGCACATGCAGAGATTTGAAATGGTCCGTGGTACAGTAGTTGTGTCTGTATA
TTCTCTTGTAGAATATTAGAACAAGGGATTTGCAGTTTACAGAGAGAAGAAGGCTTGGCGAGGTGTTTGGAAATACACTCAGAAACCTGA
GGAAATTTGTGGAAAGAGAGGCTTATTATTTCTAGAAATATGCTAGAGTWCGTTTTGATTGTGCACCTGAGGAATTAATAGATTAAGTA
GTTTATAAGGACTGGGGTTAATAGAATACTGGCAGTGAAGTTGTCTTAGGACTTCTTAATTGGATAATCAGTGAAGTCACCAGATCC
CAGTTAGAGACAGTTCCAAGTTTACAAAACGCAAGATAACTGTCCAAGAGCTGTAATCATAGGGTGACTAATGTCCCTGTTTACCCAGGACT
TGAAGCTATATCATAAGAAATAAAAATCTACATTTAAAAAATGGCTGTAATCATAGGGTGACTAATGTCCCTGTTTACCCAGGACT
CAGGGTTTCCCAGGCTGAGGGACAATGGGTACTAAAACCAGACAGTCCCAGGCAAACTGGGACGGTTGATCACCCTACCAATGGCCT
CATCTGTCTCATTAAAATATCTGGATTACTTCGTGCCTCAAAAATATCCTCGGCTTACCTGACTCTAGACAGTCAAGAAGCTTTATTA
ATTGTCTAATGTATGCCACTTCTGGAGGTGATATTCTGTTCAACTGATAGAGTAGCATCACTTCTGGAGATATTAGCCTGAACTCAGCAAAATA
TTGTATCTTGTGCTGATAGCCCCACATGGAATTCCAGTGAATTCTGTCCTTCTTGTGCTGTTGTCATCTGACTTAGATATACTGGCCGGGCGGTGGCTC
GGATGATCAAAATGAACCTTTCCAGTGAATTCTGTCCTTCTTGTGCTGTTGTCATCTGACTTAGATATACTGGCCGGGCGGTGGCTC
ACACCTGTAATCCCAGTACTTTGGGAGGCTGAGGTGGTTGGATCCCTTGGATCAGGAGGTTGAGACCAGCTTGGCCAATATGGTGAAT
GAAGCCCTGTCTCTACTAAAAATACAAAAATTAGTGTGCGTGGTGAAGTGTGCCTGTAATCCCAGCTACTCGGGAGGCTGAGGCAGGA
GAACTGCTTGAACCAGGGAGTCGGAGGTTGCAGTGAGCCGAGATCACCACCACTGCACTCCAGCCTGGGCAACAGAGTGAGACTCCATCTC
AAAAAAAAAAAAAATTAGCTGGATGTGGTGGCACATGCCTGTAATCCCAGCTACCTGGGGTGTCACAGGAGGCAGGAGAATCGCTTGAACCCA
GGAGACGGAGGTTGCAGTGGAGGACGAGATCAATGAACACATAAATTGAACACATAACCAAGAAAAGTATAAAAAGTCTTGTGTGAACATAATGA
ATAAAAAATAAATAAATACATAAATACGAACACATAAATTGAACACATAACCAAGAAAAGTATAAAAAGTCTTGTGTGAACATAATGA
AAATTGGCCAAAATAGGTAACAGACAGGGTCAGGGTCATGCCTCATGCCTGAATCCCAGTACTTTGGGAGGCTGAGGTGGGAGGACC
ACTTGAGGCCAGGAGCTCAAGACCAGCTTGGGCAACAAAGCGAGACCTCATCTTAATGCAATACATGCCCTGACATTGTAGTTTGCTTTCACAAAGAT
CAACTTGCTTCCTGCCTCTGCCTGCCTTCCCTAAAACCTTGTGCTACATGTTGGGGCTACAGGGATGAAAGARAATTGGTCTTGCCCTCCAGGAACCTT
TTACTGAATACTTACTCTAGGCTAAACCTTGTGCTACATGTTGGGGCTACAGGGATGAAAGARAATTGGTCTTGCCCTCCAGGAACCTT
TCATTTAGTACAGAGATTTAGTGTGTGCTGGTTGGTCTCTGTTGGTCTCTGTTCTCCCTCTCGTCTCCCCTCTCGTTCTCTATTTCTTCCCTCTCCCT
```

FIG. 3H

```
GCCTCCAGGAAGGGGGCTGGATCACTGTGGCTCATTGCTCTGTGGCTTCTGATTGAGTTCAGCCAATGGGAGGCATMATTTGGCGTG
GCAGCTCTGGCTGTTCCTCTGCAATTGCAGTTCCCTCCTCCAAGGCTCTGGCTCTCACTGGGTTCCTGTATCCAATAACAGACTCCCTT
AACTGCCCACTTCTGAAAACAGTTTCTGCATAAAGCTATTTTCATAATTTCCTCGATGTGCCTTCTGTTTCCTGCTGTGAGACCCTGATT
CAATAGGAAATAAATTATTGAAATAGAGGAAGAGACAGGTAATAATAGAGGTATACACAAGTAGAATAGATGGGCAATAAATGGCGCATT
TCGCACCATCAAGAGTGCCATGTAACAGAGTAAGAGAGGAAAATAAACTACTGTGCATTCATGCCAGTGTTAGCATTTAGGACATCTGGAAGCTAGAGG
CTAGAAGGGGCAATATACAGCAAGGAGGGGAAAATAAACTACTGTGCATTCATGCCAGTGTTAGCATTTAGGACATCTGGAAGCTAGAGG
TGGAGTGGAAAAGGAGGAGAGTGATAGGAGCTGGGGTCAGAGAGTTTCAGGGTGGGAAGGTCTTGCAGGACCTTGTAGGTAATTGTAAA
GCATTTGGATTTTATTCTGAGGGTCACTGGGGTGTCATTAGAGACTTTGAGCAAAGAGGTACATGCTCTGACTGAACTTTATTCTGTG
AACAATCAGAATCAACTAGATGGATTTAAGTATGGGTATACCATGAAGAAATTACTTAAGATCCTTGCTACTCAAAGTATGAGCCAG
GACCAGCTACACTGGCATMAGCTGGGAACTTGTTAGAAATGCAGAATCCCAAGTCCCGAGACAAACTGAATCAGAACCTGCACTTTAA
CAAGATCCCAGGTGGCCCATTTGTATGGTAGAGTTAAGAAGCATTGGTTTAAAAGATCCCTCTTGATAGGAGCATGGAAGATACATTT
GAGACAGAATAGACAAGTCAGAGACAGGTGGGAAGGGCCTAAAACAGGGCAGAAGTAGGGAGGGTAAATGAAGGAGACAAATACAAAGGAA
GAAAATGCACAGCACAGTGTAGACAATTCCTAAATACTTAAAAAAATTTTTTGAAATAAGATGATGCAACTATATTATAATATGCAAAGAA
ATGCGTAGGGAGGAAGAACAATGCACCCTTTACCAGCCTCCTCCATCATTAACACTCTTATGCAACTATATTATAATATGAAAACAATCAA
GTGACATTGCTACAACCCATAGAGCTTATTCAGATTTCACCAGTTCAGATAATGCACTCGTGTGTGTATGCATATAGCTCTGTGTAAT
TTATCATATGTGAAGCTTTGCTACCACACAATCAAGATATTCAAGCACATTGAGATTTCTGGTGTTACCTCCTTATAGCCACACG
CATTCCTCCATCATTGGGAACACCTGGGAACACAAGTAATCTGTTCATCTGTCACCCAGCTGGAGTGCAGTGTCGTGATCTTGGCTCA
CAGTGTGTATCTTTTTGGGATTGGTAACAGAGCAAGACAGGATTCTCACTCTGTCACCCAGCTGGGACTACAGACACACGCCACCTCACCTGGC
TTGCAGCCTCCACCTCCTGGGCTCAGGTGATCCTTCCACCATTTGCCTAGGCTAGTCTAGAACTCCTGGGCTCAAGTGATCCAACCGCCTTG
TAATTTTTTGTATTTTATAATGATGGGGTTCACCATTTGCCTAGGCTAGTCTAGAACTCCTGGGCTCAAGTGATCCAACCGCCTTG
GCCTCCCAAAATGCTGGGAGTACAGGCATGAGCCACCACGCCCAGCTTTTCATTCATACTTTCTTGAAGTTCATCCAAGTTGTG
TGTATCAATACTTCACTCTCCTTCCAGTTCAGTTGCTGAGTAGTAGTTAGGCTATTCCATGGCTGGAGGTGCTAGAGTTTATTCATCACATTCAACCATTGAA
GGMCATTGGGTGGCTTCCAAGTTTCCAGTTTAGGGCTATTAGTGATCAGCTAGTTGGGATGAAGAGTGGCATAAGTGGCATAAAGTAACCCTCAATGCA
TGAATGAATGGAATAGAATGGATAGGATTTAGTGATCAGCTAGTTGGGATGAAGAGTGGCATAAGTGGCATAAAGTAACCCTCAATGCA
ATGTGCAGCCAGCAAGTACCACCAAAAGAGTTTATTTGTTAACATAAACTATGAAACTTAAAATCTAAAGTAAAACTTGACAACAGTGATGCAGAAT
AATAGTATCCTTTCAAATGAAAACAGTAATTAACATAAACTATGAAACTTAAAATCTAAAGTAAAACTTGACAACAGTGATGCAGAAT
TTTTGCTCCTTAGCTCAGTTAGGTCTGTGTTCTTATCTTATGACCAGGAAGAACTAGGTACCCTGACATCAAAGAATGAGTGGCATAG
AATTATTAAGCAAAAGGAAAGCTCTCAGGAAAGAGTGGGGTTCCTGAAAGCAGGTTGCTGGTTGCCCCTTCGTAGTTGAATACAAGGG
CTTCTATATAAACCTGATGGGGCCGAGTTCCCTGTTCGTAGTTCGTATAAGGCATGAATTCCTGGTGGCTCCACCGCCCTCCCCCAGTGCGTATG
```

FIG. 3I

```
TGGGACCTTCGTCCACTAGGGACATGTTTAGACAAGCTCCCTGTGCACGTTCCCTTATCTGCACAAAACATGGGTTGGAGGTTCTCCGG
GGACCCTTCCTTACTTTCTGCCTAAACTTAAAATGGTGTTTGTTTGATTTGACATTTAAAAGATATCGCTGTTCTAAAAATTCGTGTTT
CATTTAAATATTTAAGTAAACTTAAAATGGTGTGTTTGTTTGATTTGACATTTAAAAGATATCGCTGTTCTAAAAATTCGTGTTTT
AGTTGTTTGGCTCCTATTCTACAATGTGCTATTACTATTAAGCATTCTTGTATCATGGCATTCCTCAAATAGTTTTAAATTACTTT
AATTTGAAGAAGGAACATTCTGTACAGTCACGGAAAAGTGTCAAAAATGAAAATTGAGAACCAGCCTGGGCAATATGGTATAACCCTGTGTGTACAAAA
CACTTTGGGAGGCCTAGGTGGGTGGATTGCTTGAGCCTAAGAATTGAGACCAGCCTGGGCAATATGGTATAACCCTGTGTGTACAAAA
AATACAAAAATTAGCCAGGTGTGGTGGCCCAAGCCTGTAGTCCCAGCTACTTGGGAGGTAGGGTGGGAAATCCTAGGTGACAGAATGA
GACCTGTCTCAAAAAAAAAAAAAAGAAAAAATGATAAAGGATACATATCAGGAAAAACATGCATGGTATTTGTATCATCTACTTTA
GAGTAATTCCAGTATAGTGGTTTTTTGTTGTTTTATTTTGAGAAAGGGTCTTGCGCTGTCACCCAGGCTGGAGTGCAGTG
GTACGATCTTGGCTCACTGCAACCTCCGCCTACCAGGTTCAAGCCATCCTCCAACTCAGCCTCCCAACTCAGCGAGTAGCTGGGACTACAGGTGTG
CGCCACCATGTCCAGATATCAATTTTGTATTTTTGTAGAGATGGGGATTTTGCCATGTTGCCTGGATGCCTGAATGCCTGGCCTCAAGCAATCCACCCTC
CTCAGCCTCCCAAAGTGCTGGGATTACAGGCGTGAGCCACCACACCCCAGGCCCCAGCTGTAGTCGTTTTTTCTTTTCTTTTATTCTATG
TTTTAATGAATTTACACGTTACCCAAATGTTCCTAGTTTTCTGCCTTCCCCCAGATCACTCTGGAAGATAATATTTAAGAATATACCAAAT
AAGAATATGCAAGTCCTCCCCTAAGGGTGGCAGGAAGAACACCCCTCCCCAGTGTATTTAGCGCCTCTGGCTGGGAACGGCTTCCC
CATGCTCCTAGGTGCAGGTCCTCTCTTGGCATGCAGCCTGACTCCTAACTCCCCACCACCAGTGCAGACCCACCACCAGGAGAAGGACGGCCACAGTCCCTCA
ATCCCCCTTTCCAAGATGTGCACAGCCTGACTCCTAACTCCCCACCACCAGTGCAGACCCACCACCAGGAGAAGGACGGCCACAGTCCCTCA
TCCATGTCACCAACCTTTCTCTGAGGAACCTGACTGGCACACCCCTCCTCTTAGGACAGCCAGCCAGCAGCTCGTCCACAACGTGGAAGTCCAGCTTC
CGTTCAAATCGGAGTTCTTTCTTCATGACATTTCTTGCAAAGTCCCGGAACCCACAGCTCGAACCTCCCAGTAATCAAGCCTGGCTGTCCCCAACCACC
CCATCTTCCTTGTCCTCACCCCTGGTCAGGAGAAGCCAAAAACATCAGTCAGCTTCCCAGTAATCAAGCCTGGCTTCTCACCCAGGGCT
CGCCCCAGAACAACCACCCGGCTTCTTCAGTGTAGCCAAAAGGCTATTGGAGTCTTCTCAACAACAAACAACAAAAATAAACGTGAGATGATTCTCC
GAAGAAAAGAAGAGGATTATATATAAAACGTAAAACAACATATACACACCACCCCCACAAGGCAAGGCCAGTTCACCTCAGTGCTCA
GGAGTGTTTAGAGCAGGAATGTTCTTGGGCATCTGCCTTCCCCCACCAGCACCTCAAATTCTTTCTTTCTTTCTTTCTTTCTTAGAGTTGCG
CTACTTTGCAGTGTTCATAGAATATTTGTAATAATTTTAGGCGGCTCCTAAAATTTCATGAAGCTCACTGAAGCTCAAATTCCTGGGTTCAAGTGACCCTCCACCTTC
TCCCTCTCGGTTGCAGCTGGAGTTCAGTGGAGCATGTTCATGTTCATAGCTCATGAAGCTCACTGAAGCCTCAAATTCCTGAAGCTCACTGAAGCCTCTTAGAGACAGAGTCTAGCTC
AGCCCCATGAGGACCTGGGACTACAGGTATGCCACGGTATGCCACGCTATCACCCGTCTATCTTTATTTATTTATTTAGAGACAGAGTCTAGCTC
TGTCACCCAGGCCAGAATGCAGTGACGATCTCAGCTCACTGCACCACCTCAGCCTCCCAACTTCTGCCTCCCAAGTTAAGGGTTTCTCTTGCCTCAGCCTCC
CTACTAGCTGGGATTACAGGCTTGCACCACCACGGCTAATTTTTGTATTTTTAGTAGAGATGTGGTTTCACCATGTTGGCCAGG
CAGGTCTCGAGCTCCTGACCTCAAGTGATCCACCCGCCTCGGCCTCCCAAAGTGCTGGATTACAGGCGTGAGCCACTACGCCCAGCCT
ATTTTATTTTATAATTTGTTTAGACAAGGTCTAGCTCTGTTGCCCAGGCTGGAGTGGTGCAATCACGATTCAGTGCGCCCT
```

FIG. 3J

```
GATCTCCTGGGTTCGAGTGAGCCTTAGCTCTGCTCCTGTTTAGCTCTGGTACTACAGGGTGCATGCCACCACCTAGCTAATTTTTTAAAATTTTTT
TGTAGAGACGGGGTCTCACCCTGGTCTCCAGGCTGGTCCAGTGCTGGTCTCAAACTCCTGGGCTCAAGATGCTCCCACATTGGGCGTCCCAAGTGCTG
GGATTATAGGAGTGAACTACTGTGCCCACCCAGTCTTTTAAAAAATTTCAAGAGATGGGGGTCTTGCTATATTGCCCAGGCTGGTCTCCAC
TCCTGGTGTTAAGGGATCCTCCCACCTCAGCCTCCTTGAGTAGCTGGGATGACATTACAGGCACACATGCCACCACTGGCTCTAAAAC
TTCTTCTGTGCCATTTGTGCCACTTCACCCAATTGCCTCTTGTAGTAGTAATTAATTAGGATCTAGGGTGAAAAAAGTCAACAGCTATAT
ATAGTCCTCAAAGTTTGTACGTATCTGAGCAGTCATCAGTTGCACAGTGCACAGAGGGATGAACTGCCGTCCCGCCACTCAAAAAGCATT
AGTGACCATCAGGGAACCGTCAGATGCATGCCAGACTAAAGCAGAGGTGAGGCTGTGCTGGGTGCTCTGTCTCTGCTGGTTTCCTGGTTCCCTTG
ACTTCCCTGTCTTGCTCTGTGCCTTGGGAGGTTGACCCTGAGTTGGCATCTCAGGGTCTCACTGAGCTCCAGAATCATTGTTTCCTCCCTTACCCAAGTGA
AAGGCTACTGCTCCCACAAGGCAACCACGGTCCCCGCTCCCGGTCCCTGGCTCTGCCTAAAAACCCCTAGGTATTATCCGATCTTGGTGATCAGGAGGTG
GAATAATTATGTTTATTCCAGAACCCTGACAAATGAACAGGCTAAAAGAGGCCTAAAAACTCACTTCACTTTGGCTAACAAGTGGTTCAATATTAAAAGCTTTGTCACCAGTGCAGTGGC
TTTGTTTGTTTTTTAATGCAGACACTAGTTTCTGTGACATTTCTGTGACATTTGGCTAACAAGTGGTTCAATATTAAAAGCTTTGTCACCAGTGCAGTGGC
TAAAACAAACAACAAACAACTTCTGTAGGAGCTGAGGATCACTTGAGGCTGAGGCCAGGAGTCGAGGCTGCAGTGAACCATGATCTCA
CTACTACACTCCAGCCTGGGCAACAGAGTGAGACTCTGTCTCTAACAAACAAACAACAAATAAGTATAGTTCTTCAAGCATGCAGA
CAATCTGTCTCCTTGGCCTGGGTCTCTCACTGCCTTTAGATAAAACTGGCAATAACCAAAGAGTTTCATAAGGCCTGTTGATCT
ATTTATAAGACATGCATATAATTTACTTGACCATTATCCATATATAGGCTGAGTATTCCTTATCTTACATGCGTGACGCCAAAGTGTTTCAGGTTCTGGA
GAGTCAGCACACAAGGATTCTTTTTTCCATATATACACAATTGAGATATCTTGGGATAGAACCTACATCTAAAACACAAAATCATTTATGTTC
TGTTTGGGATTTGAAATATTTGCATATACACAATTGAGATATCTTGGGATAGAACCTACATCTAAAACACAAAATCATTTATGTTC
ATATACACCTTATACACGTAGCCTGAAGGTAAATTTACACACAGGTAAATTTTAATAATTTCCACATAAAACAAAGTTTGTATACATTGAAC
CATCAGGAAGCAAGGTGTCCCTGTCTCAGCCACCACAAGGACACTCTGTAGTTGTCTTTCATTCCTGATTCCGAATTTATACGCTACT
GACAAGCAATCATTTTCTTACACTTATTCACACAAGAGCACTTAGTAAAAATATGACATATATATCTGGCATGCTCAGAAAAGCTATT
TGCAGCAGAAAGGAGCTGGGAGGGTCCCTTTTTTTCCCTTGGGACACGGAATAAATTGTGTATTATGTCCTGCATTTGACTGTGAC
CCCATCACATGAGGTTAAGTGTAGAATTTTCCACTTGTCTCTCGTGTCTTAAGGTCAGGAGTCAAAACCAGCCTGGCCAACATGGTAAACCCTGTCT
CAATCCCATCACTTTAGGAGGCCAAAGCAGGTGGGTCATTTGAGGTCAGGAGTCAAAACCAGCCTGGCCAACATGGTAAACCCTGTCT
CTACTAAAAATAAAAAAGTTAGCCTGGCATGTGGTGGCATGCCATTGCACTCCAGCCTGGGTGACAAAGCCGAGACTCTGTCTCAAAAAAAAA
CCTGGGAGGCAGAGGTTGCAGAGAGCAGAGATCACTTGCATTGGATTTTGCATTAAGTGTTCAAGCTGACAAAGCCGAGACTCTGTCTCAAAAAAAAA
AAAAAAAGGTTAGATTTTGGAGCATTTTGGATTTTGGATATATCCAATACTATATATATGCTCCGTTTATATTTCCTTAATTAATTGGACTTGGAACAACTTG
CAAACTTAACAAAACAAGTGAGATATTCCAATACTATATATATGCTCCGTTTATATTTCCTTAATTAATTGGACTTGGAACAACTTG
GCCAATTATGGAGGATTAGAGGATGAGACTTAAATGTTACTGTACAAGGGATAGAACGATTCATTCCTCTATGTTATCATAAATACTTATGGTA
```

FIG. 3K

```
TTTMCCATCCTGCTGTCATGCAGATCCAAGAACCAAATTAAAACACATTTGCCGGGGTCATAATAATGTGGCCAGAATTTAAAGAAA
AACTTGATTTTAATTATGTATGATTTTGCTTGTTTAGTCTACGGATTTCTATTTGCTTAGCTTACTCAAAATAAAGCGGGCACTT
CGAAGACTCAATAGTCTTCCATTCATGTGGGCCTTTATAATGCACGGGCCCAGATGCAATACATCTGGCGGTCTGCTTGGGTTGGCCAC
TGGATTGAAGGAGGCAGAGAAGTCTGGGATGATTCCCAAATGTCTGGATCTGGTGACAGAGAGACAGCCGGTAGAAGGTTGTCTTTGCCTGTCTGT
AAGCTGGGTTAGGAACTGTTGAAACTGAAATCCCTGAGGSYKTGCCGACAGAGAGGAAATAAGAGCACCCAGGAGACAAAGCCCAGGAAGAGAAACATCTGACG
GGTTCCAGGTAACTTCATCGAAAGAGAGTTTCAGGCAGCAGTAGAGAAATAAGAGCACCCAGGACAAAGCCCAGGAGACAAAGCCCAGGAGACAAAGCCCAGGAGACAAAGCCC
GAGGACAGAGGAAGAAAGGGTCAGGAATGAGACTGAGCAGGTGTCATGTGTCTGACACCAGAGCCTGACACATAGTACGTAGTAGACACT
CAGCAAATACCGTAACAGAGATGAATCCAAGGCTGGGGAGGTGGCTCACGCTGTAATCCCACACCTTGAGAGGCTAAGTGGGAGG
ATCTCTTGAGTCCAGGAGTTCGAGACCAGCAGGCCTGGCTCTCAAAAATAAAAATTAAACATTAAAAAAGA
GATGAATGCATAACCTGGCTGCTGAGCCAACATGGGTTGGGTGAGCCACTCTTACCAGCAGCTAATCAAAAATTTGCCTGGAATTCT
GAGGCTCCTGTCCTACGTCTTGGCTGCTCCTCCAGATCACCTTCTGGCCGGTCCCAAGTCCACTTCCGTGCTCCTTGCTCCTTCCT
CCTGGTCTCCCTCACACTTTCCTTTCTCCTACTCCCTTCCCTGTGTGCCCTGGCTCAGCCCAGCACAGGGAGAGCCCTGTGCCACCTAT
TACAGCTCACTGCACCTTTGCATCTTTCAGAAAGGAGCACCTACAAGATAACCCACCCCCACCTTTTTTTTTTTTAGTAGTA
CAGATTGCCTCTCATAGCATAATTGGGCTTCATTATTATCCTTAAAGACCCTCTTTCTGTGGCGGATTGGGATGGATAAAATAAGAAG
ATCGAGAGGTTGAAGAACCCATCTGTTTTGCCAGTGAGGGGATGAGGGCTGAGGGGATAGAATTAAAAGGATTAGGAGGGCTCAGGCACTAGAGCACTATGATTACACTGT
NGTGTCATCCCAGCTACTCAGGAGGCTGAGGCGGGCAACATATCAAGACCCTGTGTTTCTAGGGACAAAAATATNNTTTAATAATTAAAAATTAAGGG
GAATAGCCACTGCACTCTAGCCTGGGCAACATCTGCTCATCCAATTCCACAAGAAAATTCTTGTTGGTAGTGAGAGTTAGAAGTCACCGGTAGGGGGTTCCTGGATCATGAGCA
AAAGGTAACCACATCCTGCTACAANAAAAGAAGNTGGAGAGGTANGANGAGGACAATAAGTAAGAAGAGGATAGAAGAGCTAATGGCATCATCATTTACACAAAAGAGA
TGCTTAAAATCAGTTGCTCATCCAATTCCACAAAAATTCTTGTTGGTAGTGAGAGTTAGACCCTGGTGGACTGGGTAGAGCTGGGTAGGGGGTTCCTGGATCATGAGCA
CTTCTTGATGACTTTAGCAACAACAGTGCCTTTTAAAAACCAGTGCATTATTGTTGCCCTACTACTACAGGATATGCACATTTCTGCACTTGCTCTGCAGATCTCAGAAAGGATCTGTACTCGGTTGGATCTATTCCAGTCTTG
AAGGCCTGTGCAGCCAATGGCCCCCACTACTGCCACTTTGATTCTGCACTTCCCCTCACCTCACCTCAGTCCAGTTCCTAACTGCACCTTCCCCTTCTGCCCTTTGCCCTTCTCCACAATTATCCAGTCTTG
AAGAATCCAGCAGCCACCTTGATTCTGCACTTCCCCTCACCTCACCTCAGTCCAGTTCCTAACTGCACCTTCCCCTTCTGCCCTTTGCCCTTCTCCACAATTATCCAGTCTTG
CCATTCTTCAGGACAACAACAGTGGCTTCACACATGTGCCACGTGCGCCCGTATTTTCATTTGCACTGGGTCCTGAAAGGGATCTGTACTCGGTTGGATCTATTGTTGCCATCT
CTTCAAAATGTATGTATTTCTGACTTTTTTACCCTGCCCTTGTTCCCACTTGTTCCCACTTGTTCCCACTTGCTCTGCAGATCTCAGAAAGAGCCGGTGCTCCTTGT
TCTCTCACTGCACTCTGCCACACTTGGCCACCTTGTTCCCACTTGTTCCCACTTGTTCCCACTTGCTCTGCAGATCTCAGAAAGAGCCGGTGCTCCTTGT
CTTTCAGGCCAGCCGGCTTCACACATGTGCCACGTGCGCCCGTATTTTCATTTGCACTGGGTCCTGAAAGGGATCTGTACTCGGTTGGATCTATTGTTGCCATCT
TGAAACTCTTAATACTCTTTGAACACGGGACGGGCCCGTATTTTCATTTGCACTGGGTCCTGAAAGGGATCTGTACTCGGTTGGATCTATTGTTGCCATCT
ATTGTATCAGAAGTCTCCTCCTCAAAGAGCTCCTCCAAGAGAGCCTTCCTCGGCCACTTATCCTCAAGTAGCTCCTCCCCTTCTAAGTTACTGGCTATCCCA
```

```
GTTAAAACTAGATAATAAATCCATCAGTCTACCTGAGTTCTCTTACATGGCAACTCATTACAATTGGGTGCATGTGAACAGAGCAAGG
GAACTATAGTTGATTCTTCTGGAATGTAGAGGATCCCTTTTCCCCAAGGTCATCACATACAGTTGGGCACACACAGTATCTGACATAT
GCATCTCAAGAGAGTACCATGTATATCCAATAATGCATCAGCCTAATCACTTTTCAAATTCAAATAGCTTTATTTAACAGCTATAGCT
TGAACTACATATTTTATCCATGGAGAATACATATTATATTCAAATGTCTCTTTGGAAGATGTAAAAATTGTTCATATGCCACAGTATAAA
GTTCAGTAAATTTCTAAATTATAGACATTGAATAGCTTGCAGTTTAATGACATTAATAATTAACATCACACTCAAAACAATGACTTTTT
TAAAAAGGTTATCTCAAMCATTMCCCTTAAATCAAAGAGGAAATTAAAACTGTAACAAAAATAATTTGGAAAATATTTTCAATTTTA
ATGTTGAGAGTAAATTACTTTTTAAATKTATTTTATTTTTGAAAAATGTAAGTTGTAAAATACATATAACAAAATTACCATCATA
ACCATTTTAAGTGTAACGTTCAGTAGTGTTAAATACATTCATACTGTTGTGCAACCATCTCCAGAATTATTTTCATCTTGCAAAAAC
TGAAAGTCTATACATATTAAACAATGCCCCATTCCCCCCACCCCAGTCAGATTTTTAATTTAAAAATACAAGTGGAAGTTCTAATATTT
TCTATCTATCCCCTCTATCTATAAAGTTGGGGGCCACTGAATTCCAGATGCTGCTTGCATCTTTTTACTTCTGAGCATCATGGCCTCTG
GGAGTCCGTTAAGCAACTGGAGCCGCGGTAGTGTGACAGGCTGACCCCAAAGCTGTGTGTCAGCGTCACCGGACTGGTTGATGTTGCAGC
CTCACCTACTGCCCTGAGTCAGTCAGGGTTCTGGCAAGGAAAGGAGAAATGCCTGACCAGAATGCCTGCAAACCCTTCTCCCTTTTGGCAGC
AATCAAAAGATTTGAGGAAATCTAAAATAGCTCCTCATCAGGAAAATGTGAAAAATGTGAACGCCCCTCCAGCTGGGATCTTCCCTGGTGGGCTTGT
GAGCCTGGCATCTGGGAATAGAGACACTAGAATACTTCACAAAACACATTATCACATGGAATGTTTTGAACATCTG
GGTAAACCACTACTTTCATTTATGCTAAGAAAACTGGGGTTGAGATGTTTGTTAATTAACATGTTACTCCAACACTGTAATGAATG
AACTGAGATAAAGTCAGCAGATGTGTGCAGGAGACCCAGTGATTTTCTGCTTTTCCACTTCCCTGAACCTCCTGGCAAGGAGGACA
GGGTATACAGCTTTAACAAGAATATTCCACTTGGGTGGGTCAAGTAAGCAAATGTGGATTCACTCTCGGCCCTGAAGAATCCAAGCA
ACTAGTAGAATTTTGTTTATTCTTAAAAATCTTATTGTACAAAAATCATTGAATTATACTCTTAAGTTTGAGGCACTCAATTAGAAA
GTTAATCGGAAAAAAAATCTGTTTAACCCTGAGTATCCCTCCTAAAATTACTTAAAGCCTAGAATAAAGGTCAGTTTAGACAAATT
ATGAATTGGCAATATGGTGTTAGCAACCTAGTCTCTCCCAGTATTGAGTAGACTATCTGAAACTTATTAAGTAGGAAACCCTAGAGAGGTT
ATCCTCACTGTCCCCTTCCTCCACCCTCAGGTTTTATTTGTATGTTTTAATGAAATGGGGTCTTGCTCTATGTGCTCAGGCTGGTCTTGAACT
AGAGTGACTTGACCTCAAGGGATCCTGCCTCACTTCCCGAGTAGCTGGGATCACAGGCACTAGCCACCATGCCTGCTCAATGCCAGGTTAAT
CCTGGGCTCAAGGGATCCTGCCTCACTTCCCGAGTAGCTGGGATCACAGGCACTAGCCACCATGCCTGCTCAATGCCAGGTTAAT
ATAGGCTTTGATAAACTGTCAACTATAGGAATAGAGTTATAAGCGTGAATCTGCCAGTTGGTACAATGTCTAGCAGGAAACGGAAGG
CGTCGATAGGATATTCCTTAGGAATGTTTACTAGACAGAGGTCTACTTCTTCCATGGCAATGTTCACTTCCAAAACTTGGGACCTGTG
ATTTGGTAACTGTTTTTGTCCTGCTTCTCGGACGTACTAGGTATAATAATAGATGCCTTGCTTGTTTAGCTCATTAATGCAAAGACCTTGAGAAGT
ACAGATGTCTTGCCTATGATAATGGATACTAGGTATAATAATAGATGCCTTGCTTGTTTAGCTCATTAATGCAAAGACCTTGAGAAGT
AGATACTATTATTCCTATTATTCTTATTGCAAATGAGGAGGACTAAGGCTTATATGTATTAAGTAATTTGCCCAAGGGTACACAGCCAC
TGTAGTTTGGAATTGGGAATATTACTAGGATTTTGGCTTATGAGGACAATGAGCAGAATATGTAAAATTGGGACTGATTGAGAAAATCCTGG
```

FIG. 3P

```
AGGTATTGTTACTTGCCTTGGAGAAACAACTTTTTTTTTTTTTTGAGACAGAGTCTTACTCTTGTTGCCCAGGCTAAAGGACAATG
GCACGATCTTGGCTCACTGCAACCTCCGCCTCCTGGGTTCAAGCGATTCTCCTGCTTCAGCCTCCCGAAGTGGCTGGGATTACAGGCACC
CACCATGACCAGCTAATTTTTGTATTTCTAGCAGAGACAGGGTTTACTATGTTGGCCAGGCTGTTCTCAAACTCCTGACATCAGG
TGATCCACCGCCTCCAGCCTCCAAAATGCTGGAATTACAGTGTTGAGCCACTGCACCCTGCCGAAAACAACCACTTTAAGATGTTA
GATTCCAGCCAAGTGAAGTGGCTCATGCCTGCAATCCAAGCACTTTGGGAGGTCAACCTGGCAGATCACTTGAGGCCAGGAGTTCGA
GNTCAGCCTGGGNAAANTGGTGNAACTCCGTCTCTANTANAACATACAAAAATTNGCCCGGACATGGTGGCACGCACCTGTACTCCCAGC
TACTGGGGAGGCTGAGGCAGGAGAATCTCTTAAACTGGGAGGATGGAGGTTGCAGTGAGCTGAGATTGCACTGCACTCCAGCCTGG
GCGACACAGCCAGACTCTGTCTCAAAAAAAAAAAAAAGATGTAAGATTCCAAAATGTTCTACAAAGTSCAAGGACACACA
CACACTCCTGTCTGGGTCAAAATGTATATTGGCAAGCTGGGCCTGGACCAGTTTTCTTACGTGGATCATAGCAAATGCTACGTGGCTTA
GCAGCCAAACTTTACAATGAGGACAACKGACAAATCCTAGCCAGGCAGAGAAGATGTGGAAGATTGTCAGTGCCCAGGTGATTCTTTGG
GCTTAATACTCCAGAAAGGGTCATTTCCATTAGCTCTGAGGCTGTCTTCTTATGGCCAGATCCACTATACTCACTTCATTCCCCTGCA
CGATATCTCGGCATGGAGGGGGCTGGGGTTCAGAAGTGTTGCAGGGAAGCCAGAGGTTTGGGCAGGGGCACAGGAAAGGTC
TGTTGCACCATGGTGCTGACCCGTGAGGCACTCCAGGGCAGGGCTGAGGCTCGGAGGACAGGTGCCACTGCTGCTGGGCTCCTCACC
ACCCAGCAGGACTTGGCCAAGTACATATATAAATATATTTATTATATTACAAGAATAAACAAGAGAACAAAGCTTGTTTATATTC
CCATTTATATTTATTTAATATTACATTATATATACATTTAACTTGACATAGCAATTGTACTTTCTGCAATGTTTAAGGATATACAACAATTAAAGAC
ATTACAATGTAACTCAACGGGAACATTTAACTGGGAACATTTAACTGACATACAAGAATTAACTGACATAGACAGA
AGCATAAAATGAAAGAATTAAAATGTACCAGTCTTTAAACTGTAAAGCCCACTTCCCCATGCAACCAGTGGATGAAGAATTGAAGACAGA
CTTACCGGTAAATAGGTAAATCACAGTTGTTCCAGATGCATCTTCATTGTCAGGTCAGGTCAGGTCACCACACCTAGAGTAATGTCTGTC
ACATAGCAAACACTCAGTAAATACTTAGTGAACAAATGAACAGATGAACAGATGAATAAGATTTACAGTCTTCAATAGGAATCAATCAGTGCT
CTTTTTCTTAAACTAAACAGAAAGCTTTGGGAGATCTGACAGCTGCGAGGCACCTGAAGGAGAAAGAATGAAAAGCAGTTAGAATGT
GTACATTTCAAAGGGTGAAATCAACTAAGGTGCACATAGATCATGAAGAAGAAAGGCTATGCCGGGAGTCTTTGGCAGATTCCTGGGGTGAATGCAGG
TGAAACTTCTGCCTGGAAAAATAACTGCATGAGAATTTATACAACCTGCCAACCTAGCTGGTCCTCCTCTGTGAAAAATAAGGTAAGAGAAAAAGAGAG
CTCAAGATTTCACAGTTCTTAAGGCACCTATTCAGCTTACTTTATTTAATTATGTTAATTATATTAGAACGGAGATGCCTGATCTGA
TAGGGGCCTTTTGCTTTCTAGAATCTAAAATATCCTGGCTTTCTTGCCTTGTATTTGTTATTTGTGAACATGTTCCCACTAGATAAGCTCTT
TGGTCACTGAATGCATCTCTTAAAATATCCTGGCTTTCTTGCCTTGTATTTGTTATTTGTGAACATGTTACCAAATTGCATTTGGAATCATAGCA
TGAGGGCAGGGATCATATCTTATTTGTCTTCACTTATGCATTGGTGGCATCCAGTAAATGTTACCAAATATCTCTGCCTCCAAATCTTACCTTCA
TTGCAGTCTCTGATTTCAATCCACATTAATTTTTCCTTCTGGAGGCCAAATATTTAAAGATACTCTCTGCCTCCAAATCTTACCTTCA
ACATGCTTGCCTCCTTATGCATAACACACCACCACACCACCCCTTCATGTCCCCTTTGCCTACCCATG
```

FIG. 3Q

```
TATGTAGACTGGCATGTTTTCTTTTTTGTACCCTTTGGTTATCTTCTGAGCAGAGGGATCACAGAGGGTGGTGACCTGAATAGGATGAG
CTCTGCCCCACTAACGGCTCCAATTAAGCTAGATTTTCTCCCCCTTCAAGAAGTGAGCTGAATACAAAATTGAGTGGAATTTCACGCT
CCATATTAGAGCACATACTAATTAGGGTATGCTCCTGGCTTGGCAATGCCATACTCAATTACAAAGGGAGCAACTACTAAGATAATGAA
TGCGCCAAGTTAATTTGCCTCCACTATTAATGCATCTGCTCTATTTTAGAGCTACTGTGCCTGCTAATACACCAGAATATGGTGTA
ATCAGCACCAGCAGGAAGTCAGGAGAATATGGGGACCATTCCCATCTGGGTCAGTTGTGTGATCTTATGAACATTTCTTGGGGCTTTAAA
GGTTGTTTTGTGGATGAAGAGTCAAGTAAACAGAAGTGGTAGAGGGAGAGGCAGACAATCCACCCAAATTCTTTCTTTATTTTT
TTCATGAGACAGGGTCTGGCTCTTTTGCCCTGGCTAGAGGGCAGTGGTGCCATCTTGGCTTACTGCAGCCTCCACCTCCTGGGTTCAAG
TGATTCCTCCTGCCTCAGCCTCCTGAGTAGCTGGGATTACAGGCGCCCACCACCACGCCTAGCTAATTTTTGTATTTTAGTAGAGACAG
GGTTTTACCATGTTGGCCAGGCTGGTGACCTCAGGTGATCCAGGAAATTTCAGATCCTGTTTCCATAGGCAAAGGCAAAGTCAGGTATAAGAGAGGTAAGAATTATCTTAA
GTGGGCAATGTAAACCAGGAGAAATTTCAGATCCTGTTTCCATAGGCAAAGGCAAAGTCAGGTATAAGAGAGGTAAGAATTATCTTAA
AGTTAATTGCCTCATACTAGCTTGCCCAGAATATATTGATTTGAAATGACTACTGTAAGTTGACTTTAAAATTTGCAATAAGAAATG
GTCCAGGGCCGGGTGCAGTGGCTCACCCTGTATCCTGTCTGTACTAAAATACAAAAAATTAGCCAGGCATGTGGATTMCCTGAGCTCAGGAGTTCGA
GACCAGCCTGGGCAACAGGTAAAACGTGAAAACCCTGTCTGTACTAAAATACAAAAAATTAGCCAGGCATGTGGATTMCCTGAGCTCAGGAGTTCGA
CTACTCGGAAGGCTGAGACAGAAGACTCCATCTCAAATAAGAAAGAAAGAAAGAAAGAAGAAAGAAGAAAGAAGAAAGAAAGAA
AGTGACAGAGAAAGAAAGAAAGAAAGAAAGAAAGAAAGAAAGAAGAAGAGAAGAAAGAAAGAAAGAAAGAAGAAGAAAGAA
AGAAAGAAAGAAAGAAAGAAAGAAGAGTTGAGAAGAAAGAGTTCTATTTCCTTTCCATGAAGATAATGAAAAAGATCTCCCATCAGTGAAAAGCT
CAGATTGAACGGTTTTTCAGGAAGATATATCAATTGGAGGATGTGTYMAGCCAGTTGACTGTGGATGTGAATTCTCTCTTTAACAGGAGTTTTA
CATTGAGGAAGATGCACAATTGACCCAAATGGAGGAGTTGACCAAGAGTTGACTGTGGATGTGAATTCTCTCTTTAACAGGAGTTTTA
ACGTCTTCAGACAGATGCAGCAGAGAGTTGACCAAGAGTTTGACCAGAGACTTCATATCAGATACAGACTTCATATCAGACCTAACTGAGCCTTACTTTTTT
CCAGCTTCTCTAAAGAGCCGATGACAAAGACAGATCTTGAGCAATGTGGGACATTCCCAACTTCTTCCAGCTGTTTGTAATTTCAG
TGTCTCTATTATGAAAGTGTCAGTGAACAATTACTAAGATGCTGAAGGCAATAGAAGATTTACCAAAACAAGACAAGGCAAGTATT
AAAAGATTACTTTACTTAGAGGTTTACACTAAGTCAAGTTTGTTTAGCTTCAGAAATGGTAGACATTTCTGAGTCACATTGTATAG
CGTTTCTTGAAGAACTGAACTCTTTCTAGAGACAATTGTTTCAGAGCCTCTTAAAAGAAGCTTTGAAGTCTGCTAAACACTATCCCTCTTCCATCA
TCGTTGAGAACTGAACTCTTTCTAGAGACAATTGTTTCAGAGCCTCTTAAAAGCAGAAAAATGCTAATAGGTTGAGAACTTGAAAAAAACCAG
TTCCCTCATTATTATTCTTTATTATTTGTGACGGAGTCTCACTCTGTCGCCAGGCTGGAGTACAGTAGCGCTGGAGTACAGTGGTGTGATCTTGG
CTCACTGCAACCTCTGCCTCCCAGGTTCAAGCAATTCTCCTGCCTCAGCTCCCAAGTAGCTGGGACTACAGGTGTGCACCACGCC
CAGCTAATTTTTGTATTTTAGTAGAGACAGGGGTGTCAGTATCTTGGCCAAGCTGGTCTCAAACTCCCGACCTCAGGTGATCCACC
CGCCTTGGCCTCCCAAAGTGCTGGGATTGCAGGCGTGAGCCACCATGCAGCCATTTCCCTCATTATTAAGCTCATGTAGATGCTC
```

FIG. 3R

```
AGCTCTATTCTGCTAAAGCATCAGAGAGCTTCTTTAAAATTGATCTGGAATCCTCAACTCCCAGTTTGAGAAGCCCACTCTCACATATA
ACCAGAGCAATTTAGTGCCCTCCTCTGAATCACTACAATCATTCCTTAAATCATAAAAGTGATCATAAAACCACAAAAATGCTCATA
AACCCCAAACTACAGAGAATATTAGATAAGAGATTGCCTTCTACCAACACTAATCATGCCTCATGGCATCCATGTTGGAGACACATGCTG
CTTTATGTTTTAAGGCGGGCAGATATCTTCTGTGGGCTTCTATGGAGTAAGTTAGATACGGCATTCGAGAATGAGAATTGCCACGAGGGT
CAAGTGTAGGATCTGCATTCCTTTGTCACTGTATTGACCCCTAAGCCAGGTGAAGGCTGTCCCCTCTGAGATGAAAATAAAATGG
GCTCCTTCTATCTATTTTTCTTTTTTTCTTTTTTTTGAGATGGAGTGTTGCTCTGTTGTGTGCCAGGCTGTATTGGTGTG
ATCTCGGCTCACTGCAACCTCTGCCTCCTGGGTTCAATCAATTCTCCTGCCTCAGCTTCCCGAGTAGTGGGGATTACAGGTGCCGCCA
CCACGCCTGGCTAATTTTTGTATTTTTAGTAGAGACAGGGTTTCACCATGTTGGCCAGGCTGGTCTCGAACTCCTGACCTCAAGTGAT
CTGCTCACCTTGGCTTCCCAAAGTGCTGGAATTACAAGCATGAGCCACCAGCGCCCAGCCAGCACTCCT
GACCCTATCTGACTATTTTCAATTATATAGCTGTAGCTGGCAACATCTGAATCAGATTCTCAAAATCGCCATGACATTACATAACTG
GCCTCTACATAGGAGAGAGGTTTACCTTCAGAAACTGAAGCTAGGAAAACAGTGCATTACATCTTCAGGTGCCATCGTTCCATGAACAGA
GAACAGCCATCATTACTGGAAATTGTGGGTTCTATTTCAGAGTCCAGTGGACTTTTTTTATAAGTCAATTATTTGGTCTGTAGTCCAT
TCTGAGGTTGCAAATTCATCAAATATTCAGGATAAAACACCAGGCGAGTAGACTAAATCATCCAGGCTGGGTGGTATTAAGTGATTTTA
GCCTGACTGTTTACATGGATATCAACTGTCTTGGAATAACACTGAGAATATGTTCATTAGAACAAAAGGCTCCTCCCCTCCATGTTGT
GTAGCAGCCTTACACAAGCATTGGTTACATTCCCATGTGCACAGATAGTTTCCACTGTCTGCCAACATCTCAGTTGATTCAGACATGCCACAATCTAGATAATTTTT
CAACCACTGTAACCCCTCCCACACACCAGCTACGAACACATAGTTTCCACTGTCTGCCAACATTGCCTTCTCATTCACACAGCTGGGG
CCAGCCCTACTCTCAGCTGCCTCACACGCCACCCTCCCAGCCCCTCCATCTCAGTGATGACCTGGAAAGCCAAGGTCC
CCTGTGAATGCAAATAGTAAAGACAAAATAGCAACCAAAAAGTCTGTGTTACACTATTGTACTCTTCTTCTCCAGTATCCC
TCCCCTAGCCAGACAGTACACAGAAGCTACCGCAGAGAGAGACACTTTCTGGACAGGTAGTTGGTGAGGAATAAGCTACTGCCCTAGAAAA
AGCCAGGGCGCTCACAGCACTTGAATGTGGTTTTCCATCATTCCCACCACATATCCCACCCTAATCCCCAGAA
TCTGCCTAATGACTTGACACTTTGAGTTTTGCCCTTGTGGTAGGCAAAATAATGACTGCCCACACAATTGTTAATCAACTGACTTTATTTTATTTATTT
CCTGTGAATTTATGTTATGCGGCAAAGGGAAAGTAAGGATGCAGATGGAAATCAATTTGTAATCAACTGACTTTATTTTATTTATTT
ATTTTTGAGACAGAGTCTTGCTCTGTCACCCAGGCTGGAGTGCAGTGGCAGTGGAATGATCTTGGCTCACTGCAACCTCCACCTCCCGGGGTTTA
AGTGATTCTCCTGCCTCAGCCTCCCGAGTAGCTGTGATTACAGGCACTCACCACCATACCTGGCTAATTTTTGTATTTTGAGTAGAGGC
AGGGTTTCGCCATGTTGTCAGGCTGGTCTCGAACTTCTGACCTCAGGTGATCCGCCTCGGCCTCCCAAAGTGCTGGGATTACAG
GCATGAGCCATCATGCCCGGCCTCAACTTGATTTTAAAATAGAGAGAGTATGCTGGATTATCCAGATGGATTCAATGAATTCACAGGGTC
CTTAAAAAGTGGAAGAAGAGGAGCAGGAGCCGAGTAATGTAGGTGGCCTCGAGAAGAATTAATAGTAGCAGCCACAAGAGAAGGACTTGGCTCGACTTTGACGACCTTGAAGACAG
AGGAAGGGGCCAGGAGCGAGTAATGTAGGTGGCCTCGAGAACTGGTATAGAAATGAAATGGTATAGAAATGAATTCTCCTCTAGAGCCTCCGCAAAA
AACTAGCCCTACTACTGACATCTTTTTTTTTTTTTTTTTTGAGACAGAGTCTCGCTCTGTCTTCAGGCTGCTTCAGGCTGGAGTGCAGT
```

FIG. 3S

```
GGTGCGATCTTGGCTCAGTACAACCTCCGCCTCCTAGGTTCAAGCGATTCTTCTGCCTCAGCCACTGAGTAGCTGGGACTACAGGCAC
GTGCCACCACGCCCAGCTAATTTTTGCATTTTTTTTGAGACAGATGACATCTTGATTTTAGCCTAGGGAGACCCACTTCAGACT
TCTGACCTAAAAGACCAAACAATAATGAATTTGTGCTGTTCAAGCCACTGAATCTGTGGTAGCTAGAGCTAATAATAATAGTA
ACTGACCAACATTTACTGAGCAAGTTCCGTGTGGCAACCTTCATGGATGGGCCTTATTGGTCATGATTGTTTAAAGGGCCAAAATTAGA
AAAATAGCTAACACTGAATTATGAACACCAGGAAAAGGAGGAGCGGAAATAAAAAGAATCAGAAATATCTTGATAATTAATGCTATTTT
GTTGAGTATAGGTTCATTTGTTCTCATATTTCTTTCCTACCTTGGTCTTTCTGGACCTCAGTTCCTGAATCTGTTGAAAGCGAATAGG
TCCAGGAAAGTAGCTCTTGGAATTATCTTCATTTGCCTCTAATGCTGCCTTAGAGAGTGTTAGTTAACATTAATTTCGCTGGGAGAAACAGACAGGCAGG
CGTGCGGGGCCGGGAGACCTGGTTCTAATGCTGCCTTAGAGAGTGTTAGTTAACATTAATTTCGCTGGGAGAAACAGACAGGCAGG
TGGGAGAGTAGAGATGATTTAGCTCAGTGACTGCACTGGAGAATTAGTGTCATATGGGCCTAGAGGTTCTGAGGTTCTGTCAAGGCTAGACTAAGCGAG
GTGATGGATTGTGCTGTGGCTGCAGGATAGTGTCATATGGGCCTAGAATTGTCATCCTTGGTGTACATACCAGTATTAA
TCTAGATGCTAGAGATAAAATGATGATTATGACACAGCCTCTGACTTCCAGGAGTCAGTCCAGAGAAAGGAAAACAGATTAGTGAACA
ATTACATCACCATATTGTGGGTAAAATGCAGAGAAGAAGGTATGGAAGAATGACAAGAGTAAAATGGCAAGACCAAGTCCCTTCCCTCAA
GAGGCTTACAGTCTAATGGAAAAGATAAGAAAGCAAACACTACATAAAGCAGGAATTAATTCTACACTGGAAATTCTCACAGGGGCTA
TACAGGGCAAAGAAGAGAGGGTCCAGGAAAGCAGCTGGGAGAAAACGACTTTCTGGTCACCAAAGGGATGGGTGCCTTACATGCCATTCT
ATCAAACAGTGCTTCACTGTTTTAAACTATGGACTTTGCAATTTATCTCAAATAAAACGTTTCATTTTAAATGCTGAGGATTTAAT
ATGACAGAAAATCATCAGGTTGTAAATTTATATGGATTGTTAATTCTCCTAATGTCAAACACTCTATTGGGAACCGCCAATTTCTGTTGGATA
GACTTCTCTTTACACATTTTGACCCCCTGTTCATAACAGTATATGCATCTCCACACACAAAAAGAATAGTAATAAATTAAGAGTTTTTAAAATACAGAAGTCCAAGAGAAA
AAATCTTTGACCCCCTGTTCATAACAGTATATGCATCTCCACACACAAAAAGAATAGTAATAAATTAAGAGTTTTTAAAATACAGAAGTCCAAGAGAAA
TGTGTGTGTATATACATATATAGAAAATGCAAAATATAGCTTTAAAAATTATAGCTTAATCCTAGCCTATTGACATCAGAAATACTAATGATATAAGACAAATGATTTTAAAGTAATCAAATA
TCTAATATCTTGAAACTTCTTCCCAATTATACTTAATCCTATTGACATCAGAAATACTAATGATATAAGACAAATGATTTTAAAGTAATCAAATA
AAGTGGTTCACAATCACCTATTTACTTAATCCTATTGACATCAGAAATACTAATGATATAAGACAAATGATTTTAAAGTAATCAAATA
TATAAAGAACAAAATAAATGAAAGCTGCCCTCTCCACCTATGTGTTATATACTAATAAATTCTAGTAATGAGATTCTTGGATTCAAGAGT
CCTCCTAGAAAATAAAATTACATGCATTAATATATGTGTATATACTAATAAATTCTAGTAATGAGATTCTTGGATTCAAGAGT
GTGCAATTTTTAATAGCTGTTCAGTTGTCCCAGGAAATTATTGCACCAACGTGCATTCTGTGTCTAAATATAGGAAAAAGGGCCAGGG
GCGGTGGCTCATGCCTGTAATCCCAGCACTTTGGGAGGCCGAGGCGGGTGGATCATTTGAGGTCAGGAGTTCAAGAACCGCCTGGAC
AACATGGCGCAACCCCATCTCTACTAAAAGTACAAAGATTAGCTGGGCATGGTGGCTCACACCTGTAATCCCAGCTACTTGGGAGGCCTG
AGGCAGGAGAATCACTTGAACCCGGGAGGCAGAGGTTGCAGTGAGCCAAGATCCGCCACTGCACTTAGCCTGGCAACAGCAAGAC
TCTGTCTCAAAAATAAATAAATAAATAAATTAAATACATACATAGGAAAAAGATTTGAAAGCACTGGTAAGAAAAAGCTGCGGCATTGTC
TCCACTTCTTCAAAGTGCAAACTCTTATGACACTAACGTGTAAATGTTATGTTCCCTGTAGCTCCTGACCACGAGGCCTGATTTCAAA
```

FIG. 3T

FIG. 3U

```
TTGTATTTTAGTAGAGATGGGGTTTCACCATATTGGCCAGGCTGGTCTCGAACTCCTGACCTCGKGATCCTCCCACCTCAGCCTCCCA
AAGCGCTGGGATTACAGGTGTGAGCCATGCGCCTGGCCAACAAATTGTTACAATGTTAAACAACATAATATCCTAAACATATTGGCTT
TTAAAGTATCATTAGATACACCACATACTAATAAAGGTTACCTTTGGGTTTAAGATTAAAGATGATTTTAAAAATACTTCTTTCTG
TATTTCCAAACTCTTAACCATAAACATAAGATATTCCTTGACTTAGGATAGGATTATGTCACAACCATACATAAGTTTGAAAAATCAT
AAGTTGAACCATTGTAAATTGGGGACCATATGCTCAAGGAGCCTGTAAATTACATATTAATATTCTCCATTATGAAATAAGTCTTTCCATTG
TAACATATTACTTTATTTAATCACCTTGCTCAAACATCTATATGCTTGCAACTCGAAAGGAGTAAGTTTCCTTTCTAATTTTTTTATTCAA
TGCAAATTAATGCATTGCAGAGGTTCTAAACATCTATATGCTTGCAACTCGAAAGGAGTAAGTTTCCTTTCTAATTTTTTTATTCAA
TAAATAAAAAAATGAGTTTAATAGAGTCTATTAAATTAGATCATTATTCGGAGTGGTTAGTAAACCTGTTTAGAGTGACAACACTCC
CTTTCTCTCTTTTTTTTTTTTTGTGCAGAGTCTCGCTTCTGCCTCTGTCGAGTGGAGTGCAATGGCACGATCTCGGCTCACT
GCAACCTCCACTTCCCAGGTTCAAGTGATTCTCCTGCCTCAGCCTCTGAGTAGCTGGATTACAGGCAACCGCCACCATGCCCAGCTA
CTTTGTTGTATTTTAGTAGAGATGGGGTTTCACCATGTTGGTTAGGCTGGTGGGGAACTCCTGACCTCAAGTGATTTGCCTGCCTCTG
CCTCCCAAAGTGCTGGGATTACAGGCGTGAGCCACCATGCCCAGCCCTTTTCCTTTTAAATATCACCAGCCTGGGTTCTTTGTTCT
TTTTGTTTGTTTTGTTTTTGTTTTTTGTTTTTGAGACGGAGTCTTGCTCCGTNGCCCAGGCTGGAGGGCAGTGGCACAATCTTGGC
TCAGTGCAACCTCCGCCTTCTGGGTTCATGCCATTCTCCTGCCTCAGCCTCCTGAGTAGCTGGGACTACAGGCGCCCGCCACCATGCCC
GGCTAAATTTTGTATTTTAGTAGAGACGGGGTTTCACCGTGTTAGCCAGGATGGTCTCGATCTCCTGACCTCGTGATCCACCTGCCT
CGGCCTCCCAAAGTGCTGGGATTACAGGCTTGAGCCACCACGCCCAGCCCGGCCTCCAGCTGCTGTTCTTTCTCTCTCTTCCACTTCATTCTCTGTCA
TTGGGCTAGTGAGGAAGTCAGGTTACACGGGCCACAGAACAAGAACAAGGATTGTTCTTTCTCTCTCTTCCACTTCATTCTCTGTCA
GCCTCTCCCGACCTCAGTAGTTGGTCTTCTGCCATGGACACCTCTACCCCAGGTAGCTCTGATTACAACTGGACCTTTTCGCGGGGTACCTAGAGCAGTGAAGAGTG
TCCCTCTTGTGCAAATTTTCTGCCATGGACACCTCTACCCCAGGTAGCTCTGATTACAACTGGACCTTTTCGCGGGGTACCTAGAGCAGTGAAGAGTG
GGCAGAAAGCGTTTGGAAAGCGTTGCTCCAGGTAGCTCTGATTACAACTGGACCTTTTCGCGGGGTGGGGAGATCACCTGCGGTCAGGAGT
CTCTTTCTCCTGGCCAGGTGCAGTTGCTCATGGCTGTAATCCCAGCACTCTGGAAGGCCGAGGCGGGCGGATCACCTGAGGTCAGGAGT
TGAGACCAGCCTGGCCAACATGGCGAAACCCCGTTCTACTAAAAATACAAAAATTAGCCAGGCATGGTGGTATGAACCTGTAATCCCA
GCTACTCAGGAGGCTGAGGCAAGAGAATTGCTTGAACCTGGGAGGCAGAGGTTGCAGTGAGCCGAGATCAAGCCTCCAGCCTGGGCCTC
AGAGGGAGACTGTCTTGAAAAAATAATAATAATAACAGATAAAATTAAAAAAATAAAAAAGGAGTGCTCTCTCCTG
AACTGCTGACTCGAGGACTCTCTCAGCCTGTTTATCATTTGAAGAGGAAATAATATCTGCTTCGTACGAGTTGCAAGGTTATATACAGAAGCATAGGTT
ATAAAATGTCTGAAATATCAATGATTCTCATTATTCAAATATTGTTTTAAGTCACAGTTGCAAGGTTATATACAGAAGCATAGGTT
TTTATAACAGAAAAATAGACACTTAATATACTGACCTCTTACAAAAATAGTCCTGCTCAAGCATCCCATCTATGTATCATTAMCATCTA
TTCTTTTCTACCCAGCTAAAATAGTTTATTAATAATCCTTGAAGTGTCACAAGTNGAATACAGAATAAATCAGATAATACATTAAAATGC
ACCTGATAATCAATATGCACCAGATAATGGACACAGTATACATCAGATAATACAGTAATACAGTTTAGTGTTGCAAAGGT
```

FIG. 3V

```
AAAATGTAAAGAAGAATGTCCTAATGTGCTCCCATGCTGCTTAAAACTGTTATTATAAATTGCTTTTTATTATAAATATATAAAGAATGATG
TAATAGGCCAGCCATGGTGGCTCATCCCTGTAATTCCAGTCTTTGGGAGGCTGAGGCAGGTGAATCACTTGAGGTTAGGAGTTTGAGA
CCAGCCTGGCCAACATGGTGAAACCCCGTCTCTACTAAAAATATAAAAATTAGCCAGGTGTGGTGGTACGCACCTGTAGTCTCAGCTAC
TCCGGAGGCTGAGGCAGGAGAATCGCTTGAAACCAGGAAGCGGAGGTTGCAGTGGGTCAAGATCAAGCAACTGCACTCCAGCCTAGGTG
ACAGAGCGAGACTTGTCTCAGGAAAAAAAAAAATTCTCAGTCACCTAGATTGAGAAATAGAACATTACCAAAACAGATAAAGCCCCA
CTGTGTTCCCATCCACATCACATTCACTTTATCTCCTCAAAAGGAAAGTGCTATTTGAATTTAGTATTAATTATTTCCTTGCATTTCT
TCCTACTCATATCATGTGCCTATATACATATATAATAATATATACAAATGCCGATATCATACATAGCAATGTTTTACATTTCGATTTTGCATT
GTCAATGTAGAATTTTAAACTTAAAAACATGCTTCATCAGCCGGGTGTGGTGGCTCATGCCTGTAATCCCAGCATTTGGGAGGCCA
AGGCAGGCGGATCGACGAGGTCAGGAGTTCGAGACCAGCTGGCCAACATGGTGAAACCCCATCTCTATTAAAAATACAAAAAAAATA
TTAGCTGGTCATGGTGGCGCGTGCCTGTAATCCCAGCTACTCAGGAGGCTGAGGCAGGAGAATTGTTGAACCCAGGAGGCAGAGGTTG
CAGTGAGCCGAGATCGCACCATTGCACTCCAGCCTGGGTGACAGAGCGAGACTCTCAAAAAAAAAAAAGCTTCATACAAA
CATGAAAACGGGCACATGTCTGGCTGGTGGCATGGTGAAACCCGTAATCCTAAAACTACAAAAATTACAAAAATTGGAGGGCCAAGGCGGGCAATCACTTAAGG
CCAGGAGTTCGAGACCAGCTGGTCAGCATGGTGAAACCCGTCTCTACTAAAAACTACAAAAATTAGCCAGGCATGGTGGCATGCGCCT
GTAGTCCCAGCTACTCGGGAGGCTGAGGCAGGAGTGATACTCTGTCTCAAACAACCAGCAGGGTGTTGAGCTCGAGAGGTTGCAGTGAGCCAAGATTGTCACTGCA
CTCCTGCCTGGGTAACAGAGTGATACTCTGTCTCAAACAACAAACAAACAGGGGTGTTGAGCTCAAGAAGTATAAGAGAGACTGGAG
GTCAAATGTTAATTTGACTATGTAACTTATTAATGAAGGAGTTATGAAAGGTTATGAACAATTGCCACTTTCAATCCATAATCTATGGTAAT
TGCTTACAGTCAAGCAGAGACAGAATGCTGAAAGGTTATGAAAGGTTATAGATATGTTAGTATATTGCCACTTTCAATCCATAATCTATGGTAAT
TGCCATTATCATCTTTTCTATCAGACGAGAATCAACAGTAAATAGTAAAGCCAACAGCCAAGCTAGATGAAGAGATAGACAGACAGCCAACGAGTCTCTCCCTAGACCTTGAAGTGATCTTTGGGTGGACCC
TTCATGGAGTCTGGCCCTAATCAACAGTAAATAGTAAAGCCAACACGCCAAGCCAAGCTAGGACACGCCAAGCCAAGGTGAGAACCGCCTCTACAAAAATTAAAAATTAG
CTAGACAATAATTTAGTATGAGCCTGTAGTCTCAGGAGGCCTAGGCTAAGGTGAAAATACCACTTGAGCCCGGAGTTCGAGGCTGTAGT
CCGGGCATGGTGTGAGCCTGTAGTCTCAGGAGGCCTAGGCTAAGGTGAAAATACCACTTGAGCCCGGAGTTCGAGGCTGTAGT
GAGCTATGATCATGCCATTGCACTCCAGCCTGGGTAACAGAGCGAGAACCTGTCTTGAAAAAAAAAGAAAAAAGAAAAAGAAACA
AAAGGAAATGCAGCCATTTTTTTTTGCACTCAGTGAGTTTGCAAGGGGTTAGCCATGTGAATGCATGTGAATGCTGCTCTAGTTCATTCACTGTT
TCTTTTGCAATATGGCTTTTCACTCAGTGAGTTTGCAAGGGGTTAGCCATGTGAATGCATGTGAATGCTGCTTCAAGGTATTGCTATTATAAACAAATC
GTATGTTGGTCTATGTAGGCATATCACAATWATATYCATTCCCTAGCTGAAGTACATTTGCTTCAAGGTATTGCTATTATAAACAAATC
TCATACCTTTAATCAAATAATAATTTGTCTCTTCAATCAGCTNTGATTTACTTGTTCNAANACNAAGCACACAACTATAATTANAAT
TCATTACTGATAAATATAAATATTTTCCAAAACATCACAAATCTTTNTNNTNCACTATTTACTATACACTTTNGGTCTNAATTTAA
AGCGGCTTCACTATATGTGGTCTTTTCCTCTCTCCCATACTAATTACTGGTACTGGACATATACATCCAAAATCAAATAGTARTGTC
CTTTTAAGGGATAAATGGGATGTGATGTAGAAGGGCATAGTAGGGACTTCATCTGTTTTGGCAAATTTTTCTTAATATAGGTGGTA
```

FIG. 3W

FIG. 3X

```
CAAAGGCACTTCTATATAAAAACCTCCACATAAAATAAAATTATGGTTTCAATTATACATTTTTATAACAATTATTACCACTTAAGAG
CATTTACTGGGTGTCAGGCAATGTTCTAAGACTTTTCCATATATCAGATCATTTAATACCCTCAATGACCCTATAAGGAAGTAGAAT
TCTTTCCCCAGTTTTCAAATGAGGCACAGAGGAGGTTAAGCAACTTGTCTGAGCTCACACAGCTAGTAAATGGTAGAACTAGAATTCA
AACTCAAGCAGTATTTCTAGAATCAGTGAACGTAACCACTTTGCTAAACTGCCTGTGAAGTTACTTTTCTCAAAACAGCTCCTATTT
CACCATGTAAAGAAAAGTACAAACCATAAATAGCAAGTGCTGAAGAGAAGCCTTATGAAGAGAAATATACAAATTCCAGCAAGTGAAA
ACGGTTGTGGTCCCTGGTTGTATAATAGTTACATGGGTGTTGACTTTACAATTATTTAAACCAAACATAAATACTTTATGCAGTTTTA
TGTATGTTATACTCACAGAAAGAGAAGGGAAAAATTTTTAAATCATTCTCTTAAGGTTACATCAAGTTGGGTATCAGTTCAGTTCCATT
TAAATGATTCAAATCAAAGTCTGTGCATTTGAGAATTCATTAAGAGAGTAACATACATGTTATTCATTAAGAGTAACATAAATTTGCA
TTGATTCTTGCCAAAATCACACTCACCATACAACCATAAATTGTAAATTTCTAGGAAAACTCAGTACAAAACTTGGTGCAATGCAATAAAGTT
GTGGCACAGACAGTAATACTCAGCAAACATCCCCACCTCTCTCATATTTTCCAGCTCCCCTTGTGGTTAAACGTTGCCATGTGGCAA
GTTCTGGCCAGTGAAGCGTGAGCAAAACTGAAAAGGGTTCTTTGTAGATTGAGACAGTGAAGAGCCTATGTGTGCTCATCTATTCTCTT
TTTCTGCTGAGGGCACAAAGAAAGTCCTGAAATCATGTGCTACAGCTATGAGATAAATCTTTGTTGCATGAAGCCCTAGGAATGCCAGGACTAATCTG
CTGGTGTGGAGCCCTTGTAATGGACACATAACATGAACAAGAAATAAATCTTTACTATTAAATTACATTGAATGTGTATTGGGATTTAGTAAACTTCTACTGT
TACCTCAGCACACAAACCCAGCCTATCCTGACTAAGGTGGTATTAAATACATTGAATGTGTATTGGGATTTAGTAAACTTCTACTGT
ATAATCCTTCTTCTGTAGGTAGTTCCAAGGATTCATGAAGGAAATATTTCCAAACAAGATGAACAATGATGACAGTAAGCATTCT
GCCTTCCTCTTAATTCACACTCAAGATCCCTCTTGAAGCAGAGTTCTAACTTCATTGGCTACGTAGTGACAAAGCTCTAC
AGCATTTTAAGGAACATTTTAAAACCTGGTAAGCAGAGCATGCCTGGTTAGGAATGCCTGTTGACAGGAATAGTTAATTCTCAAAGGGA
AAAACAAAACTTGTTTCAAATATACCTGGAAAACATGTTAACCTCATTAATAAAGACATGAAAACAAACAAGATGGCATTTTCTGCCTA
TCAGATTTGCAAATTAAAAAAAACCCAGGAAATCCTGATAGGAAATGTGATGAAATGGGAATTCTCATATATCATGTATTGGTGGGAAC
ATAATTGGTTTTGCATTTTTTGAAAGCTATTTGATTGATGAAMAKTCTCCCTCCAAGATCTAGATTTGCAGCATTATTTAAATATTAAAGTTGGCC
ATCAATCCTAAGGRATAAATCTAAATTTGATGAAMAKTCTCCCTCCAAGATCTAGATTTGCAGCATTATTTAAATATTAAAGTTGGCC
GGGGCGCAGTGGCTCATGCCTGTAATCCCAGCACTTTGGGAGGCTGAGGCGGGCGGATCAGGAGGTCAGGAGATTGAGACCATCCTGGAT
AACACGGAGAAATGGCGTGTCTCATGCCTGTAATCCCAGCACTTTGGGAGGCTGAGGCGGGCGGATCAGGAGGTCAGGAGATTGAGACCATCCTGGAT
AGGCAGGAGAATGGCGTGAAACGCTGAGGCAGARCTTGCAGTGAGCAGGAGATCGGCCACTGCCTGCACTCCAGCCTGGGCGACAGAGCAAGA
CTCTGTTTAAAAAAAAAAAAAAAAAAAAAAAAAAATTAGCCGGGCATGGTGGCGGGCATGGTGGCGGGCGCCTGTAGTCCCAGCTACTCGGGAGGCTG
TGTGTAAAAACAAGAGAATGATTAAGTAKATTATGACTAAATACACTCAATACATTTATGAAACGTTAAAATATTCAAAAATTTAA
ATAATGACTTGCTAACTACTTTAACAAGAGCTTTATTATCAGCTAGTCTTGGAGGTAATAGTATTATCATGATTTTTCAGAAAAGATC
CTGAGGCTCAGTGTCCAAGGTCCAATGAACTGAACTACTCAGGTCGGAGGTGGTAGAGCAGCAGCATGTGGAGCCAGTTCTCTCCGACTCCATCA
TCACACTGCACGGCTTCCTGTTAAGATATTTGCTCAAAAAATGCGAGATATAAAAATCTGGGTAATATGCGAGTAAATCTGGGTAATATGCGGTAATATGTGGGTAAT
```

FIG. 3Y

```
ACATTTTAAATTATTCATGAGACCTTGTAGTAGGTCACCATCAATGTGTAATTAAGCCAGATGTGACAGGATTTGTTGCCTCTCCCTT
TACTTCTGAATTTTGGAGGCCTTTTTTTTTCTAGTTGTATCAGTCAGCCAACCAATATCTTTTTAGCATCTACTAAGTTTAGATACG
GGAACTGGTACTCTGAAAGAGAAAATGAGAAATTTGACAAGATCCTGTCCCAAGGAGCTTCCTATCCAACAGGGGCACAAGACAGATA
GATAGACACACACACACACACACACACACAGATACTTGGTAGGAAGATACTTCTGAGCTCAGTATATTCCCTTTCTCACTGTCCTTCTATC
CTCTGGGAGTCAGGGGAGGGGTGTTCACATTCTGCTCTTTCCTCTTTCTCTTTCCCTCCTGTCCTCTCCCACTCTGCTCCCTTTCCTTTTCTTTCT
CCCTCTCTTCCTCTCTTTCTGTTCTGTCACCCATACTGGAGTAGCTGGGATTACAGGCGCACACACAGTGGCACGATCTGGCTCACTGCAACCTCGGCCTCCCAGGT
TTTTTTTTGAGACAGAGTCTTGTTCTGTCACCCATACTGGAGTAGCTGGGATTACAGGCGCACACACCACCATGCCTGGCTAATTTTTGTGTTTTTTAGTAG
TCAAATGATTCTTGTGCCTCAGCCTCCTGAGTAGCTGGGATTACAGGCGTGCTTGAACTCCTGACCTCAAGTAATCCACCCACCCTTGGCCTCCCAAAGTGCTGGGATC
AGACAGGGTTTCACCATGTTGGCCAGGCTGGTCTTGAACTCCTGACCTCAAGTAATCCATCAATTAATTAAATATAAATGTAGATACACACAGGC
ACAGGGCATGAGCCACCACACTGGCCTCCTCCCTTCTTAAAAATACATCAATTAATTAAATATAAATGTAGATACACACAGGC
AGAATCAAAGTGTATAGGTTGGAGAGGAGACTGTTCCAAAAGGGGGATGGCATGGGCAAATACGGCAAGAAAGAGTAGAGCATCTAGG
TACTGAGGGTGCTGGGAAGTCCTGCTAAAAATACGGCAGAAGAGTAGAGCATCTAGGTACTAGGGTGCTGAGGGTGCTAAAG
TGGTCCCCTCCCACTGTGGGGCCTTTGAGTTTCCCTGTGCCAGGTACCTGCCCTCTGTGAGTTTGAGTTCTTTCTTTGGTTGCAAGCA
ACCAAGACAGCTCAGCTAGAGAAATGGATACCGACTCATGAGTCAGAGGGGAAGCTGGACGTCTATGCCCAGAGCAGCAGA
AACGGGTCAGGTCTAGAGTCACTCTGCTCAAGATGTGACTTGCCAGGAGGAATCTGGCTGGCCCAGCTGGCTGGGACATGTGTCTACCTCTAGACCA
TTAGTCCTCAGATCACTCTGCTCAAGATGTGACTTGCCAGGAGGAATCTGGCTGGCCCAGCTGGCTGGGACATGTGTCTACCTCTAGACCA
GGAGAGGAGAGTCTTGGTTGACAGTCCCATGTAGTACCCTTGTTTACTGAGTCATCAACAGATCTCAGTTCAAATAGTC
ACTTCTCAGGGCAATATACCCTCTCTACCCATAAAACTAGGGCAACATACCCTCTCTCCCTTTCACACATGACCATAACACCATG
TAGCACTCAACTCTGTAAGTTGACATTTACCCATGTGACTCTTTATGAACGTTCATCTGCCTGGCACAGGCAAACCCTCAGTCCATGAGGGTA
CCACCGTTCTAGGGTTTTGCTCTTCTCTTTGCTCAGTGGGACTTAGGACTCTGCTCAGTGGGACTTAGGACTCTGATTTGTTGAAT
AAATTAATTAATAAACACGTGTAAATGAATATCAGTAGATACAACAAGAGTAACAGTAGGCAAGGTGGAAGCAAAGGTGGGAAGAG
GTCAGGGCTCGAGTCTGGGCTGTCGGGTGTGGAGTCTGAGGTTCACTCTACAGCCTGGTGAGACGTAGGTTTTAGAGAAAGGAAGCCTCA
TGCTGGTGCCCCAGTGGGTACTGACTATGCATTTGTAGCCAAATCAAAGTATTTCCCATAAAGTCATCTATCTCTTCCCAGTTGTTGGG
ACTTCCAATGGCAATGGGAATTAAGATACTGAGTAATTGAGTAGTTTTAAAATTCTAAAAGTAACAAAATCACAACTACCAAACATTTACTAACAAGGCACACAAGGAGTGATTTTCAC
AGGCAATGTAATGTTTTCTTTTTTATGTAGTTTTAAAATTCTAAAAGTAACAAAATCACAACTACCAAACATTTACTACCTATTTTCTTAGATTYCCAAGA
TATCCATAATCCCACCATCTTAACACAACCACTATTATTCATTGTTTTCCTTATTCACATTTTCACATTTTCACTATTTTTCTTAGATTYCCAAGA
AATAGAATTACTTGTTTAGAGGTTATTACATCTTATTGTTCTGGATATATATCTTATTGTTCTGGATATATATATATCTATATATATAGCTAAATTAATAACAG
CAATGTCTGCAGTACCACTTTCTCAAATGCTAACTGGCATTTCAATTTTCAATTTGAGACAGTCTCTCTCTCTGTTGCCCAGGCAGGATTGCAGT
GGCATGATCTCGGCTCACGGCAACCTCCACCTCCCAGGTTCAAGCGACTCTCATGCCTCAGCCTCCCAAGTAGCTGGGATTACAGGTGT
```

FIG. 3Z

```
GCACCACCACACTTGGCTAATTTTTGTATTTTTAGTAGAGATGTGTTTTACCATGTTGGCCGGGCTGGTCTCAAACTCCTGGCCTCA
AGTGATCCTTCCACCTCAGCCTCCCCAAGGCTGGTATTACAGGCATGAGCCACTGCCTGGCCTGGCATTTCAATTTTAAAATCTTCA
GTAATAAATGAAAATTTTATCTTATTGTTATAATTTTATGGTTTTTATTATTCATGAGAATAAACATTTCCAAGTTGTTTACTG
ACTGAATTTCTTTTGTGCACCTTACTGGTATCATGGATAAAATTTGTCAATTTCTGATTATATCAATGCATTCAGGTCCCAAA
CCTGCCAAAGTTTAAAGAGAAAGATACTAAGGGAAAAACCAGGAAAAGAATGGTAGAAAAGAATCACCCTGGCATTTCAATCACGTAAA
CATTTGCTAGGTGCCCTAGCTGCAGGTATACAGCTCACTGAAACATGAATTCCAATTTATAGGGTGAAATATATATTTAGAACCCTCT
TCTGGAACTTTCTTCTAGTTATCTAGCATCCTAAGTGCCTGGACGTTCCTGATTGGTTGCAATGTGTTTTATTCCCATCCCCAAGTT
TCATAGCTGCCGGCCCTGGGATCTACAGTCCACAGGCTGTAACACAATATCTTGCACATCCTGAGTCTTTAATAAGCTTTTGTAGATGGG
CTCTTACCATCATCATCGTGAAAGGCAAATATACAAAATTTGTTGACTAATGTAATGAGTCATGAGTAACAGAAGTTACTGACCA
AACACTAGTGCATGTAGAGTTCAGAATAAACACTTTATTATCACATCAGAGGAAAAGACCATCTTAGAGGCTCAACAACCAGGAAAG
CTGTGACGATTTCTTCAAATTGTTAAGAATATCCATGCATATGGGTTTCACATTATTTGCTACACACAGTACCAATTTTTCCAAAGC
CAACAGCAGGTATTCTATTACCATCCTGGACTTTACTCAGGTAAGATGCATCCTATATCCAGTAAGTAAGTAGAATTATCTCTTCATCTGGGACCTGAA
TTGCTGCTTTTTTTTAAGGTAAGAAGATCTAATGCAATAAACACAGTTGCAGGAAAGTATGTTAGCTATATACTCAGTAAGTAGCTATATACTCAAGTATGT
ATCCTGAAATAAAAAAAGGATAATAATACTCAAATTGAGTAAATACTAAATCACCTAGGTGTCTATGTTCTATCATCGACTTTTGAA
TTGAATGGCTAGCTAGTTCTTTCCTTTAGTTGCTTTGCACTTAAAATATATATAATTGACTTTTTGGAAAAAAATCTAAGATTCATTGCTTTG
TACATTAGTAGTTCTTTCCTTTAGTTGCTTTGCACTTAAAATATATATATAATTGACTTTTTGGAAAAAAATCTAAGATTCACTTCCTAAT
TAACAAAATGTTCTTCCTTTAGTTCTGTATAGTCTTTTTAAATTGTGGTAAAATACACACATGGCATTAATTACCATTTTATCTCCTAAACT
TTTTGTAAAGACCAATAGGTTCGTATAGTCTTTTTTTAAATTGTGGTAAAATACACACATGGCATTAATTACCATTTTATCTTCCTAAACT
AGTGCACAATTGTGGCATTAAGACTACACTCAGTGCTGTGCAACCATCACCACCGTCCATCTTCAGAACCTTTTTATCTTCTAAACT
GAAACTCTGTACTCGTTAAGCACTCACTTCCGTTCCCATCCCCAGCCCGTAGCAACCACGACTGTACTTTCTATGAATTGACTA
CTCTAGGTACTGCATGTAGGTGGAATCATACAGTATTGTCTTCATTTGTTTGTTTTTGTAAGACAGGGTCTCAC
TCTGTCGCCCAGGCTGGAGTGCAGTGGTGCAATCACAGTATTGTGCAATGGTTATTTCACTTAGTGCCATGTTTCAAGGTTCA
TCCATGTTGTTGCATGTCTCAGAACTTCCTTTTAGGCTAATATCTGCATGTGTTGAACGTGGGTGTGCTACATAGTTACTTTTAAAATTG
ATGGACACTTGGGTTGCTTCCATCTTTGACATACGTATTTTATGGAAAACACAAGATTTCCTGGCTGACGCTCAACCTCATAGTTACTTTTAAAATTG
GCACAACAGGCGCTGTCTTTTTGACATACGTATTTGTGTCAGTATATACTAAGGATTACAATGAGGCCAACGTGGGGATTACGTGGATTACGTGAGGATT
TGCAACACAATAATGAGGAGAGCACGGTCCTCACACGTGTCAGTATATACTAAGGATTACAATGAGGCCAACGTGGGGATTACGTGGATTACGTGAGGATT
AAGAAATGTAGGCAGGCACGGTGCCTCACACGTGTCAGTATATACTAAGGATTACAATGAGGCCAACGTGGGGATTACGTGGATTACGTGAGGATT
CGAAACCAGCCTGGCCAACATGGTGAAAACCTGTATCTACTAAAATACAAAATTGGCCAGGCGTGGTGGCGCATGCCTGTAATCCCA
GCTACTCAGGAGGCTGAGATGGGAGGAATTGCTTGAACCTGGGAGGCAGAGGTTGCCACTGAGCCAAGATTGTGCCACTGCTACTCCAGCCT
```

FIG. 3AA

```
GGGCAACAGAGCGAGACTCTTTTTTAATAAATAAATAAATAAATATATAAAGAGAAAGCGTAATGAAAGAGAGAACTCTGAACTT
TAAAGAACTTTTCACCCAGTCTCTTGATCTATCTGACAGAAAAGGCTTGTCAGAGAAAGTTAGAGTTCAGAGGCAGCCAATTGAATATAAT
TAACTCCAAATGAAGATAAACCTTTCTAAATCATACTGAAGGCTATAAAGGCTCTAAAAAATGAGAATTATGTTATTTTTTTGAGACAGGGTCT
TACTCTATTGCCCAGGCTGGAGTGCAGTGGCATGATCTGGGCTCACTGAAGCCTGACCTCCTTGGCTCAGGTGATCCTCCCACCTCAGC
CTCCTGAGTAGCTGGGACTACAGGCTACTACCATGCCCGTCTATTTTGTATTTTTTAGTAGAGATGGGGTTTCTCCATGTTGTCCAGG
CTGGTCTCAAACTCCCAGGCTCAAGCAATCTGCCCGCCTCAGCCTCCCAAAGTGCTGTAATTACAGGCATGAGCCACTGCTCCTGGCAG
GGAACTAATAGAATCTGGGTTCTTCGGTGTGCAATAAAYCTCAAATACAGCTATTCAACCATAGATTTAAATATTTGTTAGTGAAGG
TGACAAAAAATAAGTGATTAAGAGAAGAAGATTTTGCATGCAGGCTGAACTGGATTTCATCCTGGCTATCAAAAGCTTATAGAGTGGAAAGAGAGTGGGGAAGTGA
GGCTCAAAACAGCTAAATGGAAAGAAAGATTTTGCATGCAGGCTGAACTGGATTTCATCCTGGCTACTATATTCTCCAGATGTGTCACT
TTGGCCAAGATCCTTAATCTCAGTGTCAGTTCAGTACTATCTGCAGTTCAGACATCCCCCTTGGGGTCTTGGAACATATCCCCGTGGATAASG
TCAGTTACCCGAGATCAACTGCGGTTTTAAAATATTATGTGGAAAATTCCAGAAATACATAGTAAGTTTCAATTGCATGCCATTAAAT
CTCATGCTGTCCTGACCCCTTCCTCTCCGGAGGTGAATGCTCCCTTGTCCAGTGGCTCCACGATGGCTCCAAAGCACAAGATAGGGATGCCGGCATACTGTTATA
CTTAGGAACCCTTTCTGTCAAGGAACCCTTACTTTACTTAATTATGGCCCAAAGCACAAGATAGGGATGCCGGCATACTGTTATA
ATTGTTCTATTTTATTATTAGTTATTGTTGTTCATCTCTACCTGTGACTAATTATGACTCTCAAAAACGTTAATTTCTGCTTCCTTTACCT
GAAAAAAACATGGTATGTATAAGGTTCAGTACTATCTGCAGTTCAGACATCCCCCTTGGGGTCTTGGAACATATCCCCGTGGATAASG
GGAAACTACTGTAAAAGTTTGTSTTTATAGAGTAGTTSTSAGAACTACATGATTCATAATGACTCTCAAAAACGTTAATTTTCTGCTTCCTTTACCT
TGGTAGTAGCAACAATAAAAAAAATAATTATCAAGTAACTGATTCATAATGACTCTCAAAAACGTTAATTTTCTGCTTCCTTTACCT
AAGTTTACCTACTAGTTTGTAAAGGGAAGGTTTTTCTATATAAGTTGAAAGAATAGCAAAATTGTTATTTCCCAGCATCGTAAAG
AAACTGAAAAAGTTGCAACATACTTGCATGTCATTTATTCTAGAATGTACCAAATGGAATCTAAATATCATCGCAATTGACCCAGCATCATCCATTTAAACAAATATA
ATTAGCAGGTCATCCCTCTTTAAAATGAGAAATTTATCTCATTACATCTTTGTTGATCAACACAATTTGATCATTTTAATTTAAAATTAAGAACATCCTGT
CAAGTTTTCTTAACAATGAGAAATTTATCTCATTACATCTTTGTTGATCAACACAATTTGATCATTTTAATTTAAAATTAAGAACATCCTGT
GACATCAAATTCTAGGTATGAAATATTTATTCTAGATTGGGTGATCATTATTATTAAAAATTTAAACAAATAACATAAA
TATACTACAAATTCTATGACTACTAAACATATAAAAGTAAAATTTTCTTCCTAGAACAAGACAGGATTAAGCATCATGACCGTCCCTATTGGGGATG
TCCAATAAGTTAACGTATCCACTATTACTTACTTATTATTTCTTCCTAGAACAAGACAGGATTAAGCATCATGACCGTCCCTATTGGGGATG
TTTTATAGATGCAAGCACTGTGGCACCTACTGGTATAAATGCACCTGCTGATTGGAATGTCTCTTCCCCAGATCTTCCCTGCTGGTT
TCTTCCCAGTATTCAGGTCTCAGCTCAAGTGACTTCCTCAAATGAGGCCTCCTGGTGATCAGATCTGTGATGTCTTGTTGGTTACTTTGGTTGTCAC
TGTTTAGTGCTATACCCATTAATTTACTATCATCACACTTGTCACTATCTGCACTATCTGCAGATGTCTTGTTGGTTACTTTGTNGTGTTGTCAC
TGCCAGAATATCAGTTCTATGAAGAAAAGGGCCTTGTCTATTTGACACTTATAGANATGTGNAGGNACGACATACAAATGGCCAATG
```

FIG. 3BB

```
GGCATATGGAAAAACGCTTGACTTCAAGAGTACTNATGGNTATNACCAACATTTATGGAGTAACTACTTTGAAAAGAACCATTCTGTCT
TTACTATCAAGCCAAGATACTCAAGGAAGGCAGAAGTGGAAGCTCCATGTGGGCAGAGGAGCCTAGTCTTGAGATGTGATTTAGCT
GGTATTTGGGTGAAACAAATAAACCAGCCTCAAAATAACACAAGGGGCCGGGTGCAGTGGCTCACGCCTGTATCCCAGCACTTTGGGAG
GCTCGAGGCAGGCAGATTACTTCAGGTGAGGAGTTCGAGACCAGCCTGGCTAACATGGTGAACCTCCAT
```

FIG. 3CC

| Brain Regions | HKNG 1 mRNA expression in normal brain | | | | |
|---|---|---|---|---|---|
| | Gray Matter | White Matter | Neuron | Astrocytes | Oligodendrocytes |
| Frontal cortex(1) | +++ | - | ++ | - | - |
| Motor cortex(2) | +++ | - | ++ | - | - |
| Parietal cortex(3) | +++ | - | ++ | - | - |
| Occipital cortex(4) | +++ | - | ++ | - | - |
| Hippocampal formation(5) | | | | | |
| CA1 | +++ | - | ++ | - | - |
| CA2 | +++ | - | ++ | - | - |
| CA3 | na | na | na | na | na |
| CA4 | +++ | - | ++ | - | - |
| Dentate gyrus | ++ | - | ++ | - | - |
| subiculum | +++ | - | ++ | - | - |
| parahippocampal gyri | +++ | - | ++ | - | - |
| Caudate/Putamen(6) | +/- | - | +/- | - | - |
| GPi/GPe/Putamen(7) | | | | | |
| GPi | + | - | + | - | - |
| GPe | + | - | + | - | - |
| Putamen | +/- | - | +/- | - | - |
| Amygdala(8) | ++ | - | ++ | - | - |
| Thalamus(9)medial | ++ | - | ++ | - | - |
| Substantia nigra level(10) | | | | | |
| SNc(substantia nigra pars compacta) | ++ | - | ++ | - | - |
| SNr(substantia nigra pars reticulata) | + | - | + | - | - |
| Red Nucleus | + | - | + | - | - |
| 3rd cranial nerve nuclei | + | - | + | - | - |
| superior colliculus | | | | | |
| Upper pons(11) | | | | | |
| Locus coeruleus | + | - | + | - | - |

FIG.4A

FIG.4B

| Region | Col1 | Col2 | Col3 | Col4 |
|---|---|---|---|---|
| pontine nuclei | +++ | ++ | – | – |
| Lower pons(12) | + | – | – | – |
| locus coeruleus | +++ | ++ | – | – |
| pontine nuclei | ++ | + | – | – |
| raphe nucleus(midline) | ++ | +++ | – | – |
| Medulla(13) | + | – | – | – |
| Inferior olivary nucleus | ++ | + | – | – |
| 12th cranial nerve nuclei | + | ++ | – | – |
| nucleus ambiguus(multipolar lower motor neurons) | + | + | – | – |
| Cerebellum(14) | | | | |
| Purkinje cells | ++ | ++ | – | – |
| Granular layer | + | +/– | – | – |
| Molecular layer | + | + | – | – |
| Temporal pole(15) | +++ | ++ | – | – |
| Cingulate cortex(16) | +++ | ++ | – | – |
| Anterior thalamus(17) | ? | ? | – | – |
| Subthalamic nucleus | ++ | ++ | – | – |
| Ventral anterior N.(VA),Ventral lateral N.(VL) | na | na | na | na |
| Hippocampal formation(18) | na | na | na | na |
| CA1 | +++ | ++ | – | – |
| CA2 | +++ | ++ | – | – |
| CA3 | +++ | ++ | – | – |
| CA4 | +++ | ++ | – | – |
| subiculum | ++ | + | – | – |
| parahippocampal gyri | ++ | + | – | – |
| cervical cord (rostral position) | | | | |
| anterior motor nuclei | | | | |
| sensory nuclei group | | | | |

| pedigree | Affected Individuals | Phenotype | a.a. change | exon | comment | nt change | nt position |
|---|---|---|---|---|---|---|---|
| 30124 | 3010189 | scz | R331T | 8 | 3 of 4 affected individuals | AGA -> ACT | 51,641 51,642 |
|  | 3010185 | scz |  |  |  |  |  |
|  | 3010184 | scz |  |  |  |  |  |
| 30105 | 3010027 | scz | I23T | 3 | the only affected individual | ATT -> ACT | 35,044 |
| 31102 | 3110017 | major depr | E202K | 7 | all three affected individual (also seen once in Costa Rica) | GAA -> AAA | 45,487 |
|  | 3110014 | scz |  |  |  |  |  |
|  | 3110003 | scz |  |  |  |  |  |
| 30120 | 3010155 | scz | E202K | 7 | one of the affected individuals | GAA -> AAA | 45,487 |
| 30126 | 3010203 | scz | intronic | 10 | 3 of 4 affected individuals | insertion: GAATGCCTGGTTAG 21 base pairs 3' of exon 10 | after 63,417 |
|  | 3010210 | scz |  |  |  |  |  |
|  | 3010204 | scz |  |  |  |  |  |
| 30140 | 3011486 | scz | intronic | 6 | one of the two affected individuals | A -> T (24bp downstream of exon 6) | 43,450 |
| 32301 | 3210041 | scz |  |  | two of the three affected individuals |  |  |
|  | 3210051 | scz |  |  |  |  |  |

FIG.5A

| pedigree | Affected Individuals | Phenotype | a.a. change | exon | comment | nt change | nt position |
|---|---|---|---|---|---|---|---|
| 30120 | 3010155 | scz | L34L | 4 | one of the two affected individuals | CTC -> CTA | 36,307 |
| 32200 | 3210104 | scz | L34L | 4 | both affected individuals | CTC -> CTA | 36,307 |
|  | 3210009 | scz |  |  |  |  |  |
| 31109 | 3110013 | scz | I23T | 3 | one of the two affected individuals | ATT -> ACT | 35,044 |

FIG.5B

| a.a. change | exon | nt change | position |
|---|---|---|---|
| non-coding 5'-UTR | 1 | G->C (35 bp upstream from 3' endo of exon 1) | 15,385 |
| L42L (silent) | 4 | CTG -> CTA | 36,331 |
| V123G | 6 | GTT -> GGT | 43,184 |
| non-coding (intronic) | 6 | A -> T (24 bp downstream from exon 6) | 43,350 |
| V30I | 7 | GTC -> ATC | 45,571 |

FIG.5C

```
AGTTGCGTCCCTCTCTGTTGCCAGGCTGGAGTTCAGTGGCATGTTCATAGCTC
ACTGAAGCCTCAAATTCNTGGGTTCAAGTGACCCTCCTACCTCAGCCCCATGA
GGACCTGGGACTACAGTTCCCTCCCTTTGGAACGCAGCGTGGGCACCTGCAA
CGCAGAGACCACTGTATCTCCGGTGCAGAATGTAATGAGTGCCTGATACATT
TGCCGAATAAACTATTCCAAGGGTTGAACTTGCTGGAAGCAANAGAAGCACT
ATTCTGGTAACAGCGGGAACATGAAGCCGCCACTCTTGGTGTTTATTGTGTGT
CTGCTGTGGTTGAAAGACAGTCACTGCGCACCCACTTGGAAGGACAAAACTG
CTATCAGTGAAAACCTGAAGAGTTTTTCTGA
```

FIG.6A

```
AGTTGCGTCCCTCTCTGTTGCCAGGCTGGAGTTCAGTGGCATGTTCTTAGCTC
ACTGAAGCCTCAAATTCCTGGGTTCAAGTGACCCTCCCACCTCAGCCCCATGA
GGACCTGGGACTACAGATGGAGTCTTGCTCTCGTTGCCCAGACTGGAGTGCA
CTGCTGCGATCTCAGCTCACTGCAACCTCTACCTCCCAGGTTCAAGCGATTCT
CCTGCCTCAGCCTCTCGAGTGGCTGGGACTATAGTAACAGCGGGAACATGAA
GCCGCCACTCTTGGTGTTTATTGTGTGTCCGCTGTGGTTGAAAGACAGTCACT
GCGCACCCACTTGGAAGGACAAAACTGCTATCAGTGAAAACCTGAAGAGTTT
TTCT
```

FIG.6B

```
                                                                                          79
CTTGGAGTCAACTGAGTGTGGACTGAAACTTCCAAAAACTGACATGAGGAGTCACTGGAGAATCATGATCAAGGAGCTA
                                                       M   K   L                           3
CACACTCTGACTTAACTTTATTCTGTGGACAATGAGAGACAACTGCAAGGATTAACAGTGAGAAC ATG AAG CTG         153
 P   L   L   M   F   P   V   C   L   L   W   L   K   D   C   H   C   A   P   T          23
CCA CTT TTG ATG TTT CCC GTG TGT CTG CTA TGG TTG AAA GAC TGT CAT TGT GCA CCT ACT         213
 W   K   D   K   T   A   I   S   E   N   A   N   S   F   S   E   A   G   E   I          43
TGG AAG GAC AAA ACT GCC ATC AGT GAA AAC GCG AAC AGT TTT TCT GAG GCT GGG GAG ATA         273
 D   V   D   G   E   V   K   I   A   L   I   G   M   K   Q   M   K   I   M   M          63
GAC GTA GAT GGA GAG GTG AAG ATA GCT TTG ATT GGC ATG AAA CAG ATG AAA ATC ATG ATG         333
 E   R   R   E   E   E   H   S   K   L   M   K   T   L   K   K   C   K   E   E          83
GAA AGG AGA GAG GAA GAA CAC AGC AAA CTA ATG AAA ACC TTG AAG AAG TGC AAA GAA GAA         393
 K   Q   E   A   L   K   L   M   N   E   V   H   E   H   L   E   E   E   E   S         103
AAG CAG GAG GCC CTG AAA CTT ATG AAT GAA GTT CAT GAA CAC CTG GAG GAG GAA GAA AGC         453
 L   C   Q   V   S   L   A   D   S   W   D   E   C   R   A   C   L   E   S   N         123
TTA TGC CAG GTT TCT CTG GCA GAT TCC TGG GAT GAA TGC AGG GCT TGC CTG GAA AGT AAC         513
 C   M   R   F   D   T   T   C   Q   P   A   W   S   S   V   K   N   M   V   E         143
TGC ATG AGG TTT GAT ACC ACC TGC CAA CCT GCA TGG TCC TCT GTG AAA AAT ATG GTG GAA         573
 Q   F   F   R   K   I   Y   Q   F   L   F   P   L   Q   E   N   D   R   S   G         163
CAG TTT TTC AGG AAG ATC TAT CAG TTT CTG TTT CCT CTC CAG GAA AAT GAC AGA AGT GGC         633
 P   V   S   K   G   V   T   E   E   D   A   Q   V   S   H   I   E   H   V   F         183
CCT GTC AGC AAA GGG GTC ACT GAG GAA GAT GCG CAG GTG TCA CAC ATA GAG CAT GTG TTC         693
```

FIG. 7A

| | | | | | | | | | | | | | | | | | | | |
|---|---|---|---|---|---|---|---|---|---|---|---|---|---|---|---|---|---|---|---|
| S | Q | L | S | A | D | V | T | S | L | F | N | R | S | L | Y | V | F | K | Q | 203 |
| AGC | CAG | CTG | AGC | GCA | GAT | GTG | ACA | TCT | CTC | TTC | AAC | AGA | AGC | CTT | TAC | GTC | TTC | AAA | CAG | 753 |
| L | R | R | E | F | D | Q | A | F | Q | S | Y | F | T | S | G | T | D | V | T | 223 |
| CTG | CGG | CGA | GAA | TTT | GAC | CAG | GCT | TTT | CAG | TCA | TAT | TTC | ACA | TCG | GGG | ACT | GAC | GTT | ACA | 813 |
| E | P | F | F | P | S | L | S | K | E | P | A | Y | R | A | D | A | E | P | 243 |
| GAG | CCT | TTC | TTT | CCA | TCT | TTG | TCC | AAG | GAG | CCA | GCC | TAC | AGA | GCA | GAT | GCT | GAG | CCA | 873 |
| S | W | A | I | P | N | V | Q | L | L | C | N | L | S | F | T | D | P | K | Q | 263 |
| AGC | TGG | GCC | ATT | CCC | AAT | GTC | CAG | CTG | CTC | TGC | AAC | TTG | AGT | TTC | ACA | GAT | CCT | AAA | CAA | 933 |
| S | V | S | E | K | L | I | T | T | L | R | A | T | E | D | P | P | K | Q | D | 283 |
| AGT | GTC | AGT | GAA | AAA | CTC | ATC | ACA | ACC | CTG | CGT | GCC | ACA | GAG | GAC | CCT | CCA | AAA | CAA | GAC | 993 |
| K | D | S | N | Q | G | G | P | I | S | K | I | L | P | E | Q | D | R | G | S | 303 |
| AAA | GAC | TCC | AAC | CAG | GGA | GGC | CCG | ATT | TCA | AAG | ATA | CTA | CCT | GAG | CAA | GAC | AGA | GGC | TCA | 1053 |
| D | G | K | L | G | Q | N | L | S | D | D | C | P | N | V | F | R | K | Q | K | 323 |
| GAT | GGG | AAA | CTT | GGC | CAG | AAT | TTG | TCT | GAT | GAC | TGC | CCT | AAT | GTG | TTT | CGC | AAG | AGA | AAA | 1113 |
| C | Q | D | Y | L | S | R | S | N | Q | Q | Y | D | Q | V | Y | R | E | L | N | 343 |
| TGC | CAG | GAT | TAT | CTA | TCT | AGA | TCC | AAT | CAG | CAA | TAC | GAC | CAG | GTG | TAC | AGA | GAA | CTC | AAT | 1173 |
| E | A | L | R | L | V | S | D | T | L | L | M | E | K | M | R | E | Q | V | Q | M | T | 363 |
| GAG | GCC | CTC | CGA | CTG | GTC | AGT | GAC | ACG | CTT | CTG | ATG | GAG | AAG | ATG | AGA | GAG | CAG | GTG | CAG | ATG | ACC | 1233 |
| Q | Y | H | L | E | D | T | L | L | M | E | K | M | R | E | Q | F | G | W | 383 |
| CAG | TAT | CAC | CTG | GAA | GAC | ACC | ACG | CTT | CTG | ATG | GAG | AAG | ATG | AGA | GAG | CAG | TTT | GGC | TGG | 1293 |

FIG.7B

```
 V   S   E   L   A   Y   Q   S   P   G   A   E   D   I   F   N   P   V   K   V    403
GTT TCT GAA CTG GCA TAC CAG TCC CCA GGA GCT GAG GAC ATC TTT AAT CCA GTG AAA GTA   1353

M   V   A   L   S   A   H   E   G   N   S   S   D   Q   D   D   T   V   V   P    423
ATG GTA GCC CTA AGT GCT CAT GAA GGA AAT TCT TCT GAT CAA GAT GAC ACA GTG GTT CCT   1413

S   S   L   L   P   S   S   N   F   T   L   S   S   P   L   E   K   S   A   G    443
TCA AGC CTC CTG CCT TCC TCT AAC TTC ACA CTC AGC CCT CTT GAA AAG AGT GCT GGC       1473

N   A   N   F   I   D   H   V   E   K   V   L   Q   H   F   K   E   H   F        463
AAC GCT AAC TTC ATT GAT CAC GTG GTA GAG AAG GTT CTT CAG CAC TTT AAG GAG CAC TTT   1533

K   T   W   *                                                                     467
AAA ACT TGG TAA                                                                   1545

GAAGATTTAGTCCATCCTATAATCAGCAAGAATTACACCCTTCGGCCAAGACCTGAGAATTCTGAAAATACAAAGCAGGC  1624

TAACACAATGAACACAGCTGCATGAAAGTTAGGTATATATTAGGAAGCACTATTGGTTTACTTTGTTGAATGGAAGTTT  1703

AATAGCTATTCAAATTGAGTTAATATAAAATTTCTTCCTAAAAAAGTAAAATGTACATATGTAGAATATGATGCATTAG  1782

TTCTTTGTATACTAAATAAATAAATACTGAGTCCCCT                                             1815
```

FIG.7C

CTTGGAGTCAACTGAGTGTGGACTGAAACTTCCAAAAACTGACATGAGGAGTCACTGGAGAATCATGATCAAGGAGCTA                                                                                    79

CACACTCTGACTTAACTTTATTCTGTGGACAATGAGAGACAACTGCAAGGATTAACAGTGAGAAC ATG AAG CTG                                                                                        153
                                                                                                                                                                      M   K   L      3

P   L   L   M   F   P   V   C   L   L   W   L   K   D   C   H   C   A   P   T                                                                                        213
CCA CTT CTG ATG TTT CCC GTG TGT CTG CTA TGG TTG AAA GAC TGT CAT TGT GCA CCT ACT                                                                                       23

W   K   D   K   T   A   I   S   E   N   A   N   S   F   S   E   A   G   E   I                                                                                        273
TGG AAG GAC AAA ACT GCC ATC AGT GAA AAC GCG AAC AGT TTT TCT GAG GCT GGG GAG ATA                                                                                       43

D   V   D   G   E   V   K   I   A   L   I   G   I   K   Q   M   K   I   M   M                                                                                        333
GAC GTA GAT GGA GAG GTG AAG ATA GCT TTG ATT GGC ATT AAA CAG ATG AAA ATC ATG ATG                                                                                       63

E   R   R   E   E   E   H   S   K   L   M   K   T   L   K   K   C   K   E   E                                                                                        393
GAA AGG AGA GAG GAA GAA CAC AGC AAA CTA ATG AAA ACC TTG AAG AAG TGC AAA GAA GAA                                                                                       83

K   Q   E   A   L   K   L   M   N   E   V   H   E   H   L   E   E   E   E   S                                                                                        453
AAG CAG GAG GCC CTG AAA CTT ATG AAT GAA GTT CAT GAA CAC CTG GAG GAG GAA GAA AGC                                                                                       103

L   C   Q   V   S   L   A   D   S   W   D   E   C   R   A   C   L   E   S   N                                                                                        513
TTA TGC CAG GTT TCT CTG GCA GAT TCC TGG GAT GAA TGC AGG GCT TGC CTG GAA AGT AAC                                                                                       123

C   M   R   F   D   T   T   C   Q   P   A   W   S   S   V   K   N   M   E   N                                                                                        573
TGC ATG AGG TTT GAT ACC ACC TGC CAA CCT GCA TGG TCC TCT GTG AAA AAT ATG GAA AAT                                                                                       143

D   R   S   G   P   V   S   K   G   V   T   E   E   D   A   Q   V   S   H   I                                                                                        633
GAC AGA AGT GGC CCT GTC AGC AAA GGG GTC ACT GAG GAA GAT GCG CAG GTG TCA CAC ATA                                                                                       163

E   H   V   F   S   Q   L   S   A   D   V   T   S   L   F   N   R   S   L   Y                                                                                        693
GAG CAT GTG TTC AGC CAG CTG AGC GCA GAT GTG ACA TCT CTC TTC AAC AGA AGC CTT TAC                                                                                       183

FIG.8A

| | | | | | | | | | | |
|---|---|---|---|---|---|---|---|---|---|---|
| V | F | K | Q | L | R | R | E | F | D | Q | A | F | Q | S | Y | F | T | S | G | 203 |
| GTC | TTC | AAA | CAG | CTG | CGG | CGA | GAA | TTT | GAC | CAG | GCT | TTT | CAG | TCA | TAT | TTC | ACA | TCG | GGG | 753 |
| T | D | V | T | E | P | F | F | F | P | S | L | S | K | E | P | A | Y | R | A | 223 |
| ACT | GAC | GTT | ACA | GAG | CCT | TTC | TTT | TTT | CCA | TCT | TTG | TCC | AAG | GAG | CCA | GCC | TAC | AGA | GCA | 813 |
| D | A | E | P | S | W | A | I | P | N | V | F | Q | L | L | C | N | L | S | F | 243 |
| GAT | GCT | GAG | CCA | AGC | TGG | GCC | ATT | CCC | AAT | GTC | TTC | CAG | CTG | CTC | TGC | AAC | TTG | AGT | TTC | 873 |
| S | V | Y | Q | S | V | S | E | K | L | I | T | T | L | R | A | C | N | L | D | 263 |
| TCA | GTT | TAT | CAA | AGT | GTC | AGT | GAA | AAA | CTC | ATC | ACA | ACC | CTG | CGT | GCC | TGC | AAT | TTG | GAC | 933 |
| P | K | Q | D | S | N | Q | Q | G | P | I | S | K | I | L | P | E | Q | 283 |
| CCA | AAA | CAA | GAC | TCC | AAC | CAG | CAG | GGC | CCG | ATT | TCA | AAG | ATA | CTA | CCT | GAG | CAA | 993 |
| D | R | G | S | D | G | K | L | Q | N | L | S | D | D | C | V | N | F | R | K | 303 |
| GAC | AGA | GGC | TCA | GAT | GGG | AAA | CTT | CAG | AAT | TTG | TCT | GAT | GAC | TGC | GTT | AAT | TTT | CGC | AAG | 1053 |
| R | C | Q | K | Q | D | Y | L | R | L | V | S | D | C | P | N | Q | P | E | L | Y | 323 |
| AGA | TGC | CAG | AAA | TGC | CAG | GAT | TAT | CTA | CGA | CTG | GTC | AGT | TCT | GAT | TGT | CCT | AAT | CAG | CCT | GAA | CTA | TAC | 1113 |
| R | E | L | N | E | A | L | R | H | L | E | D | T | T | L | M | E | K | M | R | E | 343 |
| AGA | GAA | CTC | AAT | GAG | GCC | CTC | CGA | CAT | CTG | GAA | GAC | ACC | CTT | CTG | ATG | GAG | AAG | ATG | AGA | GAG | 1173 |
| V | Q | M | T | Q | Y | H | L | E | D | T | T | L | M | E | K | M | R | E | 363 |
| | | | | | | | | | | | | | | | | | | | | |
| V | Q | M | T | Q | Y | | | | | | | | | | | | | | | |
| GTG | CAG | ATG | ACC | CAG | TAT | | | | | | | | | | | | | | | |

FIG. 8B

```
P   V   K   V   M   V   A   L   S   A   H   E   G   N   S   S   D   Q   D   D    403
CCA GTG AAA GTA ATG GTA GCC CTA AGT GCT CAT GAA GGA AAT TCT TCT GAT CAA GAT GAC  1353

T   V   V   P   S   S   L   L   P   S   S   N   F   T   L   S   S   P   L   E    423
ACA GTG GTT CCT TCA AGC CTC CTG CCT TCC TCT AAC TTC ACA CTC AGC CCT CTT GAA      1413

K   S   A   G   N   A   N   F   I   D   H   V   V   E   K   V   L   Q   H   F    443
AAG AGT GCT GGC AAC GCT AAC TTC ATT GAT CAC GTG GTA GAG AAG GTT CTT CAG CAC TTT  1473

K   E   H   F   K   T   W   *                                                    451
AAG GAG CAC TTT AAA ACT TGG TAA                                                  1497

GAAGATTTAGTCCATCCTATAATCAGCAAGAATTACACCTTCGGCCAAGACCTGAGAATTCTGAAAATACAAAGCAGGC  1576
TAACACAATGAACACAGCTGCATGAAAGTTAGGTATATATTAGGAAGCACTATTGGTTTACTTTGTTGAATGGAAGTTT  1655
AATAGCTATTCAAATTGAGTTAATAATATAAAAATTTCTTCCTAAAAGTAACATATGTAGAATATGATGCATTAG      1734
TTCTTTGTATACTAAATAAATACTGAGTCCCCT                                                1767
```

FIG.8C

```
CTTGGAGTCAACTGAGTGTGGACTGAAACTTCCAAAAACTGACATGAGGAGTCACTGGAGAATCATGATCAAGGAGCTA                                              79

M   K   L                                                                          3
CACACTCTGACTTAACTTTATTCTGTGGACAATGAGAGACAACTGCAAGGATTAACAGTGAGAAC ATG AAG CTG                                               153

P   L   L   M   F   P   V   C   L   L   L   W   L   K   D   C   H   C   A   P   T                                          23
CCA CTT TTG ATG TTT CCC GTG TGT CTG CTG CTA TGG TTG AAA GAC TGT CAT TGT GCA CCT ACT                                         213

W   K   D   K   T   A   I   S   E   N   A   N   S   F   S   E   A   G   E   I                                              43
TGG AAG GAC AAA ACT GCC ATC AGT GAA AAC GCG AAC AGT TTT TCT GAG GCT GGG GAG ATA                                             273

D   V   D   G   E   V   K   I   A   L   I   G   I   K   Q   M   K   I   M   M                                              63
GAC GTA GAT GGA GAG GTG AAG ATA GCT TTG ATT GGC ATT AAA CAG ATG AAA ATC ATG ATG                                             333

E   R   R   E   E   E   H   S   K   L   M   K   T   L   K   K   C   K   E   E                                              83
GAA AGG AGA GAG GAA GAA CAC AGC AAA CTA ATG AAA ACC TTG AAG AAG TGC AAA GAA GAA                                             393

K   Q   E   A   L   K   L   N   E   V   H   E   H   L   E   E   E   E   S                                                 103
AAG CAG GAG GCC CTG AAA CTT ATG AAT GAA GTT CAT GAA CAC CTG GAG GAG GAA GAA AGC                                             453

L   C   Q   V   S   L   A   D   S   Q   P   A   W   S   S   S   V   K   N                                                 123
TTA TGC CAG GTT TCT CTG GCA GAT TCC CAA CCT GCA TGG TCC TCT GTG AAA AAT                                                     513

C   M   R   F   D   T   T   C   Q   P   S   W   A   I   P   N   V   F   Q   L   P                                         143
TGC ATG AGG TTT GAT ACC ACC TGC CAA AGC TGG GCC ATT CCC AAT GTC TTC CAG CTG CCA                                             573

A   Y   R   A   D   A   E   P   S   Y   Q   S   S   E   K   L   I   T   L   R   A                                         163
GCC TAC AGA GCA GAT GCT GAG CCA AGC TAT CAA AGT GAA AAA CTC ATC ACA CTG CGT GCC                                             633

N   L   S   F   S   V   Y   Q   S   V   S   E   K   L   I   T   L   R   A                                                 183
AAC TTG AGT TTC TCA GTT TAT CAA AGT GTC AGT GAA AAA CTC ATC ACA CTG CGT GCC                                                 693
```

FIG.9A

```
  T   E   D   P   P   K   Q   D   K   D   S   N   Q   G   G   P   I   S   K   I   203
 ACA GAG GAC CCT CCA AAA CAA GAC AAA GAC TCC AAC CAG GGA GGC CCG ATT TCA AAG ATA  753

L   P   E   Q   D   R   G   S   D   G   K   N   L   G   Q   N   L   S   D   V   223
 CTA CCT GAG CAA GAC AGA GGC TCA GAT GGG AAA CTT GGC CAG AAT TTG TCT GAT TGC GTT  813

N   F   R   K   C   Q   K   C   Q   D   Y   L   S   D   D   C   P   N   V   V   243
 AAT TTT CGC AAG TGC CAG AAA TGC CAG GAT TAT CTA TCT GAT GAC TGC CCT AAT GTG GTG  873

P   E   L   Y   R   E   L   N   E   A   L   R   L   V   S   R   S   N   Q   Q   263
 CCT GAA CTA TAC AGA GAA CTC AAT GAG GCC CTC CGA CTG GTC AGT AGA TCC AAT CAG CAA  933

Y   D   Q   V   Q   M   T   Q   Y   H   L   E   D   T   L   L   M   E   283
 TAC GAC CAG GTG CAG ATG ACC CAG TAT CAC CTG GAA GAC ACC ACG CTT CTG ATG GAG  993

K   M   R   E   Q   F   G   W   V   K   V   S   E   L   A   Y   Q   S   P   G   A   E   303
 AAG ATG AGA GAG CAG TTT GGC TGG GTT AAA GTA ATG GTA CTG GAA CTG GCA TAC CAG TCC CCA GGA GCT GAG 1053

D   I   F   N   P   D   T   V   P   S   M   V   A   L   S   S   L   P   S   S   N   S   323
 GAC ATC TTT AAT CCA GAC ACA GTG CCA TCC ATG GTA GCC CTA AGC AGT CTC CCT TCC TCC AAT TCT 1113

D   Q   D   D   L   E   K   S   A   G   N   A   N   F   I   D   H   S   S   N   F   T   L   S   343
 GAT CAA GAT GAC CTC GAA AAG AGT GCT GGC AAC GCT AAC TTC ATT GAT CAC TCC TCT AAC TTC ACA CTC AGC 1173

S   P   L   H   F   K   E   H   F   K   T   W   *             363
 AGC CCT CTT CAG CAC TTT AAA GAG CAC TTT AAA ACT TGG TAA          1233

L   Q                                                          375
 CTT CAG CAC TTT AAG GAG AAG GTT                                 1269
```

FIG.9B

GAAGATTTAGTCCATCCTATAATCAGCAAGAATTACACCTTCGGCCAAGACCTGAGAATTCTGAAATACAAAGCAGGC 1348

TAACACAATGAACACAGCTGCATGAAAGTTAGGTATATATTAGGAAGCACTATTGGTTTACTTTGTTGAATGGAAGTTT 1427

AATAGCTATTCAAATTGAGTTAATATAAAAATTTCTTCCTAAAAAGTAAAAATGTACATATGTAGAATATGATGCATTAG 1506

TTCTTTGTATACTAAATAAATACTGAGTCCCCT 1539

FIG.9C

```
CTTGGAGTCAACTGAGTGTGGACTGAAACTTCCAAAAACTGACATGAGGAGTCACTGGAGAATCATGATCAAGGAGCTA 79
                                                           M   K   L    3
CACACTCTGACTTAACTTTATTCTGTGGACAATGAGAGACAACTGCAAGGATTAACAGTGAGAAC ATG AAG CTG 153

P   L   M   F   P   V   C   L   L   W   L   K   D   C   H   C   A   P   T     23
CCA CTT ATG TTT CCC GTG TGT CTG CTG CTA TGG TTG AAA GAC TGT CAT TGT GCA CCT ACT 213

W   K   D   K   T   A   I   S   E   N   A   N   S   F   S   E   A   G   E   I   43
TGG AAG GAC AAA ACT GCC ATC AGT GAA AAC GCG AAC AGT TTT TCT GAG GCT GGG GAG ATA 273

D   V   D   G   E   V   K   I   A   L   I   G   I   K   Q   M   K   I   M   M   63
GAC GTA GAT GGA GAG GTG AAG ATA GCT TTG ATT GGC ATT AAA CAG ATG AAA ATC ATG ATG 333

E   R   R   E   E   H   S   K   L   M   K   T   L   K   K   C   K   E   E       83
GAA AGG AGA GAG GAA CAC AGC AAA CTA ATG AAG ACC TTG AAG AAG TGC AAA GAA GAA     393

K   Q   E   A   L   K   L   M   N   E   V   H   E   H   L   E   E   E   S      103
AAG CAG GAG GCC CTG AAA CTG ATG AAT GAA GTT CAT GAA CAC CTG GAG GAG GAA AGC     453

L   C   Q   V   S   L   A   D   S   W   D   E   C   R   A   C   L   E   S   N  123
TTA TGC CAG GTT TCT CTG GCA GAT TCC TGG GAT GAA TGC AGG GCT TGC CTG GAA AGT AAC 513

C   M   R   F   D   T   T   C   Q   P   A   W   S   V   K   N   M   P   A      143
TGC ATG AGG TTT GAT ACC ACC TGC CAA CCT GCA TGG TCC TCT GTG AAA AAT ATG CCA GCC 573

Y   R   A   D   A   E   P   S   W   A   I   P   N   V   F   Q   L   L   C   N  163
TAC AGA GCA GAT GCT GAG CCA AGC TGG GCC ATT CCC AAT GTC TTC CAG CTG CTC TGC AAC 633

L   S   F   S   V   Y   Q   S   V   S   E   K   L   I   T   L   R   A   T      183
TTG AGT TTC TCA GTT TAT CAA AGT GTC AGT GAA AAA CTC ATC ACA ACC CTG CGT GCC ACA 693
```

FIG.10A

```
E   D   P   P   K   Q   D   K   D   S   N   Q   G   G   P   I   S   K   I   L    203
GAG GAC CCT CCA AAA CAA GAC AAA GAC TCC AAC CAG GGA GGC CCG ATT TCA AAG ATA CTA   753

P   E   Q   D   R   G   S   D   G   K   L   G   Q   N   L   S   D   C   V   N    223
CCT GAG CAA GAC AGA GGC TCA GAT GGG AAA CTT GGC CAG AAT TTG TCT GAT TGC GTT AAT   813

F   R   K   R   C   Q   K   C   Q   D   Y   L   S   D   D   C   P   N   V   P    243
TTT CGC AAG AGA TGC CAG AAA TGC CAG GAT TAT CTA TCT GAT GAC TGC CCT AAT GTG CCT   873

E   L   Y   R   E   L   N   E   A   L   R   L   V   S   R   T   L   M   Q   Y    263
GAA CTA TAC AGA GAA CTC AAT GAG GCC CTC CGA CTG GTC AGT AGA TCC AAT CAG CAA TAC   933

D   Q   V   V   Q   M   T   Q   H   L   E   D   T   L   T   S   P   A   E   D    283
GAC CAG GTG GTG CAG ATG ACC CAG TAT CAC CTG GAA GAC ACC ACG CTT CTG ATG GAG GAC   993

M   R   E   Q   F   G   W   V   K   V   M   V   S   E   L   A   L   S   S   D    303
ATG AGA GAG CAG TTT GGC TGG GTT AAA GTA ATG GTT TCT GAA CTG GCA CTG AGT TCC GAG GCT   1053

I   F   N   P   V   K   V   M   V   P   S   S   L   P   S   N   F   T   L   S    323
ATC TTT AAT CCA GTG AAA GTA ATG GTT CCT TCA AGC CTC CTG TCT AAC TTC ACA CTC TCT GAT   1113

Q   D   D   T   V   V   P   S   A   L   P   S   S   N   H   V   E   K   V   L    343
CAA GAT GAC ACA GTG GTT CCT TCA AGC GCT CTA CTC CCT TCC AAC CAC GTG GAG AAG GTT CTT   1173

P   L   E   K   S   A   G   N   A   N   F   I   D   H   V   E   K   V   L   363
CCT CTT GAA AAG AGT GCT GGC AAC GCT AAC TTC ATT GAT CAC GTG GAG AAG GTT CTT   1233

Q   H   F   K   E   H   F   K   T   W   *                                         374
CAG CAC TTT AAG GAG CAC TTT AAA ACT TGG TAA                                       1266
```

FIG.10B

```
GAAGATTTAGTCCATCCTATAATCAGCAAGAATTACACCTTCGGCCAAGACCTGAGAATTCTGAAAATACAAAGCAGGC  1345

TAACACAATGAACACAGCTGCATGAAAGTTAGGTATATATTAGGAAGCACTATTGGTTTACTTTGTTGAATGGAAGTTT  1424

AATAGCTATTCAAATTGAGTTAATATATAAAAATTTCTTCCTAAAAAGTAAAATGTACATATGTAGAATATGATGCATTAG  1503

TTCTTTGTATACTAAATAAATACTGAGTCCCCT  1536
```

FIG.10C

```
                    M   K   P   P   L   V   F       8
GCAACCTCGTTGGTGAGAGCCTGCAGTTAGTGTCACGGGGAAAC ATG AAG CCG CCA CTC TTG GTG TTT  69

I   V   Y   L   L   R   D   C   Q   C   A   P   T   G   K   D   R   T       28
ATT GTG TAT CTG CTG CGG AGA GAC TCT CAG TGT GCG CCT ACA GGG AAG GAC CGA ACT  129

S   I   R   E   D   P   K   G   F   S   K   A   G   E   I   D   V   E   E   48
TCC ATC CGT GAA GAC CCG AAG GGT TTT TCC AAG GCT GGG GAG ATA GAC GTA GAT GAG 189

V   K   K   A   L   I   G   M   K   Q   M   K   R   E   E   R   E   E       68
GTG AAG AAG GCT TTG ATT GGC ATG AAG CAG ATG AAA ATC CTG ATG GAA AGA AGA GAG 249

E   H   S   K   L   M   R   T   L   K   K   C   R   E   E   K   Q   L       88
GAA CAT AGC AAA CTA ATG AGA ACA CTG AAG AAA TGC AGA GAA GAA AAG CAG CTG     309

K   L   M   N   E   V   Q   E   H   L   E   E   E   R   L   Q   V   S      108
AAG CTT ATG AAT GAA GTT CAA GAA CAT CTA GAA GAG GAA AGG CTA CAG GTG TCT    369

L   M   G   S   W   D   E   C   K   S   C   L   E   S   D   C   M   R   F   Y  128
CTG ATG GGT TCC TGG GAC GAA TGC AAA TCT TGC CTG GAA AGT GAC TGC ATG AGA TTT TAT  429

T   T   C   Q   S   S   M   K   S   T   I   E   R   V   F   R   K         148
ACA ACC TGC CAA AGC AGT ATG AAA TCC ACG ATT GAA CGG GTT TTC CGG AAG         489

I   Y   Q   F   L   P   F   H   E   D   D   E   K   E   L   P   V   G   E  168
ATA TAT CAG TTT CTC TTT CCT TTC CAT GAA GAT GAA AAA GAG CTT CCT GTT GGT GAG  549

K   F   T   E   E   D   V   Q   L   M   Q   I   E   N   V   F   S   Q   L   T  188
AAG TTC ACT GAG GAA GAT GTA CAG CTG ATG CAG ATA GAG AAT GTG TTC AGC CAG CTG ACC  609

FIG.11A
```

```
V   D   V   G   F   L   Y   N   M   S   F   H   V   F   K   Q   M   Q   Q   E   208
GTG GAT GTG GGA TTT CTC TAT AAC ATG AGC TTT CAC GTC TTC AAA CAG ATG CAG CAA GAA   669

F   D   L   A   F   Q   S   Y   F   M   S   D   T   D   S   M   E   P   Y   F   228
TTT GAC CTG GCT TTT CAA TCA TAC TTT ATG TCA GAC ACA GAC TCC ATG GAG CCT TAC TTT   729

F   P   A   F   S   K   E   P   A   K   K   A   H   P   M   Q   S   W   D   I   248
TTT CCA GCT TTT TCC AAA GAG CCA GCA AAA GCA CAT CCT ATG CAG AGT TGG GAC ATT       789

F   S   F   F   Q   L   F   C   N   F   S   L   S   V   Y   Q   S   V   S   A   268
CCC AGC TTC TTC CAG CTG TTT TGT AAT TTC AGC CTC TCT GTT TAT CAA AGT GTC AGC GCA   849

T   V   T   E   M   L   K   A   I   E   D   L   S   K   Q   D   K   D   S   A   288
ACA GTT ACA GAG ATG CTG AAG GCC ATT GAG GAC TTA TCC AAA CAA GAC AAA GAT TCT GCC   909

H   G   G   P   S   S   T   T   W   P   V   R   G   R   G   L   C   G   E   P   308
CAC GGT GGA CCG AGT TCC ACG ACG TGG CCT GTG CGG GGC AGA GGG CTG TGT GGA GAA CCT   969

G   Q   N   S   S   E   C   L   Q   F   H   A   R   C   Q   K   A   D   Q   Y   328
GGC CAG AAC TCG TCC GAA TGT CTC CAA TTT CAT GCA AGA TGC CAG AAA GCG GAT CAG TAC   1029

L   W   A   D   C   P   A   V   P   E   L   Y   T   K   A   D   E   A   L   E   348
CTA TGG GCA GAC TGC CCT GCT GTT CCT GAA CTA TAC ACA AAG GCG GAT GAG GCC CTT GAG   1089

L   V   N   I   S   N   Q   Q   Y   A   Q   V   L   Q   L   Q   M   T   H   H   368
TTG GTC AAC ATA TCC AAT CAG CAG TAT GCC CAG GTA CTC CAG CTC CAG ATG ACC CAG CAT   1149

E   D   T   T   Y   L   M   E   K   M   R   E   Q   F   G   W   V   T   E   L   388
GAG GAC ACC ACG TAT CTG ATG GAG AAG ATG AGA GAG CAG TTT GGT TGG GTA ACA GAG CTG   1209
```

FIG. 11B

```
A    S    Q    T    P    G    S    E    N    I    F    S    F    I    K    V    P    G    V    408
GCC  AGC  CAG  ACC  CCA  GGA  AGC  GAG  AAC  ATC  TTC  AGT  TTC  ATA  AAG  GTA  CCA  GGT  GTT  1269

H    E    G    N    F    S    K    Q    D    E    K    M    I    D    I    S    I    L    P    S    428
CAC  GAA  GGA  AAT  TTC  TCC  AAA  CAA  GAT  GAA  AAG  ATG  ATA  GAC  ATA  AGC  ATT  CTG  CCT  TCC  1329

S    N    F    T    L    T    I    P    L    E    E    S    A    E    S    S    D    F    I    S    448
TCT  AAT  TTC  ACA  CTC  ACC  ATC  CCT  CTT  GAA  GAA  AGT  GCT  GAG  AGT  TCC  GAC  TTC  ATT  AGC  1389

Y    M    L    A    K    A    V    Q    H    F    K    E    H    F    K    S    W    *         466
TAC  ATG  CTG  GCC  AAA  GCT  GTA  CAG  CAT  TTT  AAG  GAA  CAT  TTT  AAA  TCT  TGG  TAA       1443

GCAGAGTATTTGATTAGGGACGTTTGCTGATAGGAATAGATTTAAAAGGGAAAAATGACAAAACTAGCTTTTGA 1522
ATACCTTGAAAACGTATTCAACCTCAATTCATTAATAATCAAGGCATGAAAACTAAGACAAGTTAGCAGTTTTACCTATTGA 1601
ATTTTCAAATTAAAAAAAAAATCCTGATAGAATGCAATGAAATGAGAATTCTTATATGTGATTGATGCCAGAAACAAACTG 1680
GTTTTGTCTTTTTGAAAAGTTATTCAATTATACATATCAAGAGTCATCAAATTTCTTTTAATATAATAATTCCACTTC 1759
TGGAATCAATCCAAAGGAGTAAATCTAAAATTGAATTGAAGTGTCTAAAAACCAGAAATGGTTAAAAGCTGTGGCTAAATATGCTCC 1838
TAGTAAACTGTTAAAAACTGAATGTCATCTGAATGTCTAAAAATTTAAAATTTATAAAGCATCGTCGAACAAGAGTTATTCT 1917
AAATATCTTATAAACCATTAAAAATATTATTATTATTACTATCTTCCAGAAAAGAAACTTGAGACTCAGGGTCCAAGTGTTAGTTG 1996
AAGCCTATCTATAAGGCAAATATCTTTGGGACCCCTTGGACTGTAGCCACCAGGCTCCTCCTGTCCGTGGGATTCTTCAGACAGG 2075
CTCAGTCATGTCTGACTCTTTGGGACCCCTTGGACTGTAGCCACCAGGCTCCTCCTGTCCGTGGGATTCTTCAGACAGG 2154
AATACTGGGGCAGGTTGCTATTTCCTTCTCCAGGAAATCTTCCAGGATGGAACCCAGGTCTCCTGCATTGCA 2233
GGTAGATGCTTTACTATCTGAGCAACCAAATGAATTACTCAAGTCAGTAGGGGGGTAGAGGCAAATTTAACTTAGTTT 2312
CTCTGAATCATAATTGCCACACATTAAACTGGTTCCTGTTGGGACATTTGGTTGAAAAAATAAAGTGAAAAATGAGTATA 2391
AAACTCTATAAATGTAATGATCAAAACGAAAAAAAATCTACAATCTGCATTAAAAATAAAAAAGGGTTGGCAGG 2464
```

FIG. 11C

```
                                                                              M   K   P   P   L      5
CAGAAGCTGGTGGCAACCTCGTTGGTGAGAGCCTGCAGTTAGTGTCACGGGGAAAC ATG AAG CCG CCA CTC     72

L   V   F   I   V   Y   L   L   R   L   R   D   C   Q   C   A   P   T   G   K   25
TTG GTG TTT ATT GTG TAT CTG CTG CGG CTG AGA GAC TGT CAG TGT GCG CCT ACA GGG AAG  132

D   R   T   S   I   R   E   D   P   K   G   F   S   K   A   G   E   I   D   V   45
GAC CGA ACT TCC ATC CGT GAA GAC CCG AAG GGT TTT TCC AAG GCT GGG GAG ATA GAC GTA  192

D   E   E   V   K   K   A   L   I   G   M   K   Q   M   M   K   I   L   M   E   R   65
GAT GAA GAG GTG AAG AAG GCT TTG ATT GGC ATG AAG CAG ATG ATG AAA ATC CTG ATG GAA AGA 252

R   E   E   H   S   K   L   M   R   T   L   K   K   C   R   E   E   K   Q   85
AGA GAG GAG CAT AGC AAA CTA ATG AGA ACA CTG AAG AAA TGC AGA GAA GAA AAG CAG      312

E   A   L   K   L   M   N   E   V   Q   E   H   L   E   E   E   R   L   C   105
GAG GCC CTG AAG CTG ATG AAT GAA GTT CAA GAA CAT CTA GAA GAG GAA AGG CTA TGC      372

Q   V   S   L   M   G   S   W   D   E   C   K   S   C   L   E   S   D   C   M   125
CAG GTG TCT CTG ATG GGT TCC TGG GAC GAA TGC AAA TCT TGC CTG GAA AGT GAC TGC ATG  432

R   F   Y   T   T   Q   F   L   F   P   F   H   E   D   D   E   K   E   L   R   V   145
AGA TTT TAT ACA ACC TGC CAA AGC TTT CTC CCT TTC CAT GAA GAC GAT GAA AAA GAG CTT GAA CGG GTT 492

F   R   K   I   Y   Q   F   L   F   P   F   H   E   D   D   E   K   E   L   P   165
TTC CGG AAG ATA TAT CAG TTT CTC CCT TTC CAT GAA GAC GAT GAA AAA GAG CTT CCT      552

V   G   E   K   F   T   E   E   D   V   Q   L   M   Q   I   E   N   V   F   S   185
GTT GGT GAG AAG TTC ACT GAG GAA GAT GTA CAG ATG CTG ATG CAG ATA GAG AAT GTG TTC AGC 612
```

FIG.12A

```
Q   L   T   V   D   V   G   F   L   Y   N   M   S   F   H   V   F   K   Q   M   205
CAG CTG ACC GTG GAT GTG GGA TTT CTC TAT AAC ATG AGC TTT CAC GTC TTC AAA CAG ATG 672

Q   E   F   P   A   L   A   F   Q   S   Y   F   M   P   A   K   D   S   M   E   225
CAG GAA TTT GAC CTG GCT TTT CAA TCA TAC TTT ATG CCA ACA GAC TCA TCC ATG GAG 732

P   Y   F   F   P   A   F   S   K   E   P   A   K   K   A   H   P   M   Q   S   245
CCT TAC TTT TTT CCA GCT TTT TCC AAA GAG CCA GCA AAA AAA GCA CAT CCT ATG CAG AGT 792

W   D   I   P   S   F   F   Q   L   F   C   N   F   S   L   S   V   Y   Q   S   265
TGG GAC ATT CCC AGC TTC TTC CAG CTG TGT AAT TTC AGC CTC TCT GTT TAT CAA AGT 852

V   S   A   T   V   T   E   M   L   K   A   I   E   D   L   S   K   Q   D   K   285
GTC AGC GCA ACA GTT ACA GAG ATG CTG AAG GCC ATT GAG GAC TTA TCC AAA CAA GAC AAA 912

D   S   A   H   G   G   P   S   S   T   W   P   V   R   G   H   A   R   C   L   305
GAT TCT GCC CAC GGT GGA CCG AGT TCC ACG TGG CCT GTG CGG GGC AGA TGC CTG TGT 972

G   E   P   G   Q   N   S   S   E   C   L   Q   F   H   A   R   C   Q   K   C   325
GGA GAA CCT GGC CAG AAC TCG TCC GAA TGT CTC CAA TTT CAT GCA AGA TGC CAG AAA TGT 1032

Q   D   Y   L   W   A   D   C   P   A   V   P   E   L   Y   T   K   A   D   E   345
CAG GAT TAC CTA TGG GCA GAC TGC CCT GCT GTT CCT GAA CTA TAC ACA AAG GCG GAT GAG 1092

A   L   E   L   V   N   I   S   N   Q   Q   Y   A   Q   V   L   Q   M   T   Q   365
GCC CTT GAG TTG GTC AAC ATA TCC AAT CAG CAG TAT GCC CAG GTA CTC CAG ATG ACC CAG 1152

H   H   L   E   D   T   T   Y   L   M   E   K   M   R   E   Q   F   G   W   V   385
CAT CAC TTG GAG GAC ACC ACG TAT CTG ATG GAG AAG ATG AGA GAG CAG TTT GGT TGG GTA 1212
```

FIG.12B

```
 T   E   L   A   S   Q   T   P   G   S   E   N   I   F   S   F   I   K   V  405
ACA GAG CTG GCC AGC CAG ACC CCA GGA AGC GAG AAC ATC TTC AGT TTC ATA AAG GTA GTT 1272

P   G   V   H   E   G   N   F   S   K   Q   D   E   K   M   I   D   I   S  425
CCA GGT GTT CAC GAA GGA AAT TTC TCC AAA CAA GAT GAA AAG ATG ATA GAC ATA AGC ATT 1332

L   P   S   S   N   F   T   L   T   I   P   L   E   E   S   A   E   S   D  445
CTG CCT TCC TCT AAT TTC ACA CTC ACC ATC CCT CTT GAA GAA AGT GCT GAG AGT TCC GAC 1392

F   I   S   Y   M   L   A   K   A   V   Q   H   F   K   E   H   F   K   S   W  465
TTC ATT AGC TAC ATG CTG GCC AAA GCT GTA CAG CAT TTT AAG GAA CAT TTT AAA TCT TGG 1452

*                                                                               466
TAA                                                                             1455

GCAGAGTATTTGATTAGGGACGTTTGCTGATAGGAATAGATGGTTCTTAAAAGGGAAAAATGACAAAACTAGCTTTTGA 1534

ATACCTTGAAAACGTATTCAACCTCATTAATAATCAAAGGCATGAAAACTAAGACAAGTTAGACAGTTTTTACCTATTGA 1613

ATTTTCAAATTAAAAAAAAAATCCTGATAGAATGCAATGAAATGAGAATTCTTATATGTGATTGCCAGAAACAAACTG 1692

GTTTTGTCTTTTTGAAAAGTTATTCAATTATACATATCAAGAGTCATCAAATTTCTTTTAATATAATAATTCCACTTC 1771

TGGAATCAATCCAAAGGAGTAAATCTAAAATTGAATTGAAGTTCCCACCCCAAGATCAATATTTGCAAATTATTTAAAA 1850

TAGTAAACTGTTAAAAACTGAATGTCATCTGAATGTCTAAAAACCAGAAATGGTTAAAAGCTGTGGCTAAATATGCTCC 1929

AAATATCTTATAAACCATTAAAATATTTATAAATTTACTATCTTCCAGAAAAGAAACTTGAGACTCAGGTCCAAGTGTTAGTTG 2008

AAGCCTATCTATAAGGCAAATATTATTATTACTATCTTCCAGAAAAGAAACTTGAGACTCAGGTCCAAGTGTTAGTTG 2087

CTCAGTCATGTCTGACTCTTTGAGACCCCTTGGACTGTGGCCACCAGGCTCCTCTGTCCATGGGATTCTTCAGACAAG 2166
```

FIG.12C

```
AATACTGGAGCAGGTTGCTATTCCTTCTCCCAGGAAATCTTCCCTATCCAGGGATGGAACCCAGGTCTCCTGCATTGCA    2245

GGTAGATGCTTTACTATCTGAGCAACCAAATGAATTACTCAGTCAGTAGGGGTAGAGGCAAATTTAACTTAGTTTT      2324

CTCTGAATCATAATTGCCACATTAAACTGGTTCCTGTGGGACATTTGGTTGAAAAAAATAAAGTGAAAAATGAGTATA    2403

AAACTCTATAAATGTAATGATCAAAAGGAAAAAAAAATCTACAATCTGCATTAAAAATAAAAAGGGTTGGCAGGAATTAC  2482

GGTTGGAAATGGATGATTTTTTTCATCTTTGATATTTACAATTTCTATAATGAATAAATAATTTTGA               2561

GATTTCAAATTAGAAGATATGTTGCTAAATAGCTAGGTAAATGTAGAACACTGTATCAATGTGTTCTCATCTTT        2640

AAACTTTAGTATAAGTACTTCTATTCCATGGTAATCCTACAGTAAGACGAAATGTAAATCTGTTCGGTCTACAGGAAAA   2719

ACAACTAAAATGACATTTCAGACGTACATTACCATCTCTGTTAGGATAATCTTCTGAATTAATGGCACAATTAGAACTGT  2798

ACATAGTATTCTCCTTTGGTAAAATGGTCAATCTTAAAGAAGCATTAAATGTAATTCTAAGTTATTACTCATAAGGGA    2877

CCTTGTAGGTAGGTCCCTATCAATGTATAATTAAGCTGGGTATTTCTAGATTCGCTGCCTCTCCCTTTATCTCTGAATG   2956

TTGGAGAGGTTGTTGGGTCATCAATCAACCAATATCTTTTAGCATCTTCTAAGTGAAGGC                      3016
```

FIG. 12D

```
                                                                              M   K    2
GTGAAGGTCCTTACAGAAGCTGGTGGCAACCTCGTTGGTGAGAGCCTGCAGTTAGTGTCACGGGGAAAC ATG AAG  76

P   P   I   L   V   F   I   V   Y   L   L   Q   L   R   D   C   Q   A   P    22
CCG CCA ATC TTG GTG TTT ATC GTG TAT CTG CAG CTG AGA GAC TGT CAG TGT GCG CCT  136

T   G   K   D   R   T   S   I   R   E   D   P   K   G   F   S   K   A   G   E    42
ACA GGG AAG GAC CGA ACT TCC ATC CGT GAA GAC CCG AAG GGT TTT TCC AAG GCT GGG GAG  196

I   D   V   D   E   E   V   K   K   A   L   I   G   M   M   K   Q   M   K   I   L    62
ATA GAC GTA GAT GAA GAG GTG AAG AAG GCT TTG ATT GGC ATG ATG AAG CAG ATG AAA ATC CTG  256

M   E   R   R   E   E   E   E   H   S   K   L   M   R   T   L   K   K   C   R   E    82
ATG GAA AGA AGA GAG GAG GAA GAA CAT AGC AAA CTA ATG AGA ACC CTG AAG AAA TGC AGA GAA  316

E   K   Q   E   E   A   L   K   L   M   N   E   V   Q   E   H   L   E   E   E   E   102
GAA AAG CAG GAG GAG GCC CTG AAG CTT ATG AAT GAA GTT CAA GAA CAT CTA GAA GAG GAA GAA  376

R   L   C   Q   V   S   L   M   G   S   W   D   E   C   K   S   C   L   E   S   122
AGG CTA TGC CAG GTG TCT CTG ATG GGT TCC TGG GAC GAA TGC AAA TCT TGC CTG GAA AGT    436

D   C   M   R   F   Y   T   T   C   Q   S   F   L   F   P   F   H   E   D   D   E   K   142
GAC TGC ATG AGA TTT TAT ACA ACC TGC CAA AGC AGT TGG TCC TCT ATG AAA GAC GAT GAA AAA  496

E   R   V   F   R   K   I   Y   Q   E   K   F   T   E   E   D   V   Q   L   M   Q   E   162
GAA CGG GTT TTC CGG AAG ATA TAT CAG GAG AAG TTC ACT GAG GAA GAT GTA CAG CTG ATG CAG  556

E   L   P   V   G   E   K   F   G   V   P   L   E   D   V   Q   L   M   Q   I   E   N   182
GAG CTT CCT GTT GGT GAG AAG TTC GGT GTT CCT CTT GAA GAT GTA CAG CTG ATG CAG ATA GAG AAT 616
```

FIG.13A

```
V   F   S   Q   L   T   V   D   V   G   F   L   Y   N   M   S   F   H   V   F   202
GTG TTC AGC CAG CTG ACC GTG GAC GTG GGA TTT CTC TAT AAC ATG AGC TTT CAC GTC TTC 676

K   Q   M   Q   Q   E   F   D   L   A   F   Q   S   Y   F   M   S   D   T   D   222
AAA CAG ATG CAG CAA GAA TTT GAC CTG GCT TTT CAA TCA TAC TTT ATG TCA GAC ACA GAC 736

S   M   E   P   Y   F   F   P   A   F   S   K   E   P   A   K   K   A   H   P   242
TCC ATG GAG CCT TAC TTT TTT CCA GCT TTT TCC AAA GAG CCA GCA AAA AAA GCA CAT CCT 796

M   Q   S   W   D   I   P   S   F   F   Q   L   C   N   F   S   L   S   L   V   262
ATG CAG AGT TGG GAC ATT CCC AGC TTC TTC CAG CTG TTT TGT AAT TTC AGC CTC TCT GTT 856

Y   Q   S   V   S   A   T   V   T   E   M   L   K   A   I   E   D   L   S   K   282
TAT CAA AGT GTC AGC GCA ACA GTT ACA GAG ATG CTG AAG GCC ATT GAG GAC TTA TCC AAA 916

Q   D   K   D   S   A   H   G   G   P   S   S   T   W   P   V   R   G   R   R   302
CAA GAC AAA GAT TCT GCC CAC GGT GGA CCG AGT TCC ACG TGG CCT GTG CGG GGC AGA 976

G   L   C   G   E   P   Q   N   Q   C   L   Q   F   H   A   R   C   322
GGG CTG TGT GGA GAA CCT GGC CAG AAC TCG TCC GAA TGT CTC CAA TTT CAT GCA AGA TGC 1036

Q   K   C   Q   D   Y   L   W   A   D   C   P   A   V   P   E   L   Y   T   K   342
CAG AAA TGT CAG GAT TAC CTA TGG GCA GAC TGC CCT GCT GTT CCT GAA CTA TAC ACA AAG 1096

A   D   E   A   L   E   L   V   N   I   S   N   Q   Q   Y   A   Q   V   L   Q   362
GCG GAT GAG GCC CTT GAG TTG GTC AAC ATA TCC AAT CAG CAG TAT GCC CAG GTA CTC CAG 1156

M   T   Q   H   H   L   E   D   T   Y   L   M   E   K   M   R   E   Q   F   382
ATG ACC CAG CAT CAC TTG GAG GAC ACG TAT CTG ATG GAG AAG ATG AGA GAG CAG TTT 1216
```

FIG. 13B

| | | | | | | | | | | |
|---|---|---|---|---|---|---|---|---|---|---|
| G | W | V | T | E | L | A | S | Q | T | P | G | S | E | N | I | F | S | F | I | 402 |
| GGT | TGG | GTA | ACA | GAG | CTG | GCC | AGC | CAG | ACC | CCA | GGA | AGC | GAG | AAC | ATC | TTC | AGT | TTC | ATA | 1276 |
| K | V | V | P | G | V | H | E | G | N | F | S | K | Q | D | E | K | M | I | D | 422 |
| AAG | GTA | GTT | CCA | GGT | GTT | CAC | GAA | GGA | AAT | TTC | TCC | AAA | CAA | GAT | GAA | AAG | ATG | ATA | GAC | 1336 |
| I | S | I | L | P | S | N | F | T | L | T | I | P | L | E | E | S | A | E | E | 442 |
| ATA | AGC | ATT | CTG | CCT | TCC | AAT | TTC | ACA | CTC | ACC | ATC | CCT | CTT | GAA | GAA | AGT | GCT | GAG | GAG | 1396 |
| S | S | D | F | I | S | Y | M | L | A | K | A | V | Q | H | F | K | E | H | F | 462 |
| AGT | TCC | GAC | TTC | ATT | AGC | TAC | ATG | CTG | GCC | AAA | GCT | GTA | CAG | CAT | TTT | AAG | GAA | CAT | TTT | 1456 |
| K | S | W | * | | | | | | | | | | | | | | | | | 466 |
| AAA | TCT | TGG | TAA | | | | | | | | | | | | | | | | | 1468 |

```
GCAGAGTATTTGATTAGGGACGTTTGCTGATAGGAATAGATGGTTCTTAAAAGGGAAAAATGACAAAACTAGCTTTTGA    1547
ATACCTTGAAAACGTATTCAACCTCATTCAATAATCCTGATAATAGAATGCAATGAAATGAGAATTCTTATATGTGATTGCCAGAAAACAAACTGG    1626
ATTTTCAAATTAAAAAAAAATCCTGATAATTATTCAATTCAATATACATATCAAGAGTCATCAAATTTCTTTTAATATAATAATTCCACTTCT    1705
TTTTGTCTTTTTGAAAAGGAGTAAATCTAAAATTGAATGTCTAAAAACTGAAGTTCCCACCCAGATCAATATTTGCAATTATTTAAAAT    1784
GGAATCAATCCAAAGGAGTAAATCTAAAATTGAATGTCTAAAAACTGAAGTTCCCACCCAGATCAATATTTGCAATTATTTAAAAT    1863
AGTAAACTGTTAAAAACTGAATGTCATCTGAATGTCTAAAAACTGAAGTTCCCACCCAGATCAATATTTGCAATTATTTAAAAT    1942
AATATCTTATAAAACCATTAAAATATTATTATTACTATCTTCCAGAAAAGAAACTTGAGACTCAGGTCCAAGTGTCAGTTGC    2021
AGCCTATCTATAAGGCAAATATTATTATTACTATCTTCCAGAAAAGAAACTTGAGACTCAGGTCCAAGTGTCAGTTGC    2100
TCAGTCATGTGTCTGACTCTTTGAGACCCCTTGAGACCCCTTCCTCCAGGATGGAACCCAGGTCTCCTCCTGCATTGCAG    2179
ATACTGGAGCAGGTTGCTATTTCCTTCTGAGCAACCAAATGAATTACTCAAGTCAGTAGGGGGTAGAGGCAAATTTAACTTAGTTTC    2258
GTAGATGCTTTACTATCTGAGCAACCAAATGAATTACTCAAGTCAGTAGGGGGTAGAGGCAAATTTAACTTAGTTTC    2337
TCTGAATCATAATTGCCACCATTAAACTGTTCCTGTTGGGACATTTGGTTGAAAAAAATAAAGTGAAAAATGAGTATAA    2416
AACTCTATAAATGTAATGATCAAAACGAAAAAAATCTACAATCTGCATTAAAAAATAAAAAGGGTTGGCAGG    2488
```

FIG.13C

FIG.14A

| | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | T | G | A | T | G | T | T | T | C | C | C | G | T | G | T | C | T | G | C | T | A | T | G | G | T | T | G | A | A | A | G | A | C | T | G | T | C | A | Majority |
| | | | | 170 | | | | | | | 180 | | | | | | | 190 | | | | | | | 200 | | | | | | | | | | | | | | | |
| 161 | T | G | A | T | G | T | T | T | C | C | C | C | G | T | G | T | C | T | G | C | T | A | T | G | G | T | T | G | A | A | A | G | A | C | T | G | T | C | A | gphkng1815-1. |
| 161 | T | G | A | T | G | T | T | T | C | C | C | C | G | T | G | T | C | T | G | C | T | A | T | G | G | T | T | G | A | A | A | G | A | C | T | G | T | C | A | gp7b-1. |
| 161 | T | G | A | T | G | T | T | T | C | C | C | C | G | T | G | T | C | T | G | C | T | A | T | G | G | T | T | G | A | A | A | G | A | C | T | G | T | C | A | gp7c-1. |
| 161 | T | G | A | T | G | T | T | T | C | C | C | C | G | T | G | T | C | T | G | C | T | A | T | G | G | T | T | G | A | A | A | G | A | C | T | G | T | C | A | gp7d-1. |
| | T | T | G | T | G | C | C | A | C | C | T | A | C | T | T | T | G | G | A | A | G | G | A | C | A | A | A | A | C | T | G | C | C | A | T | C | A | G | T | G | A | A | Majority |
| | | | | 210 | | | | | | | 220 | | | | | | | 230 | | | | | | | 240 | | | | | | | | | | | | | | | | | | |
| 201 | T | T | G | T | G | C | C | A | C | C | T | A | C | T | T | T | G | G | A | A | G | G | A | C | A | A | A | A | C | T | G | C | C | A | T | C | A | G | T | G | A | A | gphkng1815-1. |
| 201 | T | T | G | T | G | C | C | A | C | C | T | A | C | T | T | T | G | G | A | A | G | G | A | C | A | A | A | A | C | T | G | C | C | A | T | C | A | G | T | G | A | A | gp7b-1. |
| 201 | T | T | G | T | G | C | C | A | C | C | T | A | C | T | T | T | G | G | A | A | G | G | A | C | A | A | A | A | C | T | G | C | C | A | T | C | A | G | T | G | A | A | gp7c-1. |
| 201 | T | T | G | T | G | C | C | A | C | C | T | A | C | T | T | T | G | G | A | A | G | G | A | C | A | A | A | A | C | T | G | C | C | A | T | C | A | G | T | G | A | A | gp7d-1. |
| | A | A | C | G | C | G | A | A | C | A | G | T | T | T | T | T | C | T | G | A | G | G | C | T | G | G | G | G | A | G | A | T | A | G | A | C | G | T | A | G | Majority |
| | | | | 250 | | | | | | | 260 | | | | | | | 270 | | | | | | | 280 | | | | | | | | | | | | | | | |
| 241 | A | A | C | G | C | G | A | A | C | A | G | T | T | T | T | T | C | T | G | A | G | G | C | T | G | G | G | G | A | G | A | T | A | G | A | C | G | T | A | G | gphkng1815-1. |
| 241 | A | A | C | G | C | G | A | A | C | A | G | T | T | T | T | T | C | T | G | A | G | G | C | T | G | G | G | G | A | G | A | T | A | G | A | C | G | T | A | G | gp7b-1. |
| 241 | A | A | C | G | C | G | A | A | C | A | G | T | T | T | T | T | C | T | G | A | G | G | C | T | G | G | G | G | A | G | A | T | A | G | A | C | G | T | A | G | gp7c-1. |
| 241 | A | A | C | G | C | G | A | A | C | A | G | T | T | T | T | T | C | T | G | A | G | G | C | T | G | G | G | G | A | G | A | T | A | G | A | C | G | T | A | G | gp7d-1. |
| | A | T | G | G | A | G | A | G | G | T | G | A | A | G | A | T | A | G | C | T | T | T | G | A | T | T | G | G | C | C | A | T | T | A | A | A | C | A | G | A | T | Majority |
| | | | | 290 | | | | | | | 300 | | | | | | | 310 | | | | | | | 320 | | | | | | | | | | | | | | | |
| 281 | A | T | G | G | A | G | A | G | G | T | G | A | A | G | A | T | A | G | C | T | T | T | G | A | T | T | G | G | C | C | A | T | T | A | A | A | C | A | G | A | T | gphkng1815-1. |
| 281 | A | T | G | G | A | G | A | G | G | T | G | A | A | G | A | T | A | G | C | T | T | T | G | A | T | T | G | G | C | C | A | T | T | A | A | A | C | A | G | A | T | gp7b-1. |
| 281 | A | T | G | G | A | G | A | G | G | T | G | A | A | G | A | T | A | G | C | T | T | T | G | A | T | T | G | G | C | C | A | T | T | A | A | A | C | A | G | A | T | gp7c-1. |
| 281 | A | T | G | G | A | G | A | G | G | T | G | A | A | G | A | T | A | G | C | T | T | T | G | A | T | T | G | G | C | C | A | T | T | A | A | A | C | A | G | A | T | gp7d-1. |

FIG.14B

```
                                                                                                    Majority
       330                  340                  350                  360
G A A A A T C A T G A T G G A A A G G A G A G G A A G A A C A C A G C A A A
321    G A A A A T C A T G A T G G A A A G G A G A G G A A G A A C A C A G C A A A    gphkng1815-1.
321    G A A A A T C A T G A T G G A A A G G A G A G G A A G A A C A C A G C A A A    gp7b-1.
321    G A A A A T C A T G A T G G A A A G G A G A G G A A G A A C A C A G C A A A    gp7c-1.
321    G A A A A T C A T G A T G G A A A G G A G A G G A A G A A C A C A G C A A A    gp7d-1.

Majority
       370                  380                  390                  400
C T A A T G A A A C C T T G A A G A A G T G C A A A G A A G A A A A G C A G G
361    C T A A T G A A A C C T T G A A G A A G T G C A A A G A A G A A A A G C A G G    gphkng1815-1.
361    C T A A T G A A A C C T T G A A G A A G T G C A A A G A A G A A A A G C A G G    gp7b-1.
361    C T A A T G A A A C C T T G A A G A A G T G C A A A G A A G A A A A G C A G G    gp7c-1.
361    C T A A T G A A A C C T T G A A G A A G T G C A A A G A A G A A A A G C A G G    gp7d-1.

Majority
       410                  420                  430                  440
A G G C C C T G A A A C T T A T G A A T G A A G T T C A T G A A C A C C T G G A
401    A G G C C C T G A A A C T T A T G A A T G A A G T T C A T G A A C A C C T G G A    gphkng1815-1.
401    A G G C C C T G A A A C T T A T G A A T G A A G T T C A T G A A C A C C T G G A    gp7b-1.
401    A G G C C C T G A A A C T T A T G A A T G A A G T T C A T G A A C A C C T G G A    gp7c-1.
401    A G G C C C T G A A A C T T A T G A A T G A A G T T C A T G A A C A C C T G G A    gp7d-1.

Majority
       450                  460                  470                  480
G G A G G A A G A A A G C T T A T G C C C A G G T T T C T C T G G C A G A T T C C
441    G G A G G A A G A A A G C T T A T G C C C A G G T T T C T C T G G C A G A T T C C    gphkng1815-1.
441    G G A G G A A G A A A G C T T A T G C C C A G G T T T C T C T G G C A G A T T C C    gp7b-1.
441    G G A G G A A G A A A G C T T A T G C C C A G G T T T C T C T G G C A G A T T C C    gp7c-1.
441    G G A G G A A G A A A G C T T A T G C C C A G G T T T C T C T G G C A G A T T C C    gp7d-1.
```

FIG.14C

```
                                                        490              500              510              520
        TGGGATGAATGCAGGGCCTTGCCCTGGAAAAGTAACTGCATGA  Majority 481   TGGGATGAATGCAGGGCCTTGCCCTGGAAAAGTAACTGCATGA  gphkng1815-1.
  481   TGGGATGAATGCAGGGCCTTGCCCTGGAAAAGTAACTGCATGA  gp7b-1.
  481   TGGGATGAATGCAGGGCCTTGCCCTGGAAAAGTAACTGCATGA  gp7c-1.
  481   TGGGATGAATGCAGGGCCTTGCCCTGGAAAAGTAACTGCATGA  gp7d-1.

530              540              550              560
        GGTTTGATACCACCCTGCCAACCCTGCCATGGTCCTCTGTGAA  Majority 521   GGTTTGATACCACCCTGCCAACCCTGCCATGGTCCTCTGTGAA  gphkng1815-1.
  521   GGTTTGATACCACCCTGCCAACCCTGCCATGGTCCTCTGTGAA  gp7b-1.
  521   GGTTTGATACCACCCTGCCAACCCTGCCATGGTCCTCTGTGAA  gp7c-1.
  521   GGTTTGATACCACCCTGCCAACCCTGCCATGGTCCTCTGTGAA  gp7d-1.

570              580              590              600
        AAATATGG------------------------------------  Majority 561   AAATATGGTGGAACAGTTTTCAGGAAGATCTATCAGTTT       gphkng1815-1.
  561   AAATATGG-----------------------------------  gp7b-1.
  561   AAATATGG-----------------------------------  gp7c-1.
  561   AAATATG-------------------------------------  gp7d-1.

610              620              630              640
        -------AAAATGACAGAAGTGGCCCTGTCA  Majority 601   CTGTTTCCTCTCCAGGAAAATGACAGAAGTGGCCCTGTCA  gphkng1815-1.
  569   ------------AAAATGACAGAAGTGGCCCTGTCA        gp7b-1.
  569   ------------AAAATGACAGAAGTGGCCCTGTCA        gp7c-1.
  568   -------------------------------              gp7d-1.
```

FIG.14D

```
                                                              Majority
GCAAAGGGTCACTGAGGAAGATGCCCAGGTGTCACACAT
         650              660              670          680
641  GCAAAGGGTCACTGAGGAAGATGCCCAGGTGTCACACAT              gphkng1815-1.
593  GCAAAGGGGTCACTGAGGAAGATGCCCAGGTGTCACACAT             gp7b-1.
569  ---------------------------------------              gp7c-1.
568  ---------------------------------------              gp7d-1.

Majority
AGAGCCATGTGTTCAGCCCAGCTGAGCCGCAGATGTGACATCT
         690              700              710          720
681  AGAGCCATGTGTTCAGCCCAGCTGAGCCGCAGATGTGACATCT          gphkng1815-1.
633  AGAGCCATGTGTTCAGCCCAGCTGAGCCGCAGATGTGACATCT          gp7b-1.
569  -------------------------------------------          gp7c-1.
568  -------------------------------------------          gp7d-1.

Majority
CTCTTCAACAGAAGCCTTTTACGTCTTCAAACAGCTGCGGC
         730              740              750          760
721  CTCTTCAACAGAAGCCTTTTACGTCTTCAAACAGCTGCCCC            gphkng1815-1.
673  CTCTTCAACAGAAGCCTTTTACGTCTTCAAACAGCTGCCCC            gp7b-1.
569  ----------------------------------------             gp7c-1.
568  ----------------------------------------             gp7d-1.

Majority
GAGAATTTGACCAGGCCTTTTCAGTCATATTTCACATCGGG
         770              780              790          800
761  GAGAATTTGACCAGGCCTTTTCAGTCATATTTCACATCGGG            gphkng1815-1.
713  GAGAATTTGACCAGGCCTTTTCAGTCATATTTCACATCGGG            gp7b-1.
569  ----------------------------------------             gp7c-1.
568  ----------------------------------------             gp7d-1.
```

FIG. 14E

```
                 GACTGACGTTACAGAGCCTTTCTTTTTCCATCTTTGTCC     Majority
                         810         820         830   840

801       GACTGACGTTACAGAGCCTTTCTTTTTCCATCTTTGTCC     gpkng1815-1.
       753       GACTGACGTTACAGAGCCTTTCTTTTTCCATCTTTGTCC     gp7b-1.
       569       ---------------------------------------     gp7c-1.
       568       ---------------------------------------     gp7d-1.

AAGGAGCCCAGCCCTACAGAGCCAGATGCTGAGCCAAGCTGGG   Majority
                         850         860         870   880

841       AAGGAGCCCAGCCCTACAGAGCCAGATGCTGAGCCAAGCTGGG   gpkng1815-1.
       793       AAGGAGCCCAGCCCTACAGAGCCAGATGCTGAGCCAAGCTGGG   gp7b-1.
       569       ----AGCCCAGCCCTACAGAGCCAGATGCTGAGCCAAGCTGGG   gp7c-1.
       568       -------CCAGCCCTACAGAGCCAGATGCTGAGCCAAGCTGGG   gp7d-1.

CCATTCCCAATGTCTTCCAGCTGCTCTGCAACTTGAGTTT    Majority
                         890         900         910   920

881       CCATTCCCAATGTCTTCCAGCTGCTCTGCAACTTGAGTTT    gpkng1815-1.
       833       CCATTCCCAATGTCTTCCAGCTGCTCTGCAACTTGAGTTT    gp7b-1.
       605       CCATTCCCAATGTCTTCCAGCTGCTCTGCAACTTGAGTTT    gp7c-1.
       602       CCATTCCCAATGTCTTCCAGCTGCTCTGCAACTTGAGTTT    gp7d-1.

CTCAGTTTATCAAAGTGTCAGTGAAAAACTCATCACAACC    Majority
                         930         940         950   960

921       CTCAGTTTATCAAAGTGTCAGTGAAAAACTCATCACAACC    gpkng1815-1.
       873       CTCAGTTTATCAAAGTGTCAGTGAAAAACTCATCACAACC    gp7b-1.
       645       CTCAGTTTATCAAAGTGTCAGTGAAAAACTCATCACAACC    gp7c-1.
       642       CTCAGTTTATCAAAGTGTCAGTGAAAAACTCATCACAACC    gp7d-1.
```

FIG. 14F

```
        CTGCGTGCCACAGAGGACCCTCCAAAACAAGACAAAGACT   Majority
                   970       980       990      1000

961   CTGCGTGCCACAGAGGACCCTCCAAAACAAGACAAAGACT   gphkng1815-1.
  913   CTGCGTGCCACAGAGGACCCTCCAAAACAAGACAAAGACT   gp7b-1.
  685   CTGCGTGCCACAGAGGACCCTCCAAAACAAGACAAAGACT   gp7c-1.
  682   CTGCGTGCCACAGAGGACCCTCCAAAACAAGACAAAGACT   gp7d-1.

CCAACCAGGGAGGCCCCGATTTCAAAGATACTACCTGAGCA   Majority
                  1010      1020      1030      1040

1001   CCAACCAGGGAGGCCCCGATTTCAAAGATACTACCTGAGCA   gphkng1815-1.
  953   CCAACCAGGGAGGCCCCGATTTCAAAGATACTACCTGAGCA   gp7b-1.
  725   CCAACCAGGGAGGCCCCGATTTCAAAGATACTACCTGAGCA   gp7c-1.
  722   CCAACCAGGGAGGCCCCGATTTCAAAGATACTACCTGAGCA   gp7d-1.

AGACAGAGGCTCAGATGGGAAACTTGGCCAGAATTTGTCT   Majority
                  1050      1060      1070      1080

1041   AGACAGAGGCTCAGATGGGAAACTTGGCCAGAATTTGTCT   gphkng1815-1.
  993   AGACAGAGGCTCAGATGGGAAACTTGGCCAGAATTTGTCT   gp7b-1.
  765   AGACAGAGGCTCAGATGGGAAACTTGGCCAGAATTTGTCT   gp7c-1.
  762   AGACAGAGGCTCAGATGGGAAACTTGGCCAGAATTTGTCT   gp7d-1.

GATTGCGTTAATTTTTCGGCAAGAGATGCCAGAAAATGCCAGG   Majority
                  1090      1100      1110      1120

1081   GATTGCGTTAATTTTTCGGCAAGAGATGCCAGAAAATGCCAGG   gphkng1815-1.
 1033   GATTGCGTTAATTTTTCGGCAAGAGATGCCAGAAAATGCCAGG   gp7b-1.
  805   GATTGCGTTAATTTTTCGGCAAGAGATGCCAGAAAATGCCAGG   gp7c-1.
  802   GATTGCGTTAATTTTTCGGCAAGAGATGCCAGAAAATGCCAGG   gp7d-1.
```

FIG. 14G

```
                    ATTATCTATCTGATGACTGCCCTAATGTGCCTGAACTATA   Majority
                                1130         1140         1150         1160
     1121           ATTATCTATCTGATGACTGCCCTAATGTGCCTGAACTATA   gphkng1815-1.
     1073           ATTATCTATCTGATGACTGCCCTAATGTGCCTGAACTATA   gp7b-1.
      845           ATTATCTATCTGATGACTGCCCTAATGTGCCTGAACTATA   gp7c-1.
      842           ATTATCTATCTGATGACTGCCCTAATGTGCCTGAACTATA   gp7d-1.

CAGAGAACTCAATGAGGCCCTCCGACTGGTCAGTAGATCC   Majority
                                1170         1180         1190         1200
     1161           CAGAGAACTCAATGAGGCCCTCCGACTGGTCAGTAGATCC   gphkng1815-1.
     1113           CAGAGAACTCAATGAGGCCCTCCGACTGGTCAGTAGATCC   gp7b-1.
      885           CAGAGAACTCAATGAGGCCCTCCGACTGGTCAGTAGATCC   gp7c-1.
      882           CAGAGAACTCAATGAGGCCCTCCGACTGGTCAGTAGATCC   gp7d-1.

AATCAGCCAATACGACCAGGTGGTGCAGATGACCCAGTATC   Majority
                                1210         1220         1230         1240
     1201           AATCAGCCAATACGACCAGGTGGTGCAGATGACCCAGTATC   gphkng1815-1.
     1153           AATCAGCCAATACGACCAGGTGGTGCAGATGACCCAGTATC   gp7b-1.
      925           AATCAGCCAATACGACCAGGTGGTGCAGATGACCCAGTATC   gp7c-1.
      922           AATCAGCCAATACGACCAGGTGGTGCAGATGACCCAGTATC   gp7d-1.

ACCTGGAAGACACCACGCTTCTGATGGAGAAGATGAGAGA   Majority
                                1250         1260         1270         1280
     1241           ACCTGGAAGACACCACGCTTCTGATGGAGAAGATGAGAGA   gphkng1815-1.
     1193           ACCTGGAAGACACCACGCTTCTGATGGAGAAGATGAGAGA   gp7b-1.
      965           ACCTGGAAGACACCACGCTTCTGATGGAGAAGATGAGAGA   gp7c-1.
      962           ACCTGGAAGACACCACGCTTCTGATGGAGAAGATGAGAGA   gp7d-1.
```

FIG. 14H

FIG.14I

|  |  | Majority |
|---|---|---|
| ACACTCAGCCCCTCTTGAAAAGAGTGCTGGCAACGCTA | 1480 | |
| 1441 ACACTCAGCCCCTCTTGAAAAGAGTGCTGGCAACGCTA | | gphkng1815-1. |
| 1393 ACACTCAGCCCCTCTTGAAAAGAGTGCTGGCAACGCTA | | gp7b-1. |
| 1165 ACACTCAGCCCCTCTTGAAAAGAGTGCTGGCAACGCTA | | gp7c-1. |
| 1162 ACACTCAGCCCCTCTTGAAAAGAGTGCTGGCAACGCTA | | gp7d-1. |

|  |  | Majority |
|---|---|---|
| ACTTCATTGATCACGTGGTAGAGAAGGTTCTTCAGCACTT | 1520 | |
| 1481 ACTTCATTGATCACGTGGTAGAGAAGGTTCTTCAGCACTT | | gphkng1815-1. |
| 1433 ACTTCATTGATCACGTGGTAGAGAAGGTTCTTCAGCACTT | | gp7b-1. |
| 1205 ACTTCATTGATCACGTGGTAGAGAAGGTTCTTCAGCACTT | | gp7c-1. |
| 1202 ACTTCATTGATCACGTGGTAGAGAAGGTTCTTCAGCACTT | | gp7d-1. |

|  |  | Majority |
|---|---|---|
| TAAGGAGCACTTTAAAAACTTGGTAAGAAGATTTAGTCCAT | 1560 | |
| 1521 TAAGGAGCACTTTAAAAACTTGGTAAGAAGATTTAGTCCAT | | gphkng1815-1. |
| 1473 TAAGGAGCACTTTAAAAACTTGGTAAGAAGATTTAGTCCAT | | gp7b-1. |
| 1245 TAAGGAGCACTTTAAAAACTTGGTAAGAAGATTTAGTCCAT | | gp7c-1. |
| 1242 TAAGGAGCACTTTAAAAACTTGGTAAGAAGATTTAGTCCAT | | gp7d-1. |

|  |  | Majority |
|---|---|---|
| CCTATAATCAGCAAGAATTACACCTTCGGCCAAGACCTGA | 1600 | |
| 1561 CCTATAATCAGCAAGAATTACACCTTCGGCCAAGACCTGA | | gphkng1815-1. |
| 1513 CCTATAATCAGCAAGAATTACACCTTCGGCCAAGACCTGA | | gp7b-1. |
| 1285 CCTATAATCAGCAAGAATTACACCTTCGGCCAAGACCTGA | | gp7c-1. |
| 1282 CCTATAATCAGCAAGAATTACACCTTCGGCCAAGACCTGA | | gp7d-1. |

FIG.14J

FIG.14K

```
         TATGTAGAATATGATGCATTAGTTCTTTGTATACTAAAATA  Majority
                   1770          1780          1790          1800
1761     TATGTAGAATATGATGCATTAGTTCTTTGTATACTAAAATA  gphkng1815-1.
1713     TATGTAGAATATGATGCATTAGTTCTTTGTATACTAAAATA  gp7b-1.
1485     TATGTAGAATATGATGCATTAGTTCTTTGTATACTAAAATA  gp7c-1.
1482     TATGTAGAATATGATGCATTAGTTCTTTGTATACTAAAATA  gp7d-1.

AATACTGAGTCCCCT  Majority
                 1810
1801     AATACTGAGTCCCCT  gphkng1815-1.
1753     AATACTGAGTCCCCT  gp7b-1.
1525     AATACTGAGTCCCCT  gp7c-1.
1522     AATACTGAGTCCCCT  gp7d-1.
```

FIG. 14L

```
gphkng1815_aa_  1    MKLPLLMFPVCLLWLKDCHCAPTWKDKTAISENANSFSEAGEIDVDGEVKIALIGIKQMKIMMERREEHSKLMKTLKKC   80
gp7b_aa_             MKLPLLMFPVCLLWLKDCHCAPTWKDKTAISENANSFSEAGEIDVDGEVKIALIGIKQMKIMMERREEHSKLMKTLKKC
gp7c_aa_             MKLPLLMFPVCLLWLKDCHCAPTWKDKTAISENANSFSEAGEIDVDGEVKIALIGIKQMKIMMERREEHSKLMKTLKKC
gp7d_aa_             MKLPLLMFPVCLLWLKDCHCAPTWKDKTAISENANSFSEAGEIDVDGEVKIALIGIKQMKIMMERREEHSKLMKTLKKC gphkng1815_aa_ 81    KEEKQEALKLMNEVHEHLEEEESLCQVSLADSWDECRACLESNCMRFDTTCQPAWSSVKNMVEQFFRKIYQFLFPLQEND  160
gp7b_aa_             KEEKQEALKLMNEVHEHLEEEESLCQVSLADSWDECRACLESNCMRFDTTCQPAWSSVKN..............MEND
gp7c_aa_             KEEKQEALKLMNEVHEHLEEEESLCQVSLADSWDECRACLESNCMRFDTTCQPAWSSVKN
gp7d_aa_             KEEKQEALKLMNEVHEHLEEEESLCQVSLADSWDECRACLESNCMRFDTTCQPAWSSVKN gphkng1815_aa_ 161   RSGPVSKGVTEEDAQVSHIEHVFSQLSADVTSLFNRSLYVFKQLRREFDQAFQSYFTSGTDVTEPFFFPSLSKEPAYRAD  240
gp7b_aa_             RSGPVSKGVTEEDAQVSHIEHVFSQLSADVTSLFNRSLYVFKQLRREFDQAFQSYFTSGTDVTEPFFFPSLSKEPAYRAD
gp7c_aa_             ..............................................................MEPAYRAD
gp7d_aa_             ..............................................................MPAYRAD gphkng1815_aa_ 241   AEPSWAIPNVFQLLCNLSFSVYQSVSEKLITTLRATEDPPKQDKDSNQGPISKILPEQDRGSDGKLGQNLSDCVNFRKR  320
gp7b_aa_             AEPSWAIPNVFQLLCNLSFSVYQSVSEKLITTLRATEDPPKQDKDSNQGPISKILPEQDRGSDGKLGQNLSDCVNFRKR
gp7c_aa_             AEPSWAIPNVFQLLCNLSFSVYQSVSEKLITTLRATEDPPKQDKDSNQGPISKILPEQDRGSDGKLGQNLSDCVNFRKR
gp7d_aa_             AEPSWAIPNVFQLLCNLSFSVYQSVSEKLITTLRATEDPPKQDKDSNQGPISKILPEQDRGSDGKLGQNLSDCVNFRKR gphkng1815_aa_ 321   CQKCQDYLSDDCPNVPELYRELNEALRLVSRSNQQYDQVVQMTQYHLEDTTLLMEKMREQFGWVSELAYQSPGAEDIFNP  400
gp7b_aa_             CQKCQDYLSDDCPNVPELYRELNEALRLVSRSNQQYDQVVQMTQYHLEDTTLLMEKMREQFGWVSELAYQSPGAEDIFNP
gp7c_aa_             CQKCQDYLSDDCPNVPELYRELNEALRLVSRSNQQYDQVVQMTQYHLEDTTLLMEKMREQFGWVSELAYQSPGAEDIFNP
gp7d_aa_             CQKCQDYLSDDCPNVPELYRELNEALRLVSRSNQQYDQVVQMTQYHLEDTTLLMEKMREQFGWVSELAYQSPGAEDIFNP gphkng1815_aa_ 401   VKVMVALSAHEGNSSDQDDTVVPSSLLPSSNFTLSSPLEKSAGNANFIDHVVEKVLQHFKEHFKTW  466
gp7b_aa_             VKVMVALSAHEGNSSDQDDTVVPSSLLPSSNFTLSSPLEKSAGNANFIDHVVEKVLQHFKEHFKTW
gp7c_aa_             VKVMVALSAHEGNSSDQDDTVVPSSLLPSSNFTLSSPLEKSAGNANFIDHVVEKVLQHFKEHFKTW
gp7d_aa_             VKVMVALSAHEGNSSDQDDTVVPSSLLPSSNFTLSSPLEKSAGNANFIDHVVEKVLQHFKEHFKTW
```

FIG. 14M

```
bhkng1   1  ------------------------------------------------------GCAACCTCGTTGGTGTGAGAGCCTGCAGTTAGTGTCACGGCGGAAACATGAAGCCGC   80
bhkng2      ------------CAGAAGCTGGTGGCAACCTCGTTGGTGTGAGAGCCTGCAGTTAGTGTCACGGCGGAAACATGAAGCCGC
bhkng3      GTGAAGGTCCTTACAGAAGCTGGTGGCAACCTCGTTGGTGTGAGAGCCTGCAGTTAGTGTCACGGCGGAAACATGAAGCCGC
           81                                                                                160 bhkng1      CACTCTTGGTGTTTATTGTGTATCTCGCTGCGGCTGAGAGACTGTCAGTGTGCGCCTACAGGGAAGGACCGAACTTCCATC
bhkng2      CACTCTTGGTGTTTATTGTGTATCTCGCTGCGGCTGAGAGACTGTCAGTGTGCGCCTACAGGGAAGGACCGAACTTCCATC
bhkng3      CAATCTTGGTGTTTATCGTGTATCTCGCTGCAGCTGAGAGACTGTCAGTGTGCGCCTACAGGGAAGGACCGAACTTCCATC
          161                                                                                240 bhkng1      CGTGAAGACCCGAAGGGTTTTTCCAAGGCTGGGGAGATAGACGTAGATGAAGAGGTGAAGAAGGCTTTGATTGGCATGAA
bhkng2      CGTGAAGACCCGAAGGGTTTTTCCAAGGCTGGGGAGATAGACGTAGATGAAGAGGTGAAGAAGGCTTTGATTGGCATGAA
bhkng3      CGTGAAGACCCGAAGGGTTTTTCCAAGGCTGGGGAGATAGACGTAGATGAAGAGGTGAAGAAGGCTTTGATTGGCATGAA
          241                                                                                320 bhkng1      GCAGATGAAAATCCTGATGGAAAGAAGAGAAGAGAAGAGGAGGAACATAGCAAACTAATGAGAACACTGAAGAAATGCAGAAGAAGAAA
bhkng2      GCAGATGAAAATCCTGATGGAAAGAAGAGAAGAGAAGAGGAGGAACATAGCAAACTAATGAGAACACTGAAGAAATGCAGAAGAAGAAA
bhkng3      GCAGATGAAAATCCTGATGGAAAGAAGAGAAGAGAAGAGGAGGAACATAGCAAACTAATGAGAACACTGAAGAAATGCAGAAGAAGAAA
          321                                                                                400 bhkng1      AGCAGGAGGCCCTGAAGCTTATGAATGAAGTTCAAGAACATCTAGAAGAGAAGAAGAAAGGCTATGCCAGGTGTCTCTGATG
bhkng2      AGCAGGAGGCCCTGAAGCTTATGAATGAAGTTCAAGAACATCTAGAAGAGAAGAAGAAAGGCTATGCCAGGTGTCTCTGATG
bhkng3      AGCAGGAGGCCCTGAAGCTTATGAATGAAGTTCAAGAACATCTAGAAGAGAAGAAGAAAGGCTATGCCAGGTGTCTCTGATG
          401                                                                                480 bhkng1      GGTTCCTGGGACGAATGCAAATCTTGCCTGGAAAGTGACTGCATGAGATTTTATACAACCTGCCAAAGCAGTTGGTCCTC
bhkng2      GGTTCCTGGGACGAATGCAAATCTTGCCTGGAAAGTGACTGCATGAGATTTTATACAACCTGCCAAAGCAGTTGGTCCTC
bhkng3      GGTTCCTGGGACGAATGCAAATCTTGCCTGGAAAGTGACTGCATGAGATTTTATACAACCTGCCAAAGCAGTTGGTCCTC
          481                                                                                560 bhkng1      TATGAAATCCACGATTGAACGGGTTTTCCGGAAGATATATCAGTTTCTTCCTTTCCTTTCCTTCCTTCCATGAAGACGATGAAAAAGAGC
bhkng2      TATGAAATCCACGATTGAACGGGTTTTCCGGAAGATATATCAGTTTCTTCCTTTCCTTTCCTTCCTTCCATGAAGACGATGAAAAAGAGC
bhkng3      TATGAAATCCACGATTGAACGGGTTTTCCGGAAGATATATCAGTTTCTTCCTTTCCTTTCCTTCCTTCCATGAAGACGATGAAAAAGAGC
```

FIG. 15A

```
          561                                                                    640
bhkng1    TTCCTGTTGGTGAGAAGTTCACTGAGGAAGATGTACAGCTGATGCAGATAGAGAATGTGTTCAGCCAGTGACCGTGGAT
bhkng2    TTCCTGTTGGTGAGAAGTTCACTGAGGAAGATGTACAGCTGATGCAGATAGAGAATGTGTTCAGCCAGTGACCGTGGAT
bhkng3    TTCCTGTTGGTGAGAAGTTCACTGAGGAAGATGTACAGCTGATGCAGATAGAGAATGTGTTCAGCCAGTGACCGTGGAC
          641                                                                    720
bhkng1    GTGGGATTTCTCTATAACATGAGCTTTCACGTCTTCAAACAGATGCAGCAAGAATTTGACCTGGCTTTTCAATCATACTT
bhkng2    GTGGGATTTCTCTATAACATGAGCTTTCACGTCTTCAAACAGATGCAGCAAGAATTTGACCTGGCTTTTCAATCATACTT
bhkng3    GTGGGATTTCTCTATAACATGAGCTTTCACGTCTTCAAACAGATGCAGCAAGAATTTGACCTGGCTTTTCAATCATACTT
          721                                                                    800
bhkng1    TATGTCAGACACAGACTCCATGGAGCCTTACTTTTTTCCAGCTGTTTGTAATTTCAGCCTCTCTGTTTATCAAAGTGTCAGCGCAACAGTT
bhkng2    TATGTCAGACACAGACTCCATGGAGCCTTACTTTTTTCCAGCTGTTTGTAATTTCAGCCTCTCTGTTTATCAAAGTGTCAGCGCAACAGTT
bhkng3    TATGTCAGACACAGACTCCATGGAGCCTTACTTTTTTCCAGCTGTTTGTAATTTCAGCCTCTCTGTTTATCAAAGTGTCAGCGCAACAGTT
          801                                                                    880
bhkng1    AGAGTTGGGACATTCCCAGCTTCTTCCAGCTTCTTCCAGCTGTTTGTAATTTCAGCCTCTCTGTTTATCAAAGTGTCAGCGCAACAGTT
bhkng2    AGAGTTGGGACATTCCCAGCTTCTTCCAGCTTCTTCCAGCTGTTTGTAATTTCAGCCTCTCTGTTTATCAAAGTGTCAGCGCAACAGTT
bhkng3    AGAGTTGGGACATTCCCAGCTTCTTCCAGCTTCTTCCAGCTGTTTGTAATTTCAGCCTCTCTGTTTATCAAAGTGTCAGCGCAACAGTT
          881                                                                    960
bhkng1    ACAGAGATGCTGAAGGCCATTGAGGACTTATCCAAACAAGACAAAGATTCTGCCCACGGTGACCGGTGAGTTCCAGACGCGTG
bhkng2    ACAGAGATGCTGAAGGCCATTGAGGACTTATCCAAACAAGACAAAGATTCTGCCCACGGTGACCGGTGAGTTCCAGACGCGTG
bhkng3    ACAGAGATGCTGAAGGCCATTGAGGACTTATCCAAACAAGACAAAGATTCTGCCCACGGTGACCGGTGAGTTCCAGACGCGTG
          961                                                                    1040
bhkng1    GCCTGTGCGGGGCAGAGGGCAGACTGCCCTGCTGTTCCTGAACTGTCCAGAACTGTCTCCAATTTCATGCAAGATGCCAGA
bhkng2    GCCTGTGCGGGGCAGAGGGCAGACTGCCCTGCTGTTCCTGAACTGTCCAGAACTGTCTCCAATTTCATGCAAGATGCCAGA
bhkng3    GCCTGTGCGGGGCAGAGGGCAGACTGCCCTGCTGTTCCTGAACTGTCCAGAACTGTCTCCAATTTCATGCAAGATGCCAGA
          1041                                                                   1120
bhkng1    AATGTCAGGATTACCTATGGGCAGACTGCCCTGCTGTTCCTGAACTATACACAAAGGGGATGAGGCCCTTGAGTTGGTC
bhkng2    AATGTCAGGATTACCTATGGGCAGACTGCCCTGCTGTTCCTGAACTATACACAAAGGCGGATGAGGCCCTTGAGTTGGTC
bhkng3    AATGTCAGGATTACCTATGGGCAGACTGCCCTGCTGTTCCTGAACTATACACAAAGGGGATGAGGCCCTTGAGTTGGTC
```

FIG. 15B

```
         1121                                                                                    1200
bhkng1   AACATATCCAATCAGCAGTATGCCCAGGTACTCCAGATGACCCAGCATCACTTGGAGGACACCACGTATCTGATGGAGAA
bhkng2   AACATATCCAATCAGCAGTATGCCCAGGTACTCCAGATGACCCAGCATCACTTGGAGGACACCACGTATCTGATGGAGAA
bhkng3   AACATATCCAATCAGCAGTATGCCCAGGTACTCCAGATGACCCAGCATCACTTGGAGGACACCACGTATCTGATGGAGAA
         1201                                                                                    1280
bhkng1   GATGAGAGAGCAGTTTGGTTGGGTAACAGAGAGCTGGCCAGCAGACCCCAGGAAGGAGAACATCTTCAGTTTCATAAAGG
bhkng2   GATGAGAGAGCAGTTTGGTTGGGTAACAGAGAGCTGGCCAGCAGACCCCAGGAAGGAGAACATCTTCAGTTTCATAAAGG
bhkng3   GATGAGAGAGCAGTTTGGTTGGGTAACAGAGAGCTGGCCAGCAGACCCCAGGAAGGAGAACATCTTCAGTTTCATAAAGG
         1281                                                                                    1360
bhkng1   TAGTTCCAGGTGTTCACGAAGGAAATTTCTCCAAACAAGATGAAAAGATGATAGACATAAGCATTCTGCCTTCCTCTAAT
bhkng2   TAGTTCCAGGTGTTCACGAAGGAAATTTCTCCAAACAAGATGAAAAGATGATAGACATAAGCATTCTGCCTTCCTCTAAT
bhkng3   TAGTTCCAGGTGTTCACGAAGGAAATTTCTCCAAACAAGATGAAAAGATGATAGACATAAGCATTCTGCCTTCCTCTAAT
         1361                                                                                    1440
bhkng1   TTCACACTCCACCATCCCTCTTGAAGAAAGTGCTGAGAGTTCCGACTTCATTAGCTACATGTCGGCCAAAGCTGTACAGCA
bhkng2   TTCACACTCCACCATCCCTCTTGAAGAAAGTGCTGAGAGTTCCGACTTCATTAGCTACATGTCGGCCAAAGCTGTACAGCA
bhkng3   TTCACACTCCACCATCCCTCTTGAAGAAAGTGCTGAGAGTTCCGACTTCATTAGCTACATGTCGGCCAAAGCTGTACAGCA
         1441                                                                                    1520
bhkng1   TTTTAAGGAACATTTTAAATCTTGGTAAGCAGAGTATTTGATTAGGGACGTTTGCTGATAGGAATAGATGGTTCTTAAAA
bhkng2   TTTTAAGGAACATTTTAAATCTTGGTAAGCAGAGTATTTGATTAGGGACGTTTGCTGATAGGAATAGATGGTTCTTAAAA
bhkng3   TTTTAAGGAACATTTTAAATCTTGGTAAGCAGAGTATTTGATTAGGGACGTTTGCTGATAGGAATAGATGGTTCTTAAAA
         1521                                                                                    1600
bhkng1   GGGAAAAAATGACAAAACTAGCTTTTGAATACCTTGAAAACGTATTCAACCTCATTAATAATCAAAGGCATGAAAACTAAG
bhkng2   GGGAAAAAATGACAAAACTAGCTTTTGAATACCTTGAAAACGTATTCAACCTCATTAATAATCAAAGGCATGAAAACTAAG
bhkng3   GGGAAAAAATGACAAAACTAGCTTTTGAATACCTTGAAAACGTATTCAACCTCATTAATAATCAAAGGCATGAAAACTAAG
         1601                                                                                    1680
bhkng1   ACAAGTTAGCAGTTTTTACCTATTGAATTTTCAAATTAAAAAAAAATCCTGATAGAATGCAATGAAATGAGAATTCTT
bhkng2   ACAAGTTAGCAGTTTTTACCTATTGAATTTTCAAATTAAAAAAAAATCCTGATAGAATGCAATGAAATGAGAATTCTT
bhkng3   ACAAGTTAGCAGTTTTTACCTATTGAATTTTCAAATTAAAAAAAAAA.TCCTGATAGAATGCAATGAAATGAGAATTCTT
```

FIG. 15C

```
          1681
bhkng1    ATATGTGATTGCCAGAAACAAACTGGTTTTGTCTTTTTGAAAAGTTATTCAATTATACATATCAAGAGTCATCAAATTTC    1760
bhkng2    ATATGTGATTGCCAGAAACAAACTGGTTTTGTCTTTTTGAAAAGTTATTCAATTATACATATCAAGAGTCATCAAATTTC
bhkng3    ATATGTGATTGCCAGAAACAAACTGGTTTTGTCTTTTTGAAAAGTTATTCAATTATACATATCAAGAGTCATCAAATTTC
          1761
bhkng1    TTTTAATATAATAATTCCACTTCTGGAATCAATCCAAAGGAGTAAATCTAAAATTGAATTGAAGTTCCACCCCAAGAT    1840
bhkng2    TTTTAATATAATAATTCCACTTCTGGAATCAATCCAAAGGAGTAAATCTAAAATTGAATTGAAGTTCCACCCCAAGAT
bhkng3    TTTTAATATAATAATTCCACTTCTGGAATCAATCCAAAGGAGTAAATCTAAAATTGAATTGAAGTTCCACCCCAAGAT
          1841
bhkng1    CAATATTTGCAAATTATTTAAAATAGTAAACTGTTAAAAACTGAATGTCATCTGAATGTCTAAAAACCAGAAATGGTTAA    1920
bhkng2    CAATATTTGCAAATTATTTAAAATAGTAAACTGTTAAAAACTGAATGTCATCTGAATGTCTAAAAACCAGAAATGGTTAA
bhkng3    CAATATTTGCAAATTATTTAAAATAGTAAACTGTTAAAAACTGAATGTCATCTGAATGTCTAAAAACCAGAAATGGTTAA
          1921
bhkng1    AAGCTGTGGCTAAATATGCTCCAAATATCTTATAAGCCATTAAAAATATTTATAAAATTTAAATCATGACATGACATCT    2000
bhkng2    AAGCTGTGGCTAAATATGCTCCAAATATCTTATAAAACCATTAAAAATATTTATAAAATTTAAATCATGACATGACATCT
bhkng3    AAGCTGTGGCTAAATATGCTCCAAATATCTTATAAAACCATTAAAAATATTTATTATTATTACTATCTAAATCATGACATCT
          2001
bhkng1    GCTGGAACAAGAGTTTATTCTAAGCCTATCTATAAGGCAAATATTATTACTATCTTCCAGAAAAGAAACTTGAGACT    2080
bhkng2    GCTGGAACAAGAGTTTATTCTAAGCCTATCTATAAGGCAAATATTATTACTATCTTCCAGAAAAGAAACTTGAGACT
bhkng3    GCTGGAACAAGAGTTTATTCTAAGCCTATCTATAAGGCAAATATTATTACTATTATTACTACTTCCAGAAAAGAAACTTGAGACT
          2081
bhkng1    CAGGGTCCAAGTGTTAGTTGCTCAGTCAGTCATGTCGACTCTTGGGACCCCTTGGACTGTAGCCCACCAGGCTCCTCTGTCC    2160
bhkng2    CAGGGTCCAAGTGTTAGTTGCTCAGTCAGTCATGTCGACTCTTGGGACCCCTTGGACTGTAGCCCACCAGGCTCCTCTGTCC
bhkng3    CAGGGTCCAAGTGTTAGTTGCTCAGTCAGTCATGTCGACTCTTGGGACCCCTTGAGACTGTGGCCCACCAGGCTCCTCTGTCC
          2161
bhkng1    GTGGGATTCTTCAGACAGGAATACTGGGGCAGGTTGCTATTCCTTCTCCAGGAAATCTTCCTATCCAGGATGGAACC    2240
bhkng2    ATGGGATTCTTCAGACAAGAATACTGGAGCAGGTTGCTATTCCTTCTCCAGGAAATCTTCCTATCCAGGATGGAACC
bhkng3    ATGGGATTCTTCAGACAAGAATACTGGAGCAGGTTGCTATTCCTTCTCCAGGAAATCTTCCTATCCAGGATGGAACC
```

FIG. 15D

```
           2320
bhkng1  2241
bhkng2  CAGGTCTCCTGCATTGCAGGTAGATGCTTTACTATCTGAGCAACCAAATGAATTACTCAAGTCAGTAGGGGGTAGAGGCA
bhkng3  CAGGTCTCCTGCATTGCAGGTAGATGCTTTACTATCTGAGCAACCAAATGAATTACTCAAGTCAGTAGGGGGTAGAGGCA
        CAGGTCTCCTGCATTGCAGGTAGATGCTTTACTATCTGAGCAACCAAATGAATTACTCAAGTCAGTAGGGGGTAGAGGCA
           2400
bhkng1  2321
bhkng2  AATTTAACTTAGTTTTCTCTGAATCATAATTGCCACATTAAACTGGTTCCTGTTGGGACATTTGGTTGAAAAAATAAA
bhkng3  AATTTAACTTAGTTTTCTCTGAATCATAATTGCCACATTAAACTGGTTCCTGTTGGGACATTTGGTTGAAAAAAATAAA
        AATTTAACTTAGTTTTCTCTGAATCATAATTGCCACATTAAACTGGTTCCTGTTGGGACATTTGGTTGAAAAAAATAAA
           2480
bhkng1  2401
bhkng2  GTGAAAAATGAGTATAAAACTCTATAAATGTAATGATCAAAACGAAAAAAATCTACAATCTGCATTAAAAATAAAAAGG
bhkng3  GTGAAAAATGAGTATAAAACTCTATAAATGTAATGATCAAAACGAAAAAAATCTACAATCTGCATTAAAAATAAAAAGG
        GTGAAAAATGAGTATAAAACTCTATAAATGTAATGATCAAAACGAAAAAAATCTACAATCTGCATTAAAAATAAAAAGG
           2560
bhkng1  2481
bhkng2  GTTGGCAGG.......................................................................
bhkng3  GTTGGCAGGAATTACGGTTGGAAATGGATGATTTTTTTTAACCTTTTCATCTTTTGATATTTACAATTTTCTATAATGA
        GTTGGCAGG.......................................................................
           2640
bhkng1  2561
bhkng2  .................................................................................
bhkng3  ATAAATAATTTTGAGATTTCAAATTTAGAAGATATGTTGCTAAAATAGCTAGGTAAATGTAGATTGAACACTGTATCAATG
        .................................................................................
           2720
bhkng1  2641
bhkng2  .................................................................................
bhkng3  TGTTCTCATCTTTAAACTTTAGTATAAGTACTTCTATTCCATGGTAATCCTACAGTAAGACGAAATGTAAATCTGTTCGG
        .................................................................................
           2800
bhkng1  2721
bhkng2  .................................................................................
bhkng3  TCTACAGGAAAAACAACTAAATGACATTTCAGACGTACATTACCATCTCTGTTAGGATAATCTTCTGAATTAATGGCACA
        .................................................................................
```

FIG.15E

```
            2801
bhkng1      ................................................................................
bhkng2      ATTAGAACTGTACATAGTATTCTCCTTTGGTAAAATGGTCAATCTTAAAGAAGCATTAAATGTTAATTCTAAGTTATTAC
bhkng3      ................................................................................

2881
bhkng1      ................................................................................
bhkng2      TCATAAGGGACCTTGTAGGTAGGTCCCTATCAATGTATAATTAAGCTGGGTATTTCTAGATTCGCTGCCTCTCCCTTTAT
bhkng3      ................................................................................

2961
bhkng1      .....................................................................
bhkng2      CTCTGAATGTTGGAGAGGTTGTTGGTCATCAATCAACCAATATCTTTTTAGCATCTTCTAAGTGAAGGC
bhkng3      .....................................................................
```

2880

2960

3029

FIG.15F

```
         1                                                                              80
hmhkng_aa      MKIKAEKNEGPSRSWWQLHWGDIANNSGNMKPPLLVFIVCLLWLKDSHCAPTWKDKTAISENLKSFSEVGEIDADEEVKK
bhkng1_aa      ----------------------------MKPPLLVFIVYLLRLRDCQCAPTGKDRTSIREDPKGFSKAGEIDVDEEVKK
gphkng1815_aa  ----------------------------MKLPLLMFPVCLLWLKDCHCAPTWKDKTAISENANSFSEAGEIDVDGEVKI
         81                                                                             160
hmhkng_aa      ALTGIKQMKIMMEREKEHTNLMSTLKKCREEKQEALKLLNEVQEHLEEEERLCRESLADSWGECRSCLENNCMRIYTTC
bhkng1_aa      ALIGMKQMKILMERREEHSKLMRTLKKCREEKQEALKLMNEVQEHLEEEERLCQVSLMGSWDECKSCLESDCMRFYTTC
gphkng1815_aa  ALIGIKQMKIMMERREEHSKLMKTLKCCKEEKQEALKLMNEVHEHLEEEESLCQVSLADSWDECRACLESNCMRFDTTC
         161                                                                            240
hmhkng_aa      QPSWSSVKNKIERFFRKIYQFLPFHEDNEKDLPISEKLIEEDAQLTQMEDVFSQLTVDVNSLFNRSFNVFRQMQQEFDQ
bhkng1_aa      QSSWSSMKSTIERVFRKIYQFLPFPHEDDEKELPVGEKFTEEDVQLMQIENVFSQLTVDVGFLYNMSFHVFKQMQQEFDL
gphkng1815_aa  QPAWSSVKNMVEQFFRKIYQFLPFLPQE.NDRSGPVSKGVTEEDAQVSHIEHVFSQLSADVTSLFNRSLYVFKQLRREFDQ
         241                                                                            320
hmhkng_aa      TFQSHFISDTDLTEPYFFPAFSKEPMTKADLEQCWDIPNFFQLFCNFSVSIYESVSETITKMLKAIEDLPKQDKAPDHGG
bhkng1_aa      AFQSYFMSDTDSMEPYFFPAFSKEPAKKAHPMQSWDIPSFFQLFCNFSLSVYQSVSATVTEMLKAIEDLSKQDKDSAHGG
gphkng1815_aa  AFQSYFTSGTDVTEPFFFPSLSKEPAYRADAEPSWAIPNVFQLLCNLSFSVYQSVSEKLITTLRATEDPPKQDKDSNQGG
         321                                                                            400
hmhkng_aa      LISKMLPGQDRGLCGELDQNLSRCFKFHEKCQKCQAHLSEDCPDVPALHTELDEAIRLVNVSNQQYGQILQMTRKHLEDT
bhkng1_aa      PSSTTWPVRGRGLCGEPGQNSSECLQFHARCQKCQDYLWADCPAVPELYTKADEALELVNISNQQYAQVLQMTQHHLEDT
gphkng1815_aa  PISKILPEQDRGSDGKLGQNLSDCVNFRKRCQKCQDYLSDDCPNVPELYRELNEALRLVSRSNQQYDQVVQMTQYHLEDT
         401                                                                            480
hmhkng_aa      AYLVEKMRGQFGWVSELANQAPETEIIFNSIQVVPRI..HEGNISKQDETMMTDLSILPSSNFTLKIPLEESAESSNFIG
bhkng1_aa      TYLMEKMREQFGWVTELASQTPGSENIFSFIKVVPGV..HEGNFSKQDE.KMIDISILPSSNFTLTIPLEESAESSDFIS
gphkng1815_aa  TLLMEKMREQFGWSELAYQSPGAEDIFNPVKVMVALSAHEGNSSDQDD.TVVPSSLLPSSNFTLSSPNFTLSSPLEKSAGNANFID
         481                          497
hmhkng_aa      YVVAKALQHFKEHFKTW
bhkng1_aa      YMLAKAVQHFKEHFKSW
gphkng1815_aa  HVVEKVLQHFKEHFKTW
```

FIG. 16

```
matureHKNG      ---------------------------------------APTWKDKTAIS
HKNG1-V1-IPF3   -----------MRTWDYSNSGNMKPPLLVFIVCLLWLKDSHCAPTWKDKTAIS
HKNG1-V1-IPF2   -----------MKPPLLVFIVCLLWLKDSHCAPTWKDKTAIS
HKNG1/1-V1-IPF2 -----------MKPPLLVFIVCLLWLKDSHCAPTWKDKTAIS
HKNG1-IPF1      MKIKAEKNEGPSRSWWQLHWGDIANNSGNMKPPLLVFIVCLLWLKDSHCAPTWKDKTAIS
                                                          ********** matureHKNG      ENLKSFSEVGEIDADEEVKKALTGIKQMKIMMEREKEHTNLMSTLKKCREEKQEALKLL
HKNG1-V1-IPF3   ENLKSFSEVGEIDADEEVKKALTGIKQMKIMMEREKEHTNLMSTLKKCREEKQEALKLL
HKNG1-V1-IPF2   ENLKSFSEVGEIDADEEVKKALTGIKQMKIMMEREKEHTNLMSTLKKCREEKQEALKLL
HKNG1/1-V1-IPF2 ENLKSFSEVGEIDADEEVKKALTGIKQMKIMMEREKEHTNLMSTLKKCREEKQEALKLL
HKNG1-IPF1      ENLKSFSEVGEIDADEEVKKALTGIKQMKIMMEREKEHTNLMSTLKKCREEKQEALKLL
                ************************************************************ matureHKNG      NEVQEHLEEEERLCRESLADSWGECRSCLENNCMRIYTTCQPSWSSVKNKIERFFRKIYQ
HKNG1-V1-IPF3   NEVQEHLEEEERLCRESLADSWGECRSCLENNCMRIYTTCQPSWSSVKNKIERFFRKIYQ
HKNG1-V1-IPF2   NEVQEHLEEEERLCRESLADSWGECRSCLENNCMRIYTTCQPSWSSVKNKIERFFRKIYQ
HKNG1/1-V1-IPF2 NEVQEHLEEEERLCRESLADSWGECRSCLENNCMRIYTTCQPSWSSVKNKIERFFRKIYQ
HKNG1-IPF1      NEVQEHLEEEERLCRESLADSWGECRSCLENNCMRIYTTCQPSWSSVKNKIERFFRKIYQ
                ************************************************************ matureHKNG      FLFPFHEDNEKDLPISEKLIEEDAQLTQMEDVFSQLTVDVNSLFNRSFNVFRQMQQEFDQ
HKNG1-V1-IPF3   FLFPFHEDNEKDLPISEKLIEEDAQLTQMEDVFSQLTVDVNSLFNRSFNVFRQMQQEFDQ
HKNG1-V1-IPF2   FLFPFHEDNEKDLPISEKLIEEDAQLTQMEDVFSQLTVDVNSLFNRSFNVFRQMQQEFDQ
HKNG1/1-V1-IPF2 FLFPFHEDNEKDLPISEKLIEEDAQLTQMEDVFSQLTVDVNSLFNRSFNVFRQMQQEFDQ
HKNG1-IPF1      FLFPFHEDNEKDLPISEKLIEEDAQLTQMEDVFSQLTVDVNSLFNRSFNVFRQMQQEFDQ
                ************************************************************ matureHKNG      TFQSHFISDTDLTEPYFFPAFSKEPMTKADLEQCWDIPNFFQLFCNFSVSIYESVSETIT
HKNG1-V1-IPF3   TFQSHFISDTDLTEPYFFPAFSKEPMTKADLEQCWDIPNFFQLFCNFSVSIYESVSETIT
HKNG1-V1-IPF2   TFQSHFISDTDLTEPYFFPAFSKEPMTKADLEQCWDIPNFFQLFCNFSVSIYESVSETIT
HKNG1/1-V1-IPF2 TFQSHFISDTDLTEPYFFPAFSKEPMTKADLEQCWDIPNFFQLFCNFSVSIYESVSETIT
HKNG1-IPF1      TFQSHFISDTDLTEPYFFPAFSKEPMTKADLEQCWDIPNFFQLFCNFSVSIYESVSETIT
                ************************************************************
```

FIG.17A

```
matureHKNG     KMLKAIEDLPKQDKAPDHGGLISKMLPGQDRGLCGELDQNLSRCFKFHEKCQKCQAHLSE
HKNG1-V1-IPF3  KMLKAIEDLPKQDKAPDHGGLISKMLPGQDRGLCGELDQNLSRCFKFHEKCQKCQAHLSE
HKNG1/1-V1-IPF2 KMLKAIEDLPKQDKAPDHGGLISKMLPGQDRGLCGELDQNLSRCFKFHEKCQKCQAHLSE
HKNG1-IPF1     KMLKAIEDLPKQDKAPDHGGLISKMLPGQDRGLCGELDQNLSRCFKFHEKCQKCQAHLSE
               ************************************************************ matureHKNG     DCPDVPALHTELDEAIRLVNVSNQQYGQILQMTRKHLEDTAYLVEKMRGQFGWVSELANQ
HKNG1-V1-IPF3  DCPDVPALHTELDEAIRLVNVSNQQYGQILQMTRKHLEDTAYLVEKMRGQFGWVSELANQ
HKNG1/1-V1-IPF2 DCPDVPALHTELDEAIRLVNVSNQQYGQILQMTRKHLEDTAYLVEKMRGQFGWVSELANQ
HKNG1-IPF1     DCPDVPALHTELDEAIRLVNVSNQQYGQILQMTRKHLEDTAYLVEKMRGQFGWVSELANQ
               ************************************************************ matureHKNG     APETEIIFNSIQVVPRIHEGNISKQDETMMTDLSILPSSNFTLKIPLEESAESSNFIGYV
HKNG1-V1-IPF3  APETEIIFNSIQVVPRIHEGNISKQDETMMTDLSILPSSNFTLKIPLEESAESSNFIGYV
HKNG1/1-V1-IPF2 APETEIIFNSIQVVPRIHEGNISKQDETMMTDLSILPSSNFTLKIPLEESAESSNFIGYV
HKNG1-IPF1     APETEIIFNSIQVVPRIHEGNISKQDETMMTDLSILPSSNFTLKIPLEESAESSNFIGYV
               ************************************************************ matureHKNG     VAKALQHFKEHFKTW
HKNG1-V1-IPF3  VAKALQHFKEHFKTW
HKNG1/1-V1-IPF2 VAKALQHFKEHFKTW
HKNG1-IPF1     VAKALQHFKEHFKTW
               ***************
```

FIG.17B

```
     R   H   L   Q   A   R   A   A   G   L   V   S   T   L   E   V   A   D   T      19
TG  CGT CAC CTG CAG GCC CGG GCC GCG GGG TTG GTT TCC ACC CTG GAG GTT GCT GAC ACC      57

L   C   P   R   L   T   S   S   R   W   H   R   L   Q   G   A   A   L   K          39
CTG TGC CCT CGG CTG ACT TCC AGC CGG TGG CAC AGA CGC CTC CAG GGG GCA GCA CTC AAG     117

R   I   L   G   M   T   E   L   R   P   S   L   L   P   G   W   S   V   A          59
CGC ATC TTA GGA ATG ACA GAG TTG CGT CCC TCT CTG TTG CCA GGC TGG AGT TCA GTG GCA     177

C   S   *   L   T   E   A   S   N   S   W   V   Q   V   T   L   P   Q   P          79
TGT TCT TAG CTC ACT GAA GCC TCA AAT TCC TGG GTT CAA GTG ACC CTC CCA CAG CCC         237

H   E   D   L   G   L   Q   D   T   A   K   S   L   T   R   M   I   K   A          99
CAT GAG GAC CTG GGA CTA CAG GAC ACA GCT AAA TCC CTG ACA CGG ATG AAA ATT AAA GCA     297

E   K   N   E   G   P   S   R   S   W   Q   W   L   H   I   A   N                 119
GAG AAA AAC GAA GGT CCT TCC AGA AGC TGG CAA TGG CTT CAC CTT ATT GCA AAT             357

N   S   G   N   M   K   P   P   L   V   F   I   V   C   L   L   W   L   K         139
AAC AGC GGG AAC ATG AAG CCG CCA CTC TTG GTG TTT ATT GTG TGT CTG CTG TGG TTG AAA     417

D   S   H   C   A   P   T   W   K   D   A   D   E   E   V   K   K   A   L   S     159
GAC AGT CAC TGC GCA CCC ACT TGG AAG GAC GCA GAT GAA GAG GTG AAG AAG GCT CTG AGT     477

F   S   E   V   G   E   I   D   A   D   E   E   K   E   K   E   H   T   G   I     179
TTT TCT GAG GTG GGG GAG ATA GAT GCA GAT GAA GAG AAA GAG AAA GAA CAC ACT GGT ATT     537

K   Q   M   K   I   M   M   E   R   K   E   K   H   N   L   M   S   T             199
AAG CAA ATG AAA ATC ATG ATG GAA AGA AAA GAG AAG CAC AAT CTA ATG AGC ACC             597
```

FIG.18A

```
  L    K    K    C    R    E    E    E    K    Q    E    A    L    K    L    L    N    E    V    Q    E   219
 CTG  AAG  AAA  TGC  AGA  GAA  GAA  GAA  AAG  CAG  GAG  GCC  CTG  AAA  CTT  CTG  AAT  GAA  GTT  CAA  GAA  657

H    L    E    E    E    E    N    E    R    L    C    R    E    S    L    A    D    S    W    G    E    C   239
 CAT  CTG  GAG  GAA  GAA  GAA  AAT  GAA  AGG  CTA  TGC  CGG  GAG  TCT  TTG  GCA  GAT  TCC  TGG  GGT  GAA  TGC  717

R    S    C    L    E    N    N    C    M    R    I    Y    T    C    Q    P    S    W    S   259
 AGG  TCT  TGC  CTG  GAA  AAT  AAC  TGC  ATG  AGA  ATT  TAT  ACA  ACC  TGC  CAA  CCT  AGC  TGG  TCC  777

S    V    K    N    K    L    L    T    T    E    A    *    F    Q    R    C    Y    L    G    R   279
 TCT  GTG  AAA  AAT  AAG  CTC  CTG  ACC  ACG  GAG  GCC  TGA  TTT  CAA  AGA  TGT  TAC  CTG  GGC  AGG  837

T    E    D    C    V    G    N    L    T    R    I    C    Q    D    V    S    N    F    M    K   299
 ACA  GAG  GAC  TGT  GTG  GGG  AAC  TTG  ACC  AGA  ATT  TGT  CAA  GAT  GTT  TCA  AAT  TTC  ATG  AAA  897
  N    A    K    N    V    R    L    T    Y    L    K    T    Y    L    M    Y    I    S    L    C    T   319
 AAT  GCC  AAA  AAT  GTC  AGG  CTC  ACC  TAT  CTG  AAG  ACT  GTC  CTG  ATG  TAC  ATC  AGC  CTG  TGC  ACA  957

Q    N    *    T    R    R    S    G    W    S    M    Y    P    I    S    M    A    R    F   339
 CAG  AAT  TAG  ACG  AGG  CGA  TCA  GGT  TGG  TCA  ATG  TAT  CCA  ATC  AGC  AGT  ATG  GCC  AGA  TTC  1017

S    R    *    P    G    S    T    W    R    T    P    P    I    W    W    R    R    *    E    G   359
 TCC  AGA  TGA  CCC  GGA  AGC  ACT  TGG  AGG  ACA  CCG  CCT  ATC  TGG  TGG  AGA  AGA  TGA  GAG  GGC  1077

N    L    A    G    C    L    N    W    Q    F    M    K    Q    K    Q    R    S    S    L    I   379
 AAT  TTG  GCT  GGG  TGT  CTG  AAC  TGG  CAA  TTC  ATG  AAG  CAG  AAA  CAG  AGA  TCA  TCT  TTA  ATT  1137

Q    Y    R    *    F    Q    G    F    M    K    E    I    F    P    N    K    M    Q    *   399
 CAA  TAC  AGG  TAG  TTC  CAA  GGA  TTC  ATG  AAG  GAA  ATA  TTT  CCA  AAC  AAG  ATG  CAA  TGA  1197
```

FIG. 18B

```
  *   Q   T   *   A   F   C   L   P   L   I   S   H   S   R   S   L   L   K   K   419
TGA CAG ACT TAA GCA TTC TGC CTT CCT CTA ATT TCA CAC TCA AGA TCC CTC TTG AAG AAA 1257

V   L   R   V   L   T   S   L   A   T   *   W   Q   K   L   Y   S   I   L   R   439
GTG CTG AGA GTT CTA ACT TCA TTG GCT ACG TAG CAA AAG CTC TAC AGC ATT TTA AGG 1317

N   I   L   K   P   G   K   K   I   *   C   I   L   Y   P   V   S   R   I   I   459
AAC ATT TTA AAA CCT GGT AAG AAG ATC TAA TGC ATC CTA TAT CCA GTA AGT AGA ATT ATC 1377

S   S   S   G   T   W   K   S   *   N   K   K   G   *   C   N   K   H   S   C   479
TCT TCA TCT GGG ACC TGG AAA TCC TGA AAT AAA AAA GGA TAA TGC AAT AAA CAC AGT TGC 1437

R   K   V   C   *   L   Y   T   M   K   Y   S   *   F   T   Y   V   E   W   L   499
AGG AAA GTA TGT TAG CTA TAT ACT ATG AAG TAC TCT TAG TTT ACT TAT GTT GAA TGG CTT 1497

S   Y   *   Y   S   N   *   V   K   M   K   I   P   P   *   K   I   K   R   N   519
AGC TAT TAA TAC TCA AAT TGA GTT AAA ATG AAA ATT CCT CCT TAA AAA ATC AAA CGT AAT 1557

M   Y   I   S   W   Y   I   S   S   L   Y   I   E   *   I   L   N   H   539
ATG TAT TAC ATT TCA TGG TAC ATT AGT AGT TCT TTG TAT ATT GAA TAA ATA CTA AAT CAC 1617

L                                                                              540
CTA                                                                             1620
```

FIG. 18C

SEQUENCE LISTING

<160> NUMBER OF SEQ ID NOS: 84

<210> SEQ ID NO 1
<211> LENGTH: 2055
<212> TYPE: DNA
<213> ORGANISM: Homo sapiens
<220> FEATURE:
<221> NAME/KEY: CDS
<222> LOCATION: (285)...(1769)

<400> SEQUENCE: 1

```
tgcgtcacct gcaggcccgg gccgcggggt tggtttccac cctggaggtt gctgacaccc      60
tgtgccctcg gctgacttcc agccggtggc acagacgcct ccaggggggca gcactcaagc     120 gcatcttagg aatgacagag ttgcgtccct ctctgttgcc aggctggagt tcagtggcat     180
gttcttagct cactgaagcc tcaaattcct gggttcaagt gaccctccca cctcagcccc     240
atgaggacct gggactacag gacacagcta atccctgac acgg atg aaa att aaa       296
                                           Met Lys Ile Lys
                                             1 gca gag aaa aac gaa ggt cct tcc aga agc tgg tgg caa ctt cac tgg        344
Ala Glu Lys Asn Glu Gly Pro Ser Arg Ser Trp Trp Gln Leu His Trp
  5              10                  15                  20 gga gat att gca aat aac agc ggg aac atg aag ccg cca ctc ttg gtg        392
Gly Asp Ile Ala Asn Asn Ser Gly Asn Met Lys Pro Pro Leu Leu Val
             25                  30                  35 ttt att gtg tgt ctg ctg tgg ttg aaa gac agt cac tgc gca ccc act        440
Phe Ile Val Cys Leu Leu Trp Leu Lys Asp Ser His Cys Ala Pro Thr
         40                  45                  50 tgg aag gac aaa act gct atc agt gaa aac ctg aag agt ttt tct gag        488
Trp Lys Asp Lys Thr Ala Ile Ser Glu Asn Leu Lys Ser Phe Ser Glu
     55                  60                  65 gtg ggg gag ata gat gca gat gaa gag gtg aag aag gct ttg act ggt        536
Val Gly Glu Ile Asp Ala Asp Glu Glu Val Lys Lys Ala Leu Thr Gly
 70                  75                  80 att aag caa atg aaa atc atg atg gaa aga aaa gag aag gaa cac acc        584
Ile Lys Gln Met Lys Ile Met Met Glu Arg Lys Glu Lys Glu His Thr
 85                  90                  95                 100 aat cta atg agc acc ctg aag aaa tgc aga gaa gaa aag cag gag gcc        632
Asn Leu Met Ser Thr Leu Lys Lys Cys Arg Glu Glu Lys Gln Glu Ala
             105                 110                 115 ctg aaa ctt ctg aat gaa gtt caa gaa cat ctg gag gaa gaa gaa agg        680
Leu Lys Leu Leu Asn Glu Val Gln Glu His Leu Glu Glu Glu Glu Arg
         120                 125                 130 cta tgc cgg gag tct ttg gca gat tcc tgg ggt gaa tgc agg tct tgc        728
Leu Cys Arg Glu Ser Leu Ala Asp Ser Trp Gly Glu Cys Arg Ser Cys
     135                 140                 145 ctg gaa aat aac tgc atg aga att tat aca acc tgc caa cct agc tgg        776
Leu Glu Asn Asn Cys Met Arg Ile Tyr Thr Thr Cys Gln Pro Ser Trp
 150                 155                 160 tcc tct gtg aaa aat aag att gaa cgg ttt ttc agg aag ata tat caa        824
Ser Ser Val Lys Asn Lys Ile Glu Arg Phe Phe Arg Lys Ile Tyr Gln
165                 170                 175                 180 ttt cta ttt cct ttc cat gaa gat aat gaa aaa gat ctc ccc atc agt        872
Phe Leu Phe Pro Phe His Glu Asp Asn Glu Lys Asp Leu Pro Ile Ser
             185                 190                 195 gaa aag ctc att gag gaa gat gca caa ttg acc caa atg gag gat gtg        920
Glu Lys Leu Ile Glu Glu Asp Ala Gln Leu Thr Gln Met Glu Asp Val
         200                 205                 210
```

```
ttc agc cag ttg act gtg gat gtg aat tct ctc ttt aac agg agt ttt       968
Phe Ser Gln Leu Thr Val Asp Val Asn Ser Leu Phe Asn Arg Ser Phe
        215                 220                 225 aac gtc ttc aga cag atg cag caa gag ttt gac cag act ttt caa tca      1016
Asn Val Phe Arg Gln Met Gln Gln Glu Phe Asp Gln Thr Phe Gln Ser
    230                 235                 240 cat ttc ata tca gat aca gac cta act gag cct tac ttt ttt cca gct      1064
His Phe Ile Ser Asp Thr Asp Leu Thr Glu Pro Tyr Phe Phe Pro Ala
245                 250                 255                 260 ttc tct aaa gag ccg atg aca aaa gca gat ctt gag caa tgt tgg gac      1112
Phe Ser Lys Glu Pro Met Thr Lys Ala Asp Leu Glu Gln Cys Trp Asp
                265                 270                 275 att ccc aac ttc ttc cag ctg ttt tgt aat ttc agt gtc tct att tat      1160
Ile Pro Asn Phe Phe Gln Leu Phe Cys Asn Phe Ser Val Ser Ile Tyr
            280                 285                 290 gaa agt gtc agt gaa aca att act aag atg ctg aag gca ata gaa gat      1208
Glu Ser Val Ser Glu Thr Ile Thr Lys Met Leu Lys Ala Ile Glu Asp
        295                 300                 305 tta cca aaa caa gac aaa gct cct gac cac gga ggc ctg att tca aag      1256
Leu Pro Lys Gln Asp Lys Ala Pro Asp His Gly Gly Leu Ile Ser Lys
    310                 315                 320 atg tta cct ggg cag gac aga gga ctg tgt ggg gaa ctt gac cag aat      1304
Met Leu Pro Gly Gln Asp Arg Gly Leu Cys Gly Glu Leu Asp Gln Asn
325                 330                 335                 340 ttg tca aga tgt ttc aaa ttt cat gaa aaa tgc caa aaa tgt cag gct      1352
Leu Ser Arg Cys Phe Lys Phe His Glu Lys Cys Gln Lys Cys Gln Ala
                345                 350                 355 cac cta tct gaa gac tgt cct gat gta cct gct ctg cac aca gaa tta      1400
His Leu Ser Glu Asp Cys Pro Asp Val Pro Ala Leu His Thr Glu Leu
            360                 365                 370 gac gag gcg atc agg ttg gtc aat gta tcc aat cag cag tat ggc cag      1448
Asp Glu Ala Ile Arg Leu Val Asn Val Ser Asn Gln Gln Tyr Gly Gln
        375                 380                 385 att ctc cag atg acc cgg aag cac ttg gag gac acc gcc tat ctg gtg      1496
Ile Leu Gln Met Thr Arg Lys His Leu Glu Asp Thr Ala Tyr Leu Val
    390                 395                 400 gag aag atg aga ggg caa ttt ggc tgg gtg tct gaa ctg gca aac cag      1544
Glu Lys Met Arg Gly Gln Phe Gly Trp Val Ser Glu Leu Ala Asn Gln
405                 410                 415                 420 gcc cca gaa aca gag atc atc ttt aat tca ata cag gta gtt cca agg      1592
Ala Pro Glu Thr Glu Ile Ile Phe Asn Ser Ile Gln Val Val Pro Arg
                425                 430                 435 att cat gaa gga aat att tcc aaa caa gat gaa aca atg atg aca gac      1640
Ile His Glu Gly Asn Ile Ser Lys Gln Asp Glu Thr Met Met Thr Asp
            440                 445                 450 tta agc att ctg cct tcc tct aat ttc aca ctc aag atc cct ctt gaa      1688
Leu Ser Ile Leu Pro Ser Ser Asn Phe Thr Leu Lys Ile Pro Leu Glu
        455                 460                 465 gaa agt gct gag agt tct aac ttc att ggc tac gta gtg gca aaa gct      1736
Glu Ser Ala Glu Ser Ser Asn Phe Ile Gly Tyr Val Val Ala Lys Ala
    470                 475                 480 cta cag cat ttt aag gaa cat ttt aaa acc tgg taagaagatc taatgcatcc    1789
Leu Gln His Phe Lys Glu His Phe Lys Thr Trp
485                 490                 495 tatatccagt aagtagaatt atctcttcat ctgggacctg gaaatcctga aataaaaaag    1849
gataatgcaa taaacacagt tgcaggaaag tatgttagct atatactatg aagtactctt    1909
agtttactta tgttgaatgg cttagctatt aatactcaaa ttgagttaaa atgaaaattc    1969
ctccttaaaa aatcaaacgt aatatgtatt acatttcatg gtacattagt agttctttgt    2029
```
atattgaata aatactaaat caccta                                    2055

<210> SEQ ID NO 2
<211> LENGTH: 495
<212> TYPE: PRT
<213> ORGANISM: Homo sapiens

<400> SEQUENCE: 2

```
Met Lys Ile Lys Ala Glu Lys Asn Glu Gly Pro Ser Arg Ser Trp Trp
  1               5                  10                  15

Gln Leu His Trp Gly Asp Ile Ala Asn Ser Gly Asn Met Lys Pro
             20                  25                  30

Pro Leu Leu Val Phe Ile Val Cys Leu Leu Trp Leu Lys Asp Ser His
         35                  40                  45

Cys Ala Pro Thr Trp Lys Asp Lys Thr Ala Ile Ser Glu Asn Leu Lys
 50                  55                  60

Ser Phe Ser Glu Val Gly Glu Ile Asp Ala Asp Glu Val Lys Lys
 65                  70                  75                  80

Ala Leu Thr Gly Ile Lys Gln Met Lys Ile Met Met Glu Arg Lys Glu
                 85                  90                  95

Lys Glu His Thr Asn Leu Met Ser Thr Leu Lys Lys Cys Arg Glu Glu
            100                 105                 110

Lys Gln Glu Ala Leu Lys Leu Leu Asn Glu Val Gln Glu His Leu Glu
        115                 120                 125

Glu Glu Glu Arg Leu Cys Arg Glu Ser Leu Ala Asp Ser Trp Gly Glu
    130                 135                 140

Cys Arg Ser Cys Leu Glu Asn Asn Cys Met Arg Ile Tyr Thr Thr Cys
145                 150                 155                 160

Gln Pro Ser Trp Ser Ser Val Lys Asn Lys Ile Glu Arg Phe Phe Arg
                165                 170                 175

Lys Ile Tyr Gln Phe Leu Phe Pro Phe His Glu Asp Asn Glu Lys Asp
            180                 185                 190

Leu Pro Ile Ser Glu Lys Leu Ile Glu Glu Asp Ala Gln Leu Thr Gln
        195                 200                 205

Met Glu Asp Val Phe Ser Gln Leu Thr Val Asp Val Asn Ser Leu Phe
    210                 215                 220

Asn Arg Ser Phe Asn Val Phe Arg Gln Met Gln Gln Glu Phe Asp Gln
225                 230                 235                 240

Thr Phe Gln Ser His Phe Ile Ser Asp Thr Asp Leu Thr Glu Pro Tyr
                245                 250                 255

Phe Phe Pro Ala Phe Ser Lys Glu Pro Met Thr Lys Ala Asp Leu Glu
            260                 265                 270

Gln Cys Trp Asp Ile Pro Asn Phe Gln Leu Phe Cys Asn Phe Ser
        275                 280                 285

Val Ser Ile Tyr Glu Ser Val Ser Glu Thr Ile Thr Lys Met Leu Lys
    290                 295                 300

Ala Ile Glu Asp Leu Pro Lys Gln Asp Lys Ala Pro Asp His Gly Gly
305                 310                 315                 320

Leu Ile Ser Lys Met Leu Pro Gly Gln Asp Arg Gly Leu Cys Gly Glu
                325                 330                 335

Leu Asp Gln Asn Leu Ser Arg Cys Phe Lys Phe His Glu Lys Cys Gln
            340                 345                 350

Lys Cys Gln Ala His Leu Ser Glu Asp Cys Pro Asp Val Pro Ala Leu
        355                 360                 365
```

```
His Thr Glu Leu Asp Glu Ala Ile Arg Leu Val Asn Val Ser Asn Gln
    370                 375                 380

Gln Tyr Gly Gln Ile Leu Gln Met Thr Arg Lys His Leu Glu Asp Thr
385                 390                 395                 400

Ala Tyr Leu Val Glu Lys Met Arg Gly Gln Phe Gly Trp Val Ser Glu
                405                 410                 415

Leu Ala Asn Gln Ala Pro Glu Thr Glu Ile Ile Phe Asn Ser Ile Gln
                420                 425                 430

Val Val Pro Arg Ile His Glu Gly Asn Ile Ser Lys Gln Asp Glu Thr
                435                 440                 445

Met Met Thr Asp Leu Ser Ile Leu Pro Ser Ser Asn Phe Thr Leu Lys
    450                 455                 460

Ile Pro Leu Glu Glu Ser Ala Glu Ser Ser Asn Phe Ile Gly Tyr Val
465                 470                 475                 480

Val Ala Lys Ala Leu Gln His Phe Lys Glu His Phe Lys Thr Trp
                485                 490                 495

<210> SEQ ID NO 3
<211> LENGTH: 1957
<212> TYPE: DNA
<213> ORGANISM: Homo sapiens
<220> FEATURE:
<221> NAME/KEY: CDS
<222> LOCATION: (241)...(1671)

<400> SEQUENCE: 3
tgcgtcacct gcaggcccgg gccgcggggt tggtttccac cctggaggtt gctgacaccc      60
tgtgccctcg gctgacttcc agccggtggc acagacgcct caggggggca gcactcaagc     120
gcatcttagg aatgacagag ttgcgtccct ctcggttgcc aggctggagt tcagtggcat     180
gttcatagct cactgaagcc tcaaattcct gggttcaagt gacctcccta cctcagcccc     240 atg agg acc tgg gac tac agt aac agc ggg aac atg aag ccg cca ctc      288
Met Arg Thr Trp Asp Tyr Ser Asn Ser Gly Asn Met Lys Pro Pro Leu
  1               5                  10                  15 ttg gtg ttt att gtg tgt ctg ctg tgg ttg aaa gac agt cac tcc gca      336
Leu Val Phe Ile Val Cys Leu Leu Trp Leu Lys Asp Ser His Ser Ala
             20                  25                  30 ccc act tgg aag gac aaa agt gct atc agt gaa aac ctg aag agt ttt      384
Pro Thr Trp Lys Asp Lys Ser Ala Ile Ser Glu Asn Leu Lys Ser Phe
         35                  40                  45 tct gag gtg ggg gag ata gat gca gat gaa gag gtg aag aag gct ttg      432
Ser Glu Val Gly Glu Ile Asp Ala Asp Glu Glu Val Lys Lys Ala Leu
     50                  55                  60 act ggt att aag caa atg aaa atc atg atg gaa aga aaa gag aag gca      480
Thr Gly Ile Lys Gln Met Lys Ile Met Met Glu Arg Lys Glu Lys Ala
 65                  70                  75                  80 aac cag gcc cca gaa aca gag atc atc ttt aat tca ata cag gta gtt      528
Asn Gln Ala Pro Glu Thr Glu Ile Ile Phe Asn Ser Ile Gln Val Val
                 85                  90                  95 cca agg att gaa cac acc aat cta atg agc acc ctg aag aaa tgc aga      576
Pro Arg Ile Glu His Thr Asn Leu Met Ser Thr Leu Lys Lys Cys Arg
            100                 105                 110 gaa gaa aag cag gag gcc ctg aaa ctt ctg aat gaa gtt caa gaa cat      624
Glu Glu Lys Gln Glu Ala Leu Lys Leu Leu Asn Glu Val Gln Glu His
        115                 120                 125 ctg gag gaa gaa gaa agg cta tgc cgg gag tct ttg gca gat tcc tgg      672
Leu Glu Glu Glu Glu Arg Leu Cys Arg Glu Ser Leu Ala Asp Ser Trp
    130                 135                 140
```

-continued

```
ggt gaa tgc agg tct tgc ctg gaa aat aac tgc atg aga att tat aca    720
Gly Glu Cys Arg Ser Cys Leu Glu Asn Asn Cys Met Arg Ile Tyr Thr
145                 150                 155                 160 acc tgc caa cct agc tgg tcc tct gtg aaa aat aag att gaa cgg ttt    768
Thr Cys Gln Pro Ser Trp Ser Ser Val Lys Asn Lys Ile Glu Arg Phe
                165                 170                 175 ttc agg aag ata tat caa ttt cta ttt cct ttc cat gaa gat aat gaa    816
Phe Arg Lys Ile Tyr Gln Phe Leu Phe Pro Phe His Glu Asp Asn Glu
            180                 185                 190 aaa gat ctc ccc atc agt gaa aag ctc att gag gaa gat gca caa ttg    864
Lys Asp Leu Pro Ile Ser Glu Lys Leu Ile Glu Glu Asp Ala Gln Leu
        195                 200                 205 acc caa atg gag gat gtg ttc agc cag ttg act gtg gat gtg aat tct    912
Thr Gln Met Glu Asp Val Phe Ser Gln Leu Thr Val Asp Val Asn Ser
    210                 215                 220 ctc ttt aac agg agt ttt aac gtc ttc aga cag atg cag caa gag ttt    960
Leu Phe Asn Arg Ser Phe Asn Val Phe Arg Gln Met Gln Gln Glu Phe
225                 230                 235                 240 gac cag act ttt caa tca cat ttc ata tca gat aca gac cta act gag   1008
Asp Gln Thr Phe Gln Ser His Phe Ile Ser Asp Thr Asp Leu Thr Glu
                245                 250                 255 cct tac ttt ttt cca gct ttc tct aaa gag ccg atg aca aaa gca gat   1056
Pro Tyr Phe Phe Pro Ala Phe Ser Lys Glu Pro Met Thr Lys Ala Asp
            260                 265                 270 ctt gag caa tgt tgg gac att ccc aac ttc ttc cag ctg ttt tgt aat   1104
Leu Glu Gln Cys Trp Asp Ile Pro Asn Phe Phe Gln Leu Phe Cys Asn
        275                 280                 285 ttc agt gtc tct att tat gaa agt gtc agt gaa aca att act aag atg   1152
Phe Ser Val Ser Ile Tyr Glu Ser Val Ser Glu Thr Ile Thr Lys Met
    290                 295                 300 ctg aag gca ata gaa gat tta cca aaa caa gac aaa gct cct gac cac   1200
Leu Lys Ala Ile Glu Asp Leu Pro Lys Gln Asp Lys Ala Pro Asp His
305                 310                 315                 320 gga ggc ctg att tca aag atg tta cct ggg cag gac aga gga ctg tgt   1248
Gly Gly Leu Ile Ser Lys Met Leu Pro Gly Gln Asp Arg Gly Leu Cys
                325                 330                 335 ggg gaa ctt gac cag aat ttg tca aga tgt ttc aaa ttt cat gaa aaa   1296
Gly Glu Leu Asp Gln Asn Leu Ser Arg Cys Phe Lys Phe His Glu Lys
            340                 345                 350 tgc caa aaa tgt cag gct cac cta tct gaa gac tgt cct gat gta cct   1344
Cys Gln Lys Cys Gln Ala His Leu Ser Glu Asp Cys Pro Asp Val Pro
        355                 360                 365 gct ctg cac aca gaa tta gac gag gcg atc agg ttg gtc aat gta tcc   1392
Ala Leu His Thr Glu Leu Asp Glu Ala Ile Arg Leu Val Asn Val Ser
    370                 375                 380 aat cag cag tat ggc cag att ctc cag atg acc cgg aag cac ttg gag   1440
Asn Gln Gln Tyr Gly Gln Ile Leu Gln Met Thr Arg Lys His Leu Glu
385                 390                 395                 400 gac acc gcc tat ctg gtg gag aag atg aga ggg caa ttt ggc tgg gtg   1488
Asp Thr Ala Tyr Leu Val Glu Lys Met Arg Gly Gln Phe Gly Trp Val
                405                 410                 415 tct gaa ctg cat gaa gga aat att tcc aaa caa gat gaa aca atg atg   1536
Ser Glu Leu His Glu Gly Asn Ile Ser Lys Gln Asp Glu Thr Met Met
            420                 425                 430 aca gac tta agc att ctg cct tcc tct aat ttc aca ctc aag atc cct   1584
Thr Asp Leu Ser Ile Leu Pro Ser Ser Asn Phe Thr Leu Lys Ile Pro
        435                 440                 445 ctt gaa gaa agt gct gag agt tct aac ttc att ggc tac gta gtg gca   1632
Leu Glu Glu Ser Ala Glu Ser Ser Asn Phe Ile Gly Tyr Val Val Ala
```

```
                          450                 455                 460
aaa gct cta cag cat ttt aag gaa cat ttt aaa acc tgg taagaagatc      1681
Lys Ala Leu Gln His Phe Lys Glu His Phe Lys Thr Trp
465                 470                 475 taatgcatcc tatatccagt aagtagaatt atctcttcat ctgggacctg gaaatcctga   1741
aataaaaaag gataatgcaa taaacacagt tgcaggaaag tatgttagct atatactatg   1801
aagtactctt agtttactta tgttgaatgg cttagctatt aatactcaaa ttgagttaaa   1861
atgaaaattc ctccttaaaa aatcaaacgt aaatatgtatt acatttcatg gtacattagt  1921
agttctttgt atattgaata aatactaaat caccta                             1957

<210> SEQ ID NO 4
<211> LENGTH: 477
<212> TYPE: PRT
<213> ORGANISM: Homo sapiens

<400> SEQUENCE: 4
```

Met Arg Thr Trp Asp Tyr Ser Asn Ser Gly Asn Met Lys Pro Pro Leu
1               5                   10                  15

Leu Val Phe Ile Val Cys Leu Leu Trp Leu Lys Asp Ser His Ser Ala
            20                  25                  30

Pro Thr Trp Lys Asp Lys Ser Ala Ile Ser Glu Asn Leu Lys Ser Phe
        35                  40                  45

Ser Glu Val Gly Glu Ile Asp Ala Asp Glu Val Lys Lys Ala Leu
    50                  55                  60

Thr Gly Ile Lys Gln Met Lys Ile Met Met Glu Arg Lys Glu Lys Ala
65                  70                  75                  80

Asn Gln Ala Pro Glu Thr Glu Ile Ile Phe Asn Ser Ile Gln Val Val
                85                  90                  95

Pro Arg Ile Glu His Thr Asn Leu Met Ser Thr Leu Lys Lys Cys Arg
            100                 105                 110

Glu Glu Lys Gln Glu Ala Leu Lys Leu Leu Asn Glu Val Gln Glu His
        115                 120                 125

Leu Glu Glu Glu Glu Arg Leu Cys Arg Glu Ser Leu Ala Asp Ser Trp
    130                 135                 140

Gly Glu Cys Arg Ser Cys Leu Glu Asn Asn Cys Met Arg Ile Tyr Thr
145                 150                 155                 160

Thr Cys Gln Pro Ser Trp Ser Ser Val Lys Asn Lys Ile Glu Arg Phe
                165                 170                 175

Phe Arg Lys Ile Tyr Gln Phe Leu Phe Pro Phe His Glu Asp Asn Glu
            180                 185                 190

Lys Asp Leu Pro Ile Ser Glu Lys Leu Ile Glu Glu Asp Ala Gln Leu
        195                 200                 205

Thr Gln Met Glu Asp Val Phe Ser Gln Leu Thr Val Asp Val Asn Ser
    210                 215                 220

Leu Phe Asn Arg Ser Phe Asn Val Phe Arg Gln Met Gln Gln Glu Phe
225                 230                 235                 240

Asp Gln Thr Phe Gln Ser His Phe Ile Ser Asp Thr Asp Leu Thr Glu
                245                 250                 255

Pro Tyr Phe Phe Pro Ala Phe Ser Lys Glu Pro Met Thr Lys Ala Asp
            260                 265                 270

Leu Glu Gln Cys Trp Asp Ile Pro Asn Phe Gln Leu Phe Cys Asn
        275                 280                 285

Phe Ser Val Ser Ile Tyr Glu Ser Val Ser Glu Thr Ile Thr Lys Met

```
                    290                 295                 300
Leu Lys Ala Ile Glu Asp Leu Pro Lys Gln Asp Lys Ala Pro Asp His
305                 310                 315                 320

Gly Gly Leu Ile Ser Lys Met Leu Pro Gly Gln Asp Arg Gly Leu Cys
                325                 330                 335

Gly Glu Leu Asp Gln Asn Leu Ser Arg Cys Phe Lys Phe His Glu Lys
                340                 345                 350

Cys Gln Lys Cys Gln Ala His Leu Ser Glu Asp Cys Pro Asp Val Pro
                355                 360                 365

Ala Leu His Thr Glu Leu Asp Glu Ala Ile Arg Leu Val Asn Val Ser
370                 375                 380

Asn Gln Gln Tyr Gly Gln Ile Leu Gln Met Thr Arg Lys His Leu Glu
385                 390                 395                 400

Asp Thr Ala Tyr Leu Val Glu Lys Met Arg Gly Gln Phe Gly Trp Val
                405                 410                 415

Ser Glu Leu His Glu Gly Asn Ile Ser Lys Gln Asp Glu Thr Met Met
                420                 425                 430

Thr Asp Leu Ser Ile Leu Pro Ser Ser Asn Phe Thr Leu Lys Ile Pro
                435                 440                 445

Leu Glu Glu Ser Ala Glu Ser Ser Asn Phe Ile Gly Tyr Val Val Ala
450                 455                 460

Lys Ala Leu Gln His Phe Lys Glu His Phe Lys Thr Trp
465                 470                 475

<210> SEQ ID NO 5
<211> LENGTH: 1485
<212> TYPE: DNA
<213> ORGANISM: Homo sapiens

<400> SEQUENCE: 5
atgaaaatta aagcagagaa aaacgaaggt ccttccagaa gctggtggca acttcactgg      60
ggagatattg caaataacag cgggaacatg aagccgccac tcttggtgtt tattgtgtgt     120
ctgctgtggt tgaaagacag tcactgcgca cccacttgga aggacaaaac tgctatcagt     180
gaaaacctga gagttttttc tgaggtgggg gagatagatg cagatgaaga ggtgaagaag     240
gctttgactg gtattaagca aatgaaaatc atgatggaaa gaaagagaa ggaacacacc     300 aatctaatga gcaccctgaa gaaatgcaga gaagaaaagc aggaggccct gaaacttctg     360
aatgaagttc aagaacatct ggaggaagaa gaaaggctat gccgggagtc tttggcagat     420
tcctggggtg aatgcaggtc ttgcctggaa aataactgca tgagaattta tacaaccctgc    480 caacctagct ggtcctctgt gaaaaataag attgaacggt ttttcaggaa gatatatcaa     540
tttctatttc ctttccatga agataatgaa aaagatctcc ccatcagtga aaagctcatt     600
gaggaagatg cacaattgac ccaaatggag gatgtgttca gccagttgac tgtggatgtg     660
aattctctct ttaacaggag ttttaacgtc ttcagacaga tgcagcaaga gtttgaccag     720
acttttcaat cacatttcat atcagataca gacctaactg agccttactt ttttccagct     780
ttctctaaag agccgatgac aaaagcagat cttgagcaat gttgggacat tcccaacttc     840
ttccagctgt tttgtaattt cagtgtctct atttatgaaa gtgtcagtga acaattact     900 aagatgctga aggcaataga agatttacca aaacaagaca agctcctga ccacggaggc     960 ctgatttcaa agatgttacc tgggcaggac agaggactgt gtggggaact tgaccagaat    1020
ttgtcaagat gtttcaaatt tcatgaaaaa tgccaaaaat gtcaggctca cctatctgaa    1080
```

-continued

| | |
|---|---|
| gactgtcctg atgtacctgc tctgcacaca gaattagacg aggcgatcag gttggtcaat | 1140 |
| gtatccaatc agcagtatgg ccagattctc cagatgaccc ggaagcactt ggaggacacc | 1200 |
| gcctatctgg tggagaagat gagagggcaa tttggctggg tgtctgaact ggcaaaccag | 1260 |
| gccccagaaa cagagatcat ctttaattca atacaggtag ttccaaggat tcatgaagga | 1320 |
| aatatttcca acaagatga aacaatgatg acagacttaa gcattctgcc ttcctctaat | 1380 |
| ttcacactca agatccctct tgaagaaagt gctgagagtt ctaacttcat tggctacgta | 1440 |
| gtggcaaaag ctctacagca ttttaaggaa cattttaaaa cctgg | 1485 |

<210> SEQ ID NO 6
<211> LENGTH: 1431
<212> TYPE: DNA
<213> ORGANISM: Homo sapiens

<400> SEQUENCE: 6

| | |
|---|---|
| atgaggacct gggactacag taacagcggg aacatgaagc cgccactctt ggtgtttatt | 60 |
| gtgtgtctgc tgtggttgaa agacagtcac tccgcaccca cttggaagga caaaagtgct | 120 |
| atcagtgaaa acctgaagag ttttttctgag gtgggggaga tagatgcaga tgaagaggtg | 180 |
| aagaaggctt tgactggtat taagcaaatg aaaatcatga tggaaagaaa agagaaggca | 240 |
| aaccaggccc cagaaacaga gatcatcttt aattcaatac aggtagttcc aaggattgaa | 300 |
| cacaccaatc taatgagcac cctgaagaaa tgcagagaag aaaagcagga ggccctgaaa | 360 |
| cttctgaatg aagttcaaga acatctggag gaagaagaaa ggctatgccg ggagtctttg | 420 |
| gcagattcct ggggtgaatg caggtcttgc ctggaaaata actgcatgag aatttataca | 480 |
| acctgccaac ctagctggtc ctctgtgaaa aataagattg aacggttttt caggaagata | 540 |
| tatcaatttc tatttccttt ccatgaagat aatgaaaaag atctccccat cagtgaaaag | 600 |
| ctcattgagg aagatgcaca attgacccaa atggaggatg tgttcagcca gttgactgtg | 660 |
| gatgtgaatt ctctctttaa caggagtttt aacgtcttca gacagatgca gcaagagttt | 720 |
| gaccagactt tcaatcaca tttcatatca gatacagacc taactgagcc ttacttttt | 780 |
| ccagctttct ctaaagagcc gatgacaaaa gcagatcttg agcaatgttg ggacattccc | 840 |
| aacttcttcc agctgttttg taatttcagt gtctctattt atgaaagtgt cagtgaaaca | 900 |
| attactaaga tgctgaaggc aatagaagat ttaccaaaac aagacaaagc tcctgaccac | 960 |
| ggaggcctga tttcaaagat gttacctggg caggacagag gactgtgtgg ggaacttgac | 1020 |
| cagaatttgt caagatgttt caaatttcat gaaaaatgcc aaaaatgtca ggctcaccta | 1080 |
| tctgaagact gtcctgatgt acctgctctg cacacagaat agacgaggc gatcaggttg | 1140 |
| gtcaatgtat ccaatcagca gtatggccag attctccaga tgacccggaa gcacttggag | 1200 |
| gacaccgcct atctggtgga gaagatgaga gggcaatttg ctgggtgtc tgaactgcat | 1260 |
| gaaggaaata tttccaaaca agatgaaaca atgatgacag acttaagcat tctgccttcc | 1320 |
| tctaatttca cactcaagat ccctcttgaa gaaagtgctg agagttctaa cttcattggc | 1380 |
| tacgtagtgg caaaagctct acagcatttt aaggaacatt ttaaaacctg g | 1431 |

<210> SEQ ID NO 7
<211> LENGTH: 72604
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g, or t

<400> SEQUENCE: 7

```
acattttaag ctacttatag tccttggaaa tagcaacaaa tatcttagtt attggactat      60
tataacctta gtcatcttat tactgcttga ttatgagaca ctctccctgc taatccttag     120
aacatcttgg ttcttggtac ttgactttta gcccctctga catatagttg atgtcagagt     180
gtctggcatt tcagtagtgc tctatttac aaatcccagt aaactgctcc actgtggctt     240
gtttatgtgt taatactgct tgttttctgt tataaattat ttttgctttt ggagtaagat     300
atcatcattt tgcatagcta caaatctgaa gttaaagaaa attttaaaaa tgtaattgtg     360
ggaaaataac aaatagatct gctgagatgg aggctttgac taatgtttta ataacaggca     420
acaaaacaaa gaggcaggat attttggtca caactaaacc taaattaaat cctcatacaa     480
agccccatta agataaatgc tcaaattctg gaacatttc acttgctttg ccagcaattt     540
tacccttcag agggtgtgga tctaatcagg gaacaaact accctgggct taattctcat     600
taacagggac taatttgtca agcggcagt actagctgaa gtgatgggta tggaagcatt     660
cactgtgagg attttgctga ggtgcctggc acagggtagg ggaactcacc caggctgcaa     720
gatgctaaca gttcaggttc aaggtcttag tgtggactaa ggtgcagtca ggatgggaac     780
aggtgcaact tgggccaaca tcagtatgaa gggcctgatc tgagggcagg ggaaggaggg     840
ggcattctgg gaagcaagag ttcctggtat cctgttgacc agagtcttgg cccaaggatc     900
aacgtatgaa ttaaagtaga aataccagaa acaaagaaag ttggcagaaa ctaggagaag     960
cagagtctca gccaactgga ctgggctcag ccttggctac tggcccggca gatgatagaa    1020
gagaaaacca ggaacccagg ctgaagccca gtggttgggc tggccacaca ccatgcatag    1080
ccttaaaggg gtggcctaag ggcatggtcc gctccaaaaa aggaaagggg gccccagaat    1140
atttctgaat cccactcact gccagggaag aacctctcaa ttcactcaat agtgcattct    1200
cctgcttctc aataggctaa tactctagag aatatgggga caaggggagg agggtctagt    1260
ggaacaggtc taaactggcg tttgaatttt aagataagtt aatcatacat tggctgggtc    1320
agccatgtct cttagtcttt acaaaagtag aacacaaaaa aattcaatgg aaatctacag    1380
acacctattt gcagatgagg aaacacggct atgaagattg ggaagattgg gaagaactgg    1440
ccaggtgtgg tgctcacgcc tgtaatccca gcactttggg aggccgaggc tggtggatca    1500
cttgaggtca ggagttggag accagcctgg gcaacatagt aaaaccctgt ctctactcaa    1560
attacaaaaa tcagcagggc gttgtggtgc ccacctgtaa tcccagctat gcaggaggct    1620
gaggcaggac aatcacttga acctggtagg cggaggttgc agtgagccaa aatcacgcca    1680
ctgtactcca gcctgggtga cagagcaaga ctttgtttaa aaaaaaaaa aaaaagggaa    1740
gaactaaaaa tgtaattttc aagggctat cacaaatggt cccaataaag agaaagcagg    1800
actcatgttt aagaaaccca tgagatgtgt atggacctca tggaagagct cttgctttct    1860
aatgatctac gtaacagatg aaaagcagag cataggcta aggatgaaaa tacaacagta    1920
ataaggtatt aatatattat taagaaagct aatgctccac ataagcagag gacattaaag    1980
ggactttttt ttcttaagga tatcttaatg ttttaaatga gaagacatag aaagggatag    2040
gtccaactct tgggattgtt gcaggttggt ttccatcgga agcactctga gtctgagatt    2100
tgtatgcaga aaattaattt gaatgtgctt ttcagatcac ccaggtgggg gaggaggaa    2160
accaggactg gcagagaga ggctgggctg taaccaagtc acaacaaagg tgtcagctgg    2220
tcccatggtg aattctggac ctaggatggc tgatcccaag gcattccaaa ctggggcaag    2280
```

-continued

```
gaagttgtgc tttaaaactt ctcattgact gtcagtcact gggcatgagc agtcccagg   2340 aagggggat gaccttgagc aagtggatg tcttcagcca agggcaayca ctgggaagga    2400
gaacccagct atgaactgtc agctgccaac actcccagca tctgagagga tgagggcttc  2460
aattctaagg gcagggctc caagggcagg ggtacggatg gtggaatctg ggcagtacct   2520
tgtggcttcc actacagtcc accccttgca ccacttagtt ccactggctt ttttttttt   2580 tttcttttct gagacagtct cactctgtca cccaggctgg agtgcggtgg cacgatctcg  2640
gctcgctgca acctccgcct cccaggttca agcaattctt gaacctcctg agtagctggg  2700
actacagatg tgtgccacca cacccagcta atttttgta tttttagtag agacgggggtt  2760 ttaccgtgtt agccagattg gtctcgatct cctgacctca tgatccgcct gctttggcct  2820
cccaaagtgc tgggattaca ggtgtgagcc accgcacaca gccagatcca ctggcttcta  2880
tataatttct gggtgaagct aattcaggat tctgatggac ctgtcttccc gagggaaact  2940
tgtaaaagga aagttagagg gacaaactat agcccctgcc acagcagctg ctgtcgagga  3000
caaaaatggt gctcctcatt tcccttaacc acctgaccta gattccccta acccttagtg  3060
ggcacctctg tggatggaag tggtggctca cykgkkggrw krwycmrrwy ycwymyccct  3120
gagtggtctg agctcccagt taccaggccc ttctcaggct gtggctgttg cacttacctc  3180
cccagccatc ccccactttt ttttcttgag actgggtctt gctctgtcac ccaggctgaa  3240
atgcagtggc ataacctcag ctcactgcag ccttgatctc ccaagctcaa gccatcttct  3300
cacctctgcc tcccaagtgg ctgggactac aggcacatgc caccatgccc agctaatatt  3360 ttttatttt tatttttttg tagcaatggg attttgccat gtttcccagg ctgggcttga   3420
actcctaagc tcaagctatc ctcccacctc tgcttcccaa agtgctggga ttacaggctt  3480
gagtcactgc atctggccac atttattcct tttaaacgtt aaaattgaat gcaggatcac  3540
tgagagacag gtgagtgatt accagggtgc caaacatacc cttctcctcc tttcctgcag  3600
ctctacctcc tcctgatgat caggacaatc atgtatgatg actccttttcc ttgactgctg  3660 ctctctcaga aggaacccat tgtgttgggt gagaacacat catttgaaat ttagtaagac  3720
tcttgctgtg cctatggtag aagcattccc tctctggggc caagatcttt aaatgcacag  3780
agtccaaagt cgtgggaacc aaagcagaaa ttaaaaagga gatgactggg attatggtaa  3840
gaactgtttc cacccttgat ttgctgcacc catgtgttct acctaggaga tagcacacca  3900
tatactggtt attcatttgg attacatgct gcatcccgga gaatgggcac tgcattctca  3960
ctggtcatca tgtcagagcc tgcgctgcag aggctttccc attgctctgt cagtgtgtta  4020
tagggtcagt ggatttcatg gtcatgtgcc cactgctgca cctccattct tgtaaaatgg  4080
gtcctctggt tcaatgtgat gccatgtggg atcttgtgtc aatagaataa atactcagat  4140
gttctggctg aagctttaca agcagaaaag gccaaccgat gactgaaata agcgttgagc  4200
ccagtcaaga tgagttcctg ctctttccag gatagacgga gtctagtgta gatcacttga  4260
catcaagaga ctggctggtc tccttgaggg atggtgctgt tctgcattca tcatccttga  4320
tgaatgaggg accctgctat tgggctcatg tacagccccc atctctgcca caatgagcgc  4380
tccattcatg ttcctattgt gccaacacta gggtgtctgt aatcactgaa acattattg   4440 ctatcattat tattatttt tttttttgag acagagtctc gctctgtcgc caaggctgga  4500
gtgcagtggc acgatctcag ctcactgcaa cctctgcctc ccggcttcaa gtgattctcc  4560
cgcctcagcc tccagagtag ctgggattat aggcatgcgc caccacgcct ggctaatttt  4620 tgtatttttta gtagagacag tcttttgcca tattagtctg tctggtctcg aactcctgac  4680
```

```
ctcaggtgat ctgcccgcct tggccttccg gagtgctagg attataggcg tgagccacca    4740
cttgctatta ttatgttgag aaaactgttt tcaattataa ataagaaaaa ataaaagatt    4800
atattttgcc tttattcctt ctctaatgct gttctttaag tagatgtgaa tttctgaact    4860
acatactttt tctttactct tgagaggttg tttggaggtt ccagcagggg accacagcta    4920
ctcgtatacc cttgaccaaa gactggtcct tgtctatcaa ggatggtcgt cttcttccac    4980
caagcacaca gcttctggag ggacgcacat ggagtggtga gggaggaagg ggacacccgc    5040
ctagccagct agatcagcca agcagaataa accctggtag tcaatgggt gacagtgtcg     5100 cagccagatt gccctcacat ccaactctta gtgatcttct cttaacattt cttgcaaggc    5160
aggtctactg gtacaaattc tctaattttt gcttgtttga aaagtcttt gtttcttctt     5220 cacctttttt tttttttttt tggagacaga gtctccctct gttgtccagg ctggagtgca    5280
gtggcctgat cttggctcac tgcaaactct gcctcccagg ttcaagtgat cctcattcct    5340
cagccatctg agtagctgtg gttacaggcg tgtgccacca tgcctagcta aattttgtat    5400
ttttagtaga gacgaggttt taccgtgttg gccaggatgg tcttcagcct cttaacttt     5460 taaaggataa tttcacgggg agaattctag gttagtgtat ttytctttca atactttaaa    5520
tatttcactc cactttcttc ttgcttgtgt ggttctgaag ataatgatat aattcttatt    5580
cttgtttctc tgcaggtaag gtggtttcat acctctggct tctttcgaga atttctcttt    5640
gtctttgatt tcctacagtt tgaatatgat ataattatgt atagacttgg ggctatttat    5700
cctttctggt gtagtctgag ctccctaagt ctgtggtatg gtgtcttgta attgatttgg    5760
gaaaattctc agtcattatt acttcaaata ttcttctgt tcctttgtgt ttttttaact     5820
tgtgccaact ttttaattga tacatagtat tttacatatt tatgggtac atgtgatact     5880 tcattacctg catagaatgt gtaaatgatc tagtgaaggt gtttggacta ttaccttgag    5940
tatgtatcgt ttctatgtgt tgggagcttt tcaagtcctc tcttgtaaca attttgaaat    6000
atacaatgcc ttgttgttaa ctagtcaccc tgctctgctc tcaaacacta ggatttattc    6060
cttctgtcta actgggtgtt tgtacccatt aaccaacctg tcttcatccc ctctacccac    6120 ataccttttcc cagccttggg tatctatcat tctactcttt acctccatga gatcagcctt    6180
tttaactccc acatatgagt gagaacatgt agtacttgtt ttgccgtgtc tggcttattt    6240
cacttaagat aatgaccttt tattccatcc aggtcactgc aaataacaag atttcattgc    6300
tttttctttt tatggccaaa tagtgttcca ttgtttatat agaccacatt ttactttatc    6360
catttgtaca ttgatgaaca ctgaggttga tccatatctt ggctattgtg aatagtgctg    6420
caataaacat gggggtgcag gtatcccttt aatataccga tttcttttcc tttggataaa    6480
tacccagtaa tgggattgct ggatcatgtg gtagatgtat tttaagtttt ttgagaaacc    6540
tccatactct tccatcatgg ctgtattaat ttacattccc atcaatagta tatgagttcc    6600
cttttttttc tgcatcctca ccagcatcta ttattttgt ctttataata atggcctttc      6660
taaccagggt aagatgatat ctcattgtgg ttttgatttg catctccctg atgagtagtg    6720
atgtcaagcg ttttttccata tgcccattgg ccatttgtat gtcttctttt gatgaagtct    6780
gtttgtgtcc tttgcccact gtttatgctc ctttttttct tctctctctg gtatccccct    6840
cacacatata tcagaccttt tttaattgtc ccacaattct tgcattttct gttctttttc    6900
attctttctt ctcttttgtat ttcagttttg gaagtttcta ttgatattca agctcactga    6960
ttcttcctct ggctctgttc agtctattaa taagcccttc aaagcctttc tctctctttc    7020
```

-continued

```
tttctttctc tctctctctt tctctctttc gttctttctt tctctatttc cttccttttct    7080
ttctttctct ttctttcttt ctttctcttt ctttctttct ttttctttcc ttccttcctt    7140
ccttccttcc ttccttcctt cctttctttc tttctccttc cttccttcct tccttccttt    7200
ctttctttct ccttccttcc ttccttcctt ccttccttcc ttccttcctt ccttccttcc    7260
tttctttctt tctttctttc tttctttctt tctttctttc tttctttctt tccttctttc    7320
tttcgaccag ttctcactat gttgctcagg ctagcctaga acccctgggc tcaagttatc    7380
ctctcagctc agccttcaa gtaggtggga caaatgcgcc attctatcat acccaacaat    7440
tcctcatttc tgttacagtg gtttttattt ctagcatttt cttttgattc tttcctagag    7500
tttccatctc tctgcttaca tacacatttg ttctctcata ttttccactt tttccattag    7560
ggccttcagc atattaatta gttatttca attctagcct gataattcca aaatctcggt    7620
tatatttgag tctgtatcta tgcttggttt gtctcctcag actgcgtttt ttcctttag    7680
gatgtccctt atcattttt gttgaaaaca agacatgatg tatcagataa aagtaattga    7740
ggtaaacagg cctttaatat gaggttttat gtttatctgg cttggagtta ggctgtgttt    7800
actctttgct gtaactttgg tgccagaggc taaaatttcc tctggtgccc ttgtttttgt    7860
ctctcctgtt atgttgtg ttccacagag tctccgtgaa tatggtgtga ggcttgaagt    7920
tctttagctg taaccctct tattatacag gagccttacg gatgtggtgg taatgtggga    7980
gggtgggctt aagtattcag cagtcctgtg atcaggcctc agtcttttaa taagcctgag    8040
tacttccctt tcccttctg catgttagag tggcctggag ttgggggtat ccattacccc    8100
aggttggtag gctttggtaa aaccacagtc tatcaagctg tggtaaaata gtttccctgc    8160
agtctggctt tgttaaggat aacagagggc tctgggggtt ttcaaaatt gctacttttc    8220
ctctctccct gtcagaagca caaggagatt tctcttgatc ttcaccctga gagtctggtg    8280
gggttcctgg agtaaaaact caggaaagtg tgagggcctc cacacaaagg gtctgctgaa    8340
gtttgttcca tagcctcagt tctctaatgg atctaagaag agttattgat tttcaatttg    8400
tccaacttaa ttcttgtttt gaagacagaa gtgatgactt ccaagctctt tatatgttga    8460
acccaacccc atattatttt caattagcaa ttgcatatag caatggtaca ttgcatttat    8520
agaaatataa ttgatgtttg cctgtgtatc tttttcccta ttatgttgct gaattcattt    8580
cttagttcta ggaattttc aaatacatcc cttaggatat tctgtataca taatcatgtc    8640
atctgcacat agggacagtt ttatttcttt ttctagtctg tatttcttat ttccttttct    8700
tgccttattg cagtggctag aacttgcagc actatattaa aataagagtg gtaaaagtga    8760
acattctttc tttgttgctg atcttggggg gaaagtattc agtctttcac cattgagcat    8820
aatgttagct gtaggtgttt taaatcttta tccagttgac gaagttaccc tttattccaa    8880
tttttctgag agtttatatc ataaatgtgt taaatttgt caatttttt tgcatgtatt    8940
gatatgatta tgtggtttt cttctttagt tactgcagtg ggttgcattg attgatttct    9000
attattgaac cagcctgcat tcctggaata aacccattt ggtcatgatg tataattctt    9060
tttttatat tgctgaattc tatttgctaa tattttgtta aggattttg catctgtgtt    9120
catgagggat ctgggctggt aggttttttt ccccctgca atgtctctgt ctggttttgg    9180
tattaaggta atttttttk ttttktttt gagatggagt ctcgctctgc tcacccaggc    9240
tggagtgcag tggcacgatc ttggctcact gcaacctcca cctcccaggt ttaagcgatt    9300
ctcctgcctc aggctcctga gtagctggga ctacaggtca caccaccacg cccgactaat    9360
ttggtattaa ggtaatatta tcatcataaa atgaactggg aagtgtgccc tcttcttgta    9420
```

```
tttctttttt ttttttttgag acagtcttgc tgttgcccag gctggagtac agtggtacga   9480
tcatggctca ctgcagcctc aaactcccag gctcaagtga tcttcctgcc tcagccttcc   9540
cagtacaggg gcaggctacc acatctggcc aattttttaaa ttttttcttt gtagagaggg   9600
gtctcactat gttgcccaga ggatctcaag caattcacct accttggccc ctcttcttgt   9660
attttatgga agaattattg gtgtcaattc ttcttgaaag tttcgttaga attcttcagt   9720
gaagctgtat gggcttgaag attacttttt tttctttttt ttttgagatg gaatttcact   9780
cttgtcgccc aggctgtagt gcagtggtgt gacctctgct cactacaacc tctgcctccc   9840
acgttcaggt gattcccctg ccttactcag cctctggagg agctgggatt acaggcaccc   9900
gccaccatgc ccggctaatt ttttgtattt ttagtagaga cggggtttca ccatgttgac   9960
cagactggtc tcgaactcct gacctcaagt gatccacccg cctcggcctc tcaaagtgct  10020
gggattacag gcatgagcca ccgcgcccag ctgaagattt cttttttgggg agttttaaat  10080 tatacaatca atttgcttaa taggtataag ctattcaagt tatctattt atactggatg   10140 agttgcaata gtttgtggtt tatgagttta tatggtccat ttcatctgag gtataaaatt   10200
tayttgtgta gtattgttgg tagtattccc ttgttatctt ttttatgttc acatggtata   10260
tggtgacagt cctggtttaa ttcctagtat tagtaactgg ctctctctct ctctctctct   10320
ctctctctct ctctggtcag tctttccaga ggtttgtcaa ttttgttgac tttttttcccc  10380 caaagaatca gctctttgtt tcatggattt tctgcttttc tgttttcaac ttcattgatt   10440
tctgctgttt attatttctc tccttctgtt ggttgtgagt ttgttttgct tttcttttc    10500 tacatattcg atgtgaaatc ttacattatt cactcgggac ttttcttctt ttttgatgta   10560
tgcatttagt attctaaatt tacttctkag tactgcatac tgcttgaact atgtctgaca   10620
aatattaata tattgttttt aaatcttat tcagttcagt gtattttaa aatttccttc     10680 tctgcctctt ctttgatttg ttatttagaa ttgtgttgtt attttccgag tatttacatt   10740
ttcctcttat ctttctgcat tgattccatc gtagtcagag tgcatgctct gtacagtttc   10800
agttctttca aatttattga gctttgttta atggatctgg atacagttta tcttggcata   10860
tatatatata tacacacaca tatgtatgtg ggcgcttgaa aagaaagcgt atctgctgtt   10920
tggtggaatg tttggagtgt tctataagcg gtgattagat actgttggtt gatgatgtca   10980
ttgagggtcc gataaaccctta ctgatttaaa tttatttagt ctgtcaatta ttcagagaga  11040
gaggtgttga actctgcaat gtgaattgtg gatttgtcaa tttctccttt cagttctatt   11100
agttttttct tcacatattt tacaactctg ttgtttggtg catacacatt tatgcaccaa   11160
atttaggatt gctataactt cttggtggat tgacccttt acattatata atgtctttt    11220 ctgtccctgg taattgtggt tgctctgaag tctatgttat ctcaatataa atagacaact   11280
ctgctttctt ttgattaatg tttacatgat acatcttttt ctattctttt actttcaact   11340
tacttatatt attatgtttg aagtgagctt cttgtagaca gcatgtagta ggtcatatat    11400
gtacatagat atatatattt ttttgagatg gtgtactctg tcacccaggc tggagtacag   11460
tagtgctcac tgcaacctct gcctcctggg tcaagtgatc tcgtgcckca gcckccccag   11520
tagctgggat tacaggcacg caccaccatg cccagctaat ttttgtattt ttagtagaga   11580
cgggtttaac catgatggac aggctggtct cgaactcccg acctccagcg attagcccac   11640
cttggcctcc caaagtgctg gcattacagg tgtgagccac cgtgcctggt ttaatatttt   11700
taatccactc agtctttgtc ttctactggt gtacatagac attcgcatgt aatgtaaatg   11760
```

```
ttgatatgta agagcttgaa tctgttatgt ttttgctttc tctatgtttt ctcaattttt    11820
aatttctctg ttttcttttt ttctgcttca tattggctaa tgaacacttt gaatcattcc    11880
attttgattt acctatagtg ttttttagtg tgtctctttg catagctttt ttaggggtta    11940
ctttaagtat ttcattatat gtacataact tatcacagta tattggtatc gttatttttac   12000 cagttcaagt aaagtatgga aatgtttcct ctctacattc ctttacctca tttataatat    12060
aattgtctta ggtatttctt gtacatacat tttaaaccgg atgagtgtta tttttgattt    12120
agctatcaaa taattccaaa aactcaagaa aaaaggaaa gcttactata ttgacccata     12180
ttttcattca ccatgttgtt tcttccctct ttatgcccca tagttccttc ttctattgtt    12240
ttcgtttaga gaacttccta gccattctat tggggtagat ctcctagtga caaattctct    12300
tagctttctt ttctctgtga atgtctttat ttccctcttt gttcctggag acattctca    12360 ctggatatag gattcttggc tattgggtct tttcttttgg cacttttgta agtgtgcagc    12420
ctgctgtcaa aataaaaatt aaaataaaat aaaaatgaat gttttccttt gctacgttca    12480
tgaaagtata attcactgaa tgaggaggga cacccatctc tataatctgg aggcccatgc    12540
tcacctctga atagtacatt tgcagagaaa ttggggaaat caaagtctgt tgagaccagc    12600
aagataaata aggcaaaagg atacaaaacc atatccaaag agaatggtt taaaggaact     12660 aaggctgttt ctcctaaaaa gaaaatagtt ggagacatgt gacctccaaa gaaacaggac    12720
tttttctatg gggctccaag gggtttctat gagagaatga taaaggagag atttcagctt    12780
agtctcagga agacttttca acaaccaaac ctgcccaaag atggactgcc ctgcctaagg    12840
attgtgttct gacattaagg gtatggaggt atgggttaga tgaatatttt accaaaatgc    12900
catagatatt tcaggctatt gatgttgtaa tatcatacta ggcaactcca cttcaatatg    12960
agtctctatg atgtaaaatg aaataggatg tgtttcgata gagagttgca gatttcattt    13020
tgatgttagc gaccacacaa aattactttc cctacataag aacatgttat tactctagtt    13080
gatgatgact gcttatggga aatgtgtctg ctttgttagg aatcttgcct aatatatgta    13140
taattcaaga tggtattata aagtgacata tatgatttta acatttgcac ttaaaataac    13200
acttattctg taccatgmas tgtctaggag cttctacata ttccattatt atctttattt    13260
tacaagacag ggaactaagg catggagaga ttgagtaatt tgtgcaatat tacctaccta    13320
gtaagtggta aaggaaagat tggaacccat tctggctcca ggatccaggc tcaaagccaa    13380
tatactatcc accaccccaa ctctttagtt tgatcaattt gtcaaattat tttacagtta    13440
tttatctgta aattaagggg ataattgccc agtcaataaa tgtgtcccct tcaaaggtta    13500
catacttaac caatggtgct actgggctca gaacattttt ggaactacga ttttggtggc    13560
aaccaaaaaa cctccagtac attcctctga acattctcca gaggcaagtc tttctccatg    13620
gagactgggc ttcatttttt gaattagcct gaagttgttt gaggtcaaat ctgatgaaaa    13680
gagcggctgg ggaagctgga tattttcgtt cgtgatttaa aacagtaaat gccacctaaa    13740
tgagaaggct actttctttg aatgtttgt aaactggctt tgaaggtact tctttaaaaa     13800
agaagcacaa gaaagacggt gactggcaac agcctcactg gaatacgtct ctaatcatca    13860
aggcaaccca cactcatttg gatgtgtgca tccggtgatg ttattatttt taaagttatg    13920
tgccacaaag atgcattctt tgctatacaa aagagctgtt gttaaattta taaagatata    13980
aaaaggggaa aggagaaggc accaaatgga agattcttag gcattaagtg ctcagacagc    14040
atagatcttc attagatgac gtcagggaga agagacacag actttgccat ctcaggtaga    14100
agtatcaaag tcatcagcct cctagtaaga cagacctggg tttgaagctc tgcacagcca    14160
```

```
tttcctagct ggtctggtgga aaaattactt cttgaagcct cagtgtcttt atttgtaaag   14220
taagtggaat tatattacct tgtcaggatg ttgtcagaat tagaaataat ttaaagaggt   14280
ccagcacgag caggtcaatc aagggaagat gttaaaaata caacaggtg aaatgtactc    14340 ccaaaagata aagtggatac atagatgaat cttcctcaca cacagagtat aataacctca   14400
gaaaaatatt gcctagagta acatgcctc ccaagccaac gttcatcatc aggaatacg     14460 gagaggatgt ttgggatatg gggggcatga aattttacaa ttgtagggcc ctttaacaag   14520
ggtagacttg caagttgcac tgmctttcct gccctcctct ggctacctgt tccagcatcc   14580
agagtttgtg aacctggggm ccaaggacag caccctggca tgggcaggcc cactnggcga   14640
ctctctcagg gctgctgcag ctgtgtcagt gtccccacag ggagnctgac atccagccat   14700
gaccatcgca ttaagcccag cagtcagggc aggggagcaa ctgctcagag gcacctttga   14760
cccactactt ttttcccctc ctgctttatc tgcccagagc gaggctctct ttctaatgtg   14820
tacaaggcgt tctacctatg actcgtggtc ctgccataga aatgcttttt ttttttttaa   14880
ctgaattaag ttgccaagtt tgaaaaatca gaatttcaca taagatccct atttctgtct   14940
tcttttgaaa aactgaatgt tctttccaca gtgagcccac attccttcct gacgaccatc   15000
accgttcagc tggagtagag agggctctgc tggcttcaga tccggacgcg caggtcctct   15060
gcaggccccg cccacccggc gtcacctgca ggtcccgccc accggcgtc tgcaggcccc    15120 gcccacccg cgtcacctgc aggccccgcc caccggcgt ctgcaggccc cgcccacccg     15180
gcgtcacctg caggccccgc ccaccggcg tctgcaggcc ccgccacccc ggcgtcacct    15240
gcaggccccg cccacccggc gtctgcaggc ccgccacc ctgcgtcacc tgcaggcccg     15300
ggccgcgggg ttggtttcca ccmtggaggt tgctgacacc ctgtgccctc ggctgacttc   15360
cagccggtgg cacagacgcc tccaggggc agcactcaag cgcatcttag gaatgacagg    15420
tgagarcatc ctccgggccc cagatttctc tcctcgccgc tcttgcccat ttctccggag   15480
agccagagaa agccgctccc aagtccaagg ccgagctccg cagacgcccg gcccctccgg   15540
cgcggacaga acaaagccat tgttcttgcc ggggaaggta gaaatactgt gggctgcttc   15600
agaggctgcc gagcaaaaact caggcaatct cctgggctgt tccaatacgt ttattctctt   15660
tttcaaaaca ggaggaggag gtagaggcgg ggagacacac catccctgca aaactactgg   15720
caaaaactaa gcggagccgg gtgtggtggc tcacgcctgt aatctcaaca ctttgggagg   15780 ccgaggggg ccgatcactt gaggtcagga gttggaggcc agcctggccg gcatggtgaa    15840
acacaaaaat tagtcgattg tggtggtgca tgcttgtaat cccatctact gggaggctg    15900 aggcaggaga atcgcttgaa cccgggaggc ggaggttgca gtgagccgag attgcgccac   15960
tgcactccag cctggacaac acaagtgaga ttctgtctca aaataaataa ataaataaac   16020
ccaagcagaa aaagaatcac tctgaaaacg atcacatcta actatcaatg ctcatacagt   16080
ttatggaatt atcagcccaa cttgataaaa tcagtatttg aggaaactgt ggataagccc   16140
cctgatttca atcccccattg tgccaggtcc tggttaactg aggttaacga agtaaagagc   16200
tgcagacact attaactgct accttaaacc gattactcta gcttagccta cttccacgt   16260 acagatttta ccagtggaca acatgatgct ttatcttgtt tttctctccc tgggactttt   16320
ctccagacat tgaaaacaga aatactaata aggccacttt tacctgcctg atgcaagaac   16380 agaatttca aactcaacat taatgcaact cctcagtccc tgacaatggc gggtggaaaa    16440
gtttctaaaa atatgcagca gcacaattat cgggaagaga tgagatactg ttacctaata   16500
```

```
aaaatgccat aaatagagaa tgatgaacta ccatgggaaa tgaatgcata agaggagaca   16560
tgctggaatg tgggacagta aaaatcactt aaactttgcg tgaccttgaa gaaagtcacg   16620
atgatctgtt tttccaggtc cctcaaacag tgagatgtgg ctgttttccca agtcttcctc   16680 tccagtgtaa agggtctgaa tttagacgct ttgtgagtct tccttctttc gacagcctgg   16740
agtctctctt gagtctcaag gctgcctgag ttcctctcta acatcctcta ggcagtatca   16800
gctaatgaga caatgaattc catggaggca gcagtgggaa cagaagtacc tctcttggat   16860
aatttacaac actggtgagc agagggtcag atcaccctgg ggtttgtgtc acaaccaaaa   16920
aagtggctgt ggcactgagt tcttggatgg ttttctacag ctggtccaga ttttccatgg   16980
gctcaccttt aaattaaaag aatttctgca ctttgaagaa tttgaaaaca aagccatgtg   17040
tgagaatatg agatccactc atatgccctt gcaagaaata ggttgcattc cttttccgg    17100 acttaaaaaa aaagcacccc ctctttcttt ttttcagaag gcatatatgt aaatgattcc   17160
aaattaatct ttagcatgtg cctatgttgt tctgatttac taaactttaa aaatatgtcc   17220
attgttgtct gttaacagct tttggcaact ttttcagaga ttgaaaatatg tgagcaaatt   17280 agagaaatga gtacaattat tagctagtac cattcaacaa gcgctaaaga tacaaatacc   17340
tctacaatac ataaaaggaa tgattatagt agatttata atgccatata aggttttctta   17400 tttaacttca ttcttaattc tcaaaataaa atgaaattac atagaagcaa agtaatatag   17460
ttaccagaat agtattttta catgtcttta agtgtatgtt gttgttgttg tttttaaggt   17520
aattatgtga tgttgtggaa agaacagaga cctgggttag ataaaaattcc ggttgtctac   17580 cagattgtga tagtgagcaa attacttaac ctctatgatc cttatcttat ttatctatga   17640
aacaggattg gtaatactca tatcataagg ttgaaaggat taaatgaggc actatggaaa   17700
atttctaaca tggtggtgcc tgggacagta gaagatgctt aataaagata gctttcatta   17760
ttattattag cttttttcagg tgatggtgat tgtaaatgtt taggtaattt tttaaacttt   17820
agaaataatt gattttcaaa tgattaagac tgcttatttt aatcatttat ttttatcacc   17880
agatttattt ttattaccca aaatgtcaac gactgtcata aagataaaaa ttaataataa   17940
ttggccaggt gcggtggttc acgcctgtaa tcccagcact ttgggagctg aggtgggtag   18000
atcacaaggt caggagattg agaccatcct ggctaacgcg tgaaaccccc atctctacta   18060
aaaatacaaa aaattagctg ggtgtgttgg cgggcgcctg tagtcccagc tactcatagt   18120
cccagctact caggaggctg aggcaggaga atggtgtgaa cccgggaggc ggagcttgca   18180
gtgagccgag atcgcgccac tgcactccag tctgggctac agagccagac ttcatctcaa   18240
aaaaaaaaaa aaattaataa taatttaaac ccgaagtatg aactgaatta tttcccttag   18300
tagcacatca cataggctga tgatagtttt ggtgactggt ttatctattc ttcctaaaag   18360
caaactgttg ttagatggat gatcacttgc atgttgtgac tgaactcagc agtttgggttt   18420 tatttttat tttttatttg cttcagtagc attadccttt cctaccaaga ttcgaacaat   18480
ccatttgcct ttttttccct aaaatctctc atacattgta aatactacat attggctaaa   18540
tatttcctgg acagacatga aggacacata aatcagtctc tgtatgatgt ttctcactgt   18600
aatggagttt atctggctca agaccaggac atttattgca tatcaggttt ctacagttca   18660
ggcaaaagtt tgaggataag gacttactgc aaaaagtctt ctattgttct caaccatttt   18720
ctcgcttagc acatgcagag atttgaaatg tccgtggta cagtagttgt gtctgtatat   18780
ttctcttgta gaatattaga acaagggatt tgcagtttac agagaagaag gcttggcgag   18840
gtgtttggaa atacactcag aaacctgagg aaatttgtgg aaagagaggc ttattatttc   18900
```

```
tagaaatatg ctagagtwcg ttttgattgt gcacctgagg aattaataga ttaagtagtt   18960
ttataaggac tggggttaat agaatactgg cagtgaagtt tgtcttagga cttcttaatt   19020
ggataatcag tgaagtcacc agatcccagt tagagacagt tccaagtttt acaaaacgca   19080
agataactgt ccaagagctg taatggctta atcatctttg aataatacct ctcactgaag   19140
ctatatcata agaaataaaa atctacattt taaaaaattg gctgtaatca tagggtgact   19200
aactgtccct gtttacccag gactcagggt ttcccaggct gagggacaat gggtactaaa   19260
accaggacag tcccaggcaa actgggacgg ttgatcaccc tacccaatgg cctcatctgt   19320
ctcattaaaa tatctggatt acttcgtgcc tcaaaaatat cctcggctta cctgactcta   19380
gacagtcaag aagcttttat taattgtcta atgtatgcca ctttctggag gtgatattgt   19440
tcaactgata gatgagcatc actgattgaa atattttgtg gttttcatgc tttgtatctt   19500
gtgctgatag ccccacatgg atatttctgt ttccaagttt tgtcacttc tggagatatt    19560 agcctgaact cagcaaaata ggatgatcaa aatgaacctt tccagtgaat tctgtccttc   19620
ttgtgctgtt gtcatctgac ttagatatac tggccgggcg cggtggctca cacctgtaat   19680
cccagtactt tgggaggctg aggtggttgg atcccttggg atcaggagtt tgagaccagc   19740
ctggccaata tggtgaatga agccctgtct ctactaaaaa tacaaaaatt agttgtgcgt   19800
ggtgaagtgt gcctgtaatc ccaggtactc aggaggttga ggcaggagaa ctgcttgaac   19860
cagggagtcg gaggttgcag tgagcccaga tcacaccact gcactccagc ctggcaacag   19920
agtgagactc catctcaaaa aaaaaaaaaa ttagctggat gtggtggcac atgcctgtaa   19980
tcccagctac ctggaaggct gaggcaggag aatcgcttga acccaggaga cggaggttgc   20040
agtgggacga gatcgtgcca ctgcactcca gcctgggtgt cacagcgaga ctccatctca   20100
aaaaataaaa atcaataaaa aataaataaa tacataaata aatgaacaca taaattagat   20160
ataccaagaa aagtataaaa aagtcttgtg tgaacataaa tgaaaattgg ccaaaatagg   20220
taacagacag ggtcaggcgt ggtggctcat gcctggaatc ccagtacttt gggaggctga   20280
ggtgggagga ccacttgagg ccaggagctc aagaccagct tgggcaacaa agcgagacct   20340
catctctatg aaagaaaaaa aaatttaaaa gacgtaatga acaacttgct tgccttcctg   20400
cctgccttcc ctaaaatact aagttaaatg caatacatgc cctgacattg tagtttgctt   20460
tcacaaagat ttactgaata cttactctag gctaaacctt gtgctacatg ttggggctac   20520
agggatgaaa garaattggt cttgccctcc aggaaccttt catttagtac agagatttag   20580
tgtgtgctgg ttggtctctg ttctccccct ctcctccaga tctattctct atttcttccc   20640
ctctccctgc ctccaggaag gggggctgga tcactgtggc tcattgctct gtggcttctg   20700
attgagttca gccaatggga ggcatmattt tggcgtggca gctctggctg ttcctctgca   20760
attgcagttc cctcctccaa ggctctggct ctcactgggt tcctgtatcc aataacagac   20820
tcccttaact gcccacttct gaaaacagtt tctgcataaa gctattttca taatttcctc   20880
tgatgtgcct tctgtttcct gtgtagaccc tgattcaata ggaaaataaa ttattgaaat   20940
agaggaagag acaggtaata atagaggtat acacaagtag aatgggcaa taaatggcgc    21000 attttcgcac catcaagagt gcccatgtaa cagagataag taaatgcatc ttgagctgaa   21060
cactgaagga taagaaacaa aggggagaaa gacctagaag gggcaatata cagcaaggag   21120
ggaaaataaa ctactgtgca ttcatgccag tgttagcatt taggacatct ggaagctaga   21180
ggtggagtgg aaaaggagag agtgatagga gctggggtca gagagtttca gggtggggaa   21240
```

```
ggtcttgcag gaccttgtag gtaattgtaa agcatttgga ttttattctg agggtcactg   21300
gggtgtcatt agagactttt gagcaaagag gtacatgctc tgactgaact ttattctgtg   21360
aacaatcaga atcaactaga tggatttaag tatgggtata ccatgaaaga aaattactta   21420
agatccttgc tactcaaagt atgagccagg accagctaca ctggcatmag ctgggaactt   21480
gttagaaatg cagaatccca agtccccgag acaaactgaa tcagaacctg cactttaaca   21540
agatcccagg tggcccattt gtatggtaga gtttaagaag cattggttta aagatccct    21600
cttgatagga gcatggaaga tacatttgag acagaataga caagtcagag acaggtggga   21660
agggcctaaa acagggcaga gtagggagg taaatgagga gacaaataca aaggaagaaa    21720
atgcacagca cagtgtagac aattcctaaa tacttaaaaa aattttttt gaaataatga    21780
tagattcaca ggaggttgca aagaaatgcg tagggaagaa caatgcaccc tttacccagc   21840
ctcctccatc attaacatct tatgcaacta tattataata tcgaaaacaa tcaagtgaca   21900
ttgctacaac ccatagagct tattcagatt tcaccagtta ttagatgcac tcgtgtgtgt   21960
gtatgcatat agctctgtgt aattttatca tatgtgaagc tttgctacca caatcaagat   22020
attcaagcca ttagcagaag attttctggt gttacctcct tatagccaca cgcattcctc   22080
catcattaac ccctgggaac aactaatctg ttcatctcta taattattct atttcacgaa   22140
cattttgtag atgggtacat gcagtgtgta tcttttggga ttggtaacag agcaagacag   22200
gatctcactc tgtcacccag gctggagtgc agtgtcgtga tcttggctca ttgcagcctc   22260
cacctcctgg gctcaggtga tccttccacc ccagcctcct gagtagctgg gactacagac   22320
acacgccacc tcacctggct aatttttttgt attttttataa tgatggggtt tcaccatttt   22380
gcctaggcta gtctagaact cctgggctca agtgatccaa ccgccttggc ctcccaaaat   22440
gctgggagta caggcatgag ccaccacctc caccagcttt ttcattcata ctttctttga   22500
agttcatcca agttgtgtgt atcaatactt cactccttcc agttgctgag tagtattcca   22560
tggcttggag gtgctagagt ttattcatca cattcaaccc attgaaggmc atttgggtgg   22620
cttccaagtt tccagttttg ggctattatg aacaaagtta ctatgaacat tcatatacaa   22680
tggatacttt ttgtatgaat gaatggaata gaatggatag gatttagtga tcagctatgt   22740
gggatgaaga gtggcataag tagtaaaaag taaccctcaa tgcaatgtgc agccagcaag   22800
taccacaaaa agagtttatt ttgtttcata catatatttc tatatataca tacacacact   22860
ttattaataa ccaaatagta tccttttcaa atgaaaacag taatttaaca taaactatga   22920
acttaaaatc taaagtaaaa cttgacaaca gtgatgcaga atttttttgct ccttagctca   22980
gttaggtctg tgttcttatc ttatgaccag gaagaactag gtaccctgac atcaaagaat   23040
gagtggcata gaatttatta agcaaaaagg aaagctctca ggaaagagtg gggtcctgaa   23100
agcaggttgc tggttgcccc ttcgtagttg aatacaaggg cttctatata aaacctgatg   23160
gggccgagtt ccctgttcgt ataaggcatg aattcctggt ggctccaccg ccctccccca   23220
gtgcgtatgt gggaccttcg tccactaggg acatgtttag acaagctccc tgtgcacgtt   23280
cccttatctg cacaaaacat gggttggagg ttctccgggg acccttcctt tactttctgc   23340
ctaaagcaag ctggctaact cctttcaaca atactaaaga catacagaca atggttctca   23400
gtacaatcat tttaaatatt taagtaaact taaaatggtg tttgttttga tttgacattt   23460
taaaagatat cgctgttcta aaaattctgt gtttttagtt gtttgggctc ctattctaca   23520
atgtgctatt actattaagc attcttgtat catggcattc ctcaaatagt ttttaaatta   23580
cttttaattt gaagaaggaa cattctgtac agtcacggaa agtgtcaaaa atgaaaatga   23640
```

```
ggcagggtgt ggtggctcac gcctgtaatc tccgcacttt gggaggccta ggtgggtgga    23700
ttgcttgagc ctaagaattt gagaccagcc tgggcaatat ggtataaccc tgtgtgtaca    23760
aaaaatacaa aaattagcca ggtgtggtgg cccaagcctg tagtcccagc tacttgggaa    23820
gttagggtgg gaaatcctag gtgacagaat gagaccttgt ctcaaaaaaa aaagaaaaa     23880 agaaaatgat aaaggataca tatcaggaaa acatgcatgg tattttgtat catctacttt    23940
agagtaattc cagtatagtg gttttttttgt tgttgtttgt tttattttttg agaaagggtc   24000 ttgcgctgtc acccaggctg gagtgcagtg gtacgatctt ggctcactgc aacctccgcc    24060
taccaggttc aagccatcct cccaactcag cctccagagt agctgggact acaggtgtgc    24120
gccaccatgt ccagataatt ttgtattttt tgtagagatg ggattttgcc atgttgcctg    24180
aatgcctggc ctcaagcaat ccaccctcct cagcctccca agtgctggg  attgcaggcg    24240 tgagccacca cacccagccc cagtgtagtc gttttttctt ttcttttta ttctatgttt     24300 taatgaattt acacgttacc caaatgttcc ctagttttc tgccttccaa gatcactctg      24360
gaagaatatt taagaatata ccaaataaga atatgcaagt cctcccctaa gggtggcagg    24420
aagaacaccc ctcccccaga tggtatttag cgcctctggc tgggaacggc ttccccatgc    24480
tcctaggtca gggtcctctc ttggcatgac actaccacca cagtgcagac ccacaacagg    24540
gagaaggacg gccacagtcc ctcaatcccc cttttccaag atgtgcacag cctgactcct    24600
aactccccac cactgactct aggggaaaaa cagcacaggg caggaaacga ttttccatgt    24660
caccaacctt tctctgaggg aacctactgg ccacctccct cttaggacca gcccatcgtc    24720
cacaacgtgg aagtccagct tccgttcaaa tcggagttct ttcttcatga catttctttg    24780
caaagtcccg gaacccacag ctctgagact ctggctgtcc cccaacccac cccatcttcc    24840
ttgtcctcac ccctggtcag gagaagccaa aacatcagtc agcttccag taatcaagcc     24900 tggctttctc acccagggct cgccccagaa caaccaccgg cttctttcag tgtagccaaa    24960
aggctattgg agtcttctca aatgaaagag atttttatcaa aggcttggag aagaaaagaa    25020
aaagaggatt atataataaa acgtaaaaca acaaacatat acacacaaac aaaaataaac    25080
gtgagatatg attctcccgg agtgtttaga gcaggaatgt tcttgggcat ctgccttccc    25140
ccaccagcac cccccacaag gcaaggccag ttcaccctca gtgctcacta ctttgcagtg    25200
ttcatagaat atttgtaata atttttaggcg gctccctaaa atttcttttc ttttctttc    25260 tttctttaga gttgcgtccc tctcggttgc caggctggag ttcagtggca tgttcatagc    25320
tcactgaagc ctcaaattcc tgggttcaag tgaccctcct acctcagccc catgaggacc    25380
tgggactaca ggtatgcacc gctatacccg tctatctttt atttatttat ttatttagag    25440
acagagtcta gctctgtcac ccaggccaga atgcagtgac acgatctcag ctcactgcaa    25500
cttctgcctc ccagatttaa gggttttctct tgcctcagcc tccctactag ctgggattac    25560
aggcttgcac cacctacgtc cggctaattt ttgtattttt agtagagatg tggtttcacc    25620
atgttggcca ggcaggtctc gagctcctga cctcaagtga tccacccggc gtggcctccc    25680
aaagtgctgg gattacaggc gtgagccact acgcccagcc tattttattt tataattttg    25740
ttttagacaa ggtctagctc tgttgcctgg gctggagtgt agtggtgcaa tcacgattca    25800
gtgcggccct gatctcctgg gttcgagtga gccttagcct cctgtttagc tggtactaca    25860
ggtgcatgcc accactagc taattttta aaattttttt gtagagacgg ggtctcaccc      25920
tggtgtccag gctggtctca aactcctggg ctccagtgat gctcccacat tggcgtccca    25980
```

-continued

```
aagtgctggg attataggag tgaactactg tgcccagtct ttttaaaaaa ttttcaagag   26040
attggggtct tgctatattg cccaggctgg tctccactcc tggtgttaag cgatcctccc   26100
acctcagcct ccttgagtag ctgggatgac attacaggca cacactgcca ccactggctc   26160
taaaacttct tctgtgccat tgtgcactt cacccaattg cctctttgta gtaattaatt    26220
aggatctagg gtgaaaaaaa agtcaacagc tatatatagt cctcaaagtt ttgtacgtat   26280
ctgagcagtc atcagttgca cagtgcagag ggatgaactg ccgtcccgcc acctaaaaag   26340
cattagtgac catcagggaa ccgtcagatg catgccagac taaagcagag tgaggctgtg   26400
ctgggtgctc tgtctgtggc tgcccgtgct ctcacttccc tgtcttgctc tgtgcctttg   26460
ggaggttgac cctgagttgg catctcaggg tctcagtctg ctggtttcct gsgttcccct   26520
tgaaggctac tgctcccaca aggcaaccac ggtccccgct ctggctctca ctgagctcca   26580
gaatcattgt ttcctcccct tacccaagtg agaataatta tgttttattc cagaaccctg   26640
acaaatgaag aggcctaaaa accccctagg tattatccga tcttggtgat cagggaggtg   26700
tttgttttgt tttttaatgc agacacatag ttttaaaaat tattcacttc atctactgta   26760
agaaaagtca tattaattca caattttgat taaaacaaac aaacaaacaa acaacttctg   26820 tgacatttg gctaacaagt ggttcaatat taaagctttg tccaccaggt gcagtggctc     26880
atgcctgtag tctcagtgct ttaggaggct gaggtgggag gatcacttga ggccaggagg   26940
tcgaggctgc agtgaaccat gatctcacta ctacactcca gcctgggcaa cagagtgaga   27000
ctctgtctct aacaaacaaa caaacaaata agtatagttc tttcaagcat ggcagacaat   27060
ctgtctcctt tggcctgggt ctctcactgc cttttagata aaaatctggc aataaccaaa   27120
gagttttcat aaggcctgtt gatctattta taagacatgc atataattta cttgaccatt   27180
ataataccat tataataatc taaatctatt ttctttatcg tccaataatc cacagagtca   27240
gcacacaagg attcttttt ccatatatag gctgagtatt ccttatctta catgcgtgac     27300
gccaaagtgt ttcaggttct ggatgtttg ggattttgaa atatttgcat atacacaatg     27360
agatatcttg gggatagaac ctacatctaa acacaaaatt catttatgtt tcatatacac   27420
cttatacacg tagcctgaag gtaaatttac acaatatttt taataatttt ccacataaaa   27480
caaagtttgt atacattgaa ccatcaggaa gcaaggtgtc cctgtctcag ccacccacaa   27540
ggacactctg tagttgtctt tcattcctga ttccgaattt atacgctact gacaagcaat   27600
cattttctta cacttattca cacaagagca cttagtaaaa aatatgacat atatatctgg   27660
catgctcaga aaagctattt tgcagcagaa aggagctggg agggtccttt ttttcccttg   27720
gggacacgga ataaattgtg tattatgtgc ctgcattttg actgtgaccc catcacatga   27780
ggttaagtgt agaattttcc acttgtctct ctgtgcttaa aaagtttaga ttggccaggc   27840
atggtggctc atggctgcaa tcccatcact ttaggaggcc aaagcaggtg ggtcatttga   27900
ggtcaggagt caaaccagc ctggccaaca tggtgaaacc ctgtctctac taaaaataaa    27960
aaagttagcc tggcatgttg gtgcatgctt gtaatcccag ctactcggga ggccgaggca   28020
ggagaatctc ttgaacctgg gaggcagagg ttgcagagag cagagatcac tccattgcac   28080
tccagcctgg gtgacaaagc gagactctgt ctcaaaaaaa aaaaaaaaaa aaggttagat   28140
tttggagcat tttggatttt ggattttgca ttaagtgtgt tcaagctgaa aagaaaatcc   28200
gatttgctca ggacaaactt aacaaaacaa gtgagatatt ccaatactat atatatgctc   28260
ctgtttatat ttccttaatt aatttggact tggaacaact tggccaatta tggattagag   28320
gatgagactt aaatgttact gtacaaggga tagaacgatt cattcctcta tgttatcaaa   28380
```

```
tacttatggt attttmccca tcctgctgtc atgcagatcc aagaaccaaa ttaaaacaca   28440
tttgccgggg tcataataat gtggccagaa tttaaagaaa aacttgattt ttaattatgt   28500
atgattttgc ttgtttagtc taccgatttc tatttgcttt agcttactca aaaataaagc   28560
gcggcacttc gaagactcaa tagtcttcca ttcatgtggg cctttataat gcacgggccc   28620
agatgcaata catctggcgg tctgcttggg ttggccactg gattgaagga ggcagagaag   28680
tctgggatga ttcccaaatg tctggatctg gtgacaggga gatatggcag ggcgagctta   28740
ggggaaaaag ctgggttagg aactgttgaa actgaaatcc ctgaggsytk tgccgacaga   28800
gagacagccg gtagaaggtt gtctttgcct gtctgtggtt ccaggtaact tcatcgaaag   28860
agagtttcag gcagtagaaa taagagcacc caggacaaag ccccagggaa gagaaacatc   28920
tgacggagga cagaggaaga agggtcagga atgagactga gcaggtgtca tgtgtctgac   28980
accagagcct gacacatagt acgtagtaga cactcagcaa ataccgtaac agagatgaat   29040
ccaaggctgg gggaggtggc tcacgcctgt aatccccaca ccttgagagg cctaagtggg   29100
aggatctctt gagtccagga gttcgagacc agcctgggaa acatggtgag accttgcctc   29160
taaaaaaata aaaattaaac attaaaaaaa gagatgaatg cataacctgg ctgctggagc   29220
caacatgggt tgggtgagcc cactcttacc agcagctaat caaaaatttg cctggaattc   29280
tgaggctcct gtcctacgtc ttggctgctc ctcccagatc accttctggc cggtcccaag   29340
tccacttccc gtgctccttg ctcccttcct cctggtctcc ctcacacttt cctttcctac   29400
tccccttccc tctgtggccc tggctcagcc cagcacaggg agagccctgt gccacctatt   29460
acagctcacc tgcacctttg catctttcag aaaggagcac ctacaagata cccacccccc   29520 caccttttt tttttttttt tagtagtaca gattgcctct catagcataa ttgggcttca   29580
ttattatcct taaagaccct ctttctgtgg cggattggga tggataaaat aaagaagatc   29640
gagaggttga agaacccatc ctgttttgcc agtgagaagg ggatagaatt aaaaggatta   29700
ggagggctca ggcatggtgg ctccagngtg tcatcccagc tactcaggag gctgaggcgg   29760
gaggatcact tgagcccagg agttggagac tatagagcac tatgattaca cctgtgaata   29820
gccactgcac tctagcctgg gcaacatatc aagaccctgt ttctagggac aaaaatatnn   29880
tttaataaat ttaaaaatta agggaaaggt aaccacatcc tgctacaaan aaaagaagnt   29940
ggagaggtan gangaggacc aagagctaat ggcatcattt acacaaaaag agatgcttta   30000
aaatcagttg ctcatccaat tccacaagga caataagtaa gaaagaggat agaaagtcac   30060
cggtggattt ggtcatcatt ggcttcttga tgactttagc aacaaaaatt cttgttggta   30120
gtgagagtta gaccctggtg gactgggtag ggggttcctg gatcatgagc aaaggcctgt   30180
gccagccaat ggcccccact acactctgcc ccggcctttc tcatctcaaa aatggcatc   30240 ccccatccaa agctcaagtc aagaatccag cagccacctt tgattctgca cttcccctca   30300
cctcacagtc cagtcccatc tccaaaataa gttccaaaty tcaccacttc tcattctcca   30360
aagaggmacm attatctctt tcctggtgat taaaacagct tcctaactgg sttcccttct   30420
accttgcttt cccatagtcc attcttctca ggacaacaac agtggccttt taaaaccagt   30480
gcattattgt tgccctttgg gaaatcctcc acaattatcc agtcttgctt caaaaaatgt   30540
atgtatttct gactttttac cctgccctac ttacaggata tgcacatttc tgatctccag   30600
ccaatatcac acttcttctc tcactgcact ctgccacact tggccaagtt tgttcccact   30660
cctcttgcac ttgctctcag atctcagaag aggcgtgctc cttgtctttc aggccagccg   30720
```

-continued

```
gcttcacaca tgtgccacgt gcgcccctcg ctcagaaggg atctgtactc ggtttggatc    30780
tattgttgcc atcttgaaac tcttaatact ctttgaacac ggggcccgta ttttcatttt    30840
gcactgggtc ctgaaaattg tgtagctggc tctactttca gggattgtat cagaagtctc    30900
ctcctcaaag aggccttcct cggccactta tcctcaagta gctcctcccc ttctaagtta    30960
ctggctatcc catcattccc acttaatttt cttcataaca gttgtcatgc ttttatacat    31020
tctggcttct atatttattt gtgtattgtc cagttccctc cctttggaac gcagcgtggg    31080
cacctgcaac gcagagacca ctgtatcccc ggtgcagaat gtaatgagtg cctgatacat    31140
ttgccgaata aactattcca agggttgaac ttgctggaag caagagaagc actattctgg    31200
gtaaaatgga aatttttaaat gtacttgata tttatataca tcctaatcaa taattaaatt    31260
tgtgtagtgc tgatctaaac agataaattc tggcttcatg atgatggtga agtggaatat    31320
aattttctca ttttgtattc aaactagatc ttttttcatga aaggatttga agtctagatt    31380
caatgcctac ttttgctact tatgttatat gaaactaaaa caattatttt attgtatttt    31440
tttgagatgg agtcttgctc tcgttgccca gactggagtg cactgctgcg atctcagctc    31500
actgcaacct ctacctccca ggttcaagcg attctcctgc ctcagcctct cgagtggctg    31560
ggactatagg tgcgtgccac cacacccagc taattttttgt attttttagta aagatgggct    31620
ttcaccatgt tggccaggct ggtcttgaac tcctgaccca agtgatctgc ctgcctcggc    31680
ctcccaaagt gttggattac aggcatgagc cactgtgcct ggcaataatt ttagtttagt    31740
ctgaattttt tttttttttt gagatggagt ctcgctctgt tgcccaggct ggagtgcagt    31800
gacgctatct cagctcacag aaacctccgc ctcctaggtt taagcaatcc tcctgtctca    31860
gcctcccgag tagccaagat tacaggcacc tgccaccacc cccagctaat ttttgtattt    31920
ttagtagaga tggggtttca ccatgttgac caggctggtc tcaaactcct gacccaagtg    31980
atgtgtctgc ctcagcctcc caaaatgctg ggattacagg cctgagccac tgtgcctggc    32040
ctagtctgaa tttttttaaaa aggttattgg tctaccttcc aatgacattg cactctgtgt    32100
ggctcaataa aacattttca tttataataa ctaatttgac ctgctcagca atctctaagc    32160
aagatagagt agctgtaatt cttcatttta caggtcatgt caaatcattt cgtacattcc    32220
agctatgtac gagagcttgg tgagaatatg tgaataataa tcacagaact tcagagctgg    32280
gagtaacagc tggaaatatt tcttccaata attgcatttt ttatgagagg acgatgaggt    32340
ccaagtggac aggaccatga gacaatcgtg tggcaaggaa gttgatgcaa tttgacctct    32400
taagtcagtg atctttatgt ccatcggtcc tttccagcaa gtgagttagc caacctttgc    32460
ctgcaaagga ggaaatttttt aattgaggat ttacactctg cttctaaaat tttgcttatt    32520
attgtgaata attttctta agtttattaa atgaatggct gaataaatgg acataaggaa    32580
agaaggaagg gaggaaggaa gggagggagg kaaggaaggg aggaaggaa ggaaggaagg    32640
aaagaaggaa ggaaggaagg aaaaagaaga gaggaaggaa aggaaggata agtctgatga    32700
cagctgctat tatattctac gtggataatt tatttagatc tttatacttt atcttttgtt    32760
ttacttctct tatgcatatt ctcctcaact tttttttcagt gggccagagg aggaggactg    32820
cctcttgtga ctgtggaagg acttctacca ggctaacacc cctggcctct caccctccca    32880
tttctcaccc tgcaaagcag agtgctattt gattcatgtt cttagtctgt ggatctcagt    32940
tgaggagaac tcgttagaga tttgccctct ttctgtcttt ttgagacctt actggtgcaa    33000
gacagcaaat cctagctggt gtctacagga cacatgcact cttaggttac ataactgcag    33060
ggaccactgt cattgtatcc tggagctggt tctatataag acacagcctg agcagtatat    33120
```

```
aggcttccta gtctgctcct ggccaaatgt cccagttgga agcccagagg ttgtctggct    33180
atgccagtgg caggatgggc aagtctaact caagggtgac atattagcaa gacctttatg    33240
gccatgcatc taagatgctc tgtccaagcc tgaacttagc aacaataaac ctgacatttt    33300
gaaatccatc tgattcctct attttccagt tgatgccaca tgcatcctct tgccatcttt    33360
cttaattaag atgactttgc ttctaaatct ccttaattat caagcagcta tctacaatat    33420
tttgtaatcc ccttaaatct tgagcataat gatgtcataa ttatgaaagt gmccggwttc    33480
acatgaagta ttgcttaatc ttaagaacaa atggcagct gtgaaaacag atgaagtaat    33540
tagaggaaga gcctttttgg aagcttcgag atattttcaa agtaattagt actagttagc    33600
aataaagttc tgttctgaga aattgctctt aaaggaggaa catggattaa agaaaaaat    33660 ctgctactag gaagtaagcc atcttcctat gtgtgtgatt ggttttgctt cctgaaaact    33720
ggttccgttt tcaacaaaat ttgggtctgt tgaaaagaa cacgcagatg ccagccttga    33780
tgtcaaacgg gcccaaactt ggacagtggt aaactaatga gcaatggtgc acagagtcag    33840
ggtaaaagct ggacaatttc ctatgaccaa cttttccagg actctgctct gctcttcctg    33900
agaaaaatac ccaaagtgct gcctcttcca ttggcccaac catgcatctt tcaggatagg    33960
mcacatctgt ttataggtgt ggattgtagt tgctcataag tgacattagg ctgtttaaaa    34020
taataatagt tcgagttttg ctatgagctg atctgttttc caagagagct aagagttttc    34080
cagctaaaag agggaattag tgggtaatca aggcagctga catggggtgt ggctgggcct    34140
tgaatgtgtg tcactctctg tgcccaggca gagcaaagat aaactccaga ctgcatgttg    34200
ctcagagacc aggaccaacg tcatagggcg cctaaaaggc aggtggccca gttcagaatt    34260
gtcaaggtct gacctgcttg gacaagtgct gagtacatag taaggatgga ttggctagtc    34320
tctcaaaact tgcaaacagg gcgcaggtga tcttgagatt tcaggtgccg gagagaccca    34380
tcgtgtagat tccagagttg gctatcatga ctaacagctg tctaagttgt ttttaaatga    34440
atcattaagg gctacatttt cagttcagct aatcaagtag caaattacgg tgggtctaaa    34500
atacttatct attgcattat gtatatgcta gactttatca ctttagttgg ttatatcgct    34560
tcatatacta acagtcaaaa aatgccaaac gagaaaacaa acaaacaaaa atgccacatg    34620
actgtgtaaa tacacttttc aaactgtttt atctaagagt ttactcactt tcacattgtg    34680
gcttatagta ttttcaatct aagagactaa ttttgcttac ataggaaact acatatttta    34740
aattgaaaat taaaaaaata ttttttaaggt tttaatgagt cctatcaaaa cacatttgta    34800
tataggaagg tagcccaagg tcactgttgc caattgtgta cacagcctgc cctmtagtgt    34860
tttcttctaa acagcaccaa attttagatc atagttgtaa atctcaaaat gttgggttaa    34920
taggattaaa cactgtgtca tcaaattgat aggacacagc taaatccctg acacggatga    34980
aaattaaagc agagaaaaac gaaggtcctt ccagaagctg gtggcaactt cactggggag    35040
atattgcaaa gttagtggta aatacactat attaaaaagt tttgttttgt aaatagagta    35100
atgatagaag aagagttagt tgaaatgatg tatgtaaaat gtgataactg cataattact    35160
agtacagttg ctagtttacg actgtattaa aaagacattc caaatgttga tcaaataatg    35220
gaggtttctg tggttgtttt cttttaaaa tagtaaatat acgtaaagca gataaatatc    35280 cccttttgtgg gagttaaaat aatctaactt attttatagt tttaacttta ttaaagcata    35340
cgactattct aacttatttta acttttctta gtaaagtttt aacctctgta tttagaatat    35400
ttgtaactaa tgtgtatcga attaaactca aagggaaatt cattaactga gagaaaaaa    35460
```

```
ttttaactgt gcactattca catagcataa tgggttttat aaggagtatg agaaaaatgt    35520
gtgtggttgg ttttgctttc tttaaaaata atagcgaacc acgtaggtaa aaactcactt    35580
gagaacatag acttttggag ggaaatgcca ggtgtggtgg ctcacgcctg taatcccagc    35640
actttgggag gccgaggggg gcggatcacc tgaggtcagt agttcgagac cagcctgacc    35700
cacatggaga aactccatct ctactaaaaa tacaaaatta accgggcttg gtggcgcatg    35760
cctataatcc cagctacttg ggaaggctga ggcaggagaa tcacttgaac ctgggaggtg    35820
gaggttgcgg tgggccgaga tcacgccatt gcactccagc ctgggcaaca agagcaaaac    35880
tccgtctcaa aaaaaaaaa aaaaaaaag aattttggag ggaaaaaat ccctctaaca    35940 gattcgaatt aattctgtgt ttcgagatgt ttacaaaatg aagcttggac tctgagagga    36000
tgtgatctat cctctccatt gcattgagtt tcaagtactt cacatggcgg gctttttaa    36060 ctgtcgtgaa gttaaaacca aatagggact agaatttgtt tgtttttta acttacattt    36120 caagcttcct tatgtctcag gcacattagc ataagttgtc taaagtcata aggaaaaatt    36180
gacagaaaaa tgctttggag ccccaggtgt tttcaattga tgccaacaga aactaaccaa    36240
atggaagaca tttgatgcgg gtttatttt cctttgcagt aacagcggga acatgaagcc    36300
gccactcttg gtgtttattg tgtgtctgct gtggttgaaa gacagtcact gcgcacccac    36360
ttggaaggac aaaactgcta tcagtgaaaa cctgaagagt acgtttggtt tcttacctgt    36420
gctgtgtcct gtttgcatgt tggttgtcct gctggcgttt atagtgagtc gcagttgaga    36480
gataaccata ttcgctgttt tcacggtgaa acgttctcaa ggcgcttaaa ccaggtcatc    36540
ctgacgccaa acatctgggt aaaaatagaa aattccaatc acgtctctgc aggcgttcac    36600 cttttccagat gtttgtatca tgtagataca acttgccagt ttttcactg catttttttg    36660 tatcatccag atggttggtg tcatctcagc acagctctaa tgaacagtga aatactttc    36720 tagcatttga aaaatttaaa ccattagagt aatctgtgca attgttctta aactagtgaa    36780
agaatgggtt ataattacgt tgaatctggt tgttctgtgg ccattaactt gcaactttgc    36840
ttggtgatat atactttggg tacttaatat atagaagaac aaattagcta aaatgcagct    36900 gatttgggt ctgtaataat cagagtcaag aatgagctcc tcagtaggcc acgttggcta    36960
ttttgaacag ggaatgacaa tgaattttaa acttactaag ggcttattaa aggtgtataa    37020
gacacgtcca ttgagttatt aaggaagctc gtattacatg ggatactttc taggtctcgt    37080
gcctccttat taggtaactg aagctgaaag aaagagaaat tgctgactgt gtttgaggtc    37140
cccagctggg cacttaatat aaattatgaa gaaaatgcaa aattttctct aatataaaca    37200
cacttgagtc ttaaatgaaa gaaaaaaaat ggataaatga aaacagggcc tgagcaagtg    37260
acaagaatga ggttcagtga actctatttg tttaggcgct cacaagtgag gagtagaagg    37320
tatggtccgt gtggcagctg tgtccatgtg gcagctgaca gctaattcat tatgatctgc    37380
tttcagaata tgagcctata agagaacaat taagcctctc ttttggagac atgaaaggtt    37440
ggtgaacttg gtgttttgta atctgatcag atctcaaaga aaaaattgcc acatgtctttt   37500 taggttttttc tgaggtgggg gagatagatg cagatgaaga ggtgaagaag ctttgactg    37560 gtattaagca aatgaaaatc atgatggaaa gaaagagaa ggaacacacc aatctaatga    37620
gcaccctgaa gaaatgcaga gaagaaaagc aggtacagtc attgaaaata atgtctgttc    37680
ttacacagat ctggaccaga aatactgcac ttgttagtgc gattgatgaa ttacttattt    37740
tccttagtaa taaatttcat gggtagctgc ttttatttga ggaaaagttt aagggaagct    37800
tcagatttcc ttgaagaaca tatttcgtgt aggataggct tctgcaagac tccaacccgg    37860
```

```
aatctggggg attcatctct gtttaagtgc tgctttctca aaaatagatt attcttggtc    37920
tcttctgagt taggatattg agtcaaaagt atttgaagag ttttttttt tactagatca     37980 gtggtctcca gagtttttgt ttttttgtttt ttgtttgttt ctgtttttga cagagtct    38040 cgctctgtca cccaggctgg agttgatccc gctcattgca acctccacct cctgggttca    38100
ggtgattctc ctgtctcagc ctccctagta gctgggatta caggctccta ccaccacgcc    38160
tggctaattt ttgtattttt agaagagacg gggtttcacc atgctggcca ggctggtccc    38220
gaactctggg gctcaagtga tccacctgcc tcagcctccc aaagtgctgg aattacaggc    38280
atggaccacc gtgcctggcc cagagatttt tggtctctca ttcctatgac taaaaatttt    38340
gttaccactc actcctaaat atatgcatat tcatttactc atgaattaga tacatgaatt    38400
gctaccattg atatctcaag gcacaatatg tatttaaggt gagattcatc attagcgagt    38460
gtggatataa gtccacattt caaataatct tctagatatt ttgaaacttt tagccgactt    38520
gccagatctg attagatcac catagttttc ccttgtcact tggccaataa agagctcata    38580
atgatcaagt gtcagctctg ccatttgctt ttggtccgct tgagcttaaa ttattcattt    38640
ttaaaatctg ccaagttttt ttttttttca aagaatcttg ttaagcctcc tgtccattta    38700
gtgaaggtta ctttagttaa aactagataa taaaatccat cagtctacct gagttctctt    38760
acatggcaac tcattacaat tgggtgcatg tgaacagagc aagggaacta tagttgattc    38820
ttctggaatg tagaggatcc ccttttcccc aaggtcatca catacagttg ggcacacaca    38880
gtatctgaca tatgcatctc aagagagtac catgtatatc caataatgca tcagcctaat    38940 cacttttttca aattcaaata gctttatttta acagctatag cttgaactac atattttatc    39000
catggagaat acatattata ttcaaatgtc tttggaagat gtaaaaaatt gttcatatgc    39060
cacagtataa agttcagtaa atttctaaat tatagacatt gaatagcttg cagtttaatg    39120
acattaataa ttaacatcac actcaaaaca atgactttt taaaaaaggt tatcttcaam    39180
cattmccctt aaatcaaaga ggaaattaaa actgtaacaa aaataatttg gaaaatattt    39240 tcaatttttaa tgttgagagt aaattacttt ttaaatktat tttattttt tgaaaaatgt    39300 taagttgtaa aatacatata acaaaattta ccatcataac cattttttaag tgtaacgttc    39360 agtagtgtta aatacattca tactgttgtg caaccaatct ccagaattat tttcatcttg    39420
caaaaactga agtctatac atattaaaca atgccccatt cccccacccc cagtcagatt    39480
tttaatttaa aaatacaagt ggaagttcta atattttcta tctatccctc tatctataaa    39540
gttgggggcc actgaattcc agattgctgc ttgcatcttt ttacttctga gcatcatggc    39600
ctctgggagt ccgttaagca actggagccg ggtagtgtga caggctgacc ccaaagctgt    39660
gtgtcagcgt caccggactg gttgatgttg cagcctcacc tactgccctg agtcagtcag    39720
ggttctggca aggaaaggag aatgcctgac cagcagctgc aaacccttct ccttttggc     39780 agcaatcaaa agattttgag gaaatctaaa atagctcctc atcaggaaaa tgtggaagcc    39840
cctccagctg ggatcttccc tggtgggctt gtgagcctgg ccatctggga atagagacac    39900
tagatagcac tcatacactc ttcacaaaac acattatcac atggaatgtt ttgaacatct    39960
gggtaaacca ctactttcat tttatagcta agaaaactgg ggtttgagat gtttgttaat    40020
taacatgtta ctccaacact gtaatgaatg aactgagata aagtcagcag atgtgtgcac    40080
gggggaccca gtgattttct gcttttctca cttccctgaa cctcctggca aggaggacag    40140
ggtatacagc tttaacaaga atattccact ttgggtgggt caagtaagca aatgtggatt    40200
```

-continued

```
tcacttctgg ccctgaagaa tccaagcaac tagtagaatt tttgtttatt cttaaaaatc   40260
ttattgtaca aaaattcatt gaattatact cttaagtttg aggcactcaa ttagaaagtt   40320
aatcggaaaa aaaaaatctg tttaaccctg agtatccctc cctaaaatta cttaaagcct   40380
agaataaagg tcagtttaga caaattatga attggcaaat atggtgttag caaccctagt   40440
ctcccagtat tgagccccac ccattctcaa gagtactgct cagtggtgac ccagcatcct   40500
cactgtcccc ttcctccacc cctccttatt aatatttagt gagactatct gaaacttatt   40560
aagtaggaaa ccctagagaa ggttagagtg acttgacctc caaatcaggt tttatttgta   40620
tgtgttttta atgaaatggg gtcttgctat gttgctcagg ctggtcttga actcctgggc   40680
tcaagggatc ctcctgcctc acttcccgag tagctgggat cacaggcact agccaccatg   40740
cctggctcaa tgccaggtta atatagcgct tttgataaac tgtcaactat aggaatagag   40800
ttataagcgt gaatctgcca gttggtacaa tgtctagcag gaaacggaag gcgtcgatag   40860
gatattcctt aggaatgttt actagacaga ggtctacttc ttccatggca atgtttcact   40920
tccaaaactt gggacctgtg atttggtaac tgttttttgt cctgcttctg ggcagtgaat   40980
ggaaggaagc ctgagagata ctagttatta tactggacta gttataataa cagatgtctt   41040
gcctatgata atggatacta ggtataataa tagatgcctt gcttgtttag ctcatttaat   41100
gcaaagacct tgagaagtag atactattat tcctattatt cttatttgca aatgaggaga   41160
ctaaggctta tatgtattaa gtaatttgcc caagggtaca cagccactgt agtttggaat   41220
tgggaatatt aggattttgg cttatgagga caatgagcag aatatgtaaa attgggactg   41280
attgagaaaa tcctggaggt attgttactt gccttggaga acaacttttt tttttttttt   41340
tttgagacag agtcttactc ttgttgccca ggctaaagga caatggcacg atcttggctc   41400
actgcaacct ccgcctcctg ggttcaagcg attctcctgc ttcagcctct gaagtggctg   41460
ggattacagg cacccaccat catgaccagc taattttttgt atttctagca gagacagggt   41520
tttactatgt tggccaggct gttctcaaac tcctgacatc aggtgatcca cccgcctcca   41580
gcctcccaaa atgctggaat tacagtgttg agccactgca ccctgccgaa aaacaaccac   41640
tttaagatgt tagattccag ccaagtgaag tggctcatgc ctgcaatccc aagcactttg   41700
ggaggtcaac ctgggcagat cacttgaggc caggagttcg agntcagcct gggnaaantg   41760
gtgnaactcc gtctctanta naacatacaa aaattngccc ggcatggtgg cacgcacctg   41820
tactcccagc tactggggag gctgaggcag gagaatctct taaacctggg agatggaggt   41880
tgcagtgagc tgagattgca ccactgcact ccagcctggg cgacacagcc agactctgtc   41940
tcaaaaaaaa aaaaaaaaa aaaagatgta agattccaaa attgttctac aaagtscaag   42000
gacacacaca cactcctgtc tgggtcaaaa tgtatattgg caagctgggg ccctggcagt   42060
tttcttacgt ggatcatagc aaatgctacg tggcttagca gccaaacttt acaatgagga   42120
caackgacaa atcctagcca ggcagagaag atgtggaaga ttgtcagtgc ccaggtgatt   42180
ctttgggctt aatactccag gaaagggtca tttccattag ctctgaggct gtcttcttat   42240
ggccagatcc actatactca cttcattccc ctgcacgata tctcggcatg gaggggggctg   42300 gggttcagaa gtccacactt gcagggaagc cagaggtttg gcaggggca caggaagaaa   42360 ggtctgttgc accatggtgc tgacccgtga ggcactccag gggcagggct gaggctcgca   42420
gggacaggtg ccactgctgc tgggctcctc accacccaga gcaggacttg gccaagtaca   42480
gcaagcacca aagggggag cactgggaat ataaacaaga agaacaaagc ttgtttatat   42540
tcccatttat atttatttaa tattacatta tatataaata tatttattat attacattct   42600
```

```
aattgcagag atgccatcct gcgtctcggc aattacaatg taactcaacg ggaacattta    42660
acttgacata caagaattgt actttcttgc aatgtttaag gatatacaac aattaaagac    42720
agcataaatg aaagaattaa aatgtaccag ctttataaac tgtaaagccc actttcccca    42780
tgcaccagtg gatgagaatt gaagacagac ttaccggtaa ataggtaaat cacagttgtt    42840
cccagatcgg gatggcatct tcattgtcag gtcacccaca cctagagtaa tgtctgtcac    42900
atagcaaaca ctcagtaaat acttagtgaa caaatgaatg aacagatgaa taagatttac    42960
agtcttcaat aggaatcaat cagtgctctt ttcttaaact aaacagaaag ctttggggag    43020
atctgacagc tgcgaggcac ctgaaggaga aagaatgaaa aagcagttta gaatgtgtac    43080
atttcaaagg gtgaaatcaa ctaaggtgca catagatcat gaaatggaaa ttggacttt     43140 gtttctactt ttaactagga ggccctgaaa cttctgaatg aagttcaaga acatctggag    43200
gaagaagaaa ggctatgccg ggagtctttg gcagattcct ggggtgaatg caggtcttgc    43260
ctggaaaata actgcatgag aatttataca acctgccaac ctagctggtc tctgtgaaa     43320 aataaggtaa gagaaaaaga gagctcaaga tttcacagtt cttaaggcac ctatttcagc    43380 ttacttttt attaatttat gttaatattt agaacggaga tgcctgatct gatagggcc     43440 ttttgctttc tagaatctaa tactaatgtt tacataccat cacctgtgta tacgcaattt    43500
ataaggtaga gcaccattca gtggtcactg aatgcatctc ttaaaatatc ctggctttct    43560
gccttgtatt tgttatttgt gaacatgttc ccactagata gtaagctctt tgagggcagg    43620
gatcatatct tatttgtctt cacttatgca ttggtggcat ccagtaaatg tttaccaaat    43680
tgcatttgga atcatagcat tgcagtctct gatttcaatc cacattaatt tttccttctg    43740
gaggccaaat atttaaagat actctctgcc tcccaaatct taccttcaac atgcttgcct    43800
ccttatgcat aacacacaca cacacacaca cacacacaca cacacacccc ttcatgtccc    43860
cttttgccct acccatgtat gtagactggc atgtttctt ttttgtaccc tttggttatc     43920
ttctgagcag agggatcaca gagggtggtg acctgaatag gatgagctct gccccactaa    43980
cggctccaat taagctagat ttttctcccc cttcaagaag tgagctgaat acaaaattga    44040
gtggaatttc acgctccata ttagagcaca tactaattag ggtatgctcc tggcttggca    44100
atgccatact caattacaaa gggagcaact actaagataa tgaatgcgcc aagttaattt    44160
gcctccacta ttaattgcat ctgctctatt tttagagcta ctgtcgcctg ctaatacacc    44220
agaatatggt gtaatcagca ccagcaggaa gtcaggagat atgggaccca ttcccatctg    44280
ggtcagttgt gtgatcttat gaacatttct tggggcttta aaggtttgtt tttgtggatg    44340
aagagtcaag taaacagaag ctggtagagg gagaggcaga caatccaccc aaattctttt    44400
cttttatttt tttcatgaga cagggtctgg ctcttttgcc ctggctagag ggcagtggtg    44460
ccatcttggc ttactgcagc ctccacctcc tgggttcaag tgattctcct gcctcagcct    44520
cctgagtagc tgggattaca ggcgcccacc accacgccta gctaattttt gtatttttag    44580
tagagacagg gttttaccat gttggccagg ctggtgacct caggtgatcc acacaccttg    44640
gcctcccaaa gtgaaaactt gacctttta ggctattggt gggcaatgta aaccaggaga     44700
aatttcagat cctgttttcca taggcaaagg caaagtcagg tataagaggg ttaagaaatt    44760
atcttaaagt taattgcctc atactagctt gcccagaatt attattgatt tgaaatgact    44820
actgtaagtt gactttaaaa tttgcaataa gaaatggtcc agggccgggt gcagtggctc    44880 accctgtta tccctagcac tttgggaggc ctaggcatgt ggattmcctg agctcaggag      44940
```

```
ttcgagacca gcctgggcaa cacggtaaaa ccctgtctgt actaaaatac aaaaaaaatt    45000
agccaggcat ggcggtgtgc aactgtaatc ccagctactc ggaaggctga gacagaagaa    45060
tcacttgaac ccaggaggcg gaggttgcag tgagccgaga tggtgccatt gcactccagc    45120
ctgagtgaca gagcaagact ccatctcaaa taagaaagaa agaaagaaag agagagagag    45180
agagaaagaa agagaaagaa agaaagaaag aagaaagaa agaaagaaag aaagaaagaa    45240
agaaagaaag aaagraagra agaaagaaag aaagaaagaa agaaagaaag agagaaagaa    45300
agaaagaagaa agaaagaaaa gaaaagagaa gaaagagagt tgagaaagaa aataattttt    45360
tattccatttt ctgtcccta ctctactcca cagattgaac ggttttcag gaagatatat    45420
caatttctat ttcctttcca tgaagataat gaaaagatc tccccatcag tgaaaagctc    45480
attgaggaag atgcacaatt gacccaaatg gaggatgtgt ymagccagtt gactgtggat    45540
gtgaattctc tctttaacag gagttttaac gtcttcagac agatgcagca agagtttgac    45600
cagactttc aatcacattt catatcagat acagacctaa ctgagcctta cttttttcca    45660
gctttctcta aagagccgat gacaaaagca gatcttgagc aatgttggga cattcccaac    45720
ttcttccagc tgttttgtaa tttcagtgtc tctatttatg aaagtgtcag tgaaacaatt    45780
actaagatgc tgaaggcaat agaagattta ccaaaacaag acaaaggcaa gtattaaaag    45840
attacttta cttagaggtt tacactaag tcaagttttg tttagcttca gaaatggtag    45900
acatttctga gtcacattgt atagcgtttc ttgaagagac aatttatgga aaatgtttca    45960
gagcctctta aaagaagctt tgaagtctgc taaacactat ccctcttcca tcatcgttga    46020
gaactgaact ctttctagag caaattttca aagcagaaag aaaaaatgct aataggttga    46080
gaacttgaaa aaaaaaaacc agttccctca tttattattt ctttatttat tttattttgt    46140
gacggagtct cactctgcca cccagcctgg agtacagtgg tgtgatcttg gctcactgca    46200
acctctgcct cccaggttca gcaattctc ctgcctcagc ctcccaagta gctgggacta    46260
cagttgtgca ccaccacgcc cagctaattt ttttgtattt ttagtagaga cggggggtgtc    46320
agtatcttgg ccaagctggt ctcaaactcc cgacctcagg tgatccaccc gccttggcct    46380
cccaaagtgc tgggattgca ggcgtgagcc accatgcatg gccatttccc tcatttatta    46440
aagctcatgt agatgctcag ctctattctg ctaaagcatc agagagcttc tttaaaattg    46500
atctggaatc ctcaactccc agtttgagaa gcccactctc acatataacc agagcaattt    46560
agtgccctcc tctgaatcac tacaatcatt ccttaaatca taaatgtat gcataaaacc    46620
acaaaaaatg ctcataaacc ccaaactaca gaaatattag ataagaattg ccttctacca    46680
acactaatca tgcctcatgg catccatgtt ggagacacaa tgctgcttta tgttttaagg    46740
cggcagatat cttctgtggg cttctatgga gtaagttaga taccgcattc gagaatgaga    46800
attgccacga gggtcaagtg taggatctgc atttcctttg tcactgtatt gaccccttag    46860
ccaggttgaa ggctgctccc ctctgagatg aaaaataaaa tgggctcctt ctatctatt    46920
ttcttttcct ttttcttttt ttttttttt tgagatggag tgttgctctg ttgtccaggc    46980
tgtattggtg tgatctcggc tcactgcaac ctctgcctcc tgggttcaat caattctcct    47040
gcctcagctt cccagtagtt ggggattaca ggtgcccgcc accacgcctg gctaattttt    47100
gtattttag tagagacagg ggtttcacca tgttggccag gctggtctcg aactcctgac    47160
ctcaagtgat ctgctcacct tggcttccca aagtgctgga attacaagca tgagccacca    47220
cacccagcca gccaccacac ccagccagcc accactcctg accctatctg actatttttc    47280
aattatatta gctgtagctg gcaacatctg aatcagattc tcaaaatcgc catgacatta    47340
```

```
cataactggc ctctacatag gagaggttta cctttcagaa actgaagcta ggaaacagtg   47400
cattacatcc ttcaggtgcc atcgttccat gaacagagaa cagccatcat tactggaatt   47460
gttgggttct atttcagagt ccagtggact ttttttataa gtcaattatt tggtctggta   47520
gtccattctg aggttgcaaa ttcatcaaat attcaggata acaccaggc gagtagacta    47580 aatctatcca ggctgggtgg tattaagtga ttttagcctg actgtttaca tggatatcaa   47640
ctgtcttgga ataacactga gaatatgttc attagaacaa aagggctcct cccctccatg   47700
ttgtgtagca gccttacaca agcattggtt acattcccat gtgcacagga ctgtcagtag   47760
tgattcagac atgccacaat ctagataatt tttcaaccac tgtaaccccc tcccacacac   47820
cagctacgaa cataggtttc cactgtctgc caccattgcc ttctcattca cacagctggg   47880
ggccagccct actctcagct gcctcacacg caccctcccc agccctctg cgccacttcc    47940 atctcagtga tgacctggaa agccaaggtc ccctgtgaat gcaaatagta aagacaaaaa   48000
caaaatagca accaaaaaag tctgtgttac actattgtac tcttctttct ccagtatccc   48060
tcccctagcc agacagtaca cagaagctac cgcagaggag acactgtctt cccagatgag   48120
caaatgtgga ctgtttatca agaatagtca ggcaggcgct ctacagcact tgaatgtggt   48180
ttccatcact tttctggaca ggtagttggt gaggaataag cctactgccc ctagaaaatc   48240
tgcctaatga cttgacactt tgagttttgc cccttgtggt aggcaaaata atgactgccc   48300
acaatatccc caccctaatc cccagaacct gtgaatttat gttatgcggc aaagggaaag   48360
taaggatgca gatggaaatc aatttgttaa tcaactgact ttatttttat ttatttattt   48420
tttgagacag agtcttgctc tgtcacccag gctggagtgc agtggaatga tcttggctca   48480
ctgcaacctc cacctccggg gtttaagtga ttctcctgcc tcagcctccc gagtagctgt   48540
gattacaggc actcaccacc atacctggct aattttgta ttttgagtag aggcagggtt    48600
tcgccatgtt gtccaggctg gtctcgaact tctgacctca aatgatccgc ccacctcggc   48660
ctcccaaagt gctgggatta caggcatgag ccatcatgcc cggcctcaac tgattttaaa   48720
atagagagag tatgctggat tatccagatg gattcaatgt aatcacaggg tccttaaaag   48780
tggaagaagg aggcagaaaa gaattaatag tagcagccac aagagaagga cttggctcga   48840 cttttgacgac cttgaagaca gaggaagggg ccaggagccg agtaatgtag gtggcctcga   48900
ggaactggaa atggtataga aatgaattct cctctagagc ctccgcaaaa aactagccct   48960
actgacatct ttttttttt ttttttttt tttttttttt gagacagagt ctcgctctgt    49020
cttcaggctg gagtgcagtg gtgcgatctt ggctcagtac aacctccgcc tcctaggttc   49080
aagcgattct tctgcctcag ccacctgagt agctgggact acaggcacgt gccaccacgc   49140
ccagctaatt tttgcatttt ttttttttg agacagatga catcttgatt ttagcctagg   49200
gagacccact tcagacttct gacctaaaag accaaacaat aatgaatttg tgctgtttca   49260
agccactgaa tctgtggtag ctgtagcaga gctaataata atagtaactg accaacattt   49320
actgagcaag ttccgtgtgg caaccttcat ggatgggcct tattggtcat gattgtttaa   49380
agggccaaaa ttagaaaaat agctaacact gaattatgaa caccaggaaa aggagagcgg   49440
aaataaaaag aatcagaaat atcttgataa ttaatgctat ttttgttgag ataggttca    49500 ttttgttctc atatttcttt cctaccttgg tctttctgga cctcagttcc tgaatctgtt   49560
gaaagcgaat aggtccagga aagtagctct tggaattatc ttcatttgcc ttatgaatcc   49620
ctggaaggaa cagatgagat tgagttctac tgtagcttga cccgtgcggg ggccgggaga   49680
```

```
cctggttcta atgctgcctt agagagtgtt agttaacatt aattttcgcg tgggagaaac   49740
agacaggcag gtgggagagt agatgattta gctcagtgac tgcactggaa gtagctccct   49800
ggaagggttc tgaggttctg tcaaggctag actaagcgag gtgatggatt gtgctgtggc   49860
tgcaggatgg ggaattagtg tcatatgggc ctagaatttg tcatccttgg tgtacatacc   49920
aggtattaat ctagatgcta gagataaaat gatgattatg acacagcctc tgacttccag   49980
gagctcagtc cagagaaagg aaaacagatt agtgaacaat tacatcacca tattgtgggt   50040
aaaatggcag aagaaggtat ggaagaatga caagattaaa atggcaagac caagtccctt   50100
ccctcaagag gcttacagtc taatggaaaa gataagaaag caaacactac ataaagcagg   50160
aattaattct acactggaaa ttctcacagg gggctataca gggcaaagaa gagggtccag   50220
gaaagcagct gggagaaact gactttctgg tcaccaaagg ggatgggtgc cttacatgcc   50280
attctatcaa acagtgcttc actgttttta aactatggac tttgcaattt atctcaaaat   50340
aaaacgtttc attttttaaat gctgaggatt taatatgaca gaaaatcatc aggttgtaaa   50400
ttagtaatac atgttttccta atgtcaaaca ctctattggg aaccgccaat tttctgttgg   50460
atagacttct cttttacaca tttttatatg gattgttaat tctcctaggg gaaaaaactt   50520
ctcaaaactt gattggcttt agatattttc ctaaatcttt gacccctgt tcataacagt   50580 atatgcatct ccacacacac atactcgcac acatatgtgt gtatatatat gtgtgtgtgt   50640
gtgtgtgtgt gtatacat atatatgaga atgcaaaaa aagaatagta ataaaataac   50700
cacctatcac ccactttaag aaacagacat ttctaatatc tttgaaactt cttcccaatt   50760
atagctttaa aaattaatta ttaaagagtt ttttaaaata cagaaaagtc caagagaaaa   50820
agtggttcac aatcacctat ttacttaatc ctattgacat cagaaatact aatgatataa   50880
gacaaatgat ttttaaagta atcaaatata taaaagaaca aaataaatga aagctgccct   50940
ctcctacctt atcaactccc tcttctaaaa gatagttatt ataattctt catgactcct   51000 cctagaaaat aaaattacat gcattaatat atgtgtgtat atactactaa taaatttcta   51060
gtaatgagat tcttggattc aagagtgtgc aattttttaat agctgttcag ttgtcccagg   51120
aaattattgc accaacgtgc atttctgtgt ctaaatatag gaaaaagggc caggggcggt   51180
ggctcatgcc tgtaatccca gcactttggg aggccgaggc gggtggatca tttgaggtca   51240
ggagttcaag aaccggcct ggacaacatg gcgcaacccc atctctacta aaagtacaaa   51300
gattagctgg gcttggtggc tctcacctgt aatcccagct acttgggagc ctgaggcagg   51360
agaatcactt gaacccggga ggcagaggtt gcagtgagcc aagatcccgc cactgcactt   51420
tagcctgggc aacaagcaag actctgtctc aaaaataaat aaattaaata catacataca   51480
tataggaaaa agattttgaa agcactggta agaaaaagct gcggcattgt ctccacttct   51540
tcaaagtgca aactcttatg acactaacgt gtaaatgtta tgttccctgt agctcctgac   51600
cacggaggcc tgatttcaaa gatgttacct gggcaggaca gaggactgtg tggggaactt   51660
gaccagaatt tgtcaagatg tttcaaattt catgaaaaat gccaaaaatg tcaggctcac   51720
ctatctgaag gtaaataatt gctattttgt tttttattct actttaagtt ctcaggtaca   51780
ttttgttata aagtttcggt gccacaaaag aaatagcact cgaatataaa attttcttt   51840 taattctcag caaggaaagt tacttctata gaagggtgcg cccttacaga tggagcaatg   51900
gtgagcgtgc acttgccaag ggagggaag gggttcttaa ccctgacaat gcacgtggcc   51960
cctgctgctg tgtggttccc ctattggcta gggttagacc gcacaggcta gactaattcc   52020
cattggctaa tttaaagaga gtgacgaggt gagtggtctg gagggaaaaa tggttatgac   52080
```

-continued

```
agagcatgta atcggaatga atcagggcgg agcgtgtaat cggaatgaat cagggcggag    52140
catgtaatcg gaatgaatca gggtggagcg tgtaatcgaa aaaggttgct ttacgaggaa    52200
attaagttta aaagtagaag gcaaagaatt gaacatactg acatactgat tctttggaaa    52260
gaaatttaga actcacatct aacaattttt tagggtttct ttagtattct ggacagagga    52320
caaaatctca ttctcacaag catagtggat tcatttgctt tcctccaagc acttttttgc    52380
aggctcattt ccatctgggg gcgttcaatg taggtttata aactggtgtt ttgtttgttt    52440
gttttatgag acagagtctt gctctgttgc ccaggctggn gtggcacaat ctcggctcac    52500
tgcaacctcc acctctcggg ttcaagcaat tctcctgcct cagcctgcca gtagctggg     52560 attacaggca tgtgccacca cgcccggcta atttttttg tattttttagt agggacgagg    52620 gtttcaccat attggccagg ctggtctcga actcctgacc ttgtgatccg cccacctcgg    52680
cctcccaaag tgctgggatt acaggcatga accaccgtgc ctggcctggt ttataaactt    52740
ttattattcc aaagtatgtc attctttcac tttctttaat tccctaattg ttcttgtgat    52800
tttttttatg attaatgacc aaacactatt gtgtgcaaaa gaaaaccttt gagcaaatta    52860
gcgcaactcc ttccttctta ccgcaagcaa aaagaacccc tgcccccaac catgaaagaa    52920
acctttcatt ctgtaaatca gtgtttagac aagtgaaata ttttttttgaa agtggcattg    52980 gctctttccc attggtgggt taatgaacta attagcattt aaatagggaa agtggcttct    53040
cctcccaagc cccaggaatc cttttccctc cctttctagt tccttcccca ggaaggaaat    53100
cattctccct ttcctccatc cctcccctca ttccctttcc cttctccaga ctaaagtcac    53160
tcctccaacc ccaccagggc caaattacaa cttttcttac ataaaacaag agcttttgat    53220
tcctatgctt ctgcattta tctcactaaa gccctaaggg aaggaaattt tcaaagtgtg     53280
actaatggct tacagtagga aattggaaga tacagaaggg acagaaatca acatgtcagt    53340
aaattctaca acactagcta gagatttggg gcaagtcatt tatgctgtct aggcctcagt    53400
tgagtaattt gtaaataaag gacccaagat aatctttggg ttctaacaaa attcttctgt    53460
aaaacagtgg tccccagcct tctggcacca gggactagat tcctggaaga caattttttcc   53520 aaagatggtg gggcagggg cacgtttggg gatgatcatc aggcattatt ctcctaagga    53580
gcgctcaacc tagacccttt gcatgcacag ttcacaatag ggtttgtgct cccgtgagaa    53640
tggaatgcct ccgctgatct gacagcaggc ggggctcagg cagtcatgct tgctcacctg    53700
ccgctcacct cctgctgtac agctccgttc ctaagaggct acaggctgat atgggtccgt    53760
ggcccagggg ttggggaccc ctgctataaa ggaagttcag aaaaatcaga ttataattct    53820
gatttttata aatcagaatt tataaaattc agattataat ttactaccaa gtaatagctc    53880
ttttgccctt aacttcccac agtgaagacc actggagtaa tttatatcaa cgcaaagaac    53940
aaaaagcatg gtcagtggaa actcctgccc ctcccttggc tttctctcct caatctaaca    54000
gtgagcaagt tgcaacaaat cgcgccgttc agagaaaagg gaggatggaa ttgttacaac    54060
cgtttctgtc gcccaggctg gagtgcagtg gcgcgatctt cgctcactga aacctctacc    54120
tcctgagttc aagcgattct gctgcctcag cctcctgagt agctgggatt acaggcacgc    54180
gccaccatac ctggctgatt tttgtatttt tagtagagat ggggtttcac catattggcc    54240
aggctggtct cgaactcctg acctcgkgat cctcccacct cagcctccca agcgctggg    54300 attacaggtg tgagccatcg cgcctggcca acaaattgtt acaatgttaa acaacataat    54360
atcctaaaca tattggcttt taaagtatca ttagatacac cacaatacta ataaaggtta    54420
```

```
cctttgggtt taagattaa agatgatttt taaaaatact tctttctgta ttttccaaac    54480
tcttaaccat aaacataaga tattccttga cttaggatag gattatgtca caacccatca    54540
taagtttgaa aaatcataag ttgaaccatt gtaaattggg gaccatatgt acatgtatgc    54600
atatatgata ttaaaaatta ttagacgtct ttaaaatttg acttttttaac atattacttt    54660 tatttaatca ccttgctcaa ggagcctgta aattacatat taatattctc cattatgaaa    54720
taagtctttc cattgtgcaa attaatgcat tgcagaggtt ctaaacatct atatgctttg    54780
caactcgaaa ggagtaagtt tcccttttcta attttttttat tcaattaaat aaaaaaatga    54840
gtttaataga gtctattaaa ttagatcatt attcggagtg gttagtaaac ctgtttagag    54900
tcgacaacac tcccttttctc tcttttttttt tttttttttt tttgtgccag agtctcgctc    54960
tgtcgccgag gctggagtgc aatggcacga tctcggctca ctgcaacctc cacttcccag    55020
gttcaagtga ttctcctgcc tcagcctctc gagtagctgg gattacaggc aaccgccacc    55080
atgcccagct actttgttgt atttttagta gagatggggt ttcaccatgt tggttaggct    55140
ggtggcgaac tcctgacctc aagtgatttg cctgcctctg cctcccaaag tgctgggatt    55200
acaggcgtga gccaccatgc ccagcccctt tctccttttt aaatatcacc agcctgggtt    55260
ctttgttctt tttgttttgt ttygtttttg tttttgtttt ttttgagacg gagtcttgct    55320
ccgtngccca ggctggaggg cagtggcaca atcttggctc agtgcaacct ccgccttctg    55380
ggttcatgcc attctcctgc ctcagcctcc tgagtagctg ggactacagg cgcccgccac    55440
catgcccggc taaattttttg tatttttagt agagacgggg tttcaccgtg ttagccagga    55500
tggtctcgat ctcctgacct tgtgatccac ctgcctcggc ctcccaaagt cctgggatta    55560
caggcttgag ccaccatccc tggcctccag cctgggttct tattgacact gaattctcaa    55620
gttagttggg ctagtgagga agtcaggtta cacgggccac agaacaagaa caaggattgt    55680
tctttctctc tctcttccac ttcattctct gtcagcctct cccgacctca gtagttggtc    55740
ttttctcccc cttcttttga aagcagagtc cattatacaa atggacttgt ttacttctcc    55800
acatccctct tgtgcaaatt ttctgccatg gacacctcta ccccaccttta gaatgtatat    55860 tagacaattt tgacatctag aatgtcttgt tgggcagaaa agcgtttgga aagcgttgct    55920
ccaggtagct ctgattacaa actggacctt ttcgcgggt tacctagagc agttgagagt    55980
gctctttctc ctggccaggt gcagttgctc atggctgtaa tcccagcact ctggaaggcc    56040
gaggcgggcg gatcacctgc ggtcaggagt ttgagaccag cctggccaac atggcgaaac    56100
cccgttctac taaaaataca aaaattagcc agatatggtg gtatgaacct gtaatcccag    56160
ctactcagga ggctgaggca agagaattgc ttgaacctgg gaggcagagg ttgcagtgag    56220
ctgagatcaa gcctccagcc tgggcctcag agcgagactc tgtcttgaaa aaataataat    56280
aataataaac agataaataa aatttaaaaa aataaaaaag gagtgctctc tctcctgaac    56340
tgctgactcg aggactctct cagcctgttt tatcatttgg aagaggaaat aatatatctg    56400
cttcgtacac atctttagaa gtttaaataa aatgtctgaa atatcaatga ttctcattat    56460
tcaaatattt gtttttttaag tcacagttgc aaggttatat acagaagcat aggttttat    56520 aacagaaaaa tagacactta atatactgac ctcttacaaa aatagtcctg ctcaagcatc    56580
ccatctatgt atcattamca tctatttctt tctacccagc taaaatagtt tattaataat    56640
ccttgaatgt cacaagtnga atacagaata aatcagataa tacattaaaa tgcacctgat    56700
aatcaatatg caccagataa tggacacagt atacatcaga taatacagta caaattcaat    56760
gaaagtttag tgttgcaaag gtaaaatgta aagaatgtcc taatgtgctc ccatgctgct    56820
```

```
taaaactgtt attataaatt gcttttatt ataaatatat aaagaatgat gtaataggcc   56880
agccatggtg gctcatccct gtaattccag gtctttggga ggctgaggca ggtgaatcac   56940
ttgaggttag gagtttgaga ccagcctggc caacatggtg aaaccccgtc tctactaaaa   57000
atataaaaat tagccaggtg tggtggtacg cacctgtagt ctcagctact ccggaggctg   57060
aggcaggaga atcgcttgaa accagaagcc ggaggttgca gtgggtcaag atcaagcaac   57120
tgcactccag cctaggtgac agagcgagac tttgtctcag aaaaaaaaa aaattctcag    57180 tcacctagat tgagaaatag aacattacca aaacagataa agccccactg tgttcccatc   57240
cacatcacat tcactttatc tcctcaaaag gaaagtgcta ttttgaattt agtattaatt   57300
atttccttgc atttcttcct actcatatca tgtgcctata tacatataat atatacaaat   57360
gccgatatca tacatagcaa tgttttacat ttcgattttt gcattgtcaa tgtagaattt   57420
ttaaacttaa aaacatgctt catacagccg ggtgtggtgg ctcatgcctg taatcccagc   57480
attttgggag gccaaggcag gcggatcgac gaggtcagga gttcgagacc agcctgacca   57540
acatggtgaa accccatctc tattaaaaat acaaaaaaaa atattagctg gtcatggtgg   57600
cgcgtgcctg taatcccagc tactcaggag gctgaggcag gagaattgtt tgaacccagg   57660
aggcagaggt tgcagtgagc cgagatcgca ccattgcact ccagcctggg tgacagagcg   57720
agactccatc tcaaaaaaaa aaaaaaaaag cttcatacaa acatgaaacg gcacatgtc    57780 tggctgggtg cggtggctca tgcctgtaat cccagcactt tgggaggcca aggcgggcaa   57840
tcacttaagg ccaggagttc gagaccagcc tggtcagcat ggtgaaaccc cgtctctact   57900
aaaactacaa aaattagcca ggcatggtgg catgcgcctg tagtcccagc tactcgggag   57960
gctgaggcac aagtatcact tgatcccagg aagcagaggt tgcagtgagc caagattgtg   58020
tcactgcact cctgcctggg taacagagtg atactctgtc tcaaacaaac aaacaaaaaa   58080
aacaaagaaa agaaaagaa aaagaaatg ggcacatgtc aaatgttaat ttgactatgt    58140
aacttattaa tgaaggaacc agcagggtgt tagagctggg tcaaagaagt ataagagaga   58200
ctggagtgct tacagtcaag cagagacaga atgctgaaag gttatgaaat tagatatgtt   58260
agttaatatt cgaaagggca actaaactgt aaatcttgcc attatctttt ctatcagacc   58320
aaaataattt acatctctac tagacaaaca tttgccactt ttcaatccat aatctatggg   58380
taatttcatg gagtctggcc ctaatcaaca gtaaatagta aagccaacaa aggatctctt   58440
ccctagacct tgaagtgatc tttgggtgga cccctagac aataatttag tatgacattg     58500
agaggacacg caagcctggg cagcatagtg agacccgcct ctacaaaaaa attaaaaatt   58560
agccgggcat ggtggtgtga gcctgtagtc ctagctactc aggaggctaa ggtggaaata   58620
ccacttgagc ccgggagttc gaggctgtag tgagctatga tcatgccatt gcactccagc   58680
ctgggtaaca gagcgagaac ctgtcttgaa aaaaagaaa agaaaaaga aaagaaaca     58740 aaaggaaatg cagccatttt tttttgcct tatttccaag ttctggataa ttttttcttt     58800
ttaacaatat aaatattatc acttatgtat tcttttgcaa tatggctttt cactcagtgt   58860
agtttgcaag gggttagcca tgtgaatgca tgctgctcta gttcattaat tcactgttgt   58920
atgttggtct atgtaggcat atcacaatwt atycattccc tagctgaagt acatttgctt   58980
tcaaggtatt gctattataa acaaatctca tacctttaat caaataataa ttttgtctct   59040
tcaatcagct ntgatttact tgttcnaan acnaagcaca caactataat tanaatttca    59100
ttactgataa atataaaata ttttccaaaa catcacaaat cttttntnnt ncactattta   59160
```

```
ctatacactt tnggtctnaa tttaaagcgg cttcactata tgtggttctt ttcctctctt    59220
cccatactaa ttactggtac tggacatata catccaaaat caaatagtar tgtcctttttt   59280 aagggataaa tgggatgtga tgtagaaggg gcatagtagg gacttcatct gttttggcaa    59340 atttttttctt aatataggtg gtaggcatgt ggaatttata acaaaagttc tgtctccagc   59400
ccagtttctg ttacataaaa ccatataatt aacagttaaa ctggatctgg tttgacacag    59460
atgtagacga tattaataat tactccagaa caacaggcat aactaaaaac taccacaggc    59520 aaaggggaa aatagagaat gtaagggctg ggacttaagc ccatgttgcc cacctccaag     59580
tttcatggac ttttccttc tccacattac tttcttctct gctagactgt cctgatgtac     59640
ctgctctgca cacagaatta gacgaggcga tcaggttggt caatgtatcc aatcagcagt    59700
atggccagat tctccagatg acccggaagc acttggagga caccgcctat ctggtggaga    59760
agatgagagg gcaatttggc tgggtgtctg aactggcaaa ccaggcccca gaaacagaga    59820
tcatctttaa ttcaatacag gtaaaggaga gacccaagag cagatacgga aatgacacgt    59880
gcataccttg atttcactgt taatttactt atgaattgtg tctgaatttg aaaacaagct    59940
gtaggaggta ttcatatttc cattgtgatt gccttcaggc tgacttgatt taacgtagtt    60000
catggtcttt agaaaacaag aaagtccata agaaaatca atttaaaaca caaatactt      60060 tctaatctag aaatggctat ttctgcttag agttataggg ctataactga tagaggtaac    60120
cttgaagaaa tatggccaat gtaggttttta ggagagaaga cttacaaata aagcaatttg    60180
agttcaaaat ttgactctga aacttaccag ctgagtaagc ttgggaaagt acctcaacca    60240
ttctaggcct cagtgttcca cctgtaaaat ggtaacaatc atagctatct taacgtgtac    60300
acctataaag tgattagtat agatttctta tacaaaacaa gagctctgta aattatagct    60360
cttattagtt gctgacacaa taaagccact gagttatctt gagaattaaa catttatatg    60420
ttactcgtca cataaaaata cattgccagc tgggcgcagt ggcttatgcc tgtaatccca    60480
gcactttggg aggctgaggt gggtggatca cttgaggtca ggagtttgag accagcctgg    60540
ctaatgtggc gaaaccccgt ctctaccaaa aacataaaaa attagccaag tgtgatggca    60600
cacacttgta atcccagcta ctcaggaggc tgaggcagga gaatcacttg aacccggaag    60660
gcagaggttg cagtgagctg agatcgtgcc actgcactcc agcctgggcg acagaaggag    60720
actctgtctc aaaaaaaaca aaaataaara catattgcca tcttaaattc cacctatacc    60780
atgactccca gattcagtca ataacttttt gcataacatg caagtgactt ttcttcctaa    60840
gacatccccc ctccaacaca cacacattac cttaatctac aaatgcgcca ggctagtgat    60900
tcctgatgag gctggttttg agggttccca aaaagacttg gatacaaaaa ttactgggca    60960
gagcaattga agatgcaata ttctgtgtgt agtatgttag gttatgttgg tgccctatcc    61020
agatccctgg ggatccctt taccagctcc cactggtgct ggtgctgctg ctaactgctt     61080
atctctgaaa ctttctccca aagattgccc ttggagcact tatgccccag agcttcctgc    61140
aggatcaggc tgaggctaac agtcatctga agccatatcc ttgcttagct tctttcactt    61200
ctctagtttg ctttcctcat cccttaaaa gttgcacctg agagcattct ttataaacca     61260
cttctgtcag aatctcaggc actgcttcta ggaaattaga cttatggcat tctataatcc    61320
agcatttccc tcttttttca aactacaaag ctgtggatca tgcctgattt gagaaataag    61380
tttagaaagt cacagcaagc tcattaaaaa acaaaattaa aaaccataca aaaaatagaa    61440
taggacaaag tagaaaatat tagcatgcat tgcatttcat aagtcatatg cacatcatgg    61500
aatttcattt ccatttttgta tgtgtatatg tgtgtaaaca tatatacaca tatgtagaca    61560
```

```
tacgtgtgtg ttttgaatca tgatgtcaag tgtattcatt actgcagacc acagtcaaag    61620
ggttttgaaa gccactgttc caatccctgc cagctctctg attctataac tctattagat    61680
tacacttgag gaaggtaaaa taattcaata tatttgatca tcctcgcata tatagacttt    61740
tagtttaacg aggaaaaagt cttgtattga agaataaaac ttgaagaaaa attttagcag    61800
tgctttcaac ctttagaaat ctacagtcaa tatttagttg ttttttaccat tgtcagtatt    61860 ttctattctg tgctttgatt tacttccatt ctagtgtctc ttgagtaaca taacagattt    61920
atctaaaatt ctttatgctg ataacaaagg cacttctata taaaaacctc cacataaaat    61980
aaaattatgg ttttcaatta tacatttta taacaattat taccacttaa gagcatttac    62040
tgggtgtcag gcaatgttct aagacttttt ccatatatca gatcatttaa taccctcaat    62100
gaccctataa gggaagtaga attctttccc cagtttttca aatgaggcac agaggaggtt    62160
aagcaacttg tctgagctca cacagctagt aaatggtaga actagaattc aaactcaagc    62220
agtatttctc tagaatcagt gaacgtaacc actttgctaa actgcctgtg aagttacttt    62280
tctcaaaaca gctcctattt caccatgtaa agaaaagtac aaacccataa aatagcaagt    62340
gctgaagaga agccttatga agaaatata caaattccag caagtgaaaa cggttgtggt    62400
ccctggttgt ataatagtta catgggtgtt gactttacaa ttatttaaac caaacataaa    62460
tactttatgc agttttttatg tatgttatac tcacagaaag agaagggaaa aattttaaa    62520 tcattctctt aaggttacat caagttgcgt atcagttcag ttccatttaa atgattcaaa    62580
tcaaagtctg tgcatttgag aattcattaa gagagtaaca tacatgttat tcattaagag    62640
taacataaat tttgcattga ttcttgccaa aatcacacct acaaccataa attgtaaatt    62700
tctaggaaaa ctcagtacaa aacttggtgc aatgcaataa agtttgtggc acagacagta    62760
atactcagca aacatcccac ctcctctctc atattttcca gctcccctttg tggttaaacg    62820 ttgccatgtg gcaagttctg gccagtgaag cgtgagcaaa actgaaaagg gttctttgta    62880
gattgagaca gtgaagagcc tatgtgtgct catctattct cttttttctgc tgagggcaca    62940 aagaaagtcc tgaaatcatg tgctacagct atgagataat gtgcctttgc ctaccaggct    63000
tctcagtgtt tactggtgtg gagcccttgt aatggacaca taacatgaac aagaaataaa    63060
tctttgttgc atgaagccct aggaatgcca ggactaatct gttacctcag cacaaaccca    63120
ggcctatcct gactaaggtg gtattaaatt actattgaat gtgtattggg atttagtaaa    63180
cttctactgt ataatccttc ttctgtaggt agttccaagg attcatgaag gaaatatttc    63240
caaacaagat gaaacaatga tgacagactt aagcattctg ccttcctcta atttcacact    63300
caagatccct cttgaagaaa gtgctgagag ttctaacttc attggctacg tagtggcaaa    63360
agctctacag catttaagg aacattttaa aacctggtaa gcagagtgcc tggttaggaa    63420
tgccttgttg acaggaatag ttaattctca aaagggaaaa acaaaacttg tttcaaaata    63480
cctggaaaac atgtttaacc tcattaataa agacatgaaa acaaacaaga tggcatttc    63540 tgcctatcag atttgcaaat taaaaaaaaa cccaggaaat cctgatagga atgtgatgaa    63600
atgggaattc tcatatatca tgtattggtg ggaacataat tggttttgca ttttttgaaag    63660 ctatttgatt atgcatatga agagccataa aatttccttt tgatataata attccacttc    63720
cgaaatcaat cctaaggrat aaatctaaat ttgatgaama ktctccctcc aagatctaga    63780
tttgcagcat tatttaaata ttaaaagttg gccgggcgca gtggctcatg cctgtaatcc    63840
cagcactttg ggaggctgag gcgggcggat cacgaggtca ggagattgag accatcctgg    63900
```

```
ataacacgga gaaactgcgt ctctactaaa ataaaaaaaa ttagccgggc atggtggcgg   63960
gcgcctgtag tcccagctac tcgggaggct gaggcaggag aatggcgtga acccgggagg   64020
cagarcttgc agtgagcaga gatcgcgcca ctgcactcca gcctgggcga cagagcaaga   64080
ctctgtttaa aaaaaaaaaa aaaaaaaaa atatatatat atatatatat atatatatat   64140
atatatatat atgttaaaca tactcttaat gtgtaaaaac aagagaatga ttaagtakat   64200
tatgactaaa tacactcaat acattttatg aaacgttaaa aatattcaaa aaatttaaat   64260
aatgacttgc taactacttt aacaagagct ttattatcag ctagtcttgg aggtaatagt   64320
attatcatga tttttcagaa aaagatcctg aggctcagtg tccaaggtcc aatgaactac   64380
tcaggtcgga ggtggtagag cagcatgtgg agccagttct ctctccgact ccatcatcac   64440
actgcacggc ttcctgttaa gatatttgct caaaaatgc gagatataaa aatctgggta    64500
atatgatcaa ccttaaagaa taattacatt ttaaattatt catgagacct tgttagtagg   64560
tcaccatcaa tgtgtaatta agccagatgt gacaggattt gttgcctctc cctttacttc   64620
tgaattttgg aggcctttt ttttttctag ttgtatcagt cagccaacca atatcttttt    64680
agcatctact aagtttagat acgggaactg gtactctgaa agagaaaatg agaaatttga   64740
caagatcctg tccccaagga gcttcctatc caacaggggc acaagacaga tagatagaca   64800
cacacacaca cacacacaca cacacacaca cacacacaca ctataaagca aggcaagatt   64860
tagagagtgc acaggagtgg gctctgggag ttcaggggag ggtcgttcac attctggtag   64920
ggaagatact tctgagctca gtatattccc tttctcactg tccttctatc ccctctcttc    64980
ctctcctcct ctcttttcct ctttcttctc cctcctccca ctctgtcctc tcccttctt    65040 tccttttttc tttctttctt tttttttttg agacagagtc ttgttctgtc acccatactg   65100
gagtacagtg gcacgatctc ggctcactgc aacctcggcc tcccaggttc aaatgattct   65160
tgtgcctcag cctcctgagt agctgggatt acaggcgcac accaccatgc ctggctaatt   65220
tttgtgtttt ttagtagaga cagggtttca ccatgttggc caggctggtc ttgaactcct   65280
gacctcaagt aatccaccca ccttggcctc ccaaagtgct gggatcacag gcatgagcca   65340
ccacactggc ctcctctccc tttcttaaaa atacatcaat taattaaata tataaatgta   65400
gatacacaca caggcagaat caaagtgtat aggttggaga ggagactgtt ccaaaagggg   65460
ggatggcatg ggcaaatacg gcaagaaaga gtagagcatc taggtactga gggtgctggg   65520
aagtcctgct aaaaatacgg caagaaagag tagagcatct aggtactgag ggtgctggga   65580
agtcctgcta aagtggtccc ctcccactgt ggggcctttg agtttccctg tgccagggta   65640
cctgccctct gtgagtttga gttctttctt tggttgcaag caaccaagac cagctcagct   65700
aaaagaaatg gatggatacc gactcatgag tcagaggga agctggacgt ctatgcccag    65760
agccaggcag aaacgggtca ggtctagagt ctggaggag gaaaccgatg acagctgct     65820 tcagggccca gcgctcaggg tgaagcagct gcagttgttt ttagtcctca gatcactctg   65880
ctcaagatgt gacttgccag gaggaatctg gctggcccag ctgggacatg tgtgtctacc   65940
tctagaccag gagagaggag agtcttggtt gacagtcccc atgtagtacc cctttgttta   66000
ggttactgag tcatcaacag atctcagttc aaatagtcac ttcttcaggg gcaatatacc   66060
ctcttctacc cataaactag gggcaacata ccctctctcc cctttcacac atgaccataa   66120
caccatgtag cactcaactc ttgtaagttg acatttaccc atgtgactct ttatgaacgt   66180
tcatctccat cccgagacct acagtccatg agggtaccac cgttctaggg ttttttgctct   66240 tctcttttgtc agtggggact taggactctg cctggcacag ggcaaaccct caatatttgt   66300
```

```
tgaataaatt aattaataaa cacgtgtaaa tgaatatcag tagactacaa caagagtaac   66360
agtaggcgaa ggtggaaggc aaaggtggga agaggtcagg gctctgagtg ctgggctgtg   66420
gagtctgagg ttcactctac agcgctggtg agacacgata ggttttagag aaaggaagcc   66480
tcatgctggt gccccagtgg gtactgacta tgcatttgta gccaaatcaa agtatttccc   66540
ataaagtcat ctatctcttc ccagttgttg ggacttccaa tggcaatggg aattaagata   66600
ctgagtaatt gggagatcaa gcaaattatt tactaacaag gcacacgaag tgatttttca   66660
caggcaatgt taatgttttt cttttttatg tagttttaaa attctaaaag taacaaaatc   66720
acaactacca aacatttaga cgacaaaaat tatccataat cccaccatct taacacaacc   66780
actattatca tttgttttcc ttattcacat tttctaccta ttttcttaga ttyccaagaa   66840
atagaattac ttgtttagag gttattaaca tcttattgtt ctggatatat atatatatat   66900
agctatatat agctaaattt aataacagca atgtctgcag taccactttc tcaaatgcta   66960
actggcattt caattttttg agacagtctc tctctgttgc ccaggcagga ttgcagtggc   67020
atgatctcgg ctcacggcaa cctccacctc ccaggttcaa gcgactctca tgcctcagcc   67080
tcccaagtag ctgggattac aggtgtgcac caccacactt ggctaatttt tgtattttt    67140 agtagagatg tgttttacc atgttggccg ggctggtctc aaactcctgg cctcaagtga    67200
tccttccacc tcagcctccc caagggctgg tattacaggc atgagccact gcctggcctg    67260
gcatttcaat ttttaaaatc ttcagtaata aatgaaaatt tttatcttat tgttataatt   67320
tttatggttt tttattattc atgagaataa acattttcca agtttgttta ctgactgaat   67380 ttctttttg tgcaccttac ttggtatcat ggataaaatt ttgtcaattt tctgattata    67440
tcaatgcatt cagggtccca aacctgccaa agtttaaaga gaaagatact aagggaaaaa   67500
ccaggaaaag atggtagaaa agaatcaccc tggcattttc aatcacgtaa acatttgcta   67560
ggtgccctag ctgcaggtat acagctcact gaaacatgaa ttccaatttt atagggtgaa   67620
atatatattt agaaccctct tctgaacttt tcttctagtt atctagcatc ctaagtgcct   67680
ggacgttcct gattggtttg caatgtgttt tatttcccat ccccaagttt catagctgcc   67740
ggccctggga tctacagtca caggctgtaa cacaatatct tgcacatcct gagtctttaa   67800
taagcttttg tagatgggct cttaccatca tcatcatcgt gaaaggcaaa tatacaaaat   67860
ttgttgacta atgtaatgag tcatgagtaa cagaagttta ctgaccaaac actacgtgca   67920
tgtagagttc agaataaaca ctttattatc acatcagagg aaaagaccat cttagaggct   67980
caacaaccca ggaaagctgt gacgatttct tcaaattgtt aagaatatcc atgcatatgg   68040
gtttcacatt attttgctac acacagtacc aattttttcca aaagccaaca gcaggtattc   68100
tattacccat cctggacttt tactccaaga aaaatacac tgagtctgtg agtaatttat    68160
tagtattttg atcattgctg cttttttttt tttttaagg taagaagatc taatgcatcc    68220
tatatccagt aagtagaatt atctcttcat ctgggacctg gaaatcctga aataaaaaag   68280
gataatgcaa taaacacagt tgcaggaaag tatgttagct atatactatg aagtactctt   68340
agtttactta tgttgaatgg cttagctatt aatactcaaa ttgagttaaa atgaaaattc   68400
ctccttaaaa aatcaaacgt aatatgtatt acatttcatg gtacattagt agttctttgt   68460
atattgaata aatactaaat cacctaggtg tctatgttct atcacatcta caaacatgtc   68520
acttcctaat taacaaaatg ttcttccttt agtttgcttt tgcacttaaa atatatataa   68580 ttgactttt tggaaaaaaa tctaagattc attgctttgt tttgtaaaga ccaataggtt    68640
```

```
ctgtatagtc tttttttaaa ttgtggtaaa atacacatgg cattaattta ccattttaac    68700
cattttaaag tgcacaattt gtggcattaa gtacactcac gttgctgtgc aaccatcacc    68760
accgtccatc ttcagaacct ttttatcttc ctaaactgaa actctgtact cgttaagcac    68820
tcacttcccg tttccccatc ccccagcccg tagcaaccac gactgtactt tctatgaatt    68880
tgactactct aggtactgca tgtaggtgga atcatacagt atttgtcttt tgcttcattt    68940
tgttttgttt tttgttttct aagacagggt ctcactctgt cgcccaggct ggagtgcagt    69000
ggtgcaatca cagtgtcctt ttgtgactgg tttatttcac ttagtgccat gttttcaagg    69060
ttcatccatg ttgttgcatg tctcagaact tcctttttta ggctaatatt cttgcatgta    69120
tttacctagt tttgcttatc cattcagcca ttgatggaca cttgggttgc ttccatcttt    69180
tggctattgt gaataatgct gttttgaacg tgggtgtgct acatagttac ttttttaaaat   69240 tggcacaaca gcgctgtctt ttgacatacg tattttatgg aaaacacaag attttcctgg    69300
ctgacgctca acctcataat ttggaccttg gtgcaacaca ataataggag agctatgtgt    69360
cagtatatat cactaaggat tacaatgaga gtgtatacag tcagtattac aaattataaa    69420
aagaaatgta ggccaggcac ggtgcctcac acctgtaatc ccagcacttt gggaggccaa    69480
cgtgggtgga ttacctgagg acaggagttc gaaaccagcc tggccaacat ggtgaaaacc    69540
tgtatctact aaaaatacaa aaattggcca ggtgtggtgg cgcatgcctg taatcccagc    69600
tactcaggag gctgagatgg gagaattgct tgaacctggg aggcagaggt tgcactgagc    69660
caagattgtg ccactgtact ccagcctggg caacagagcg agactctttt ttaataaata    69720
aataaataaa taaatatata aagaaacgt aatgaaagag agagaactct gaactttaa     69780 agaacttttc acccagtctt gatctatctg acagaaaggc ttgtcagaga agttagagt    69840 tcagaggcag ccaattgaat ataattaact ccaaatgaag ataaaccttt tctaaatcat    69900
actgaaggct ataaaaatg agaattatgt tattttttt ttgagacagg gtcttactct     69960
attgcccagg ctggagtgca gtggcatgat ctgggctcac tgaagcctga cctccttggc    70020
tcaggtgatc ctcccacctc agcctcctga gtagctggga ctacaggtac taccatgccc    70080
gtctattttt gtatttttt agtagagatg gggtttctcc atgttgtcca ggctggtctc    70140
aaactcccag gctcaagcaa tctgcccgcc tcagcctcca aaagtgctgt aattacaggc    70200
atgagccact gctcctggca gggaactaat agaatcctgg gttcttcggt gtgcaataaa    70260
yctcaaatac agctattcaa ccatagattt taaatatttg ttagtgaagg tgacaaaaaa    70320
ataagtgatt aagagaacct attttctatc caatgagcta tcaaaagctt atagagtgga    70380
aagagagtgg gggaagtgag gctcaaaaca gctaaatgga aagaagattt tgcatgcagg    70440
ctgaactgga ttttcatcct ggctactata ttctccagat gtgtcacttt ggccaagatc    70500
cttaatctca gtgtcatcta taaggtaatt aaagtacact agtgcccac taatctgtgg     70560 ttttgctttc caagctttca gttacccgag atcaactgcg gttttaaaat attatgtgga    70620
aaattccaga aatacatagt aagttttcaa ttgcatgcca ttaaatctca tgctgtccct    70680 gacccttcc tctccggagg tgaatgctcc ctttgtccag tggctccacg atgactacat     70740
tccccaaatt gttctcttag gaacccttc tgtgttcaag gaacccttac tttacttaat     70800
tatggcccca aagcacaaga tagggatgcc ggcatactgt tataattgtt ctattttatt    70860
attagttatt gttgttcatc tctacctgtg actaattat gaattcaact ttatcatagg     70920
tatgtaggta taggaaaaaa acatggtatg tataaggttc agtactatct gcagtttcag    70980
acatcccctt gggtcttgg aacatatccc ccgtggataa sgggaaacta ctgtaaaagt    71040
```

-continued

```
ttgtsttta  tagagtagtt  stsagaacta  cattaatcca  taatgtgtgs  ctcatgatac   71100
tcattgatag  atggtagtag  caacaataaa  aaataatatt  atcaagtaac  tgattcataa   71160
ttgactctca  aaaacgttaa  ttttctgctt  tcctttacct  aagtttacct  acatgtttga   71220
atttgtaaag  ggaaggtttt  tctagaccaa  taatttcaa   atattttgc   tctcatactt   71280
cctcaaagga  aactgaaaaa  gttgcaacat  acttgcatgt  cattttcta   tataagttga   71340
aagaatagca  aattgttatt  ttcccacgca  tcgtaaagat  tagcaggtca  tccctcttta   71400
aaatgtacca  aatggaatct  aaatatcatc  gcaatttgac  ccagcatcat  ccatttaaac   71460
aaatatacaa  gtttttcttt  aacaatgaga  aattttatct  cattacattt  tctccctaaa   71520
ctcttatttc  aatctacatt  cctaagaatt  ttatcctaat  gtagtatatt  tttatgctta   71580
aatatctttt  gttgatcaac  acaattttga  tcatttttaa  attttaaaaa  ttaagaacat   71640
cctgtgacat  caaattctag  gtatgaaata  tttattctag  attgggtgat  cattataatt   71700
atttttgta   cataattgat  caaaataaca  taaatatact  acaaatttct  atgactacta   71760
aacatataaa  agtaaaattt  taaacaaata  tatctcttaa  tgagaaggaa  gagcttttta   71820
tactccaata  agttaacgta  tccactaata  attattattt  cttcctagaa  caagacagga   71880
ttaagcatca  tgaccgtccc  tattgggga   tgtttttata  gatgcaagca  ctgtggcacc   71940
tactggtata  aatgcacctg  ctgattggaa  tgttctttcc  ccagatcttc  ccctgctggt   72000
ttcttcccag  tattcaggtc  tcagctcaaa  tgtgacttcc  tcaatgaggc  ctcctggtga   72060
tcagatctaa  agcaccctct  acacaatcac  tgtttagtgc  tatacccatt  aatttactat   72120
catcacactt  gtcactatct  gcagatgtct  tgtttggtta  cttttgtngt  gtttgtcact   72180
gccagaatat  cagttctatg  aagaaaaggg  ccttgtctat  tttgacactt  ataganatga   72240
tgnaggnacg  acatacaaat  ggccaatggg  catatggaaa  aacgcttgac  ttcaagagta   72300
ctnatggnta  tnaccaacat  ttatggagta  actactttga  aaagaaccat  tctgtcttta   72360
ctatcaagcc  aagatactca  aggaaggcag  cagaagtgga  agctccatgt  gggcagagga   72420
gcctagtctt  gagatgtgat  ttagctggta  tttgggtgaa  acaaataaac  cagcctcaaa   72480
ataacacaag  gggccgggtg  cagtggctca  cgcctgtatc  ccagcacttt  gggaggctcg   72540
aggcaggcag  attacttcag  gtgaggagtt  cgagaccagc  ctggctaaca  tggtgaacct   72600
ccat                                                                    72604
```

<210> SEQ ID NO 8
<211> LENGTH: 17
<212> TYPE: DNA
<213> ORGANISM: Artificial Sequence
<220> FEATURE:
<223> OTHER INFORMATION: Primer

<400> SEQUENCE: 8
cggggttggt ttccacc                                                      17

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
gcgaggagag aaatctggg                                                    19

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
tgctcactac tttgcagtgt tc                                             22

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
tgagatcgtg tcactgcatt ct                                             22

<210> SEQ ID NO 12
<211> LENGTH: 27
<212> TYPE: DNA
<213> ORGANISM: Artificial Sequence
<220> FEATURE:
<223> OTHER INFORMATION: Primer

<400> SEQUENCE: 12
gtaaatctca aaatgttggg ttaatag                                        27

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ctaactcttc ttctatcatt actc                                           24

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tgtttattgt gtgtctgctg tg                                             22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gaacaaccaa catgcaaaca g                                              21

<210> SEQ ID NO 16
<211> LENGTH: 22
<212> TYPE: DNA
<213> ORGANISM: Artificial Sequence
<220> FEATURE:
<223> OTHER INFORMATION: Primer

```
<400> SEQUENCE: 16
cccaggtgtt ttcaattgat gc                                          22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
agcagttttg tccttccaag tg                                          22

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
gtgttttgta atctgatcag atctc                                       25

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gcagtatttc tggtccagat c                                           21

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ggtgcacata gatcatgaaa tgg                                         23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
taagctgaaa taggtgcctt aag                                         23

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
tttattccat ttctgtcccc tac                                         23

<210> SEQ ID NO 23
```

<211> LENGTH: 22
<212> TYPE: DNA
<213> ORGANISM: Artificial Sequence
<220> FEATURE:
<223> OTHER INFORMATION: Primer

<400> SEQUENCE: 23
aaggctcagt taggtctgta tc                                           22

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
caggagtttt aacgtcttca gac                                          23

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
gactcagaaa tgtctaccat ttc                                          23

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tgtctccact tcttcaaagt gc                                           22

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
caaaatgtac ctgagaactt aaag                                         24

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
cacctccaag tttcatggac                                              20

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29

```
caaggtatgc acgtgtcatt tc                                          22
```

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30

```
gaatgtgtat tgggatttag taaac                                       25
```

<210> SEQ ID NO 31
<211> LENGTH: 25
<212> TYPE: DNA
<213> ORGANISM: Artificial Sequence
<220> FEATURE:
<223> OTHER INFORMATION: Primer

<400> SEQUENCE: 31

```
ttgagaatta actattcctg tcaac                                       25
```

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32

```
ccatcctgga cttttactcc                                             20
```

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33

```
ctttcctgca actgtgttta ttg                                         23
```

<210> SEQ ID NO 34
<211> LENGTH: 147
<212> TYPE: DNA
<213> ORGANISM: Homo sapiens

<400> SEQUENCE: 34

```
ttccctccct ttggaacgca gcgtgggcac ctgcaacgca gagaccactg tatccccggt   60
gcagaatgta atgagtgcct gatacatttg ccgaataaac tattccaagg gttgaacttg  120
ctggaagcaa gagaagcact attctgg                                     147
```

<210> SEQ ID NO 35
<211> LENGTH: 123
<212> TYPE: DNA
<213> ORGANISM: Homo sapiens

<400> SEQUENCE: 35

```
atggagtctt gctctcgttg cccagactgg agtgcactgc tgcgatctca gctcactgca   60
acctctacct cccaggttca agcgattctc ctgcctcagc ctctcgagtg gctgggacta  120
tag                                                               123
```

<210> SEQ ID NO 36
<211> LENGTH: 398
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g, or t

<400> SEQUENCE: 36

```
agttgcgtcc ctctctgttg ccaggctgga gttcagtggc atgttcatag ctcactgaag      60
cctcaaattc ntgggttcaa gtgaccctcc tacctcagcc ccatgaggac ctgggactac     120
agttccctcc ctttggaacg cagcgtgggc acctgcaacg cagagaccac tgtatctccg     180
gtgcagaatg taatgagtgc ctgatacatt tgccgaataa actattccaa gggttgaact     240
tgctggaagc aanagaagca ctattctggt aacagcggga acatgaagcc gccactcttg     300
gtgtttattg tgtgtctgct gtggttgaaa gacagtcact gcgcacccac ttggaaggac     360
aaaactgcta tcagtgaaaa cctgaagagt ttttctga                             398
```

<210> SEQ ID NO 37
<211> LENGTH: 372
<212> TYPE: DNA
<213> ORGANISM: Homo sapiens

<400> SEQUENCE: 37

```
agttgcgtcc ctctctgttg ccaggctgga gttcagtggc atgttcttag ctcactgaag      60
cctcaaattc ctgggttcaa gtgaccctcc cacctcagcc ccatgaggac ctgggactac     120
agatggagtc ttgctctcgt tgcccagact ggagtgcact gctgcgatct cagctcactg     180
caacctctac ctcccaggtt caagcgattc tcctgcctca gcctctcgag tggctgggac     240
tatagtaaca gcgggaacat gaagccgcca ctcttggtgt ttattgtgtg tccgctgtgg     300
ttgaaagaca gtcactgcgc acccacttgg aaggacaaaa ctgctatcag tgaaaacctg     360
aagagttttt ct                                                         372
```

<210> SEQ ID NO 38
<211> LENGTH: 1815
<212> TYPE: DNA
<213> ORGANISM: Cavia sp.
<220> FEATURE:
<221> NAME/KEY: CDS
<222> LOCATION: (145)...(1542)

<400> SEQUENCE: 38

```
cttggagtca actgagtgtg gactgaaact tccaaaaact gacatgagga gtcactggag      60
aatcatgatc aaggagctac acactctgac ttaactttat tctgtggaca atgagagaca     120
actgcaagga ttaacagtga gaac atg aag ctg cca ctt ttg atg ttt ccc        171
                           Met Lys Leu Pro Leu Leu Met Phe Pro
                             1               5
gtg tgt ctg cta tgg ttg aaa gac tgt cat tgt gca cct act tgg aag       219
Val Cys Leu Leu Trp Leu Lys Asp Cys His Cys Ala Pro Thr Trp Lys
     10                  15                  20                  25
gac aaa act gcc atc agt gaa aac gcg aac agt ttt tct gag gct ggg       267
Asp Lys Thr Ala Ile Ser Glu Asn Ala Asn Ser Phe Ser Glu Ala Gly
                 30                  35                  40
gag ata gac gta gat gga gag gtg aag ata gct ttg att ggc att aaa       315
Glu Ile Asp Val Asp Gly Glu Val Lys Ile Ala Leu Ile Gly Ile Lys
             45                  50                  55
```

```
cag atg aaa atc atg atg gaa agg aga gag gaa gaa cac agc aaa cta    363
Gln Met Lys Ile Met Met Glu Arg Arg Glu Glu Glu His Ser Lys Leu
         60                  65                  70 atg aaa acc ttg aag aag tgc aaa gaa gaa aag cag gag gcc ctg aaa    411
Met Lys Thr Leu Lys Lys Cys Lys Glu Glu Lys Gln Glu Ala Leu Lys
     75                  80                  85 ctt atg aat gaa gtt cat gaa cac ctg gag gag gaa gaa agc tta tgc    459
Leu Met Asn Glu Val His Glu His Leu Glu Glu Glu Glu Ser Leu Cys
 90                  95                 100                 105 cag gtt tct ctg gca gat tcc tgg gat gaa tgc agg gct tgc ctg gaa    507
Gln Val Ser Leu Ala Asp Ser Trp Asp Glu Cys Arg Ala Cys Leu Glu
                110                 115                 120 agt aac tgc atg agg ttt gat acc acc tgc caa cct gca tgg tcc tct    555
Ser Asn Cys Met Arg Phe Asp Thr Thr Cys Gln Pro Ala Trp Ser Ser
            125                 130                 135 gtg aaa aat atg gtg gaa cag ttt ttc agg aag atc tat cag ttt ctg    603
Val Lys Asn Met Val Glu Gln Phe Phe Arg Lys Ile Tyr Gln Phe Leu
        140                 145                 150 ttt cct ctc cag gaa aat gac aga agt ggc cct gtc agc aaa ggg gtc    651
Phe Pro Leu Gln Glu Asn Asp Arg Ser Gly Pro Val Ser Lys Gly Val
    155                 160                 165 act gag gaa gat gcg cag gtg tca cac ata gag cat gtg ttc agc cag    699
Thr Glu Glu Asp Ala Gln Val Ser His Ile Glu His Val Phe Ser Gln
170                 175                 180                 185 ctg agc gca gat gtg aca tct ctc ttc aac aga agc ctt tac gtc ttc    747
Leu Ser Ala Asp Val Thr Ser Leu Phe Asn Arg Ser Leu Tyr Val Phe
                190                 195                 200 aaa cag ctg cgg cga gaa ttt gac cag gct ttt cag tca tat ttc aca    795
Lys Gln Leu Arg Arg Glu Phe Asp Gln Ala Phe Gln Ser Tyr Phe Thr
            205                 210                 215 tcg ggg act gac gtt aca gag cct ttc ttt ttt cca tct ttg tcc aag    843
Ser Gly Thr Asp Val Thr Glu Pro Phe Phe Phe Pro Ser Leu Ser Lys
        220                 225                 230 gag cca gcc tac aga gca gat gct gag cca agc tgg gcc att ccc aat    891
Glu Pro Ala Tyr Arg Ala Asp Ala Glu Pro Ser Trp Ala Ile Pro Asn
    235                 240                 245 gtc ttc cag ctg ctc tgc aac ttg agt ttc tca gtt tat caa agt gtc    939
Val Phe Gln Leu Leu Cys Asn Leu Ser Phe Ser Val Tyr Gln Ser Val
250                 255                 260                 265 agt gaa aaa ctc atc aca acc ctg cgt gcc aca gag gac cct cca aaa    987
Ser Glu Lys Leu Ile Thr Thr Leu Arg Ala Thr Glu Asp Pro Pro Lys
                270                 275                 280 caa gac aaa gac tcc aac cag gga ggc ccg att tca aag ata cta cct   1035
Gln Asp Lys Asp Ser Asn Gln Gly Gly Pro Ile Ser Lys Ile Leu Pro
            285                 290                 295 gag caa gac aga ggc tca gat ggg aaa ctt ggc cag aat ttg tct gat   1083
Glu Gln Asp Arg Gly Ser Asp Gly Lys Leu Gly Gln Asn Leu Ser Asp
        300                 305                 310 tgc gtt aat ttt cgc aag aga tgc cag aaa tgc cag gat tat cta tct   1131
Cys Val Asn Phe Arg Lys Arg Cys Gln Lys Cys Gln Asp Tyr Leu Ser
315                 320                 325 gat gac tgc cct aat gtg cct gaa cta tac aga gaa ctc aat gag gcc   1179
Asp Asp Cys Pro Asn Val Pro Glu Leu Tyr Arg Glu Leu Asn Glu Ala
330                 335                 340                 345 ctc cga ctg gtc agt aga tcc aat cag caa tac gac cag gtg gtg cag   1227
Leu Arg Leu Val Ser Arg Ser Asn Gln Gln Tyr Asp Gln Val Val Gln
                350                 355                 360 atg acc cag tat cac ctg gaa gac acc acg ctt ctg atg gag aag atg   1275
Met Thr Gln Tyr His Leu Glu Asp Thr Thr Leu Leu Met Glu Lys Met
            365                 370                 375
```

```
aga gag cag ttt ggc tgg gtt tct gaa ctg gca tac cag tcc cca gga    1323
Arg Glu Gln Phe Gly Trp Val Ser Glu Leu Ala Tyr Gln Ser Pro Gly
        380                 385                 390 gct gag gac atc ttt aat cca gtg aaa gta atg gta gcc cta agt gct    1371
Ala Glu Asp Ile Phe Asn Pro Val Lys Val Met Val Ala Leu Ser Ala
    395                 400                 405 cat gaa gga aat tct tct gat caa gat gac aca gtg gtt cct tca agc    1419
His Glu Gly Asn Ser Ser Asp Gln Asp Asp Thr Val Val Pro Ser Ser
410                 415                 420                 425 ctc ctg cct tcc tct aac ttc aca ctc agc agc cct ctt gaa aag agt    1467
Leu Leu Pro Ser Ser Asn Phe Thr Leu Ser Ser Pro Leu Glu Lys Ser
                430                 435                 440 gct ggc aac gct aac ttc att gat cac gtg gta gag aag gtt ctt cag    1515
Ala Gly Asn Ala Asn Phe Ile Asp His Val Val Glu Lys Val Leu Gln
                445                 450                 455 cac ttt aag gag cac ttt aaa act tgg taagaagatt tagtccatcc          1562
His Phe Lys Glu His Phe Lys Thr Trp
                460                 465 tataatcagc aagaattaca ccttcggcca agacctgaga attctgaaaa tacaaagcag  1622
gctaacacaa tgaacacagc tgcatgaaag ttaggtatat attaggaagc actattggtt  1682
tactttgttg aatggaagtt taatagctat tcaaattgag ttaatataaa aatttcttcc  1742
taaaaagtaa aatgtacata tgtagaatat gatgcattag ttctttgtat actaaataaa  1802
tactgagtcc cct                                                     1815

<210> SEQ ID NO 39
<211> LENGTH: 466
<212> TYPE: PRT
<213> ORGANISM: Cavia sp.

<400> SEQUENCE: 39

Met Lys Leu Pro Leu Met Phe Pro Val Cys Leu Leu Trp Leu Lys
 1               5                  10                  15

Asp Cys His Cys Ala Pro Thr Trp Lys Asp Lys Thr Ala Ile Ser Glu
                20                  25                  30

Asn Ala Asn Ser Phe Ser Glu Ala Gly Glu Ile Asp Val Asp Gly Glu
            35                  40                  45

Val Lys Ile Ala Leu Ile Gly Ile Lys Gln Met Lys Ile Met Met Glu
50                  55                  60

Arg Arg Glu Glu Glu His Ser Lys Leu Met Lys Thr Leu Lys Lys Cys
65                  70                  75                  80

Lys Glu Glu Lys Gln Glu Ala Leu Lys Leu Met Asn Glu Val His Glu
                85                  90                  95

His Leu Glu Glu Glu Ser Leu Cys Gln Val Ser Leu Ala Asp Ser
            100                 105                 110

Trp Asp Glu Cys Arg Ala Cys Leu Glu Ser Asn Cys Met Arg Phe Asp
        115                 120                 125

Thr Thr Cys Gln Pro Ala Trp Ser Ser Val Lys Asn Met Val Glu Gln
    130                 135                 140

Phe Phe Arg Lys Ile Tyr Gln Phe Leu Phe Pro Leu Gln Glu Asn Asp
145                 150                 155                 160

Arg Ser Gly Pro Val Ser Lys Gly Val Thr Glu Glu Asp Ala Gln Val
                165                 170                 175

Ser His Ile Glu His Val Phe Ser Gln Leu Ser Ala Asp Val Thr Ser
            180                 185                 190
```

```
Leu Phe Asn Arg Ser Leu Tyr Val Phe Lys Gln Leu Arg Arg Glu Phe
            195                 200                 205

Asp Gln Ala Phe Gln Ser Tyr Phe Thr Ser Gly Thr Asp Val Thr Glu
        210                 215                 220

Pro Phe Phe Pro Ser Leu Ser Lys Glu Pro Ala Tyr Arg Ala Asp
225                 230                 235                 240

Ala Glu Pro Ser Trp Ala Ile Pro Asn Val Phe Gln Leu Leu Cys Asn
                245                 250                 255

Leu Ser Phe Ser Val Tyr Gln Ser Val Ser Glu Lys Leu Ile Thr Thr
            260                 265                 270

Leu Arg Ala Thr Glu Asp Pro Lys Gln Asp Lys Asp Ser Asn Gln
        275                 280                 285

Gly Gly Pro Ile Ser Lys Ile Leu Pro Glu Gln Asp Arg Gly Ser Asp
        290                 295                 300

Gly Lys Leu Gly Gln Asn Leu Ser Asp Cys Val Asn Phe Arg Lys Arg
305                 310                 315                 320

Cys Gln Lys Cys Gln Asp Tyr Leu Ser Asp Asp Cys Pro Asn Val Pro
                325                 330                 335

Glu Leu Tyr Arg Glu Leu Asn Glu Ala Leu Arg Leu Val Ser Arg Ser
            340                 345                 350

Asn Gln Gln Tyr Asp Gln Val Val Gln Met Thr Gln Tyr His Leu Glu
        355                 360                 365

Asp Thr Thr Leu Leu Met Glu Lys Met Arg Glu Gln Phe Gly Trp Val
        370                 375                 380

Ser Glu Leu Ala Tyr Gln Ser Pro Gly Ala Glu Asp Ile Phe Asn Pro
385                 390                 395                 400

Val Lys Val Met Val Ala Leu Ser Ala His Glu Gly Asn Ser Ser Asp
                405                 410                 415

Gln Asp Asp Thr Val Val Pro Ser Ser Leu Leu Pro Ser Ser Asn Phe
            420                 425                 430

Thr Leu Ser Ser Pro Leu Glu Lys Ser Ala Gly Asn Ala Asn Phe Ile
        435                 440                 445

Asp His Val Val Glu Lys Val Leu Gln His Phe Lys Glu His Phe Lys
        450                 455                 460

Thr Trp
465

<210> SEQ ID NO 40
<211> LENGTH: 1767
<212> TYPE: DNA
<213> ORGANISM: Cavia sp.
<220> FEATURE:
<221> NAME/KEY: CDS
<222> LOCATION: (145)...(1494)

<400> SEQUENCE: 40
cttggagtca actgagtgtg gactgaaact tccaaaaact gacatgagga gtcactggag      60
aatcatgatc aaggagctac acactctgac ttaactttat tctgtggaca atgagagaca     120
actgcaagga ttaacagtga gaac atg aag ctg cca ctt ttg atg ttt ccc        171
                          Met Lys Leu Pro Leu Leu Met Phe Pro
                            1               5 gtg tgt ctg cta tgg ttg aaa gac tgt cat tgt gca cct act tgg aag       219
Val Cys Leu Leu Trp Leu Lys Asp Cys His Cys Ala Pro Thr Trp Lys
 10              15                  20                  25 gac aaa act gcc atc agt gaa aac gcg aac agt ttt tct gag gct ggg       267
Asp Lys Thr Ala Ile Ser Glu Asn Ala Asn Ser Phe Ser Glu Ala Gly
```

-continued

```
                     30                      35                      40
gag ata gac gta gat gga gag gtg aag ata gct ttg att ggc att aaa          315
Glu Ile Asp Val Asp Gly Glu Val Lys Ile Ala Leu Ile Gly Ile Lys
                 45                      50                      55 cag atg aaa atc atg atg gaa agg aga gag gaa gaa cac agc aaa cta          363
Gln Met Lys Ile Met Met Glu Arg Arg Glu Glu Glu His Ser Lys Leu
         60                      65                      70 atg aaa acc ttg aag aag tgc aaa gaa gaa aag cag gag gcc ctg aaa          411
Met Lys Thr Leu Lys Lys Cys Lys Glu Glu Lys Gln Glu Ala Leu Lys
 75                      80                      85 ctt atg aat gaa gtt cat gaa cac ctg gag gag gaa gaa agc tta tgc          459
Leu Met Asn Glu Val His Glu His Leu Glu Glu Glu Glu Ser Leu Cys
 90                      95                     100                     105 cag gtt tct ctg gca gat tcc tgg gat gaa tgc agg gct tgc ctg gaa          507
Gln Val Ser Leu Ala Asp Ser Trp Asp Glu Cys Arg Ala Cys Leu Glu
                    110                     115                     120 agt aac tgc atg agg ttt gat acc acc tgc caa cct gca tgg tcc tct          555
Ser Asn Cys Met Arg Phe Asp Thr Thr Cys Gln Pro Ala Trp Ser Ser
            125                     130                     135 gtg aaa aat atg gaa aat gac aga agt ggc cct gtc agc aaa ggg gtc          603
Val Lys Asn Met Glu Asn Asp Arg Ser Gly Pro Val Ser Lys Gly Val
        140                     145                     150 act gag gaa gat gcg cag gtg tca cac ata gag cat gtg ttc agc cag          651
Thr Glu Glu Asp Ala Gln Val Ser His Ile Glu His Val Phe Ser Gln
    155                     160                     165 ctg agc gca gat gtg aca tct ctc ttc aac aga agc ctt tac gtc ttc          699
Leu Ser Ala Asp Val Thr Ser Leu Phe Asn Arg Ser Leu Tyr Val Phe
170                     175                     180                     185 aaa cag ctg cgg cga gaa ttt gac cag gct ttt cag tca tat ttc aca          747
Lys Gln Leu Arg Arg Glu Phe Asp Gln Ala Phe Gln Ser Tyr Phe Thr
                190                     195                     200 tcg ggg act gac gtt aca gag cct ttc ttt ttt cca tct ttg tcc aag          795
Ser Gly Thr Asp Val Thr Glu Pro Phe Phe Phe Pro Ser Leu Ser Lys
            205                     210                     215 gag cca gcc tac aga gca gat gct gag cca agc tgg gcc att ccc aat          843
Glu Pro Ala Tyr Arg Ala Asp Ala Glu Pro Ser Trp Ala Ile Pro Asn
        220                     225                     230 gtc ttc cag ctg ctc tgc aac ttg agt ttc tca gtt tat caa agt gtc          891
Val Phe Gln Leu Leu Cys Asn Leu Ser Phe Ser Val Tyr Gln Ser Val
    235                     240                     245 agt gaa aaa ctc atc aca acc ctg cgt gcc aca gag gac cct cca aaa          939
Ser Glu Lys Leu Ile Thr Thr Leu Arg Ala Thr Glu Asp Pro Pro Lys
250                     255                     260                     265 caa gac aaa gac tcc aac cag gga ggc ccg att tca aag ata cta cct          987
Gln Asp Lys Asp Ser Asn Gln Gly Gly Pro Ile Ser Lys Ile Leu Pro
                270                     275                     280 gag caa gac aga ggc tca gat ggg aaa ctt ggc cag aat ttg tct gat         1035
Glu Gln Asp Arg Gly Ser Asp Gly Lys Leu Gly Gln Asn Leu Ser Asp
            285                     290                     295 tgc gtt aat ttt cgc aag aga tgc cag aaa tgc cag gat tat cta tct         1083
Cys Val Asn Phe Arg Lys Arg Cys Gln Lys Cys Gln Asp Tyr Leu Ser
        300                     305                     310 gat gac tgc cct aat gtg cct gaa cta tac aga gaa ctc aat gag gcc         1131
Asp Asp Cys Pro Asn Val Pro Glu Leu Tyr Arg Glu Leu Asn Glu Ala
    315                     320                     325 ctc cga ctg gtc agt aga tcc aat cag caa tac gac cag gtg gtg cag         1179
Leu Arg Leu Val Ser Arg Ser Asn Gln Gln Tyr Asp Gln Val Val Gln
330                     335                     340                     345 atg acc cag tat cac ctg gaa gac acc acg ctt ctg atg gag aag atg         1227
```

```
                                                                           1275
Met Thr Gln Tyr His Leu Glu Asp Thr Thr Leu Leu Met Glu Lys Met
            350                 355                 360
aga gag cag ttt ggc tgg gtt tct gaa ctg gca tac cag tcc cca gga           1275
Arg Glu Gln Phe Gly Trp Val Ser Glu Leu Ala Tyr Gln Ser Pro Gly
            365                 370                 375
gct gag gac atc ttt aat cca gtg aaa gta atg gta gcc cta agt gct           1323
Ala Glu Asp Ile Phe Asn Pro Val Lys Val Met Val Ala Leu Ser Ala
    380                 385                 390
cat gaa gga aat tct tct gat caa gat gac aca gtg gtt cct tca agc           1371
His Glu Gly Asn Ser Ser Asp Gln Asp Asp Thr Val Val Pro Ser Ser
395                 400                 405
ctc ctg cct tcc tct aac ttc aca ctc agc agc cct ctt gaa aag agt           1419
Leu Leu Pro Ser Ser Asn Phe Thr Leu Ser Ser Pro Leu Glu Lys Ser
410                 415                 420                 425
gct ggc aac gct aac ttc att gat cac gtg gta gag aag gtt ctt cag           1467
Ala Gly Asn Ala Asn Phe Ile Asp His Val Val Glu Lys Val Leu Gln
                430                 435                 440
cac ttt aag gag cac ttt aaa act tgg taagaagatt tagtccatcc                 1514
His Phe Lys Glu His Phe Lys Thr Trp
                445                 450 tataatcagc aagaattaca ccttcggcca agacctgaga attctgaaaa tacaaagcag         1574
gctaacacaa tgaacacagc tgcatgaaag ttaggtatat attaggaagc actattggtt         1634
tactttgttg aatggaagtt taatagctat tcaaattgag ttaatataaa aatttcttcc         1694
taaaaagtaa aatgtacata tgtagaatat gatgcattag ttctttgtat actaaataaa         1754
tactgagtcc cct                                                            1767

<210> SEQ ID NO 41
<211> LENGTH: 450
<212> TYPE: PRT
<213> ORGANISM: Cavia sp.

<400> SEQUENCE: 41

Met Lys Leu Pro Leu Met Phe Pro Val Cys Leu Leu Trp Leu Lys
1               5                   10                  15

Asp Cys His Cys Ala Pro Thr Trp Lys Asp Lys Thr Ala Ile Ser Glu
                20                  25                  30

Asn Ala Asn Ser Phe Ser Glu Ala Gly Glu Ile Asp Val Asp Gly Glu
            35                  40                  45

Val Lys Ile Ala Leu Ile Gly Ile Lys Gln Met Lys Ile Met Met Glu
    50                  55                  60

Arg Arg Glu Glu Glu His Ser Lys Leu Met Lys Thr Leu Lys Lys Cys
65                  70                  75                  80

Lys Glu Glu Lys Gln Glu Ala Leu Lys Leu Met Asn Glu Val His Glu
                85                  90                  95

His Leu Glu Glu Glu Ser Leu Cys Gln Val Ser Leu Ala Asp Ser
            100                 105                 110

Trp Asp Glu Cys Arg Ala Cys Leu Glu Ser Asn Cys Met Arg Phe Asp
        115                 120                 125

Thr Thr Cys Gln Pro Ala Trp Ser Ser Val Lys Asn Met Glu Asn Asp
    130                 135                 140

Arg Ser Gly Pro Val Ser Lys Gly Val Thr Glu Glu Asp Ala Gln Val
145                 150                 155                 160

Ser His Ile Glu His Val Phe Ser Gln Leu Ser Ala Asp Val Thr Ser
                165                 170                 175

Leu Phe Asn Arg Ser Leu Tyr Val Phe Lys Gln Leu Arg Arg Glu Phe
```

```
                    180              185              190
Asp Gln Ala Phe Gln Ser Tyr Phe Thr Ser Gly Thr Asp Val Thr Glu
        195              200              205

Pro Phe Phe Pro Ser Leu Ser Lys Glu Pro Ala Tyr Arg Ala Asp
    210              215              220

Ala Glu Pro Ser Trp Ala Ile Pro Asn Val Phe Gln Leu Leu Cys Asn
225              230              235              240

Leu Ser Phe Ser Val Tyr Gln Ser Val Ser Glu Lys Leu Ile Thr Thr
                245              250              255

Leu Arg Ala Thr Glu Asp Pro Pro Lys Gln Asp Lys Asp Ser Asn Gln
            260              265              270

Gly Gly Pro Ile Ser Lys Ile Leu Pro Glu Gln Asp Arg Gly Ser Asp
        275              280              285

Gly Lys Leu Gly Gln Asn Leu Ser Asp Cys Val Asn Phe Arg Lys Arg
    290              295              300

Cys Gln Lys Cys Gln Asp Tyr Leu Ser Asp Asp Cys Pro Asn Val Pro
305              310              315              320

Glu Leu Tyr Arg Glu Leu Asn Glu Ala Leu Arg Leu Val Ser Arg Ser
                325              330              335

Asn Gln Gln Tyr Asp Gln Val Val Gln Met Thr Gln Tyr His Leu Glu
            340              345              350

Asp Thr Thr Leu Leu Met Glu Lys Met Arg Glu Gln Phe Gly Trp Val
        355              360              365

Ser Glu Leu Ala Tyr Gln Ser Pro Gly Ala Glu Asp Ile Phe Asn Pro
    370              375              380

Val Lys Val Met Val Ala Leu Ser Ala His Glu Gly Asn Ser Ser Asp
385              390              395              400

Gln Asp Asp Thr Val Val Pro Ser Ser Leu Leu Pro Ser Ser Asn Phe
                405              410              415

Thr Leu Ser Ser Pro Leu Glu Lys Ser Ala Gly Asn Ala Asn Phe Ile
            420              425              430

Asp His Val Val Glu Lys Val Leu Gln His Phe Lys Glu His Phe Lys
        435              440              445

Thr Trp
    450

<210> SEQ ID NO 42
<211> LENGTH: 1539
<212> TYPE: DNA
<213> ORGANISM: Cavia sp.
<220> FEATURE:
<221> NAME/KEY: CDS
<222> LOCATION: (145)...(1266)

<400> SEQUENCE: 42
cttggagtca actgagtgtg gactgaaact tccaaaaact gacatgagga gtcactggag    60
aatcatgatc aaggagctac acactctgac ttaactttat tctgtggaca atgagagaca   120
actgcaagga ttaacagtga gaac atg aag ctg cca ctt ttg atg ttt ccc      171
                         Met Lys Leu Pro Leu Leu Met Phe Pro
                           1               5 gtg tgt ctg cta tgg ttg aaa gac tgt cat tgt gca cct act tgg aag    219
Val Cys Leu Leu Trp Leu Lys Asp Cys His Cys Ala Pro Thr Trp Lys
 10              15              20              25 gac aaa act gcc atc agt gaa aac gcg aac agt ttt tct gag gct ggg    267
Asp Lys Thr Ala Ile Ser Glu Asn Ala Asn Ser Phe Ser Glu Ala Gly
                30              35              40
```

```
gag ata gac gta gat gga gag gtg aag ata gct ttg att ggc att aaa    315
Glu Ile Asp Val Asp Gly Glu Val Lys Ile Ala Leu Ile Gly Ile Lys
            45                  50                  55 cag atg aaa atc atg atg gaa agg aga gag gaa gaa cac agc aaa cta    363
Gln Met Lys Ile Met Met Glu Arg Arg Glu Glu Glu His Ser Lys Leu
        60                  65                  70 atg aaa acc ttg aag aag tgc aaa gaa gaa aag cag gag gcc ctg aaa    411
Met Lys Thr Leu Lys Lys Cys Lys Glu Glu Lys Gln Glu Ala Leu Lys
    75                  80                  85 ctt atg aat gaa gtt cat gaa cac ctg gag gag gaa gaa agc tta tgc    459
Leu Met Asn Glu Val His Glu His Leu Glu Glu Glu Glu Ser Leu Cys
90                  95                  100                 105 cag gtt tct ctg gca gat tcc tgg gat gaa tgc agg gct tgc ctg gaa    507
Gln Val Ser Leu Ala Asp Ser Trp Asp Glu Cys Arg Ala Cys Leu Glu
                110                 115                 120 agt aac tgc atg agg ttt gat acc acc tgc caa cct gca tgg tcc tct    555
Ser Asn Cys Met Arg Phe Asp Thr Thr Cys Gln Pro Ala Trp Ser Ser
            125                 130                 135 gtg aaa aat atg gag cca gcc tac aga gca gat gct gag cca agc tgg    603
Val Lys Asn Met Glu Pro Ala Tyr Arg Ala Asp Ala Glu Pro Ser Trp
        140                 145                 150 gcc att ccc aat gtc ttc cag ctg ctc tgc aac ttg agt ttc tca gtt    651
Ala Ile Pro Asn Val Phe Gln Leu Leu Cys Asn Leu Ser Phe Ser Val
    155                 160                 165 tat caa agt gtc agt gaa aaa ctc atc aca acc ctg cgt gcc aca gag    699
Tyr Gln Ser Val Ser Glu Lys Leu Ile Thr Thr Leu Arg Ala Thr Glu
170                 175                 180                 185 gac cct cca aaa caa gac aaa gac tcc aac cag gga ggc ccg att tca    747
Asp Pro Pro Lys Gln Asp Lys Asp Ser Asn Gln Gly Gly Pro Ile Ser
                190                 195                 200 aag ata cta cct gag caa gac aga ggc tca gat ggg aaa ctt ggc cag    795
Lys Ile Leu Pro Glu Gln Asp Arg Gly Ser Asp Gly Lys Leu Gly Gln
            205                 210                 215 aat ttg tct gat tgc gtt aat ttt cgc aag aga tgc cag aaa tgc cag    843
Asn Leu Ser Asp Cys Val Asn Phe Arg Lys Arg Cys Gln Lys Cys Gln
        220                 225                 230 gat tat cta tct gat gac tgc cct aat gtg cct gaa cta tac aga gaa    891
Asp Tyr Leu Ser Asp Asp Cys Pro Asn Val Pro Glu Leu Tyr Arg Glu
    235                 240                 245 ctc aat gag gcc ctc cga ctg gtc agt aga tcc aat cag caa tac gac    939
Leu Asn Glu Ala Leu Arg Leu Val Ser Arg Ser Asn Gln Gln Tyr Asp
250                 255                 260                 265 cag gtg gtg cag atg acc cag tat cac ctg gaa gac acc acg ctt ctg    987
Gln Val Val Gln Met Thr Gln Tyr His Leu Glu Asp Thr Thr Leu Leu
                270                 275                 280 atg gag aag atg aga gag cag ttt ggc tgg gtt tct gaa ctg gca tac    1035
Met Glu Lys Met Arg Glu Gln Phe Gly Trp Val Ser Glu Leu Ala Tyr
            285                 290                 295 cag tcc cca gga gct gag gac atc ttt aat cca gtg aaa gta atg gta    1083
Gln Ser Pro Gly Ala Glu Asp Ile Phe Asn Pro Val Lys Val Met Val
        300                 305                 310 gcc cta agt gct cat gaa gga aat tct tct gat caa gat gac aca gtg    1131
Ala Leu Ser Ala His Glu Gly Asn Ser Ser Asp Gln Asp Asp Thr Val
    315                 320                 325 gtt cct tca agc ctc ctg cct tcc tct aac ttc aca ctc agc agc cct    1179
Val Pro Ser Ser Leu Leu Pro Ser Ser Asn Phe Thr Leu Ser Ser Pro
330                 335                 340                 345 ctt gaa aag agt gct ggc aac gct aac ttc att gat cac gtg gta gag    1227
Leu Glu Lys Ser Ala Gly Asn Ala Asn Phe Ile Asp His Val Val Glu
```

-continued

```
                           350                 355                 360
aag gtt ctt cag cac ttt aag gag cac ttt aaa act tgg taagaagatt        1276
Lys Val Leu Gln His Phe Lys Glu His Phe Lys Thr Trp
                365                 370 tagtccatcc tataatcagc aagaattaca ccttcggcca agacctgaga attctgaaaa     1336
tacaaagcag gctaacacaa tgaacacagc tgcatgaaag ttaggtatat attaggaagc     1396
actattggtt tactttgttg aatggaagtt taatagctat tcaaattgag ttaatataaa     1456
aatttcttcc taaaaagtaa aatgtacata tgtagaatat gatgcattag ttctttgtat     1516
actaaataaa tactgagtcc cct                                              1539
```

<210> SEQ ID NO 43
<211> LENGTH: 374
<212> TYPE: PRT
<213> ORGANISM: Cavia sp.

<400> SEQUENCE: 43

```
Met Lys Leu Pro Leu Leu Met Phe Pro Val Cys Leu Leu Trp Leu Lys
 1               5                  10                  15

Asp Cys His Cys Ala Pro Thr Trp Lys Asp Lys Thr Ala Ile Ser Glu
            20                  25                  30

Asn Ala Asn Ser Phe Ser Glu Ala Gly Glu Ile Asp Val Asp Gly Glu
        35                  40                  45

Val Lys Ile Ala Leu Ile Gly Ile Lys Gln Met Lys Ile Met Met Glu
    50                  55                  60

Arg Arg Glu Glu Glu His Ser Lys Leu Met Lys Thr Leu Lys Lys Cys
65                  70                  75                  80

Lys Glu Glu Lys Gln Glu Ala Leu Lys Leu Met Asn Glu Val His Glu
                85                  90                  95

His Leu Glu Glu Glu Ser Leu Cys Gln Val Ser Leu Ala Asp Ser
            100                 105                 110

Trp Asp Glu Cys Arg Ala Cys Leu Glu Ser Asn Cys Met Arg Phe Asp
        115                 120                 125

Thr Thr Cys Gln Pro Ala Trp Ser Ser Val Lys Asn Met Glu Pro Ala
    130                 135                 140

Tyr Arg Ala Asp Ala Glu Pro Ser Trp Ala Ile Pro Asn Val Phe Gln
145                 150                 155                 160

Leu Leu Cys Asn Leu Ser Phe Ser Val Tyr Gln Ser Val Ser Glu Lys
                165                 170                 175

Leu Ile Thr Thr Leu Arg Ala Thr Glu Asp Pro Pro Lys Gln Asp Lys
            180                 185                 190

Asp Ser Asn Gln Gly Gly Pro Ile Ser Lys Ile Leu Pro Glu Gln Asp
        195                 200                 205

Arg Gly Ser Asp Gly Lys Leu Gly Gln Asn Leu Ser Asp Cys Val Asn
    210                 215                 220

Phe Arg Lys Arg Cys Gln Lys Cys Gln Asp Tyr Leu Ser Asp Cys
225                 230                 235                 240

Pro Asn Val Pro Glu Leu Tyr Arg Glu Leu Asn Glu Ala Leu Arg Leu
                245                 250                 255

Val Ser Arg Ser Asn Gln Gln Tyr Asp Gln Val Gln Met Thr Gln
            260                 265                 270

Tyr His Leu Glu Asp Thr Thr Leu Leu Met Glu Lys Met Arg Glu Gln
        275                 280                 285

Phe Gly Trp Val Ser Glu Leu Ala Tyr Gln Ser Pro Gly Ala Glu Asp
```

-continued

```
                        290                 295                 300
Ile Phe Asn Pro Val Lys Val Met Val Ala Leu Ser Ala His Glu Gly
305                 310                 315                 320

Asn Ser Ser Asp Gln Asp Asp Thr Val Val Pro Ser Ser Leu Leu Pro
                325                 330                 335

Ser Ser Asn Phe Thr Leu Ser Ser Pro Leu Glu Lys Ser Ala Gly Asn
            340                 345                 350

Ala Asn Phe Ile Asp His Val Val Glu Lys Val Leu Gln His Phe Lys
        355                 360                 365

Glu His Phe Lys Thr Trp
    370

<210> SEQ ID NO 44
<211> LENGTH: 1536
<212> TYPE: DNA
<213> ORGANISM: Cavia sp.
<220> FEATURE:
<221> NAME/KEY: CDS
<222> LOCATION: (145)...(1263)

<400> SEQUENCE: 44
cttggagtca actgagtgtg gactgaaact tccaaaaact gacatgagga gtcactggag        60
aatcatgatc aaggagctac acactctgac ttaactttat tctgtggaca atgagagaca      120
actgcaagga ttaacagtga gaac atg aag ctg cca ctt ttg atg ttt ccc        171
                            Met Lys Leu Pro Leu Leu Met Phe Pro
                              1               5 gtg tgt ctg cta tgg ttg aaa gac tgt cat tgt gca cct act tgg aag        219
Val Cys Leu Leu Trp Leu Lys Asp Cys His Cys Ala Pro Thr Trp Lys
 10              15                  20                  25 gac aaa act gcc atc agt gaa aac gcg aac agt ttt tct gag gct ggg        267
Asp Lys Thr Ala Ile Ser Glu Asn Ala Asn Ser Phe Ser Glu Ala Gly
             30                  35                  40 gag ata gac gta gat gga gag gtg aag ata gct ttg att ggc att aaa        315
Glu Ile Asp Val Asp Gly Glu Val Lys Ile Ala Leu Ile Gly Ile Lys
         45                  50                  55 cag atg aaa atc atg atg gaa agg aga gag gaa gaa cac agc aaa cta        363
Gln Met Lys Ile Met Met Glu Arg Arg Glu Glu Glu His Ser Lys Leu
     60                  65                  70 atg aaa acc ttg aag aag tgc aaa gaa gaa aag cag gag gcc ctg aaa        411
Met Lys Thr Leu Lys Lys Cys Lys Glu Glu Lys Gln Glu Ala Leu Lys
 75                  80                  85 ctt atg aat gaa gtt cat gaa cac ctg gag gag gaa gaa agc tta tgc        459
Leu Met Asn Glu Val His Glu His Leu Glu Glu Glu Glu Ser Leu Cys
 90                  95                 100                 105 cag gtt tct ctg gca gat tcc tgg gat gaa tgc agg gct tgc ctg gaa        507
Gln Val Ser Leu Ala Asp Ser Trp Asp Glu Cys Arg Ala Cys Leu Glu
             110                 115                 120 agt aac tgc atg agg ttt gat acc acc tgc caa cct gca tgg tcc tct        555
Ser Asn Cys Met Arg Phe Asp Thr Thr Cys Gln Pro Ala Trp Ser Ser
         125                 130                 135 gtg aaa aat atg cca gcc tac aga gca gat gct gag cca agc tgg gcc        603
Val Lys Asn Met Pro Ala Tyr Arg Ala Asp Ala Glu Pro Ser Trp Ala
     140                 145                 150 att ccc aat gtc ttc cag ctg ctc tgc aac ttg agt ttc tca gtt tat        651
Ile Pro Asn Val Phe Gln Leu Leu Cys Asn Leu Ser Phe Ser Val Tyr
155                 160                 165 caa agt gtc agt gaa aaa ctc atc aca acc ctg cgt gcc aca gag gac        699
Gln Ser Val Ser Glu Lys Leu Ile Thr Thr Leu Arg Ala Thr Glu Asp
170                 175                 180                 185
```

```
cct cca aaa caa gac aaa gac tcc aac cag gga ggc ccg att tca aag      747
Pro Pro Lys Gln Asp Lys Asp Ser Asn Gln Gly Gly Pro Ile Ser Lys
            190                 195                 200 ata cta cct gag caa gac aga ggc tca gat ggg aaa ctt ggc cag aat      795
Ile Leu Pro Glu Gln Asp Arg Gly Ser Asp Gly Lys Leu Gly Gln Asn
                205                 210                 215 ttg tct gat tgc gtt aat ttt cgc aag aga tgc cag aaa tgc cag gat      843
Leu Ser Asp Cys Val Asn Phe Arg Lys Arg Cys Gln Lys Cys Gln Asp
            220                 225                 230 tat cta tct gat gac tgc cct aat gtg cct gaa cta tac aga gaa ctc      891
Tyr Leu Ser Asp Asp Cys Pro Asn Val Pro Glu Leu Tyr Arg Glu Leu
        235                 240                 245 aat gag gcc ctc cga ctg gtc agt aga tcc aat cag caa tac gac cag      939
Asn Glu Ala Leu Arg Leu Val Ser Arg Ser Asn Gln Gln Tyr Asp Gln
250                 255                 260                 265 gtg gtg cag atg acc cag tat cac ctg gaa gac acg ctt ctg atg          987
Val Val Gln Met Thr Gln Tyr His Leu Glu Asp Thr Thr Leu Leu Met
                270                 275                 280 gag aag atg aga gag cag ttt ggc tgg gtt tct gaa ctg gca tac cag     1035
Glu Lys Met Arg Glu Gln Phe Gly Trp Val Ser Glu Leu Ala Tyr Gln
            285                 290                 295 tcc cca gga gct gag gac atc ttt aat cca gtg aaa gta atg gta gcc    1083
Ser Pro Gly Ala Glu Asp Ile Phe Asn Pro Val Lys Val Met Val Ala
        300                 305                 310 cta agt gct cat gaa gga aat tct tct gat caa gat gac aca gtg gtt    1131
Leu Ser Ala His Glu Gly Asn Ser Ser Asp Gln Asp Asp Thr Val Val
    315                 320                 325 cct tca agc ctc ctg cct tcc tct aac ttc aca ctc agc agc cct ctt    1179
Pro Ser Ser Leu Leu Pro Ser Ser Asn Phe Thr Leu Ser Ser Pro Leu
330                 335                 340                 345 gaa aag agt gct ggc aac gct aac ttc att gat cac gtg gta gag aag    1227
Glu Lys Ser Ala Gly Asn Ala Asn Phe Ile Asp His Val Val Glu Lys
                350                 355                 360 gtt ctt cag cac ttt aag gag cac ttt aaa act tgg taagaagatt          1273
Val Leu Gln His Phe Lys Glu His Phe Lys Thr Trp
            365                 370 tagtccatcc tataatcagc aagaattaca ccttcggcca agacctgaga attctgaaaa   1333
tacaaagcag gctaacacaa tgaacacagc tgcatgaaag ttaggtatat attaggaagc   1393
actattggtt tactttgttg aatggaagtt taatagctat tcaaattgag ttaatataaa   1453
aatttcttcc taaaaagtaa aatgtacata tgtagaaat gatgcattag ttctttgtat   1513
actaaataaa tactgagtcc cct                                           1536

<210> SEQ ID NO 45
<211> LENGTH: 373
<212> TYPE: PRT
<213> ORGANISM: Cavia sp.

<400> SEQUENCE: 45

Met Lys Leu Pro Leu Leu Met Phe Pro Val Cys Leu Leu Trp Leu Lys
 1               5                  10                  15

Asp Cys His Cys Ala Pro Thr Trp Lys Asp Lys Thr Ala Ile Ser Glu
            20                  25                  30

Asn Ala Asn Ser Phe Ser Glu Ala Gly Glu Ile Asp Val Asp Gly Glu
        35                  40                  45

Val Lys Ile Ala Leu Ile Gly Ile Lys Gln Met Lys Ile Met Met Glu
    50                  55                  60
```

```
Arg Arg Glu Glu Glu His Ser Lys Leu Met Lys Thr Leu Lys Lys Cys
 65                  70                  75                  80

Lys Glu Glu Lys Gln Glu Ala Leu Lys Leu Met Asn Glu Val His Glu
                 85                  90                  95

His Leu Glu Glu Glu Ser Leu Cys Gln Val Ser Leu Ala Asp Ser
                100                 105                 110

Trp Asp Glu Cys Arg Ala Cys Leu Glu Ser Asn Cys Met Arg Phe Asp
                115                 120                 125

Thr Thr Cys Gln Pro Ala Trp Ser Ser Val Lys Asn Met Pro Ala Tyr
130                 135                 140

Arg Ala Asp Ala Glu Pro Ser Trp Ala Ile Pro Asn Val Phe Gln Leu
145                 150                 155                 160

Leu Cys Asn Leu Ser Phe Ser Val Tyr Gln Ser Val Ser Glu Lys Leu
                165                 170                 175

Ile Thr Thr Leu Arg Ala Thr Glu Asp Pro Pro Lys Gln Asp Lys Asp
                180                 185                 190

Ser Asn Gln Gly Gly Pro Ile Ser Lys Ile Leu Pro Glu Gln Asp Arg
                195                 200                 205

Gly Ser Asp Gly Lys Leu Gly Gln Asn Leu Ser Asp Cys Val Asn Phe
210                 215                 220

Arg Lys Arg Cys Gln Lys Cys Gln Asp Tyr Leu Ser Asp Asp Cys Pro
225                 230                 235                 240

Asn Val Pro Glu Leu Tyr Arg Glu Leu Asn Glu Ala Leu Arg Leu Val
                245                 250                 255

Ser Arg Ser Asn Gln Gln Tyr Asp Gln Val Val Gln Met Thr Gln Tyr
                260                 265                 270

His Leu Glu Asp Thr Thr Leu Leu Met Glu Lys Met Arg Glu Gln Phe
                275                 280                 285

Gly Trp Val Ser Glu Leu Ala Tyr Gln Ser Pro Gly Ala Glu Asp Ile
290                 295                 300

Phe Asn Pro Val Lys Val Met Val Ala Leu Ser Ala His Glu Gly Asn
305                 310                 315                 320

Ser Ser Asp Gln Asp Asp Thr Val Val Pro Ser Ser Leu Leu Pro Ser
                325                 330                 335

Ser Asn Phe Thr Leu Ser Ser Pro Leu Glu Lys Ser Ala Gly Asn Ala
                340                 345                 350

Asn Phe Ile Asp His Val Val Glu Lys Val Leu Gln His Phe Lys Glu
                355                 360                 365

His Phe Lys Thr Trp
    370

<210> SEQ ID NO 46
<211> LENGTH: 2464
<212> TYPE: DNA
<213> ORGANISM: Bos sp.

<400> SEQUENCE: 46
gcaacctcgt tggtgagagc ctgcagttag tgtcacggcg aaacatgaa gccgccactc      60 ttggtgttta ttgtgtatct gctgcggctg agagactgtc agtgtgcgcc tacagggaag    120
gaccgaactt ccatccgtga agacccgaag ggttttttcca aggctgggga gatagacgta    180
gatgaagagg tgaagaaggc tttgattggc atgaagcaga tgaaaatcct gatggaaaga    240
agagaggagg aacatagcaa actaatgaga acactgaaga aatgcagaga agaaaagcag    300
gaggccctga agcttatgaa tgaagttcaa gaacatctag aagaggaaga aaggctatgc    360
```

```
caggtgtctc tgatgggttc ctgggacgaa tgcaaatctt gcctggaaag tgactgcatg    420 agatttata caacctgcca aagcagttgg tcctctatga aatccacgat tgaacgggtt    480
ttccggaaga tatatcagtt tctctttcct ttccatgaag acgatgaaaa agagcttcct    540
gttggtgaga agttcactga ggaagatgta cagctgatgc agatagagaa tgtgttcagc    600
cagctgaccg tggatgtggg atttctctat aacatgagct tcacgtctt caaacagatg    660 cagcaagaat ttgacctggc ttttcaatca tactttatgt cagacacaga ctccatggag    720
ccttactttt ttccagcttt ttccaaagag ccagcaaaaa aagcacatcc tatgcagagt    780
tgggacattc ccagcttctt ccagctgttt tgtaatttca gcctctctgt ttatcaaagt    840
gtcagcgcaa cagttacaga gatgctgaag gccattgagg acttatccaa acaagacaaa    900
gattctgccc acgtggacc gagttccacg acgtggcctg tgcggggcag agggctgtgt    960
ggagaacctg gccagaactc gtccgaatgt ctccaatttc atgcaagatg ccagaaatgt    1020
caggattacc tatgggcaga ctgccctgct gttcctgaac tatacacaaa ggcggatgag    1080
gcccttgagt tggtcaacat atccaatcag cagtatgccc aggtactcca gatgacccag    1140
catcacttgg aggacaccac gtatctgatg gagaagatga gagagcagtt tggttgggta    1200
acagagctgg ccagccagac cccaggaagc gagaacatct tcagtttcat aaaggtagtt    1260
ccaggtgttc acgaaggaaa tttctccaaa caagatgaaa agatgataga cataagcatt    1320
ctgccttcct ctaatttcac actcaccatc cctcttgaag aaagtgctga gagttccgac    1380
ttcattagct acatgctggc caaagctgta cagcatttta aggaacattt taaatcttgg    1440
taagcagagt atttgattag ggacgtttgc tgataggaat agatggttct taaaagggaa    1500
aaatgacaaa actagctttt gaataccttg aaaacgtatt caacctcatt aataatcaaa    1560
ggcatgaaaa ctaagacaag ttagcagttt ttacctattg aattttcaaa ttaaaaaaaa    1620
aaatcctgat agaatgcaat gaaatgagaa ttcttatatg tgattgccag aaacaaactg    1680
gttttgtctt tttgaaaagt tattcaatta tacatatcaa gagtcatcaa atttcttttt    1740
aatataataa ttccacttct ggaatcaatc caaaggagta aatctaaaat tgaattgaag    1800
ttcccacccc aagatcaata tttgcaaatt atttaaaata gtaaactgtt aaaaactgaa    1860
tgtcatctga atgtctaaaa accagaaatg gttaaaagct gtggctaaat atgctccaaa    1920
tatcttataa aaccattaaa aatatttata aaatttaaat catgacatga catctgctgg    1980
aacaagagtt tattctaagc ctatctataa ggcaaatatt attattacta tcttccagaa    2040
aagaaacttg agactcaggg tccaagtgtt agttgctcag tcatgtctga ctctttggga    2100
ccccttggac tgtagcccac caggctcctc tgtccgtggg attcttcaga caggaatact    2160
ggggcaggtt gctatttcct tctccaggaa atcttcccta tccagggatg gaacccaggt    2220
ctcctgcatt gcaggtagat gctttactat ctgagcaacc aaatgaatta ctcaagtcag    2280 taggggtag aggcaaattt taacttagtt ttctctgaat cataattgcc acattaaact    2340
ggttcctgtt gggacatttg gttgaaaaaa ataaagtgaa aaatgagtat aaaactctat    2400
aaatgtaatg atcaaaacga aaaaaaatct acaatctgca ttaaaaataa aaagggttgg    2460
cagg                                                                2464
```

<210> SEQ ID NO 47
<211> LENGTH: 3016
<212> TYPE: DNA
<213> ORGANISM: Bos sp.

-continued

```
<400> SEQUENCE: 47
cagaagctgg tggcaacctc gttggtgaga gcctgcagtt agtgtcacgg cggaaacatg      60
aagccgccac tcttggtgtt tattgtgtat ctgctgcggc tgagagactg tcagtgtgcg     120
cctacaggga aggaccgaac ttccatccgt gaagacccga agggttttc caaggctggg     180
gagatagacg tagatgaaga ggtgaagaag gctttgattg gcatgaagca gatgaaaatc     240
ctgatggaaa gaagagagga ggaacatagc aaactaatga gaacactgaa gaaatgcaga     300
gaagaaaagc aggaggccct gaagcttatg aatgaagttc aagaacatct agaagaggaa     360
gaaaggctat gccaggtgtc tctgatgggt tcctgggacg aatgcaaatc ttgcctggaa     420
agtgactgca tgagatttta tacaacctgc caaagcagtt ggtcctctat gaaatccacg     480
attgaacggg ttttccggaa gatatatcag tttctctttc ctttccatga agacgatgaa     540
aaagagcttc ctgttggtga agttcact gaggaagatg tacagctgat gcagatagag     600
aatgtgttca gccagctgac cgtggatgtg ggatttctct ataacatgag ctttcacgtc     660
ttcaaacaga tgcagcaaga atttgacctg gcttttcaat catactttat gtcagacaca     720
gactccatgg agccttactt ttttccagct tttttccaaag agccagcaaa aaaagcacat     780
cctatgcaga gttgggacat tcccagcttc ttccagctgt tttgtaattt cagcctctct     840
gtttatcaaa gtgtcagcgc aacagttaca gagatgctga aggccattga ggacttatcc     900
aaacaagaca aagattctgc ccacggtgga ccgagttcca cgacgtggcc tgtgcggggc     960
agaggctgt gtggagaacc tggccagaac tcgtccgaat gtctccaatt tcatgcaaga    1020
tgccagaaat gtcaggatta cctatgggca gactgccctg ctgttcctga actatacaca    1080
aaggcggatg aggcccttga gttggtcaac atatccaatc agcagtatgc ccaggtactc    1140
cagatgaccc agcatcactt ggaggacacc acgtatctga tggagaagat gagagagcag    1200
tttggttggg taacagagct ggccagccag accccaggaa gcgagaacat cttcagtttc    1260
ataaaggtag ttccaggtgt tcacgaagga aatttctcca acaagatgaa aagatgata    1320
gacataagca ttctgccttc ctctaatttc acactcacca tccctcttga gaaagtgct    1380
gagagttccg acttcattag ctacatgctg gccaaagctg tacagcattt taaggaacat    1440
tttaaatctt ggtaagcaga gtatttgatt agggacgttt gctgatagga atagatggtt    1500
cttaaaaggg aaaaatgaca aaactagctt ttgaatacct tgaaaacgta ttcaacctca    1560
ttaataatca aaggcatgaa aactaagaca agttagcagt ttttacctat tgaattttca    1620
aattaaaaaa aaaaatcctg atagaatgca atgaaatgag aattcttata tgtgattgcc    1680
agaaacaaac tggttttgtc tttttgaaaa gttattcaat tatacatatc aagagtcatc    1740
aaatttcttt ttaatataat aattccactt ctggaatcaa tccaaaggag taaatctaaa    1800
attgaattga agttcccacc ccaagatcaa tatttgcaaa ttatttaaaa tagtaaactg    1860
ttaaaaactg aatgtcatct gaatgtctaa aaaccagaaa tggttaaaag ctgtggctaa    1920
atatgctcca aatatcttat aaaaccatta aaaatattta taaaatttaa atcatgacat    1980
gacatctgct ggaacaagag tttattctaa gcctatctat aaggcaaata ttattattac    2040
tatcttccag aaaagaaact tgagactcag ggtccaagtg ttagttgctc agtcatgtct    2100
gactctttga gaccccttgg actgtggccc accaggctcc tctgtccatg ggattcttca    2160
gacaagaata ctggagcagg ttgctatttc cttctccagg aaatcttccc tatccaggga    2220
tggaacccag gtcctgca ttgcaggtag atgcttact atctgagcaa ccaaatgaat    2280
tactcaagtc agtaggggt agaggcaaat tttaacttag ttttctctga atcataattg    2340
```

-continued

```
ccacattaaa ctggttcctg ttgggacatt tggttgaaaa aaataaagtg aaaaatgagt      2400
ataaaactct ataaatgtaa tgatcaaaac gaaaaaaaat ctacaatctg cattaaaaat      2460
aaaaagggtt ggcaggaatt acggttggaa atggatgatt ttttttaacc ttttcatctt      2520
ttgatatttt acaattttct ataatgaata ataattttg agatttcaaa ttagaagata       2580
tgttgctaaa atagctaggt aaatgtagat tgaacactgt atcaatgtgt tctcatcttt      2640
aaactttagt ataagtactt ctattccatg gtaatcctac agtaagacga aatgtaaatc      2700
tgttcggtct acaggaaaaa caactaaatg acatttcaga cgtacattac catctctgtt      2760
aggataatct tctgaattaa tggcacaatt agaactgtac atagtattct cctttggtaa      2820
aatggtcaat cttaaagaag cattaaatgt taattctaag ttattactca taagggacct      2880
tgtaggtagg tccctatcaa tgtataatta agctgggtat ttctagattc gctgcctctc      2940
cctttatctc tgaatgttgg agaggttgtt ggtcatcaat caaccaatat cttttagca       3000 tcttctaagt gaaggc                                                      3016
```

```
<210> SEQ ID NO 48
<211> LENGTH: 2488
<212> TYPE: DNA
<213> ORGANISM: Bos sp.
<220> FEATURE:
<221> NAME/KEY: CDS
<222> LOCATION: (71)...(1465)

<400> SEQUENCE: 48
gtgaaggtcc ttacagaagc tggtggcaac ctcgttggtg agagcctgca gttagtgtca       60
cggcggaaac atg aag ccg cca atc ttg gtg ttt atc gtg tat ctg ctg         109
            Met Lys Pro Pro Ile Leu Val Phe Ile Val Tyr Leu Leu
              1               5                  10 cag ctg aga gac tgt cag tgt gcg cct aca ggg aag gac cga act tcc        157
Gln Leu Arg Asp Cys Gln Cys Ala Pro Thr Gly Lys Asp Arg Thr Ser
         15                  20                  25 atc cgt gaa gac ccg aag ggt ttt tcc aag gct ggg gag ata gac gta        205
Ile Arg Glu Asp Pro Lys Gly Phe Ser Lys Ala Gly Glu Ile Asp Val
 30                  35                  40                  45 gat gaa gag gtg aag aag gct ttg att ggc atg aag cag atg aaa atc        253
Asp Glu Glu Val Lys Lys Ala Leu Ile Gly Met Lys Gln Met Lys Ile
                 50                  55                  60 ctg atg gaa aga aga gag gag gaa cat agc aaa cta atg aga acc ctg        301
Leu Met Glu Arg Arg Glu Glu Glu His Ser Lys Leu Met Arg Thr Leu
             65                  70                  75 aag aaa tgc aga gaa gaa aag cag gag gcc ctg aag ctt atg aat gaa        349
Lys Lys Cys Arg Glu Glu Lys Gln Glu Ala Leu Lys Leu Met Asn Glu
         80                  85                  90 gtt caa gaa cat cta gaa gag gaa gaa agg cta tgc cag gtg tct ctg        397
Val Gln Glu His Leu Glu Glu Glu Glu Arg Leu Cys Gln Val Ser Leu
     95                  100                 105 atg ggt tcc tgg gac gaa tgc aaa tct tgc ctg gaa agt gac tgc atg        445
Met Gly Ser Trp Asp Glu Cys Lys Ser Cys Leu Glu Ser Asp Cys Met
110                 115                 120                 125 aga ttt tat aca acc tgc caa agc agt tgg tcc tct atg aaa tcc acg        493
Arg Phe Tyr Thr Thr Cys Gln Ser Ser Trp Ser Ser Met Lys Ser Thr
                 130                 135                 140 att gaa cgg gtt ttc cgg aag ata tat cag ttt ctc ttt cct ttc cat        541
Ile Glu Arg Val Phe Arg Lys Ile Tyr Gln Phe Leu Phe Pro Phe His
             145                 150                 155 gaa gac gat gaa aaa gag ctt cct gtt ggt gag aag ttc act gag gaa        589
```

```
                Glu Asp Asp Glu Lys Glu Leu Pro Val Gly Glu Lys Phe Thr Glu Glu
                        160                 165                 170 gat gta cag ctg atg cag ata gag aat gtg ttc agc cag ctg acc gtg        637
Asp Val Gln Leu Met Gln Ile Glu Asn Val Phe Ser Gln Leu Thr Val
    175                 180                 185 gac gtg gga ttt ctc tat aac atg agc ttt cac gtc ttc aaa cag atg        685
Asp Val Gly Phe Leu Tyr Asn Met Ser Phe His Val Phe Lys Gln Met
190                 195                 200                 205 cag caa gaa ttt gac ctg gct ttt caa tca tac ttt atg tca gac aca        733
Gln Gln Glu Phe Asp Leu Ala Phe Gln Ser Tyr Phe Met Ser Asp Thr
                210                 215                 220 gac tcc atg gag cct tac ttt ttt cca gct ttt tcc aaa gag cca gca        781
Asp Ser Met Glu Pro Tyr Phe Phe Pro Ala Phe Ser Lys Glu Pro Ala
            225                 230                 235 aaa aaa gca cat cct atg cag agt tgg gac att ccc agc ttc ttc cag        829
Lys Lys Ala His Pro Met Gln Ser Trp Asp Ile Pro Ser Phe Phe Gln
        240                 245                 250 ctg ttt tgt aat ttc agc ctc tct gtt tat caa agt gtc agc gca aca        877
Leu Phe Cys Asn Phe Ser Leu Ser Val Tyr Gln Ser Val Ser Ala Thr
    255                 260                 265 gtt aca gag atg ctg aag gcc att gag gac tta tcc aaa caa gac aaa        925
Val Thr Glu Met Leu Lys Ala Ile Glu Asp Leu Ser Lys Gln Asp Lys
270                 275                 280                 285 gat tct gcc cac ggt gga ccg agt tcc acg acg tgg cct gtg cgg ggc        973
Asp Ser Ala His Gly Gly Pro Ser Ser Thr Thr Trp Pro Val Arg Gly
                290                 295                 300 aga ggg ctg tgt gga gaa cct ggc cag aac tcg tcc gaa tgt ctc caa       1021
Arg Gly Leu Cys Gly Glu Pro Gly Gln Asn Ser Ser Glu Cys Leu Gln
            305                 310                 315 ttt cat gca aga tgc cag aaa tgt cag gat tac cta tgg gca gac tgc       1069
Phe His Ala Arg Cys Gln Lys Cys Gln Asp Tyr Leu Trp Ala Asp Cys
        320                 325                 330 cct gct gtt cct gaa cta tac aca aag gcg gat gag gcc ctt gag ttg       1117
Pro Ala Val Pro Glu Leu Tyr Thr Lys Ala Asp Glu Ala Leu Glu Leu
    335                 340                 345 gtc aac ata tcc aat cag cag tat gcc cag gta ctc cag atg acc cag       1165
Val Asn Ile Ser Asn Gln Gln Tyr Ala Gln Val Leu Gln Met Thr Gln
350                 355                 360                 365 cat cac ttg gag gac acc acg tat ctg atg gag aag atg aga gag cag       1213
His His Leu Glu Asp Thr Thr Tyr Leu Met Glu Lys Met Arg Glu Gln
                370                 375                 380 ttt ggt tgg gta aca gag ctg gcc agc cag acc cca gga agc gag aac       1261
Phe Gly Trp Val Thr Glu Leu Ala Ser Gln Thr Pro Gly Ser Glu Asn
            385                 390                 395 atc ttc agt ttc ata aag gta gtt cca ggt gtt cac gaa gga aat ttc       1309
Ile Phe Ser Phe Ile Lys Val Val Pro Gly Val His Glu Gly Asn Phe
        400                 405                 410 tcc aaa caa gat gaa aag atg ata gac ata agc att ctg cct tcc tct       1357
Ser Lys Gln Asp Glu Lys Met Ile Asp Ile Ser Ile Leu Pro Ser Ser
    415                 420                 425 aat ttc aca ctc acc atc cct ctt gaa gaa agt gct gag agt tcc gac       1405
Asn Phe Thr Leu Thr Ile Pro Leu Glu Glu Ser Ala Glu Ser Ser Asp
430                 435                 440                 445 ttc att agc tac atg ctg gcc aaa gct gta cag cat ttt aag gaa cat       1453
Phe Ile Ser Tyr Met Leu Ala Lys Ala Val Gln His Phe Lys Glu His
                450                 455                 460 ttt aaa tct tgg taagcagagt atttgattag ggacgtttgc tgataggaat          1505
Phe Lys Ser Trp
            465
```

```
agatggttct taaaagggaa aaatgacaaa actagctttt gaataccttg aaaacgtatt    1565
caacctcatt aataatcaaa ggcatgaaaa ctaagacaag ttagcagttt ttacctattg    1625
aattttcaaa ttaaaaaaaa aatcctgata gaatgcaatg aaatgagaat tcttatatgt    1685
gattgccaga acaaactgg ttttgtcttt ttgaaaagtt attcaattat acatatcaag     1745
agtcatcaaa tttcttttta atataataat tccacttctg gaatcaatcc aaaggagtaa    1805
atctaaaatt gaattgaagt tcccacccca agatcaatat ttgcaaatta tttaaaatag   1865
taaactgtta aaaactgaat gtcatctgaa tgtctaaaaa ccagaaatgg ttaaaagctg    1925
tggctaaata tgctccaaat atcttataaa accattaaaa atatttataa aatttaaatc    1985
atgacatgac atctgctgga acaagagttt attctaagcc tatctataag gcaaatatta    2045
ttattactat cttccagaaa agaaacttga gactcagggt ccaagtgtta gttgctcagt    2105
catgtctgac tctttgagac cccttggact gtagcccacc aggctcctct gtccatggga    2165
ttcttcagac aagaatactg gagcaggttg ctatttcctt ctccaggaaa tcttccctat    2225
ccagggatgg aacccaggtc tcctgcattg caggtagatg ctttactatc tgagcaacca    2285
aatgaattac tcaagtcagt aggggtaga ggcaatttt aacttagttt tctctgaatc     2345
ataattgcca cattaaactg gttcctgttg ggacatttgg ttgaaaaaaa taaagtgaaa    2405
aatgagtata aaactctata aatgtaatga tcaaaacgaa aaaaaatcta caatctgcat    2465
taaaaataaa aagggttggc agg                                           2488
```

<210> SEQ ID NO 49
<211> LENGTH: 465
<212> TYPE: PRT
<213> ORGANISM: Bos sp.

<400> SEQUENCE: 49

```
Met Lys Pro Pro Ile Leu Val Phe Ile Val Tyr Leu Leu Gln Leu Arg
 1               5                  10                  15

Asp Cys Gln Cys Ala Pro Thr Gly Lys Asp Arg Thr Ser Ile Arg Glu
            20                  25                  30

Asp Pro Lys Gly Phe Ser Lys Ala Gly Glu Ile Asp Val Asp Glu Glu
        35                  40                  45

Val Lys Lys Ala Leu Ile Gly Met Lys Gln Met Lys Ile Leu Met Glu
    50                  55                  60

Arg Arg Glu Glu His Ser Lys Leu Met Arg Thr Leu Lys Lys Cys
65                  70                  75                  80

Arg Glu Glu Lys Gln Glu Ala Leu Lys Leu Met Asn Glu Val Gln Glu
                85                  90                  95

His Leu Glu Glu Glu Arg Leu Cys Gln Val Ser Leu Met Gly Ser
            100                 105                 110

Trp Asp Glu Cys Lys Ser Cys Leu Glu Ser Asp Cys Met Arg Phe Tyr
        115                 120                 125

Thr Thr Cys Gln Ser Ser Trp Ser Ser Met Lys Ser Thr Ile Glu Arg
    130                 135                 140

Val Phe Arg Lys Ile Tyr Gln Phe Leu Phe Pro Phe His Glu Asp Asp
145                 150                 155                 160

Glu Lys Glu Leu Pro Val Gly Glu Lys Phe Thr Glu Asp Val Gln
                165                 170                 175

Leu Met Gln Ile Glu Asn Val Phe Ser Gln Leu Thr Val Asp Val Gly
            180                 185                 190

Phe Leu Tyr Asn Met Ser Phe His Val Phe Lys Gln Met Gln Gln Glu
```

```
                 195                 200                 205
    Phe Asp Leu Ala Phe Gln Ser Tyr Phe Met Ser Asp Thr Asp Ser Met
                     210                 215                 220

Glu Pro Tyr Phe Phe Pro Ala Phe Ser Lys Pro Ala Lys Lys Ala
    225                 230                 235                 240

His Pro Met Gln Ser Trp Asp Ile Pro Ser Phe Phe Gln Leu Phe Cys
                    245                 250                 255

Asn Phe Ser Leu Ser Val Tyr Gln Ser Val Ser Ala Thr Val Thr Glu
                    260                 265                 270

Met Leu Lys Ala Ile Glu Asp Leu Ser Lys Gln Asp Lys Asp Ser Ala
                    275                 280                 285

His Gly Gly Pro Ser Ser Thr Thr Trp Pro Val Arg Gly Arg Gly Leu
                    290                 295                 300

Cys Gly Glu Pro Gly Gln Asn Ser Ser Glu Cys Leu Gln Phe His Ala
    305                 310                 315                 320

Arg Cys Gln Lys Cys Gln Asp Tyr Leu Trp Ala Asp Cys Pro Ala Val
                    325                 330                 335

Pro Glu Leu Tyr Thr Lys Ala Asp Glu Ala Leu Glu Leu Val Asn Ile
                    340                 345                 350

Ser Asn Gln Gln Tyr Ala Gln Val Leu Gln Met Thr Gln His His Leu
                    355                 360                 365

Glu Asp Thr Thr Tyr Leu Met Glu Lys Met Arg Glu Gln Phe Gly Trp
    370                 375                 380

Val Thr Glu Leu Ala Ser Gln Thr Pro Gly Ser Glu Asn Ile Phe Ser
    385                 390                 395                 400

Phe Ile Lys Val Val Pro Gly Val His Glu Gly Asn Phe Ser Lys Gln
                    405                 410                 415

Asp Glu Lys Met Ile Asp Ile Ser Ile Leu Pro Ser Ser Asn Phe Thr
                    420                 425                 430

Leu Thr Ile Pro Leu Glu Glu Ser Ala Glu Ser Ser Asp Phe Ile Ser
                    435                 440                 445

Tyr Met Leu Ala Lys Ala Val Gln His Phe Lys Glu His Phe Lys Ser
        450                 455                 460

Trp
    465

<210> SEQ ID NO 50
<211> LENGTH: 8
<212> TYPE: PRT
<213> ORGANISM: Homo sapiens

<400> SEQUENCE: 50

Asp Tyr Lys Asp Asp Asp Asp Lys
1               5

<210> SEQ ID NO 51
<211> LENGTH: 446
<212> TYPE: PRT
<213> ORGANISM: Homo sapiens

<400> SEQUENCE: 51

Ala Pro Thr Trp Lys Asp Lys Thr Ala Ile Ser Glu Asn Leu Lys Ser
1               5                   10                  15

Phe Ser Glu Val Gly Glu Ile Asp Ala Asp Glu Glu Val Lys Lys Ala
                20                  25                  30

Leu Thr Gly Ile Lys Gln Met Lys Ile Met Glu Arg Lys Glu Lys
```

```
              35                  40                  45
Glu His Thr Asn Leu Met Ser Thr Leu Lys Lys Cys Arg Glu Glu Lys
        50                  55                  60
Gln Glu Ala Leu Lys Leu Leu Asn Glu Val Gln Glu His Leu Glu Glu
 65                  70                  75                  80
Glu Glu Arg Leu Cys Arg Glu Ser Leu Ala Asp Ser Trp Gly Glu Cys
                85                  90                  95
Arg Ser Cys Leu Glu Asn Asn Cys Met Arg Ile Tyr Thr Thr Cys Gln
               100                 105                 110
Pro Ser Trp Ser Ser Val Lys Asn Lys Ile Glu Arg Phe Phe Arg Lys
               115                 120                 125
Ile Tyr Gln Phe Leu Phe Pro Phe His Glu Asp Asn Glu Lys Asp Leu
           130                 135                 140
Pro Ile Ser Glu Lys Leu Ile Glu Glu Asp Ala Gln Leu Thr Gln Met
145                 150                 155                 160
Glu Asp Val Phe Ser Gln Leu Thr Val Asp Val Asn Ser Leu Phe Asn
               165                 170                 175
Arg Ser Phe Asn Val Phe Arg Gln Met Gln Gln Glu Phe Asp Gln Thr
           180                 185                 190
Phe Gln Ser His Phe Ile Ser Asp Thr Asp Leu Thr Glu Pro Tyr Phe
           195                 200                 205
Phe Pro Ala Phe Ser Lys Glu Pro Met Thr Lys Ala Asp Leu Glu Gln
210                 215                 220
Cys Trp Asp Ile Pro Asn Phe Phe Gln Leu Phe Cys Asn Phe Ser Val
225                 230                 235                 240
Ser Ile Tyr Glu Ser Val Ser Glu Thr Ile Thr Lys Met Leu Lys Ala
               245                 250                 255
Ile Glu Asp Leu Pro Lys Gln Asp Lys Ala Pro Asp His Gly Gly Leu
           260                 265                 270
Ile Ser Lys Met Leu Pro Gly Gln Asp Arg Gly Leu Cys Gly Glu Leu
           275                 280                 285
Asp Gln Asn Leu Ser Arg Cys Phe Lys Phe His Glu Lys Cys Gln Lys
           290                 295                 300
Cys Gln Ala His Leu Ser Glu Asp Cys Pro Asp Val Pro Ala Leu His
305                 310                 315                 320
Thr Glu Leu Asp Glu Ala Ile Arg Leu Val Asn Val Ser Asn Gln Gln
               325                 330                 335
Tyr Gly Gln Ile Leu Gln Met Thr Arg Lys His Leu Glu Asp Thr Ala
           340                 345                 350
Tyr Leu Val Glu Lys Met Arg Gly Gln Phe Gly Trp Val Ser Glu Leu
           355                 360                 365
Ala Asn Gln Ala Pro Glu Thr Glu Ile Ile Phe Asn Ser Ile Gln Val
370                 375                 380
Val Pro Arg Ile His Glu Gly Asn Ile Ser Lys Gln Asp Glu Thr Met
385                 390                 395                 400
Met Thr Asp Leu Ser Ile Leu Pro Ser Ser Asn Phe Thr Leu Lys Ile
               405                 410                 415
Pro Leu Glu Glu Ser Ala Glu Ser Ser Asn Phe Ile Gly Tyr Val Val
           420                 425                 430
Ala Lys Ala Leu Gln His Phe Lys Glu His Phe Lys Thr Trp
           435                 440                 445

<210> SEQ ID NO 52
```

```
<211> LENGTH: 44
<212> TYPE: DNA
<213> ORGANISM: Artificial Sequence
<220> FEATURE:
<223> OTHER INFORMATION: Primer

<400> SEQUENCE: 52
tttttctgaa ttcgccacca tgaaaattaa agcagagaaa aacg                44

<210> SEQ ID NO 53
<211> LENGTH: 69
<212> TYPE: DNA
<213> ORGANISM: Artificial Sequence
<220> FEATURE:
<223> OTHER INFORMATION: Primer

<400> SEQUENCE: 53
tttttgtcga cttatcactt gtcgtcgtcg tccttgtagt cccaggtttt aaaatgttcc      60
ttaaaatgc                                                             69

<210> SEQ ID NO 54
<211> LENGTH: 40
<212> TYPE: DNA
<213> ORGANISM: Artificial Sequence
<220> FEATURE:
<223> OTHER INFORMATION: Primer

<400> SEQUENCE: 54
tttttctgaa ttcaccatga ggacctggga ctacagtaac                40

<210> SEQ ID NO 55
<211> LENGTH: 41
<212> TYPE: DNA
<213> ORGANISM: Artificial Sequence
<220> FEATURE:
<223> OTHER INFORMATION: Primer

<400> SEQUENCE: 55
tttttctctc gagaccatga aaattaaagc agagaaaaac g                41

<210> SEQ ID NO 56
<211> LENGTH: 47
<212> TYPE: DNA
<213> ORGANISM: Artificial Sequence
<220> FEATURE:
<223> OTHER INFORMATION: Primer

<400> SEQUENCE: 56
tttttggatc cgctgctgcc caggttttaa aatgttcctt aaaatgc            47

<210> SEQ ID NO 57
<211> LENGTH: 40
<212> TYPE: DNA
<213> ORGANISM: Primer

<400> SEQUENCE: 57
tttttctctc gagaccatga ggacctggga ctacagtaac                40

<210> SEQ ID NO 58
<211> LENGTH: 37
<212> TYPE: DNA
<213> ORGANISM: Artificial Sequence
<220> FEATURE:
<223> OTHER INFORMATION: Primer

<400> SEQUENCE: 58
```
tttttctgaa ttcaccatga agccgccact cttggtg					37

<210> SEQ ID NO 59
<211> LENGTH: 60
<212> TYPE: DNA
<213> ORGANISM: Artificial Sequence
<220> FEATURE:
<223> OTHER INFORMATION: Primer

<400> SEQUENCE: 59
tttttggatc cgctgcggcc tccgtggtca ggagcttatt tttcacagag gaccagctag					60

<210> SEQ ID NO 60
<211> LENGTH: 36
<212> TYPE: DNA
<213> ORGANISM: Artificial Sequence
<220> FEATURE:
<223> OTHER INFORMATION: Primer

<400> SEQUENCE: 60
tttttctctc gaggactaca ggacacagct aaatcc					36

<210> SEQ ID NO 61
<211> LENGTH: 45
<212> TYPE: DNA
<213> ORGANISM: Artificial Sequence
<220> FEATURE:
<223> OTHER INFORMATION: Primer

<400> SEQUENCE: 61
tttttggatc cttatcacca ggttttaaaa tgttccttaa aatgc					45

<210> SEQ ID NO 62
<211> LENGTH: 37
<212> TYPE: DNA
<213> ORGANISM: Artificial Sequence
<220> FEATURE:
<223> OTHER INFORMATION: Primer

<400> SEQUENCE: 62
tttttctgaa ttcaccatga agccgccact cttggtg					37

<210> SEQ ID NO 63
<211> LENGTH: 40
<212> TYPE: DNA
<213> ORGANISM: Artificial Sequence
<220> FEATURE:
<223> OTHER INFORMATION: Primer

<400> SEQUENCE: 63
tttttctctc gagaccatga ggacctggga ctacagtaac					40

<210> SEQ ID NO 64
<211> LENGTH: 466
<212> TYPE: PRT
<213> ORGANISM: Homo sapiens

<400> SEQUENCE: 64

Met Lys Pro Pro Leu Leu Val Phe Ile Val Cys Leu Leu Trp Leu Lys
 1               5                  10                  15

Asp Ser His Cys Ala Pro Thr Trp Lys Asp Lys Thr Ala Ile Ser Glu
            20                  25                  30

Asn Leu Lys Ser Phe Ser Glu Val Gly Glu Ile Asp Ala Asp Glu Glu
        35                  40                  45

```
Val Lys Lys Ala Leu Thr Gly Ile Lys Gln Met Lys Ile Met Met Glu
    50                  55                  60

Arg Lys Glu Lys Glu His Thr Asn Leu Met Ser Thr Leu Lys Lys Cys
65                  70                  75                  80

Arg Glu Glu Lys Gln Glu Ala Leu Lys Leu Leu Asn Glu Val Gln Glu
                85                  90                  95

His Leu Glu Glu Glu Arg Leu Cys Arg Glu Ser Leu Ala Asp Ser
                100                 105                 110

Trp Gly Glu Cys Arg Ser Cys Leu Glu Asn Asn Cys Met Arg Ile Tyr
            115                 120                 125

Thr Thr Cys Gln Pro Ser Trp Ser Ser Val Lys Asn Lys Ile Glu Arg
        130                 135                 140

Phe Phe Arg Lys Ile Tyr Gln Phe Leu Phe Pro Phe His Glu Asp Asn
145                 150                 155                 160

Glu Lys Asp Leu Pro Ile Ser Glu Lys Leu Ile Glu Glu Asp Ala Gln
                165                 170                 175

Leu Thr Gln Met Glu Asp Val Phe Ser Gln Leu Thr Val Asp Val Asn
            180                 185                 190

Ser Leu Phe Asn Arg Ser Phe Asn Val Phe Arg Gln Met Gln Gln Glu
        195                 200                 205

Phe Asp Gln Thr Phe Gln Ser His Phe Ile Ser Asp Thr Asp Leu Thr
210                 215                 220

Glu Pro Tyr Phe Phe Pro Ala Phe Ser Lys Glu Pro Met Thr Lys Ala
225                 230                 235                 240

Asp Leu Glu Gln Cys Trp Asp Ile Pro Asn Phe Phe Gln Leu Phe Cys
            245                 250                 255

Asn Phe Ser Val Ser Ile Tyr Glu Ser Val Ser Glu Thr Ile Thr Lys
            260                 265                 270

Met Leu Lys Ala Ile Glu Asp Leu Pro Lys Gln Asp Lys Ala Pro Asp
        275                 280                 285

His Gly Gly Leu Ile Ser Lys Met Leu Pro Gly Gln Asp Arg Gly Leu
        290                 295                 300

Cys Gly Glu Leu Asp Gln Asn Leu Ser Arg Cys Phe Lys Phe His Glu
305                 310                 315                 320

Lys Cys Gln Lys Cys Gln Ala His Leu Ser Glu Asp Cys Pro Asp Val
                325                 330                 335

Pro Ala Leu His Thr Glu Leu Asp Glu Ala Ile Arg Leu Val Asn Val
            340                 345                 350

Ser Asn Gln Gln Tyr Gly Gln Ile Leu Gln Met Thr Arg Lys His Leu
        355                 360                 365

Glu Asp Thr Ala Tyr Leu Val Glu Lys Met Arg Gly Gln Phe Gly Trp
    370                 375                 380

Val Ser Glu Leu Ala Asn Gln Ala Pro Glu Thr Glu Ile Ile Phe Asn
385                 390                 395                 400

Ser Ile Gln Val Val Pro Arg Ile His Glu Gly Asn Ile Ser Lys Gln
                405                 410                 415

Asp Glu Thr Met Met Thr Asp Leu Ser Ile Leu Pro Ser Ser Asn Phe
            420                 425                 430

Thr Leu Lys Ile Pro Leu Glu Glu Ser Ala Glu Ser Ser Asn Phe Ile
        435                 440                 445

Gly Tyr Val Val Ala Lys Ala Leu Gln His Phe Lys Glu His Phe Lys
    450                 455                 460
```

-continued

```
Thr Trp
465

<210> SEQ ID NO 65
<211> LENGTH: 1622
<212> TYPE: DNA
<213> ORGANISM: Homo sapiens
<220> FEATURE:
<221> NAME/KEY: CDS
<222> LOCATION: (3)...(1622)

<400> SEQUENCE: 65 tg cgt cac ctg cag gcc cgg gcc gcg ggg ttg gtt tcc acc ctg gag      47
   Arg His Leu Gln Ala Arg Ala Ala Gly Leu Val Ser Thr Leu Glu
   1               5                  10                  15 gtt gct gac acc ctg tgc cct cgg ctg act tcc agc cgg tgg cac aga     95
Val Ala Asp Thr Leu Cys Pro Arg Leu Thr Ser Ser Arg Trp His Arg
             20                  25                  30 cgc ctc cag ggg gca gca ctc aag cgc atc tta gga atg aca gag ttg    143
Arg Leu Gln Gly Ala Ala Leu Lys Arg Ile Leu Gly Met Thr Glu Leu
         35                  40                  45 cgt ccc tct ctg ttg cca ggc tgg agt tca gtg gca tgt tct tag ctc    191
Arg Pro Ser Leu Leu Pro Gly Trp Ser Ser Val Ala Cys Ser  *  Leu
     50                  55                  60 act gaa gcc tca aat tcc tgg gtt caa gtg acc ctc cca cct cag ccc    239
Thr Glu Ala Ser Asn Ser Trp Val Gln Val Thr Leu Pro Pro Gln Pro
             65                  70                  75 cat gag gac ctg gga cta cag gac aca gct aaa tcc ctg aca cgg atg    287
His Glu Asp Leu Gly Leu Gln Asp Thr Ala Lys Ser Leu Thr Arg Met
         80                  85                  90 aaa att aaa gca gag aaa aac gaa ggt cct tcc aga agc tgg tgg caa    335
Lys Ile Lys Ala Glu Lys Asn Glu Gly Pro Ser Arg Ser Trp Trp Gln
95                  100                 105                 110 ctt cac tgg gga gat att gca aat aac agc ggg aac atg aag ccg cca    383
Leu His Trp Gly Asp Ile Ala Asn Asn Ser Gly Asn Met Lys Pro Pro
                115                 120                 125 ctc ttg gtg ttt att gtg tgt ctg ctg tgg ttg aaa gac agt cac tgc    431
Leu Leu Val Phe Ile Val Cys Leu Leu Trp Leu Lys Asp Ser His Cys
            130                 135                 140 gca ccc act tgg aag gac aaa act gct atc agt gaa aac ctg aag agt    479
Ala Pro Thr Trp Lys Asp Lys Thr Ala Ile Ser Glu Asn Leu Lys Ser
        145                 150                 155 ttt tct gag gtg ggg gag ata gat gca gat gaa gag gtg aag aag gct    527
Phe Ser Glu Val Gly Glu Ile Asp Ala Asp Glu Glu Val Lys Lys Ala
    160                 165                 170 ttg act ggt att aag caa atg aaa atc atg atg gaa aga aaa gag aag    575
Leu Thr Gly Ile Lys Gln Met Lys Ile Met Met Glu Arg Lys Glu Lys
175                 180                 185                 190 gaa cac acc aat cta atg agc acc ctg aag aaa tgc aga gaa gaa aag    623
Glu His Thr Asn Leu Met Ser Thr Leu Lys Lys Cys Arg Glu Glu Lys
                195                 200                 205 cag gag gcc ctg aaa ctt ctg aat gaa gtt caa gaa cat ctg gag gaa    671
Gln Glu Ala Leu Lys Leu Leu Asn Glu Val Gln Glu His Leu Glu Glu
            210                 215                 220 gaa gaa agg cta tgc cgg gag tct ttg gca gat tcc tgg ggt gaa tgc    719
Glu Glu Arg Leu Cys Arg Glu Ser Leu Ala Asp Ser Trp Gly Glu Cys
        225                 230                 235 agg tct tgc ctg gaa aat aac tgc atg aga att tat aca acc tgc caa    767
Arg Ser Cys Leu Glu Asn Asn Cys Met Arg Ile Tyr Thr Thr Cys Gln
    240                 245                 250 cct agc tgg tcc tct gtg aaa aat aag ctc ctg acc acg gag gcc tga    815
```

```
Pro Ser Trp Ser Ser Val Lys Asn Lys Leu Leu Thr Thr Glu Ala
255                 260                 265 ttt caa aga tgt tac ctg ggc agg aca gag gac tgt gtg ggg aac ttg      863
Phe Gln Arg Cys Tyr Leu Gly Arg Thr Glu Asp Cys Val Gly Asn Leu
270                 275                 280                 285 acc aga att tgt caa gat gtt tca aat ttc atg aaa aat gcc aaa aat      911
Thr Arg Ile Cys Gln Asp Val Ser Asn Phe Met Lys Asn Ala Lys Asn
                    290                 295                 300 gtc agg ctc acc tat ctg aag act gtc ctg atg tac ctc tgc aca          959
Val Arg Leu Thr Tyr Leu Lys Thr Val Leu Met Tyr Leu Leu Cys Thr
                305                 310                 315 cag aat tag acg agg cga tca ggt tgg tca atg tat cca atc agc agt     1007
Gln Asn  *  Thr Arg Arg Ser Gly Trp Ser Met Tyr Pro Ile Ser Ser
                320                 325                 330 atg gcc aga ttc tcc aga tga ccc gga agc act tgg agg aca ccg cct     1055
Met Ala Arg Phe Ser Arg  *  Pro Gly Ser Thr Trp Arg Thr Pro Pro
                335                 340                 345 atc tgg tgg aga aga tga gag ggc aat ttg gct ggg tgt ctg aac tgg     1103
Ile Trp Trp Arg Arg  *  Glu Gly Asn Leu Ala Gly Cys Leu Asn Trp
                350                 355                 360 caa acc agg ccc cag aaa cag aga tca tct tta att caa tac agg tag     1151
Gln Thr Arg Pro Gln Lys Gln Arg Ser Ser Leu Ile Gln Tyr Arg
                365                 370                 375 ttc caa gga ttc atg aag gaa ata ttt cca aac aag atg aaa caa tga     1199
Phe Gln Gly Phe Met Lys Glu Ile Phe Pro Asn Lys Met Lys Gln  *
                380                 385                 390 tga cag act taa gca ttc tgc ctt cct cta att tca cac tca aga tcc     1247
 *  Gln Thr  *  Ala Phe Cys Leu Pro Leu Ile Ser His Ser Arg Ser
                    395                 400                 405 ctc ttg aag aaa gtg ctg aga gtt cta act tca ttg gct acg tag tgg     1295
Leu Leu Lys Lys Val Leu Arg Val Leu Thr Ser Leu Ala Thr  *  Trp
                410                 415                 420 caa aag ctc tac agc att tta agg aac att tta aaa cct ggt aag aag     1343
Gln Lys Leu Tyr Ser Ile Leu Arg Asn Ile Leu Lys Pro Gly Lys Lys
                425                 430                 435 atc taa tgc atc cta tat cca gta agt aga att atc tct tca tct ggg     1391
Ile  *  Cys Ile Leu Tyr Pro Val Ser Arg Ile Ile Ser Ser Ser Gly
                440                 445                 450 acc tgg aaa tcc tga aat aaa aaa gga taa tgc aat aaa cac agt tgc     1439
Thr Trp Lys Ser  *  Asn Lys Lys Gly  *  Cys Asn Lys His Ser Cys
                455                 460                 465 agg aaa gta tgt tag cta tat act atg aag tac tct tag ttt act tat     1487
Arg Lys Val Cys  *  Leu Tyr Thr Met Lys Tyr Ser  *  Phe Thr Tyr
                470                 475                 480 gtt gaa tgg ctt agc tat taa tac tca aat tga gtt aaa atg aaa att     1535
Val Glu Trp Leu Ser Tyr  *  Tyr Ser Asn  *  Val Lys Met Lys Ile
                    485                 490 cct cct taa aaa atc aaa cgt aat atg tat tac att tca tgg tac att     1583
Pro Pro      Lys Ile Lys Arg Asn Met Tyr Tyr Ile Ser Trp Tyr Ile
495                 500                 505 agt agt tct ttg tat att gaa taa ata cta aat cac cta                 1622
Ser Ser Ser Leu Tyr Ile Glu      Ile Leu Asn His Leu
510                 515                 520

<210> SEQ ID NO 66
<211> LENGTH: 61
<212> TYPE: PRT
<213> ORGANISM: Homo sapiens

<400> SEQUENCE: 66
```

```
Arg His Leu Gln Ala Arg Ala Ala Gly Leu Val Ser Thr Leu Glu Val
 1               5                  10                  15

Ala Asp Thr Leu Cys Pro Arg Leu Thr Ser Ser Arg Trp His Arg Arg
            20                  25                  30

Leu Gln Gly Ala Ala Leu Lys Arg Ile Leu Gly Met Thr Glu Leu Arg
            35                  40                  45

Pro Ser Leu Leu Pro Gly Trp Ser Ser Val Ala Cys Ser
 50                  55                  60

<210> SEQ ID NO 67
<211> LENGTH: 208
<212> TYPE: PRT
<213> ORGANISM: Homo sapiens

<400> SEQUENCE: 67

Leu Thr Glu Ala Ser Asn Ser Trp Val Gln Val Thr Leu Pro Pro Gln
 1               5                  10                  15

Pro His Glu Asp Leu Gly Leu Gln Asp Thr Ala Lys Ser Leu Thr Arg
            20                  25                  30

Met Lys Ile Lys Ala Glu Lys Asn Glu Gly Pro Ser Arg Ser Trp Trp
            35                  40                  45

Gln Leu His Trp Gly Asp Ile Ala Asn Ser Gly Asn Met Lys Pro
 50                  55                  60

Pro Leu Val Phe Ile Val Cys Leu Leu Trp Leu Lys Asp Ser His
65                  70                  75                  80

Cys Ala Pro Thr Trp Lys Asp Lys Thr Ala Ile Ser Glu Asn Leu Lys
            85                  90                  95

Ser Phe Ser Glu Val Gly Glu Ile Asp Ala Asp Glu Val Lys Lys
            100                 105                 110

Ala Leu Thr Gly Ile Lys Gln Met Lys Ile Met Met Glu Arg Lys Glu
            115                 120                 125

Lys Glu His Thr Asn Leu Met Ser Thr Leu Lys Lys Cys Arg Glu Glu
130                 135                 140

Lys Gln Glu Ala Leu Lys Leu Leu Asn Glu Val Gln Glu His Leu Glu
145                 150                 155                 160

Glu Glu Glu Arg Leu Cys Arg Glu Ser Leu Ala Asp Ser Trp Gly Glu
            165                 170                 175

Cys Arg Ser Cys Leu Glu Asn Asn Cys Met Arg Ile Tyr Thr Thr Cys
            180                 185                 190

Gln Pro Ser Trp Ser Ser Val Lys Asn Lys Leu Leu Thr Thr Glu Ala
            195                 200                 205

<210> SEQ ID NO 68
<211> LENGTH: 50
<212> TYPE: PRT
<213> ORGANISM: Homo sapiens

<400> SEQUENCE: 68

Phe Gln Arg Cys Tyr Leu Gly Arg Thr Glu Asp Cys Val Gly Asn Leu
 1               5                  10                  15

Thr Arg Ile Cys Gln Asp Val Ser Asn Phe Met Lys Asn Ala Lys Asn
            20                  25                  30

Val Arg Leu Thr Tyr Leu Lys Thr Val Leu Met Tyr Leu Leu Cys Thr
            35                  40                  45

Gln Asn
 50
```

<210> SEQ ID NO 69
<211> LENGTH: 19
<212> TYPE: PRT
<213> ORGANISM: Homo sapiens

<400> SEQUENCE: 69

Thr Arg Arg Ser Gly Trp Ser Met Tyr Pro Ile Ser Ser Met Ala Arg
1               5                   10                  15

Phe Ser Arg

<210> SEQ ID NO 70
<211> LENGTH: 14
<212> TYPE: PRT
<213> ORGANISM: Homo sapiens

<400> SEQUENCE: 70

Pro Gly Ser Thr Trp Arg Thr Pro Pro Ile Trp Trp Arg Arg
1               5                   10

<210> SEQ ID NO 71
<211> LENGTH: 25
<212> TYPE: PRT
<213> ORGANISM: Homo sapiens

<400> SEQUENCE: 71

Glu Gly Asn Leu Ala Gly Cys Leu Asn Trp Gln Thr Arg Pro Gln Lys
1               5                   10                  15

Gln Arg Ser Ser Leu Ile Gln Tyr Arg
            20                  25

<210> SEQ ID NO 72
<211> LENGTH: 15
<212> TYPE: PRT
<213> ORGANISM: Homo sapiens

<400> SEQUENCE: 72

Phe Gln Gly Phe Met Lys Glu Ile Phe Pro Asn Lys Met Lys Gln
1               5                   10                  15

<210> SEQ ID NO 73
<211> LENGTH: 26
<212> TYPE: PRT
<213> ORGANISM: Homo sapiens

<400> SEQUENCE: 73

Ala Phe Cys Leu Pro Leu Ile Ser His Ser Arg Ser Leu Leu Lys Lys
1               5                   10                  15

Val Leu Arg Val Leu Thr Ser Leu Ala Thr
            20                  25

<210> SEQ ID NO 74
<211> LENGTH: 18
<212> TYPE: PRT
<213> ORGANISM: Homo sapiens

<400> SEQUENCE: 74

Trp Gln Lys Leu Tyr Ser Ile Leu Arg Asn Ile Leu Lys Pro Gly Lys
1               5                   10                  15

Lys Ile

<210> SEQ ID NO 75
<211> LENGTH: 18

<212> TYPE: PRT
<213> ORGANISM: Homo sapiens

<400> SEQUENCE: 75

Cys Ile Leu Tyr Pro Val Ser Arg Ile Ile Ser Ser Ser Gly Thr Trp
1               5                   10                  15

Lys Ser

<210> SEQ ID NO 76
<211> LENGTH: 4
<212> TYPE: PRT
<213> ORGANISM: Homo sapiens

<400> SEQUENCE: 76

Asn Lys Lys Gly
1

<210> SEQ ID NO 77
<211> LENGTH: 10
<212> TYPE: PRT
<213> ORGANISM: Homo sapiens

<400> SEQUENCE: 77

Cys Asn Lys His Ser Cys Arg Lys Val Cys
1               5                   10

<210> SEQ ID NO 78
<211> LENGTH: 7
<212> TYPE: PRT
<213> ORGANISM: Homo sapiens

<400> SEQUENCE: 78

Leu Tyr Thr Met Lys Tyr Ser
1               5

<210> SEQ ID NO 79
<211> LENGTH: 9
<212> TYPE: PRT
<213> ORGANISM: Homo sapiens

<400> SEQUENCE: 79

Phe Thr Tyr Val Glu Trp Leu Ser Tyr
1               5

<210> SEQ ID NO 80
<211> LENGTH: 7
<212> TYPE: PRT
<213> ORGANISM: Homo sapiens

<400> SEQUENCE: 80

Val Lys Met Lys Ile Pro Pro
1               5

<210> SEQ ID NO 81
<211> LENGTH: 20
<212> TYPE: PRT
<213> ORGANISM: Homo sapiens

<400> SEQUENCE: 81

Lys Ile Lys Arg Asn Met Tyr Tyr Ile Ser Trp Tyr Ile Ser Ser Ser
1               5                   10                  15

Leu Tyr Ile Glu
            20

-continued

```
<210> SEQ ID NO 82
<211> LENGTH: 5
<212> TYPE: PRT
<213> ORGANISM: Homo sapiens

<400> SEQUENCE: 82

Ile Leu Asn His Leu
 1               5

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
agttgcgtcc ctctctgttg                                              20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
gcttcatgtt cccgctgtta                                              20
```

METHODS AND COMPOSITIONS FOR DIAGNOSING AND TREATING CHROMOSOME-18P RELATED DISORDERS

This is a continuation-in-part of U.S. application Ser. No. 09/236,134, filed on Jan. 22, 1999 which claims priority under 35 U.S.C. § 119(e)(1) of provisional application No. 60/078,044 filed on Mar. 16, 1998, of provisional application No. 60/088,312 filed on Jun. 5, 1998, and of provisional application No. 60/106,056 filed on Oct. 28, 1998, each of which is incorporated herein by reference in its entirety.

1. INTRODUCTION

The present invention relates, first, to the HKNG1 gene, shown herein to be associated with central nervous system-related disorders, e.g., neuropsychiatric disorders, in particular, bipolar affective disorder and schizophrenia and with myopia-related disorders. The invention includes recombinant DNA molecules and cloning vectors comprising sequences of the HKNG1 gene, and host cells and non-human host organisms engineered to contain such DNA molecules and cloning vectors. The present invention further relates to HKNG1 gene products, and to antibodies directed against such HKNG1 gene products. The present invention also relates to methods of using the HKNG1 gene and gene product, including drug screening assays, and diagnostic and therapeutic methods for the treatment of HKNG1-mediated disorders, including HKNG1-mediated neuropsychiatric disorders such as bipolar affective disorder, as well as HKNG1-mediated myopia disorders such as early-onset autosomal dominant myopia.

2. BACKGROUND OF THE INVENTION

There are only a few psychiatric disorders in which clinical manifestations of the disorder can be correlated with demonstrable defects in the structure and/or function of the nervous system. Well-known examples of such disorders include Huntington's disease, which can be traced to a mutation in a single gene and in which neurons in the striatum degenerate, and Parkinson's disease, in which dopaminergic neurons in the nigro-striatal pathway degenerate. The vast majority of psychiatric disorders, however, presumably involve subtle and/or undetectable changes, at the cellular and/or molecular levels, in nervous system structure and function. This lack of detectable neurological defects distinguishes "neuropsychiatric" disorders, such as schizophrenia, attention deficit disorders, schizoaffective disorder, bipolar affective disorders, or unipolar affective disorder, from neurological disorders, in which anatomical or biochemical pathologies are manifest. Hence, identification of the causative defects and the neuropathologies of neuropsychiatric disorders are needed in order to enable clinicians to evaluate and prescribe appropriate courses of treatment to cure or ameliorate the symptoms of these disorders.

One of the most prevalent and potentially devastating of neuropsychiatric disorders is bipolar affective disorder (BAD), also known as bipolar mood disorder (BP) or manic-depressive illness, which is characterized by episodes of elevated mood (mania) and depression (Goodwin, et al., 1990, Manic Depressive Illness, Oxford University Press, New York). The most severe and clinically distinctive forms of BAD are BP-I (severe bipolar affective (mood) disorder), which affects 2–3 million people in the United States, and SAD-M (schizoaffective disorder manic type). They are characterized by at least one full episode of mania, with or without episodes of major depression (defined by lowered mood, or depression, with associated disturbances in rhythmic behaviors such as sleeping, eating, and sexual activity). BP-I often co-segregates in families with more etiologically heterogeneous syndromes, such as with a unipolar affective disorder such as unipolar major depressive disorder (MDD), which is a more broadly defined phenotype (Freimer and Reus, 1992, in The Molecular and Genetic Basis of Neurological Disease, Rosenberg, et al., eds., Butterworths, New York, pp. 951–965; McInnes and Freimer, 1995, Curr. Opin. Genet. Develop., 5, 376–381). BP-I and SAD-M are severe mood disorders that are frequently difficult to distinguish from one another on a cross-sectional basis, follow similar clinical courses, and segregate together in family studies (Rosenthal, et al., 1980, Arch. General Psychiat. 37, 804–810; Levinson and Levitt, 1987, Am. J. Psychiat. 144, 415–426; Goodwin, et al., 1990, Manic Depressive Illness, Oxford University Press, New York). Hence, methods for distinguishing neuropsychiatric disorders such as these are needed in order to effectively diagnose and treat afflicted individuals.

Currently, individuals are typically evaluated for BAD using the criteria set forth in the most current version of the American Psychiatric Association's Diagnostic and Statistical Manual of Mental Disorders (DSM). While many drugs have been used to treat individuals diagnosed with BAD, including lithium salts, carbamazepine and valproic acid, none of the currently available drugs are adequate. For example, drug treatments are effective in only approximately 60–70% of individuals diagnosed with BP-I. Moreover, it is currently impossible to predict which drug treatments will be effective in, for example, particular BP-I affected individuals. Commonly, upon diagnosis, affected individuals are prescribed one drug after another until one is found to be effective. Early prescription of an effective drug treatment, therefore, is critical for several reasons, including the avoidance of extremely dangerous manic episodes, the risk of progressive deterioration if effective treatments are not found, and the risk of substantial side effects of current treatments.

The existence of a genetic component for BAD is strongly supported by segregation analyses and twin studies (Bertelson, et al., 1977, Br. J. Psychiat. 130, 330–351; Freimer and Reus, 1992, in The Molecular and Genetic Basis of Neurological Disease, Rosenberg, et al., eds., Butterworths, New York, pp. 951–965; Pauls, et al., 1992, Arch. Gen. Psychiat. 49, 703–708). Efforts to identify the chromosomal location of genes that might be involved in BP-I, however, have yielded disappointing results in that reports of linkage between BP-I and markers on chromosomes X and 11 could not be independently replicated nor confirmed in the re-analyses of the original pedigrees, indicating that with BAD linkage studies, even extremely high lod scores at a single locus, can be false positives (Baron, et al., 1987, Nature 326, 289–292; Egeland, et al., 1987, Nature 325, 783–787; Kelsoe, et al., 1989, Nature 342, 238–243; Baron, et al., 1993, Nature Genet. 3, 49–55).

Recent investigations have suggested possible localization of BAD genes on chromosomes 18p and 21q, but in both cases the proposed candidate region is not well defined and no unequivocal support exists for either location (Berrettini, et al., 1994, Proc. Natl. Acad. Sci. U.S.A. 91, 5918–5921; Murray, et al., 1994, Science 265, 2049–2054; Pauls, et al., 1995, Am. J. Hum. Genet. 57, 636–643; Maier, et al., 1995, Psych. Res. 59, 7–15; Straub, et al., 1994, Nature Genet. 8, 291–296).

Mapping genes for common diseases believed to be caused by multiple genes, such as BAD, may be complicated by the typically imprecise definition of phenotypes, by etiologic heterogeneity, and by uncertainty about the mode of genetic transmission of the disease trait. With neuropsychiatric disorders there is even greater ambiguity in distinguishing individuals who likely carry an affected genotype from those who are genetically unaffected. For example, one can define an affected phenotype for BAD by including one or more of the broad grouping of diagnostic classifications that constitute the mood disorders: BP-I, SAD-M, MDD, and bipolar affective (mood) disorder with hypomania and major depression (BP-II).

Thus, one of the greatest difficulties facing psychiatric geneticists is uncertainty regarding the validity of phenotype designations, since clinical diagnoses are based solely on clinical observation and subjective reports. Also, with complex traits such as neuropsychiatric disorders, it is difficult to genetically map the trait-causing genes because: (1) neuropsychiatric disorder phenotypes do not exhibit classic Mendelian recessive or dominant inheritance patterns attributable to a single genetic locus, (2) there may be incomplete penetrance, i.e., individuals who inherit a predisposing allele may not manifest disease; (3) a phenocopy phenomenon may occur, i.e., individuals who do not inherit a predisposing allele may nevertheless develop disease due to environmental or random causes; (4) genetic heterogeneity may exist, in which case mutations in any one of several genes may result in identical phenotypes.

Despite these difficulties, however, identification of the chromosomal location, sequence and function of genes and gene products responsible for causing neuropsychiatric disorders such as bipolar affective disorders is of great importance for genetic counseling, diagnosis and treatment of individuals in affected families.

3. SUMMARY OF THE INVENTION

The present invention relates, first, to the discovery, identification, and characterization of novel nucleic acid molecules that are associated with central nervous system-related disorders and processes, e.g., human neuropsychiatric disorders, such as schizophrenia, attention deficit disorder, schizoaffective disorder, dysthymic disorder, major depressive disorder, and bipolar affective disorder (BAD) including severe bipolar affective (mood) disorder (BP-I), bipolar affective (mood) disorder with hypomania and major depression (BP-II). The invention further relates to the discovery, identification, and characterization of proteins encoded by such nucleic acid molecules, or by degenerate, e.g., allelic or homologous, variants thereof. The invention further relates to the discovery, identification, and characterization of novel nucleic acid molecules that are associated with human myopia or nearsightedness, such as early-onset, autosomal dominant myopia, as well as to the discovery, identification, and characterization of proteins encoded by such nucleic acid molecules or by degenerate variants thereof.

In particular, the nucleic acid molecules of the present invention represent, first, nucleic acid sequences corresponding to the gene referred to herein as HKNG1. As demonstrated in the Examples presented below in Sections 6, 8 and 14, the HKNG1 gene is associated with human CNS-related disorders, e.g., neuropsychiatric disorders, in particular BAD. The HKNG1 gene is associated with other human neuropsychiatric disorders as well, such as schizophrenia. As demonstrated in the Example presented below in Section 14, the HKNG1 gene is also associated with human myopia, such as early-onset autosomal dominant myopia.

In addition to the positive correlation between mutations within the HKNG1 gene and individuals exhibiting symptoms of BAD, described in Section 6 and 8, the present invention is further based, in part, on Applicants' discovery of novel HKNG1 cDNA sequences. Applicants' discovery of such cDNA sequences has led to the elucidation of the HKNG1 genomic (that is, upstream untranslated, intron/exon, and downstream untranslated) structure, and to the discovery of full-length and alternately spliced HKNG1 variants and the polypeptides encoded by such variants. These discoveries are described in Sections 7 and 10, below. Applicants' discovery of such cDNA sequences has also led to the elucidation of novel mammalian (e.g., guinea pig and bovine) HKNG1 sequences, and to the discovery of novel allelic variants and polymorphisms of such sequences. These discoveries are described in Section 10 below.

The invention encompasses nucleic acid molecules which comprise the following nucleotide sequences: (a) nucleotide sequences (e.g., SEQ ID NOS: 1, 3, 5, 6, 36, and 37) that comprise a human HKNG1 gene and/or encode a human HKNG1 gene product (e.g., SEQ ID NO: 2; SEQ ID NO: 4), as well as allelic variants, homologs and orthologs thereof, including nucleotide sequences (e.g., SEQ ID NOS:38, 40, 42, 44, and 46–48) that encode non-human HKNG1 gene products (e.g., SEQ ID NOS:39, 41, 43, 45, and 49); (b) nucleotide sequences comprising the novel HKNG1 sequences disclosed herein that encode mutants of the HKNG1 gene product in which sequences encoding all or a part of one or more of the HKNG1 domains is deleted or altered, or fragments thereof; (c) nucleotide sequences that encode fusion proteins comprising a HKNG1 gene product (e.g., SEQ ID NO: 2; SEQ ID NO: 4), or a portion thereof fused to a heterologous polypeptide; and (d) nucleotide sequences within the HKNG1 gene, as well as chromosome 18p nucleotide sequences flanking the HKNG1 gene, which can be utilized, e.g., as primers, in the methods of the invention for identifying and diagnosing individuals at risk for or exhibiting an HKNG1-mediated disorder, such as BAD or schizophrenia, or for diagnosing individuals at risk for or exhibiting a form of myopia such as early-onset autosomal dominant myopia. The nucleic acid molecules of (a) through (d), above, can include, but are not limited to, cDNA, genomic DNA, and RNA sequences.

The invention also encompasses the expression products of the nucleic acid molecules listed above; i.e., peptides, proteins, glycoproteins and/or polypeptides that are encoded by the above HKNG1 nucleic acid molecules.

The compositions of the present invention further encompass agonists and antagonists of the HKNG1 gene product, including small molecules (such as small organic molecules), and macromolecules (including antibodies), as well as nucleotide sequences that can be used to inhibit HKNG1 gene expression (e.g., antisense and ribozyme molecules, and gene or regulatory sequence replacement constructs) or to enhance HKNG1 gene expression (e.g., expression constructs that place the HKNG1 gene under the control of a strong promoter system).

The compositions of the present invention further include cloning vectors and expression vectors containing the nucleic acid molecules of the invention, as well as hosts which have been transformed with such nucleic acid molecules, including cells genetically engineered to contain the nucleic acid molecules of the invention, and/or cells genetically engineered to express the nucleic acid molecules of the invention. In addition to host cells and cell lines, hosts also include transgenic non-human animals (or progeny thereof), particularly non-human mammals, that have been engineered to express an HKNG1 transgene, or "knockouts" that have been engineered to not express HKNG1.

Transgenic non-human animals of the invention include animals engineered to express an HKNG1 transgene at higher or lower levels than normal, wild-type animals. The transgenic animals of the invention also include animals engineered to express a mutant variant or polymorphism of an HKNG1 transgene which is associated with HKNG1-mediated disorder, for example an HKNG1-mediated neuropsychiatric disorders, such as BAD and schizophrenia, or, alternatively, a myopia disorder such as early-onset autosomal dominant myopia. The transgenic animals of the invention further include the progeny of such genetically engineered animals.

The invention further relates to methods for the treatment of HKNG1-mediated disorders in a subject, such as HKNG1-mediated neuropsychiatric disorders and HKNG1-mediated myopia disorders, wherein such methods comprise administering a compound which modulates the expression of a HKNG1 gene and/or the synthesis or activity of a HKNG1 gene product so symptoms of the disorder are ameliorated.

The invention further relates to methods for the treatment of HKNG1-mediated disorders in a subject, such as HKNG1-mediated neuropsychiatric disorders and HKNG1-mediated myopia disorders, resulting from HKNG1 gene mutations or aberrant levels of HKNG1 expression or activity, wherein such methods comprise supplying the subject with a nucleic acid molecule encoding an unimpaired HKNG1 gene product such that an unimpaired HKNG1 gene product is expressed and symptoms of the disorder are ameliorated.

The invention further relates to methods for the treatment of HKNG1-mediated disorders in a subject, such as HKNG1-mediated neuropsychiatric disorders and HKNG1-mediated myopia disorders, resulting from HKNG1 gene mutations or from aberrant levels of expression or activity, wherein such methods comprise supplying the subject with a cell comprising a nucleic acid molecule that encodes an unimpaired HKNG1 gene product such that the cell expresses the unimpaired HKNG1 gene product and symptoms of the disorder are ameliorated.

The invention also encompasses pharmaceutical formulations and methods for treating HKNG1-mediated disorders, including neuropsychiatric disorders, such as BAD and schizophrenia, and myopia disorders, such as early-onset autosomal dominant myopia, involving HKNG1 gene.

In addition, the present invention is directed to methods that utilize the HKNG1 nucleic acid sequences, chromosome 18p nucleotide sequences flanking the HKNG1 human gene and/or HKNG1 gene product sequences for mapping the chromosome 18p region, and for the diagnostic evaluation, genetic testing and prognosis of a HKNG1-mediated disorder, such as a HKNG1-mediated neuropsychiatric disorder or a HKNG1-mediated myopia disorder. For example, in one embodiment, the invention relates to methods for diagnosing HKNG1-mediated disorders, wherein such methods comprise measuring HKNG1 gene expression in a patient sample, or detecting a HKNG1 polymorphism or mutation in the genome of a mammal, including a human, suspected of exhibiting such a disorder. In one embodiment, nucleic acid molecules encoding HKNG1 can be used as diagnostic hybridization probes or as primers for diagnostic PCR analysis for the identification of HKNG1 gene mutations, allelic variations and regulatory defects in the HKNG1 gene which correlate with neuropsychiatric disorders such as BAD or schizophrenia.

The invention still further relates to methods for identifying compounds which modulate the expression of the HKNG1 gene and/or the synthesis or activity of the HKNG1 gene products, including therapeutic compounds, which reduce or eliminate the symptoms of HKNG1-mediated disorders, including HKNG1-mediated neuropsychiatric disorders such as BAD and schizophrenia. In particular, cellular and non-cellular assays are described that can be used to identify compounds that interact with the HKNG1 gene product, e.g., modulate the activity of the HKNG1 and/or bind to the HKNG1 gene product. Such cell-based assays of the invention utilize cells, cell lines, or engineered cells or cell lines that express the HKNG1 gene product.

In one embodiment, such methods comprise contacting a compound to a cell that expresses a HKNG1 gene, measuring the level of HKNG1 gene expression, gene product expression or gene product activity, and comparing this level to the level of HKNG1 gene expression, gene product expression or gene product activity produced by the cell in the absence of the compound, such that if the level obtained in the presence of the compound differs from that obtained in its absence, a compound that modulates the expression of the HKNG1 gene and/or the synthesis or activity of the HKNG1 gene products has been identified.

In another embodiment, such methods comprise contacting a compound to a cell that expresses a HKNG1 gene and also comprises a reporter construct whose transcription is dependent, at least in part, on HKNG1 expression or activity. In such an embodiment, the level of reporter transcription is measured and compared to the level of reporter transcription in the cell in the absence of the compound. If the level of reporter transcription obtained in the presence of the compound differs from that obtained in its absence, a compound that modulates expression of HKNG1 or genes involved in HKNG1-related pathways or signal transduction has been identified.

In yet another embodiment, such methods comprise administering a compound to a host, such as a transgenic animal, that expresses an HKNG1 transgene or a mutant HKNG1 transgene associated with an HKNG1-mediated disorder such as a neuropsychiatric disorder (e.g., BAD or schizophrenia), or to an animal, e.g., a knock-out animal, that does not express HKNG1, and measuring the level of HKNG1 gene expression, gene product expression, gene product activity, or symptoms of an HKNG1-mediated disorder such as an HKNG1-mediated neuropsychiatric disorder (e.g., BAD or schizophrenia). The measured level is compared to the level obtained in a host that is not exposed to the compound, such that if the level obtained when the host is exposed to the compound differs from that obtained in a host not exposed to the compound, a compound modulates the expression of the mammalian HKNG1 gene and/or the synthesis or activity of the mammalian HKNG1 gene products, and/or the symptoms of an HKNG1-mediated disorder such as a neuropsychiatric disorder (e.g., BAD or schizophrenia), has been identified.

The present invention still further relates to pharmacogenomic and pharmacogenetic methods for selecting an effective drug to administer to an individual having a HKNG1-mediated disorder. Such methods are based on the detection of genetic polymorphisms in the HKNG1 gene or variations in HKNG1 gene expression due to, e.g., altered methylation, differential splicing, or post-translational modification of the HKNG1 gene product which can affect the safety and efficacy of a therapeutic agent.

As briefly discussed above, the present invention is based, in part, on the genetic and physical mapping of the HKNG1 gene to a specific portion of the short arm of human chromosome 18 that is associated with human neuropsychiatric disorders, in particular, bipolar affective disorder. These results are described in the Example presented, below, in Section 6. The invention is also based on the elucidation of the HKNG1 nucleotide sequence, amino acid sequence and expression pattern, as described in the Example presented, below, in Section 7. The invention is further based on the identification of specific mutations and/or polymorphisms within the HKNG1 gene which positively correlate with neuropsychiatric disorders, in particular, BAD, as described in the Example presented below in Section 8. These mutations include a point mutation discovered in an individual affected by BAD which is absent from the corresponding wild-type nucleic acid derived from non-affected individuals and linkage disequilibrium of three markers showing cosegregation with a population of individuals with BAD. This mutation is a single base mutation which results in a mutant HKNG1 gene product comprising substitution of a lysine residue for the wild-type glutamic acid residue at HKNG1 amino acid position 202 of the polypeptide of SEQ ID NO:2 or the HKNG1 amino acid residue 184 of the polypeptide of SEQ ID NO:4. These mutations further include the mutations discovered in schizophrenic and BAD patients that are detailed in FIGS. 5A–5C.

3.1. DEFINITIONS

As used herein, the following terms shall have the abbreviations indicated.

BAC, bacterial artificial chromosomes
BAD, bipolar affective disorder(s)
BP, bipolar mood disorder
BP-I, severe bipolar affective (mood) disorder
BP-II, bipolar affective (mood) disorder with hypomania and major depression
bp, base pair(s)
EST, expressed sequence tag
HKNG1, Hong Kong new gene 1
lod, logarithm of odds
MDD, unipolar major depressive disorder
ROS, reactive oxygen species
RT-PCR, reverse transcriptase PCR
SSCP, single-stranded conformational polymorphism
SAD-M, schizoaffective disorder manic type
STS, sequence tagged site
YAC, yeast artificial chromosome "HKNG1-mediated disorders" include disorders involving an aberrant level of HKNG1 gene expression, gene product synthesis and/or gene product activity relative to levels found in clinically normal individuals, and/or relative to levels found in a population whose level represents a baseline, average HKNG1 level. While not wishing to be bound by any particular mechanism, it is to be understood that disorder symptoms can, for example, be caused, either directly or indirectly, by such aberrant levels. Alternatively, it is to be understood that such aberrant levels can, either directly or indirectly, ameliorate disorder symptoms, (e.g., as in instances wherein aberrant levels of HKNG1 suppress the disorder symptoms caused by mutations within a second gene).

HKNG1-mediated disorders include, for example, central nervous system (CNS) disorders. CNS disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as bipolar affective disorder, e.g., severe bipolar affective (mood) disorder (BP-I), bipolar affective (mood) disorder with hypomania and major depression (BP-II). Further CNS-related disorders include, for example, those listed in the American Psychiatric Association's Diagnostic and Statistical manual of Mental Disorders (DSM), the most current version of which is incorporated herein by reference in its entirety.

"HKNG1-mediated processes" include processes dependent and/or responsive, either directly or indirectly, to levels of HKNG1 gene expression, gene product synthesis and/or gene product activity. Such processes can include, but are not limited to, developmental, cognitive and autonomic neural and neurological processes, such as, for example, pain, appetite, long term memory and short term memory.

4. BRIEF DESCRIPTION OF THE FIGURES

FIGS. 1A–1C. The nucleotide sequence of human HKNG1 cDNA (SEQ ID NO: 1) is depicted on the bottom line. The top line depicts the full length amino acid sequence of human HKNG1 polypeptide (SEQ ID NO: 2) encoded by the human HKNG1 cDNA sequence. The nucleotide sequence encoding SEQ ID NO:2 corresponds to SEQ ID NO:5.

FIGS. 2A–2C. Nucleotide sequence of an alternately spliced human HKNG1 variant, referred to as HKNG1-V1 (SEQ ID NO: 3) is depicted on the bottom line. The derived amino acid sequence of the human HKNG1 gene product (SEQ ID NO: 4) encoded by this alternately spliced cDNA variant is depicted on the top line. The nucleotide sequence encoding SEQ ID NO:4 corresponds to SEQ ID NO:6.

Figure 3N:
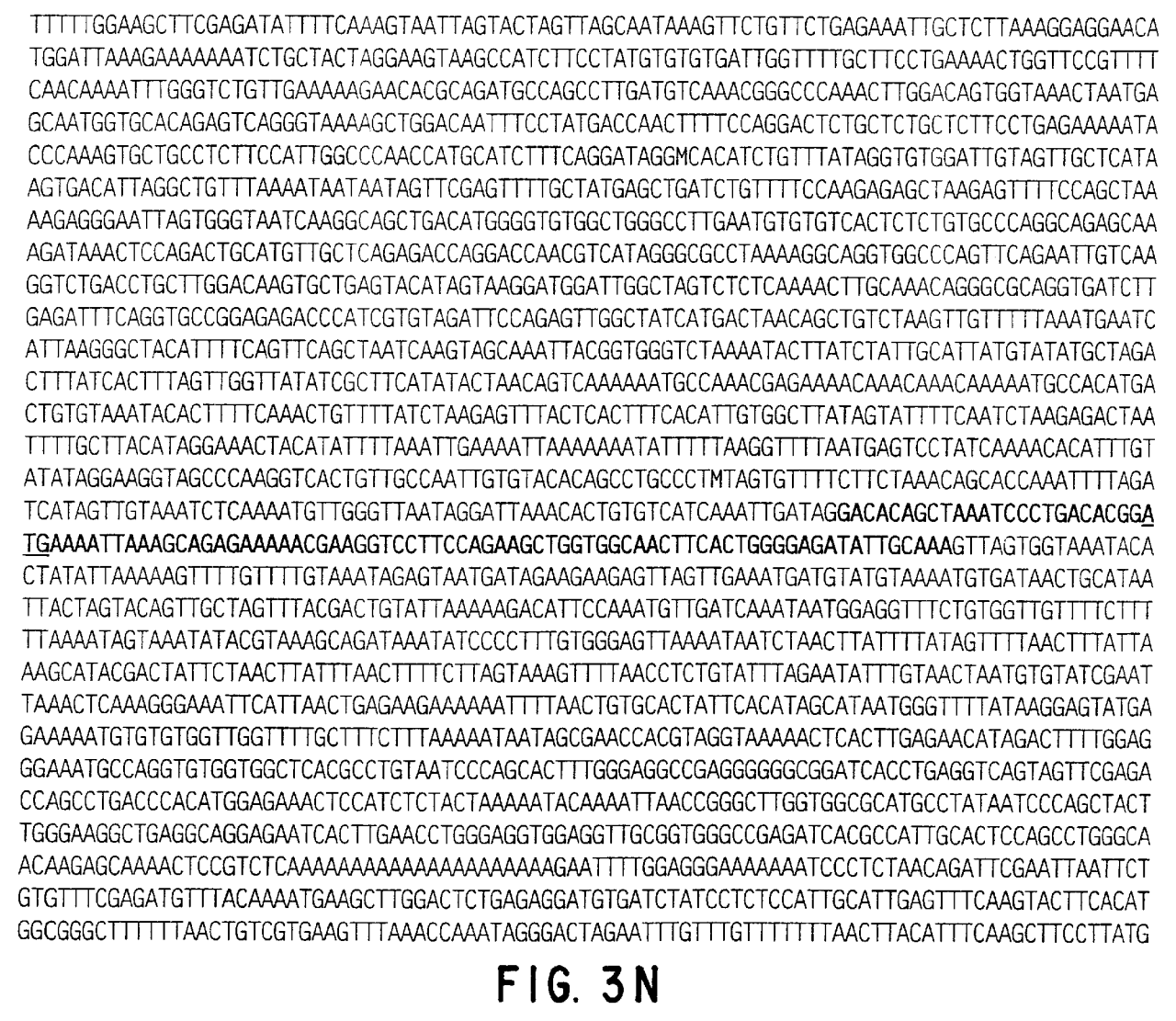

FIGS. 3A–3CC. Genomic sequence of the human HKNG1 gene (SEQ ID NO. 7). Exons are in bold and the 3' and 5' UTRs (untranslated regions) are underlined.

FIGS. 4A–4B. Summary of in situ hybridization analysis of HKNG1 mRNA distribution in normal human brain tissue.

FIGS. 5A–5C. HKNG1 polymorphisms relative to the HKNG1 wild-type sequence. These polymorphisms were isolated from a collection of schizophrenic patients of mixed ethnicity from the United States (FIG. 5A) and from the San Francisco BAD collection (FIG. 5B) and from the Costa Rican BAD samples (FIG. 5C).

FIGS. 6A–6B. Nucleotide sequence of the RT-PCR products for HKNG1-V2 (FIG. 6A; SEQ ID NO:36) and HKNG1-V3 (FIG. 6B; SEQ ID NO:37).

FIGS. 7A–7C. The cDNA sequence (SEQ ID NO:38) and the predicted amino acid sequence (SEQ ID NO:39) of the guinea pig HKNG1 ortholog gphkng1815.

FIGS. 8A–8C. The cDNA sequence (SEQ ID NO:40) and the predicted amino acid sequence (SEQ ID NO:41) of gphkng 7b, an allelic variant of the guinea pig HKNG1 ortholog gphkng1815.

FIGS. 9A–9C. The cDNA sequence (SEQ ID NO:42) and the predicted amino acid sequence (SEQ ID NO:43) of gphkng 7c, an allelic variant of the guinea pig HKNG1 ortholog gphkng1815.

FIGS. 10A–10C. The cDNA sequence (SEQ ID NO:44) and the predicted amino acid sequence (SEQ ID NO:45) of gphkng 7d, an allelic variant of the guinea pig HKNG1 ortholog gphkng1815.

FIGS. 11A–11C. The cDNA sequence (SEQ ID NO:46) and the predicted amino acid sequence (SEQ ID NO:49) of the allelic variant bhkng1 of the bovine HKNG1 ortholog.

FIGS. 12A–12D. The cDNA sequence (SEQ ID NO:47) and the predicted amino acid sequence (SEQ ID NO:49) of the allelic variant bhkng2 of the bovine HKNG1 homolgue.

FIGS. 13A–13C. The cDNA sequence (SEQ ID NO:48) and the predicted amino acid sequence (SEQ ID NO:49) of the allelic variant bhkng3 of the bovine HKNG1 homolgue.

Figure 14A:
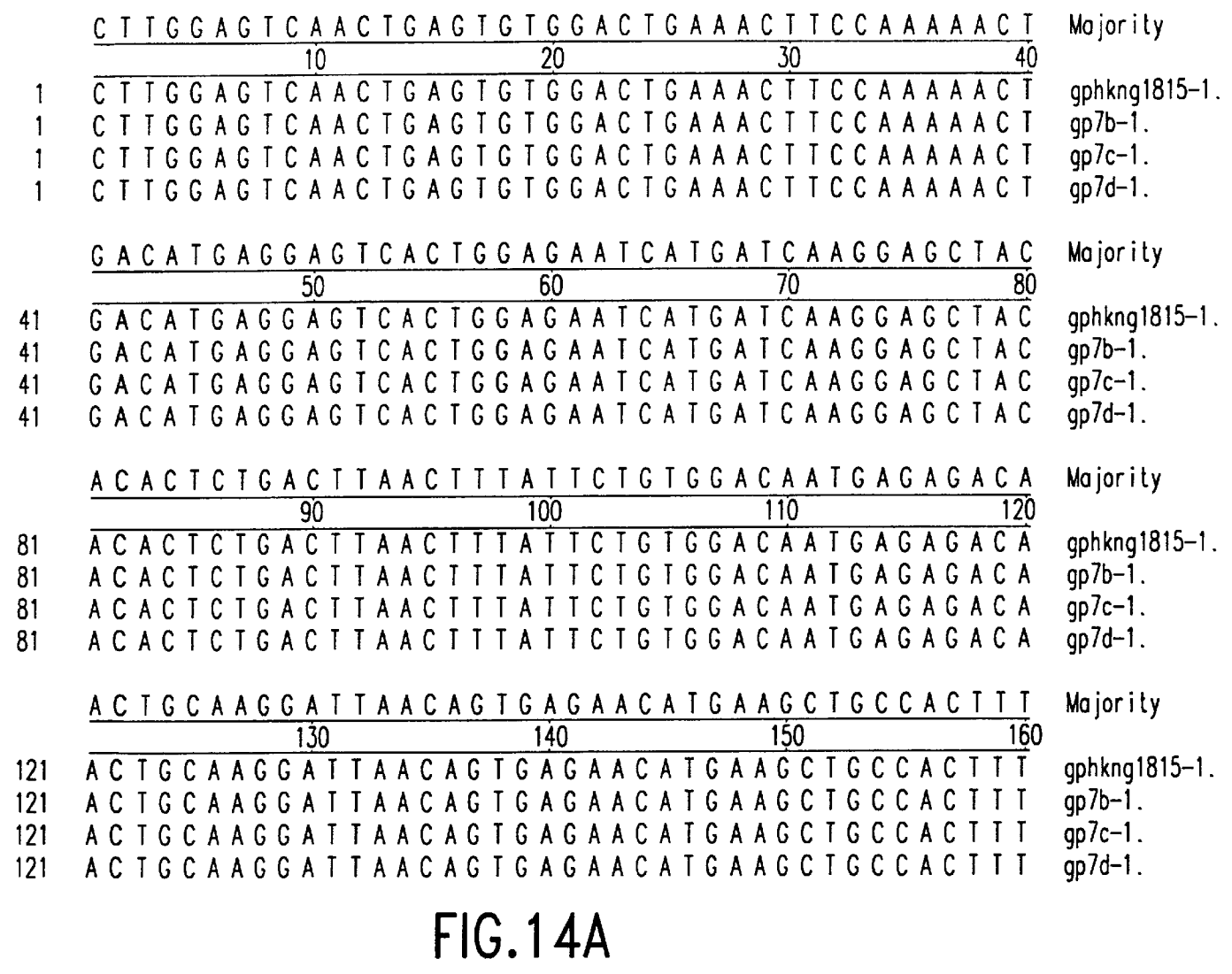
Figure 14I:
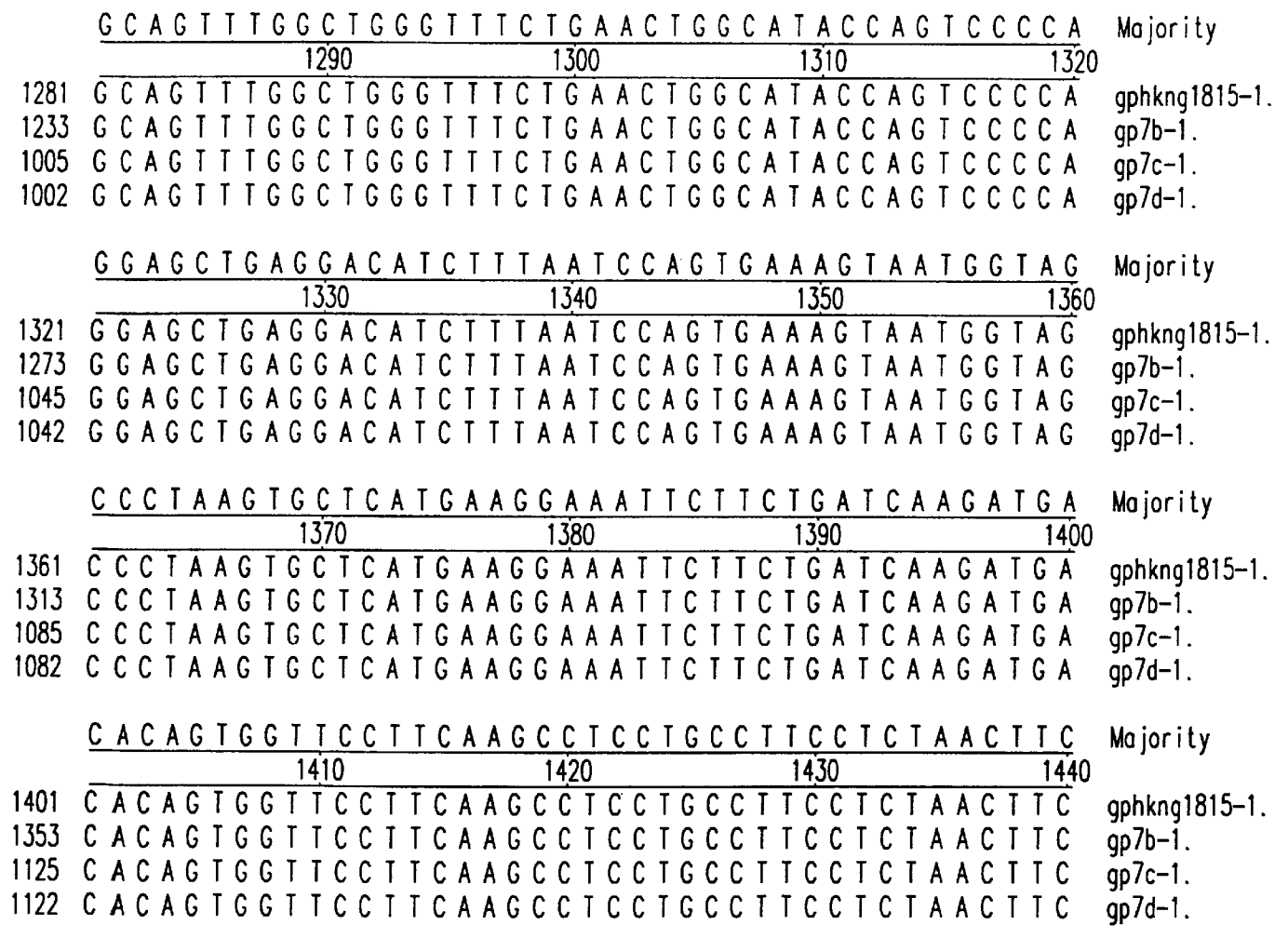
Figure 14K:
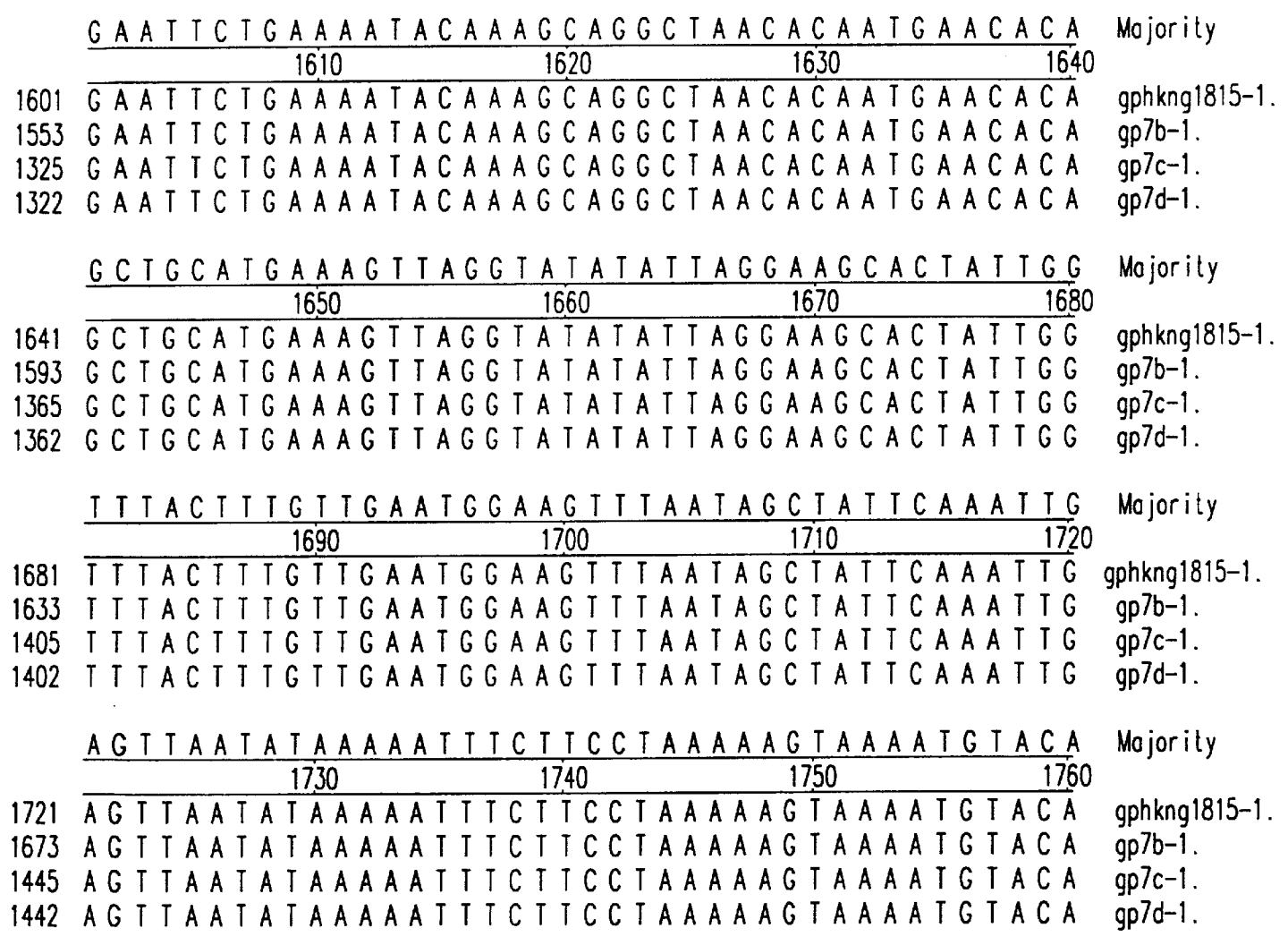

FIGS. 14A–14M. Alignments of the guinea pig HKNG1 cDNA (FIG. 14A) and predicted amino acid (FIG. 14B) sequences for gphkng1815, gphkng 7b, gphkng7c, and gphkng 7d.

FIGS. 15A–15F. Alignments of the cDNA sequences of the bovine HKNG1 allelic variants bhkng1, bhkng2, and bhkng3.

FIG. 16. Alignments of the human (hkng_aa) (SEQ ID NO: 2), bovine (bhkng1_aa) (SEQ ID NO: 49) and guinea pig (gphkng1815_aa) (SEQ ID NO: 39) HKNG1 amino acid sequences.

FIGS. 17A–17B. Alignments of the human HKNG1 protein sequences; top line: the mature secreted HKNG1 protein sequence (SEQ ID NO:51); second line: immature HKNG1 protein form 1 (IPF1; SEQ ID NO:2); third line: immature HKNG1 protein form 2 (IPF2; SEQ ID NO:64); bottom line: immature HKNG1 protein form 3 (IPF3; SEQ ID NO:4).

FIGS. 18A–18C. The nucleotide sequence of human HKNG1 splice variant HKNG1Δ7 cDNA (SEQ ID NO: 65) is depicted on the bottom line. The top line depicts the full length amino acid sequence of human HKNG1Δ7 polypeptide (SEQ ID NO: 66) encoded by the human HKNG1Δ7 cDNA sequence.

5. DETAILED DESCRIPTION OF THE INVENTION

5.1. The HKNG1 Gene

HKNG1 nucleic acid molecules are described in the section. Unless otherwise stated , the term "HKNG1 nucleic acid" refers collectively to the sequences described herein.

A human HKNG1 cDNA sequence (SEQ ID NO: 1) encoding the full length amino acid sequence (SEQ ID NO: 2) of the HKNG1 polypeptide is shown in FIGS. 1A–1C. The human HKNG1 gene encodes a secreted polypeptide of 495 amino acid residues, as shown in FIGS. 1A–1B, and SEQ ID NO: 2. The nucleotide sequence of the portion of the cDNA corresponding to the coding sequence for HKNG1 (SEQ ID NO:2) is depicted as SEQ ID NO:5.

The HKNG1 sequences of the invention also include splice variants of the HKNG1 sequences described herein. For example, an alternately spliced human HKNG1 cDNA sequence, referred to as HKNG1-V1 (SEQ ID NO: 3) encoding a human HKNG1 variant gene product (i.e., the HKNG1-V1 gene product) is shown in FIGS. 2A–2C. This splice variant of a human HKNG1 gene encodes a secreted polypeptide of 477 amino acid residues, as shown in FIGS. 2A–2C, and SEQ ID NO:4. The nucleotide sequence of the portion of the cDNA corresponding to the coding sequence for HKNG1 (SEQ ID NO:4) is depicted in SEQ ID NO:6.

Another alternately spliced human HKNG1 cDNA sequence (SEQ ID NO:65), referred to as HKNG1Δ7, encodes a second HKNG1 variant gene product (the HKNG1Δ7 gene product) which is depicted in FIGS. 18A–18C. This splice variant of the human HKNG1 gene encodes the variant polypeptide shown in FIGS. 18A–18C (SEQ ID NO:66).

The genomic structure of the human HKNG1 gene has been elucidated and is depicted in FIGS. 3A–3CC, with the HKNG1 exons indicated in bold type, and the 5'- and 3'-untranslated regions indicated by underlining. The wild-type genomic sequence of the HKNG1 gene is depicted in FIGS. 3A–3CC and SEQ ID NO:7.

Non-human homologues or orthologs mammalian orthologs, e.g., of the human HKNG1 sequences discussed above are also provided. Specifically, a guinea pig cDNA sequence (SEQ ID NO:38), referred to herein as gphkng1815, encoding the full length amino acid sequence (SEQ ID NO:39) of a guinea pig HKNG1 ortholog is shown in FIGS. 7A–7C. This guinea pig cDNA sequence encodes a gene product of 466 amino acid residues, as shown in FIGS. 7A–7C and in SEQ ID NO:39.

Allelic variants of this guinea pig HKNG1 ortholog, referred to as gphkng 7b, gphkng 7c, and gphkng 7d (SEQ ID NOS:40, 42, and 44, respectively), are shown in FIGS. 8A–10C, respectively. The allelic variants gphkng7b, gphkng7c, and gphkng7d each encode variants of the guinea pig gphkng1815 HKNG1 gene product which contain deletions of 16, 92, and 93 amino acids, respectively, as shown in FIGS. 8A–10C, in SEQ ID NOS:41, 43, and 45, respectively, and in the sequence alignment in FIG. 14B.

Bovine HKNG1 ortholog cDNA sequences (SEQ ID NOS: 46–48), referred to herein as bhkng1, bhkng2, and bhkng3, and each encoding the same bovine ortholog gene product are shown in FIGS. 11A–13C, respectively. The bovine HKNG1 allelic variants encode the same gene product, i.e., a 465 amino acid protein, as shown in FIGS. 11A–13C and in SEQ ID NO:49.

The HKNG1 gene nucleic acid molecules of the invention include: (a) nucleotide sequences and fragments thereof (e.g., SEQ ID NOS: 1, 3, 5, 6, 7, 36, 37, and 65) that encode a HKNG1 gene product (e.g., SEQ ID NOS: 2, 4 and 66), as well as homologues, orthologs and allelic variants of such sequences and fragments thereof (e.g., SEQ ID NOS:38, 40, 42, 44, and 46–48) which encode homologue or ortholog HKNG1 gene products (e.g., SEQ ID NOS:39, 41, 43, 45, and 49); (b) nucleotide sequences that encode one or more functional domains of a HKNG1 gene product including, but not limited to, nucleic acid sequences that encode a signal sequence domain, or one or more clusterin domains as described in Section 5.2 below; (c) nucleotide sequences that comprise HKNG1 gene sequences of upstream untranslated regions, intronic regions, and/or downstream untranslated regions or fragments thereof of the HKNG1 nucleotide sequences in (a) above; (d) nucleotide sequences comprising the novel HKNG1 sequences disclosed herein that encode mutants of the HKNG1 gene product in which all or a part of one or more of the domains is deleted or altered, as well as fragments thereof; (e) nucleotide sequences that encode fusion proteins comprising a HKNG1 gene product (e.g., SEQ ID NO: 2, 4, 39, 41, 43, 45, 49 and 65), or a portion thereof fused to a heterologous polypeptide; and (f) nucleotide sequences (e.g., primers) within the HKNG1 gene, and chromosome 18p nucleotide sequences flanking the HKNG1 gene which can be utilized as part of the methods of the invention for identifying and diagnosing individuals at risk for or exhibiting an HKNG1-mediated disorder, such as BAD, or myopia.

The HKNG1 nucleotide sequences of the invention further include nucleotide sequences corresponding to the nucleotide sequences of (a)–(f) above wherein one or more of the exons, or fragments thereof, have been deleted. In one preferred embodiment, the HKNG1 nucleotide sequence of the invention is a sequence wherein the exon corresponding to exon 7 of SEQ ID NO:7, or a fragment thereof, has been deleted.

The HKNG1 nucleotide sequences of the invention also include nucleotide sequences that have at least 65%, 70%, 75%, 80%, 85%, 90%, 95%, 98%, or more nucleotide sequence identity to the HKNG1 nucleotide sequences of (a)–(f) above. The HKNG1 nucleotide sequences of the invention further include nucleotide sequences that encode polypeptides having at least 65%, 70%, 75%, 80%, 85%, 90%, 95%, 98%, or higher amino acid sequence identity to the polypeptides encoded by the HKNG1 nucleotide sequences of (a)–(f), e.g., SEQ ID NOS: 2, 4, 39, 41, 43, 45, 49, and 66 above.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.*25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used (see http://www.ncbi.nlm.nih.gov). Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The HKNG1 nucleotide sequences of the invention further include: (a) any nucleotide sequence that hybridizes to a HKNG1 nucleic acid molecule of the invention under stringent conditions, e.g., hybridization to filter-bound DNA in 6× sodium chloride/sodium citrate (SSC) at about 45° C. followed by one or more washes in 0.2×SSC/0.1% SDS at about 50–65° C., or (b) under highly stringent conditions, e.g., hybridization to filter-bound nucleic acid in 6×SSC at about 45° C. followed by one or more washes in 0.1×SSC/0.2% SDS at about 68° C., or under other hybridization conditions which are apparent to those of skill in the art (see, for example, Ausubel F. M. et al., eds., 1989, Current Protocols in Molecular Biology, Vol. I, Green Publishing Associates, Inc., and John Wiley & sons, Inc., New York, at pp. 6.3.1–6.3.6 and 2.10.3). Preferably the HKNG1 nucleic acid molecule that hybridizes to the nucleotide sequence of (a) and (b), above, is one that comprises the complement of a nucleic acid molecule that encodes a HKNG1 gene product. In a preferred embodiment, nucleic acid molecules comprising the nucleotide sequences of (a) and (b), above, encode gene products, e.g., gene products functionally equivalent to an HKNG1 gene product.

Functionally equivalent HKNG1 gene products include naturally occurring HKNG1 gene products present in the same or different species. In one embodiment, HKNG1 gene sequences in non-human species map to chromosome regions syntenic to the human 18p chromosome location within which human HKNG1 lies. Functionally equivalent HKNG1 gene products also include gene products that retain at least one of the biological activities of the HKNG1 gene products, and/or which are recognized by and bind to antibodies (polyclonal or monoclonal) directed against the HKNG1 gene products.

Among the nucleic acid molecules of the invention are deoxyoligonucleotides ("oligos") which hybridize under highly stringent or stringent conditions to the HKNG1 nucleic acid molecules described above. In general, for probes between 14 and 70 nucleotides in length the melting temperature (TM) is calculated using the formula:

$$Tm(°C.)=81.5+16.6(\log[\text{monovalent cations (molar)}])+0.41(\% G+C)-(500/N)$$

where N is the length of the probe. If the hybridization is carried out in a solution containing formamide, the melting temperature is calculated using the equation Tm(° C.)=81.5+16.6(log[monovalent cations (molar)])+0.41(% G+C)–(0.61% formamide)–(500/N) where N is the length of the probe. In general, hybridization is carried out at about 20–25 degrees below Tm (for DNA-DNA hybrids) or 10–15 degrees below Tm (for RNA-DNA hybrids).

Exemplary highly stringent conditions may refer, e.g., to washing in 6×SSC/0.05% sodium pyrophosphate at 37° C. (for about 14-base oligos), 48° C. (for about 17-base oligos), 55° C. (for about 20-base oligos), and 60° C. (for about 23-base oligos).

These nucleic acid molecules may encode or act as antisense molecules, useful, for example, in HKNG1 gene regulation, and/or as antisense primers in amplification reactions of HKNG1 gene nucleic acid sequences. Further, such sequences may be used as part of ribozyme and/or triple helix sequences, also useful for HKNG1 gene regulation. Still further, such molecules may be used as components of diagnostic methods whereby, for example, the presence of a particular HKNG1 allele involved in a HKNG1-related disorder, e.g., a neuropsychiatric disorder, such as BAD, may be detected.

Fragments of the HKNG1 nucleic acid molecules can be at least 10 nucleotides in length. In alternative embodiments, the fragments can be about 20, 30, 40, 50, 60, 70, 80, 90, 100, 200, 300, 400, 500, 1000, 1500, 2000, 2500, 3000, 3500, 4000, 4500, 5000, or more contiguous nucleotides in length. Alternatively, the fragments can comprise sequences that encode at least 10, 20, 30, 40, 50, 100, 150, 200, 250, 300, 350, 400, 450 or more contiguous amino acid residues of the HKNG1 gene products. Fragments of the HKNG1 nucleic acid molecules can also refer to HKNG1 exons or introns, and, further, can refer to portions of HKNG1 coding regions that encode domains (e.g., clusterin domains) of HKNG1 gene products.

The HKNG1 nucleotide sequences of the invention can be readily obtained, for example, by standard sequencing and the sequence provided herein.

As will be appreciated by those skilled in the art, DNA sequence polymorphisms of a HKNG1 gene will exist within a population of individual organisms (e.g., within a human population). Such polymorphisms may exist, for example, among individuals within a population due to natural allelic variation. Such polymorphisms include ones that lead to changes in amino acid sequence. An allele is one of a group of genes which occur alternatively at a given genetic locus.

As used herein, the phrase "allelic variant" refers to a nucleotide sequence which occurs at a given locus or to a gene product encoded by that nucleotide sequence. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. As used herein, the terms "gene" and "recombinant gene" refer to nucleic acid molecules comprising an open reading frame encoding a polypeptide of the invention. The term can further include nucleic acid molecules comprising upstream and/or exon/intron sequences and sructure.

With respect to HKNG1 allelic variants, any and all such nucleotide variations and resulting amino acid polymorphisms or variations that are the result of natural allelic variation of the HKNG1 gene are intended to be within the scope of the present invention. Such allelic variants include, but are not limited to, ones that do not alter the functional activity of the HKNG1 gene product. Variants include, but are not limited to, variants comprising the polymorphisms summarized in FIGS. 5A–5C and a variant which encodes a full length HKNG1 polypeptide comprising a substitution of a lysine amino acid at amino acid residue 202 of the HKNG1 polypeptide shown in FIGS. 1A–1C and SEQ ID NO:2 or the HKNG1 amino acid residue 184 of the polypeptide of SEQ ID NO:4.

With respect to the cloning of additional allelic variants of the human HKNG1 gene and homologues and orthologs from other species (e.g., guinea pig, cow, mouse), the isolated HKNG1 gene sequences disclosed herein may be labeled and used to screen a cDNA library constructed from mRNA obtained from appropriate cells or tissues (e.g., brain or retinal tissues) derived from the organism (e.g., guinea pig, cow, and mouse) of interest. The hybridization conditions used should generally be of a lower stringency when the cDNA library is derived from an organism different from the type of organism from which the labeled sequence was derived, and can routinely be determined based on, e.g., relative relatedness of the target and refernce organisms.

Alternatively, the labeled fragment may be used t o screen a genomic library derived from the organism of interest, again, using appropriately stringent conditions. Appropriate stringency conditions are well known to those of skill in the art as discussed above, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989–1999, Current Protocols in Molecular Biology, Green Publishing Associates and Wiley Interscience, N.Y., both of which are incorporated herein by reference in their entirety.

Further, a HKNG1 gene allelic variant may be isolated from, for example, human nucleic acid, by performing PCR using two degenerate oligonucleotide primer pools designed on the basis of amino acid sequences within the HKNG1 gene product disclosed herein. The template for the reaction may be cDNA obtained by reverse transcription of mRNA prepared from, for example, human or non-human cell lines or tissue known or suspected to express a wild type or mutant HKNG1 gene allele (such as, for example, brain cells, including brain cells from individuals having BAD). In one embodiment, the allelic variant is isolated from an individual who has a HKNG1-mediated disorder. Such variants are described in the examples below.

The PCR product may be subcloned and sequenced to ensure that the amplified sequences represent the sequences of a HKNG1 gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the HKNG1 gene, such as, for example, brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra, or Ausubel et al., supra.

A cDNA of an allelic, e.g., mutant, variant of the HKNG1 gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying a mutant HKNG1 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant HKNG1 allele to that of the normal HKNG1 allele, the mutation(s) responsible for the loss or alteration of function of the mutant HKNG1 gene product can be ascertained.

Alternatively, a genomic library can be constructed using DNA obtained from an individual suspected of or known to carry a mutant HKNG1 allele, or a cDNA library can be constructed using RNA from a tissue known, or suspected, to express a mutant HKNG1 allele. An unimpaired HKNG1 gene or any suitable fragment thereof may then be labeled and used as a probe to identify the corresponding mutant HKNG1 allele in such libraries. Clones containing the mutant HKNG1 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant HKNG1 allele in an individual suspected of or known to carry such a mutant allele. In this manner, gene products made by the putatively mutant tissue may be expressed and screened using standard antibody screening techniques in conjunction with antibodies raised against the normal HKNG1 gene product, as described, below, in Section 5.3. (For screening techniques, see, for example, Harlow and Lane, eds., 1988, "Antibodies: A Laboratory Manual", Cold Spring Harbor Press, Cold Spring Harbor.)

In cases where a HKNG1 mutation results in an expressed gene product with altered function (e.g., as a result of a missense or a frameshift mutation), a polyclonal set of anti-HKNG1 gene product antibodies are likely to cross-react with the mutant HKNG1 gene product. Library clones detected via their reaction with such labeled antibodies can be purified and subjected to sequence analysis according to methods well known to those of skill in the art.

HKNG1 mutations or polymorphisms can further be detected using PCR amplification techniques. Primers can routinely be designed to amplify overlapping regions of the whole HKNG1 sequence including the promoter regulating region. In one embodiment, primers are designed to cover the exon-intron boundaries such that, coding regions can be scanned for mutations. Exemplary primers for analyzing HKNG1 exons are provided in Table 1, of Section 5.6, below.

The invention also includes nucleic acid molecules, preferably DNA molecules, that are the complements of the nucleotide sequences of the preceding paragraphs.

In certain embodiments, the nucleic acid molecules of the invention are present as part of nucleic acid molecules comprising nucleic acid sequences that do not contain heterologous (e.g., cloning vector or expression vector) sequences. In other embodiments, the nucleic acid molecules of the invention further comprise vector sequences, e.g., cloning vectors or expression vectors.

5.2. Protein Products of the HKNG1 Gene

HKNG1 gene products or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of HKNG1-mediated disorders, e.g., neuropsychiatric disorders, such as BAD.

The HKNG1 gene products of the invention include, but are not limited to, human HKNG1 gene products, e.g., polypeptides comprising the amino acid sequences depicted in FIGS. 1A–1C, 2A–2C, 17A–17B, and 18A–18C (i.e., SEQ ID NOS:2, 4, 51, and 66). The HKNG1 gene products of the invention also include non-human, e.g., mammalian (such as bovine or guinea pig), HKNG1 gene products. These include, but are not limited to, polypeptides comprising the amino acid sequences depicted in FIGS. 7A–13C (i.e., SEQ ID NOS:39, 41, 43, 45, and 49).

HKNG1 gene product, sometimes referred to herein as an "HKNG1 protein" or "HKNG1 polypeptide," includes those gene products encoded by the HKNG1 gene sequences depicted in FIGS. 1A–1C, 2A–2C, 7A–13C, 17A–17B, and 18A–C, as well as gene products encoded by other human allelic variants and non-human variants of HKNG1 that can be identified by the methods herein described. Among such HKNG1 gene product variants are gene products comprising HKNG1 amino acid residues encoded by the polymorphisms depicted in FIGS. 5A–5C. Such gene product variants also include a variant of the HKNG1 gene product depicted in FIG. 1A–1C (SEQ ID NO:2) wherein the amino acid residue Lys202 is mutated to a glutamic acid residue. Such HKNG1 gene product variants also include a variant of the HKNG1 gene product depicted in FIGS. 2A–2C (SEQ ID NO:4) wherein the amino acid residue Lys184 is mutated to a glutamic acid residue.

In addition, HKNG1 gene products may include proteins that represent functionally equivalent gene products. Functionally equivalent gene products may include, for example, gene products encoded by one of the HKNG1 nucleic acid molecules described in Section 5.1, above. In preferred embodiments, such functionally equivalent HKNG1 gene products are naturally occuring gene products. Functionally equivalent HKNG1 gene products also include gene products that retain at least one of the biological activities of the HKNG1 gene products described above, and/or which are recognized by and bind to antibodies (polyclonal or monoclonal) directed against HKNG1 gene products.

Equivalent HKNG1 gene product may contain deletions, including internal deletions, additions, including additions yielding fusion proteins, or substitutions of amino acid residues within and/or adjacent to the amino acid sequence encoded by the HKNG1 gene sequences described, above, in Section 5.1. Generally, deletions will be deletions of single amino acid residues, or deletions of no more than about 2, 3, 4, 5, 10 or 20 amino acid residues, either contiguous or non-contiguous. Generally, additions or substitutions, other than additions that yield fusion proteins, will be additions or substitutions of single amino acid residues, or additions or substitutions of no more than about 2, 3, 4, 5, 10 or 20 amino acid residues, either contiguous or non-contiguous. Preferably, these modifications result in a "silent" change, in that the change produces a HKNG1 gene product with the same activity as the HKNG1 gene product depicted in FIGS. 1A–1C, 2A–2C, 7A–13C, or 17A–17B.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, addition(s), deletion(s) or non-conservative alterations can produce altered, including reduced-activity, HKNG1 gene products. Such alterations can, for example, alter one or more of the biological functions of the HKNG1 gene product. Further, such alterations can be selected so as to generate HKNG1 gene products that are better suited for expression, scale up, etc. in the host cells chosen. For example, cysteine residues can be deleted or substituted with another amino acid residue in order to eliminate disulfide bridges.

As another example, altered HKNG1 gene products can be engineered that correspond to variants of the HKNG1 gene product associated with HKNG1-mediated neuropsychiatric disorders such as BAD. Such altered HKNG1 gene products include, but are not limited to, HKNG1 proteins or peptides comprising substitution of a lysine residue for the wild-type glutamic acid residue at HKNG1 amino acid position 202 in FIGS. 1A–1C (SEQ ID NO:2) or amino acid position 184 (SEQ ID NO:4) in FIGS. 2A–2C.

HKNG1 protein fragments and/or HKNG1 peptides comprise at least as many contiguous amino acid residues as necessary to represent an epitope fragment (that is to be recognized by an antibody directed to the HKNG1 protein). For example, such protein fragments or peptides comprise at least about 8 contiguous HKNG1 amino acid residues from a full length HKNG1 protein. In alternate embodiments, the HKNG1 protein fragments and peptides of the invention can comprise about 10, 20, 30, 40, 50, 60, 70, 80, 90, 100, 150, 200, 250, 300, 350, 400, 450 or more contiguous amino acid residues of a HKNG1 protein.

Peptides and/or proteins corresponding to one or more domains of the HKNG1 protein as well as fusion proteins in which a HKNG1 protein, or a portion of a HKNG1 protein such as a truncated HKNG1 protein or peptide or a HKNG1 protein domain, is fused to an unrelated protein are also within the scope of this invention. Such proteins and peptides can be designed on the basis of the HKNG1 nucleotide sequence disclosed in Section 5.1, above, and/or on the basis of the HKNG1 amino acid sequence disclosed in the Section. Fusion proteins include, but are not limited to, IgFc fusions which stabilize the HKNG1 protein or peptide and prolong half life in vivo; or fusions to any amino acid sequence that allows the fusion protein to be anchored to the cell membrane; or fusions to an enzyme, fluorescent protein, luminescent protein, or a flag epitope protein or peptide which provides a marker function.

The HKNG1 protein, the HKNG1 protein sequences described above can include a domain which comprises a signal sequence that targets the HKNG1 gene product for secretion. As used herein, a signal sequence includes a peptide of at least about 15 or 20 amino acid residues in length which occurs at the N-terminus of secretory and membrane-bound proteins and which contains at least about 70% hydrophobic amino acid residues such as alanine, leucine, isoleucine, phenylalanine, proline, tyrosine, tryptophan, or valine. In a preferred embodiment, a signal sequence contains at least about 10 to 40 amino acid residues, preferably about 19–34 amino acid residues, and has at least about 60–80%, more preferably 65–75%, and more preferably at least about 70% hydrophobic residues. A signal sequence serves to direct a protein containing such a sequence to a lipid bilayer.

In one embodiment, a HNKNG1 protein contains a signal sequence at about amino acids 1 to 49 of SEQ ID NO:2. In another embodiment, a HKNG1 protein contains a signal sequence at about amino acids 30–49 of SEQ ID NO:2. In yet another embodiment, a HKNG1 protein contains a signal sequence at about amino acid residues 1 to 31 of SEQ ID NO:4. In yet another embodiment, a HKNG1 protein contains a signal sequence at about amino acids 12–31 of SEQ ID NO:4. The signal sequence is cleaved during processing of the mature protein.

A signal sequence of a polypeptide of the invention can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described HKNG1 polypeptides having a signal sequence (that is, "immature" polypeptides), as well as to the HKNG1 signal sequences themselves and to the HNKG1 polypeptides in the absence of a signal sequence (i.e., the "mature" HKNG1 cleavage products). It is to be understood that HKNG1 polypeptides of the invention can further comprise polypeptides comprising any signal sequence having characteristics as described above and a mature HKNG1 polypeptide sequence.

In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The HKNG1 protein sequences described above can also include one or more domains which comprise a clusterin domain, i.e., domains which are identical to or substantially homologous to (i.e., 65%, 75%, 80%, 85%, 90%, 95% or more identical to) the domain corresponding to amino acid residues 134 to 160 or amino acid residues 334 to 362 of SEQ ID NO:2, or to the domain corresponding to amino acid residues 105–131 or amino acid residues 305–333 of SEQ ID No:39, or to the domain corresponding to amino acid residues 105–131 or amino acid residues 304–332 of SEQ ID NO:49. Preferably, such domains comprise cysteine amino acid residues at positions corresponding to conserved cysteine residues of the clusterin domains of SEQ ID NOS: 2, 39 or 49.

In particular, HKNG1 protein sequences described above can also include one or more domains which comprise a conserved cysteine domain. Such a domain corresponds, for example, to the domain of cysteines corresponding to Cys134, Cys145, Cys148, Cys158 and Cys160; or to Cys 334, Cys344, Cys351, Cys354, and Cys362 of SEQ ID NO:2. In an alternative embodiment, a conserved cystein domain corresponds to one or more of the domains of SEQ ID NO:39 which comprises Cys105, Cys116, Cys119, Cys124, and Cys131; or Cys305, Cys315, Cys322, Cys325, and Cys333. In yet another alternative embodiment, a conserved cysteine domain corresponds to one or more of the domains of SEQ ID NO:49 which comprises Cys105, Cys116, Cys119, Cys124, and Cys131; or Cys314, Cys321, Cys324, and Cys332.

Finally, the HKNG1 proteins of the invention also include HKNG1 protein sequences wherein domains encoded by one or more exons of the cDNA sequence, or fragments thereof, have been deleted. In one particularly preferred embodiment, the HKNG1 proteins of the invention are proteins in which the domain(s) corresponding the those domains encoded by exon 7 of SEQ ID NO:7, or fragments thereof, have been deleted.

The HKNG1 polypeptides of the invention can further comprise posttranslational modifications, including, but not limited to glycosylations, acetylations, and myrisalations.

The HKNG1 gene products, peptide fragments thereof and fusion proteins thereof, may be produced by recombinant DNA technology using techniques well known in the art. Thus, methods for preparing the HKNG1 gene products, polypeptides, peptides, fusion peptide and fusion polypeptides of the invention by expressing nucleic acid containing HKNG1 gene sequences are described herein. Methods that are well known to those skilled in the art can be used to construct expression vectors containing HKNG1 gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding HKNG1 gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the HKNG1 gene product coding sequences of the invention. Such host-expression systems represent vehicles by which the coding sequences of interest may be produced and subsequently purified, but also represent cells that may, when transformed or transfected with the appropriate nucleotide coding sequences, exhibit the HKNG1 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing HKNG1 gene product coding sequences; yeast (e.g., Saccharomyces, Pichia) transformed with recombinant yeast expression vectors containing the HKNG1 gene product coding sequences; insect cell systems infected with recombinant virus expression vectors (e.g., baculovirus) containing the HKNG1 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing HKNG1 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the HKNG1 gene product being expressed. For example, when a large quantity of such a protein is to be produced, for the generation of pharmaceutical compositions of HKNG1 gene product or for raising antibodies to HKNG1 gene product, for example, vectors that direct the expression of high levels of fusion protein products that are readily purified may be desirable. Such vectors include, but are not limited to, the *E. coli* expression vector pUR278 (Ruther et al., 1983, EMBO J. 2:1791), in which the HKNG1 gene product coding sequence may be ligated individually into the vector in frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhidrosis virus (AcNPV) is used as a vector to express foreign genes. The virus grows in *Spodoptera frugiperda* cells. The HKNG1 gene product coding sequence may be cloned individually into non-essential regions (for example the polyhedrin gene) of the virus and placed under control of an AcNPV promoter (for example the polyhedrin promoter). Successful insertion of HKNG1 gene product coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46:584; Smith, U.S. Pat. No. 4,215,051).

In mammalian host cells, a number of viral-based expression systems may be utilized. In cases where an adenovirus is used as an expression vector, the HKNG1 gene product coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing HKNG1 gene product in infected hosts. (e.g., See Logan and Shenk, 1984, Proc. Natl. Acad. Sci. U.S.A. 81:3655–3659). Specific initiation signals may also be required for efficient translation of inserted HKNG1 gene product coding sequences. These signals include the ATG initiation codon and adjacent sequences. In cases where an entire HKNG1 gene, including its own initiation codon and adjacent sequences, is inserted into the appropriate expression vector, no additional translational control signals may be needed. However, in cases where only a portion of the HKNG1 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the posttranslational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the HKNG1 gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the HKNG1 gene product. Such engineered cell lines may be particularly useful in screening and evaluation of compounds that affect the endogenous activity of the HKNG1 gene product.

A number of selection systems may be used, including but not limited to the herpes simplex virus thymidine kinase (Wigler, et al., 1977, Cell 11:223), hypoxanthine-guanine phosphoribosyltransferase (Szybalska and Szybalski, 1962, Proc. Natl. Acad. Sci. U.S.A. 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. U.S.A. 77:3567; O'Hare, et al., 1981, Proc. Natl. Acad. Sci. U.S.A. 78:1527); gpt, which confers resistance to mycophenolic acid (Mulligan and Berg, 1981, Proc. Natl. Acad. Sci. U.S.A. 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, the expression characteristics of an endogenous HKNG1 gene within a cell line or microorganism may be modified by inserting a heterologous DNA regulatory element into the genome of a stable cell line or cloned microorganism such that the inserted regulatory element is operatively linked with the endogenous HKNG1 gene. For example, an endogenous HKNG1 gene which is normally "transcriptionally silent", i.e., an HKNG1 gene which is normally not expressed, or is expressed only at very low levels in a cell line or microorganism, may be activated by inserting a regulatory element which is capable of promoting the expression of a normally expressed gene product in that cell line or microorganism. Alternatively, a transcriptionally silent, endogenous HKNG1 gene may be activated by insertion of a promiscuous regulatory element that works across cell types.

A heterologous regulatory element may be inserted into a stable cell line or cloned microorganism, such that it is operatively linked with an endogenous HKNG1 gene, using techniques, such as targeted homologous recombination, which are well known to those of skill in the art, and described e.g., in Chappel, U.S. Pat. No. 5,272,071; PCT publication No. WO 91/06667, published May 16, 1991.

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. U.S.A. 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

The HKNG1 gene products can also be expressed in transgenic animals. Animals of any species, including, but not limited to, mice, rats, rabbits, guinea pigs, pigs, micropigs, goats, sheep, cows, and non-human primates, e.g., baboons, monkeys, and chimpanzees may be used to generate HKNG1 transgenic animals. The term "transgenic," as used herein, refers to animals expressing HKNG1 gene sequences from a different species (e.g., mice expressing huma HKNG1 gene sequences), as well as animals that have been genetically engineered to overexpress endogenous (i.e., same species) HKNG1 sequences or animals that have been genetically engineered to no longer express endogenous HKNG1 gene sequences (i.e., "knock-out" animals), and their progeny.

Any technique known in the art may be used to introduce a HKNG1 gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., U.S.A. 82:6148–6152); gene targeting in embryonic stem cells (Thompson, et al., 1989, Cell 56:313–321); electroporation of embryos (Lo, 1983, Mol. Cell. Biol. 3:1803–1814); and sperm-mediated gene transfer (Lavitrano et al., 1989, Cell 57:717–723) (For a review of such techniques, see Gordon, 1989, Transgenic Animals, Intl. Rev. Cytol. 115, 171–229)

Any technique known in the art may be used to produce transgenic animal clones containing a HKNG1 transgene, for example, nuclear transfer into enucleated oocytes of nuclei from cultured embryonic, fetal or adult cells induced to quiescence (Campbell, et al., 1996, Nature 380:64–66; Wilmut, et al., Nature 385:810–813).

The present invention provides for transgenic animals that carry a HKNG1 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. U.S.A. 89:6232–6236). The regulatory sequences required for such a cell-type specific activation will depend upon the particular cell type of interest, and will be apparent to those of skill in the art. When it is desired that the HKNG1 transgene be integrated into the chromosomal site of the endogenous HKNG1 gene, gene targeting is preferred. Briefly, when such a technique is to be utilized, vectors containing some nucleotide sequences homologous to the endogenous HKNG1 gene are designed for the purpose of integrating, via homologous recombination with chromosomal sequences, into and disrupting the function of the nucleotide sequence of the endogenous HKNG1 gene. The transgene may also be selectively introduced into a particular cell type, thus inactivating the endogenous HKNG1 gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant HKNG1 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of HKNG1 gene-expressing tissue, may also be evaluated immunocytochemically using antibodies specific for the HKNG1 transgene product.

HKNG1 proteins can be used, e.g., to treat CNS-related disorders, e.g., neuropsychiatric disorders. Such HKNG1 gene products include but are not limited to soluble derivatives such as peptides or polypeptides corresponding to one or more domains of the HKNG1 gene product, particularly HKNG1 gene products, that are modified such that they are deleted for one or more hydrophobic domains. Alternatively, antibodies to the HKNG1 protein or anti-idiotypic antibodies that mimic the HKNG1 gene product (including Fab fragments), antagonists or agonists can be used to treat neuropsychiatric disorders involving HKNG1. In yet another approach, nucleotide constructs encoding such HKNG1 gene products can be used to genetically engineer host cells to express such HKNG1 gene products in vivo; these genetically engineered cells can function as "bioreactors" in the body delivering a continuous supply of HKNG1 gene product, HKNG1 peptides, soluble HKNG1 polypeptides.

5.3. Antibodies to HKNG1 Gene Products

Described herein are methods for the production of antibodies capable of specifically recognizing one or more HKNG1 gene product epitopes or epitopes of conserved variants or peptide fragments of the HKNG1 gene products. Further, antibodies that specifically recognize mutant forms of HKNG1, are encompassed by the invention. The terms "specifically bind" and "specifically recognize" refer to antibodies that bind to HKNG1 gene product epitopes at a higher affinity than they bind to non-HKNG1 (e.g., random) epitopes.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above, including the polyclonal and monoclonal antibodies described in Section 12 below. Such antibodies may be used, for example, in the detection of a HKNG1 gene product in an biological sample and may, therefore, be utilized as part of a diagnostic or prognostic technique whereby patients may be tested for abnormal levels of HKNG1 gene products, and/or for the presence of abnormal forms of such gene products. Such antibodies may also be utilized in conjunction with, for example, compound screening schemes, as described, below, in Section 5.8, for the evaluation of the effect of test compounds on HKNG1 gene product levels and/or activity. Additionally, such antibodies can be used in conjunction with the gene therapy techniques described, below, in Section 5.9.2 to, for example, evaluate the normal and/or engineered HKNG1-expressing cells prior to their introduction into the patient.

Anti-HKNG1 gene product antibodies may additionally be used in methods for inhibiting abnormal HKNG1 gene product activity. Thus, such antibodies may, therefore, be utilized as part of treatment methods for a HKNG1-mediated neuropsychiatric disorder, such as BAD or schizophrenia.

For the production of antibodies against a HKNG1 gene product, various host animals may be immunized by injection with a HKNG1 gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, such as a HKNG1 gene product, or an antigenic functional derivative thereof. For the production of polyclonal antibodies, host animals such as those described above, may be immunized by injection with HKNG1 gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81:6851–6855; Neuberger, et al., 1984, Nature 312:604–608; Takeda, et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983) ). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston, et al., 1988, Proc. Natl. Acad. Sci. U.S.A. 85:5879–5883; and Ward, et al., 1989, Nature 334:544–546) can be adapted to produce single chain antibodies against HKNG1 gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science 246:1275–1281) to allow rapid and easy identification of monoclonal Fab fragments with the desired specificity.

5.4. Uses of HKNG1 Gene Sequences Gene Products, and Antibodies

Described herein are various applications of HKNG1 gene sequences, HKNG1 gene products, including peptide fragments and fusion proteins thereof, and of antibodies directed against HKNG1 gene products and peptide fragments thereof. Such applications include, for example, mapping of chromosome 18p, prognostic and diagnostic evaluation of HKNG1-mediated disorders, including CNS-related disorders, e.g., neuropsychiatric disorders, such as BAD or schizophrenia, modulation of HKNG1-related processes, and the identification of subjects with a predisposition to such disorders, as described, below, in Section 5.5.

Additionally, such applications include methods for the treatment of a HKNG1-mediated disorders, such as BAD or schizophrenia, as described, below, in Section 5.9, and for the identification of compounds that modulate the expression of the HKNG1 gene and/or the synthesis or activity of the HKNG1 gene product, as described below, in Section 5.8. Such compounds can include, for example, other cellular products that are involved in such processes as mood regulation and in HKNG1-mediated disorders, e.g., neuropsychiatric disorders such as BAD or schizophrenia. These compounds can be used, for example, in the amelioration of HKNG1-mediated disorders and for the modulation of HKNG1-mediated processes.

Uses of the HKNG1 gene sequences, HKNG1 gene products, including peptide fragments and fusion proteins thereof, and of antibodies directed against HKNG1 gene products and/or peptide fragments thereof also include prognostic and diagnostic evaluation of a HKNG1-mediated myopia disorder such as early-onset autosomal dominant myopia, methods for the treatment of a HKNG1-mediated myopia disorder, and for the identification of compound that modulate the expression of the HKNG1 gene and/or the synthesis or activity of the HKNG1 gene product and could therefore be used in the amelioration of a HKNG1-mediated myopia such as early-onset autosomal dominant myopia. Indeed, such methods are substantially identical to the methods described, below, in Sections 5.5, 5.8, and 5.9 for the diagnosis and treatment of HKNG1-mediated disorders.

5.5. Diagnosis of HKNG1-Mediated Disorders

A variety of methods can be employed for the diagnostic and prognostic evaluation of HKNG1-mediated disorders, e.g., neuropsychiatric disorders and for the identification of subjects having a predisposition to such disorders.

Such methods may, for example, utilize reagents such as the HKNG1 gene nucleotide sequences described in Sections 5.1, and antibodies directed against HKNG1 gene products, including peptide fragments thereof, as described, above, in Section 5.3. Specifically, such reagents may be used, for example, for:

(1) the detection of the presence of HKNG1 gene mutations, or the detection of either over- or under-expression of HKNG1 gene relative to wild-type HKNG1 levels of expression;

(2) the detection of over- or under-abundance of HKNG1 gene product relative to wild-type abundance of HKNG1 gene product; and (3) the detection of an aberrant level of HKNG1 gene product activity relative to wild-type HKNG1 gene product activity levels.

HKNG1 gene nucleotide sequences can, for example, be used to diagnose a HKNG1-mediated neuropsychiatric disorder using, for example, the techniques for HKNG1 mutation/polymorphism detection described above in Section 5.1, and in Section 5.6 below.

Mutations at a number of different genetic loci may lead to phenotypes related to neuropsychiatric disorders. Ideally, the treatment of patients suffering from such neuropsychiatric disorder will be designed to target the particular genetic loci containing the mutation mediating the disorder. Genetic polymorphisms have been linked to differences in drug effectiveness. Thus, identification of alterations in the HKNG1 gene, protein or gene flanking regions, can be utilized in pharmacogenetic methods to optimize therapeutic drug treatments.

In one embodiment of the present invention, therefore, alterations, i.e., polymorphisms, in the HKNG1 gene or protein encoded by genes comprising such polymorphisms, are associated with a drug or drugs' efficacy, tolerance, or toxicity, and may be used in pharmacogenomic methods to optimize therapeutic drug treatments, including therapeutic drug treatments for one of the disorders described herein, e.g., HKNG1-mediated disorders such as schizophrenia and BAD. Such polymorphisms can be used, for example, to refine the design of drugs by decreasing the incidence of adverse events in drug tolerance studies, e.g., by identifying patient subpopulations of individuals who respond or do not respond to a particular drug therapy in efficacy studies, wherein the subpopulations have a HKNG1 polymorphism associated with drug responsiveness or unresponsiveness. The pharmacogenomic methods of the present invention can also provide tools to identify new drug targets for designing drugs and to optimize the use of already existing drugs, e.g., to increase the response rate to a drug and/or to identify and exclude non-responders from certain drug treatments (e.g., individuals having a particular HKNG1 polymorphism associated with unresponsiveness or inferior responsiveness to the drug treatment) or to decrease the undersireable side effects of certain drug treatments and/or to identify and exclude individuals with marked susceptibility to such side effects (e.g., individuals having a particular HKNG1 polymorphism associated with an undersirable side effect to the drug treatment).

In an embodiment of the present invention, polymorphisms in the HKNG1 gene sequence or flanking this sequence, or variations in HKNG1 gene expression, or activity, e.g., variations due to altered methylation, differential splicing, or post-translational modification of the HKNG1 gene product, may be utilized to identify an individual having a disease or condition resulting from a HKNG1-mediated disorder and thus define the most effective and safest drug treatment. Assays such as those described herein may be used to identify such polymorphisms or variations in HKNG1 gene expression or activity. Once a polymorphism in the HKNG1 gene or in a flanking sequence in linkage disequilibrium with a disorder-causing allele, or a variation in HKNG1 gene expression has been identified in an individual, an appropriate drug treatment can be prescribed to the individual.

For the detection of HKNG1 gene mutations or polymorphisms, any nucleated cell can be used as a starting source for genomic nucleic acid. For the detection of HKNG1 gene expression or HKNG1 gene products, any cell type or tissue in which the HKNG1 gene is expressed may be utilized.

Nucleic acid-based detection techniques are described, below, in Section 5.6. Peptide detection techniques are described, below, in Section 5.7.

The methods described herein may be performed, for example, by utilizing pre-packaged diagnostic kits. The invention therefore also encompasses kits for detecting the presence of a polypeptide or nucleic acid of the invention in a biological sample (i.e., a test sample). Such kits can be used, e.g., to determine if a subject is suffering from or is at increased risk of developing a disorder associated with a disorder-causing allele, or aberrant expression or activity of a polypeptide of the invention (e.g., a CNS disorder, including a neuropsychiatric disorder such as BAD or schizophrenia). For example, the kit can comprise a labeled compound or agent capable of detecting the polypeptide or mRNA or DNA or HKNG1 gene sequences, e.g., encoding the polypeptide in a biological sample. The kit can further comprise a means for determining the amount of the polypeptide or mRNA in the sample (e.g., an antibody which binds the polypeptide or an oligonucleotide probe which binds to DNA or mRNA encoding the polypeptide). Kits can also include instructions for observing that the tested subject is suffering from or is at risk of developing a disorder associated with aberrant expression of the polypeptide if the amount of the polypeptide or mRNA encoding the polypeptide is above or below a normal level, or if the DNA correlates with presence of a HKNG1 allele that causes a disorder.

For antibody-based kits, the kit can comprise, for example: (1) a first antibody (e.g., attached to a solid support) which binds to a polypeptide of the invention; and, optionally, (2) a second, different antibody which binds to either the polypeptide or to the first antibody and is conjugated to a detectable agent.

For oligonucleotide-based kits, the kit can comprise, for example: (1) an oligonucleotide (e.g., a detectably labeled oligonucleotide) which hybridizes to a nucleic acid sequence encoding a polypeptide of the invention, or (2) a pair of primers, such as the primers recited in Table 1, useful for amplifying a nucleic acid molecule encoding a polypeptide of the invention.

The kit can also comprise, for example, one or more buffering agents, preservatives, or protein stabilizing agents. The kit can also comprise components necessary for detecting the detectable agent (e.g., an enzyme or a substrate). The kit can also contain a control sample or a series of control samples which can be assayed and compared to the test sample. Each component of the kit is usually enclosed within an individual container and all of the various containers are within a single package along with instructions for observing whether the tested subject is suffering from or is at risk of developing a disorder associated with polymorphisms that correlate with alleles that cause HKNG1-related disorders, and/or aberrant levels of HKNG1 mRNA, polypeptides or activity.

5.6. Detection of HKNG1 Nucleic Acid Molecules

A variety of methods can be employed to screen for the presence of HKNG1 gene-specific mutations or polymorphisms (including polymorphisms flanking HKNG1 gene) and to detect and/or assay levels of HKNG1 nucleic acid sequences.

Mutations or polymorphisms within or flanking the HKNG1 gene can be detected by utilizing a number of techniques. Nucleic acid from any nucleated cell can be used as the starting point for such assay techniques, and may be isolated according to standard nucleic acid preparation procedures that are well known to those of skill in the art.

HKNG1 nucleic acid sequences may be used in hybridization or amplification assays of biological samples to detect abnormalities involving HKNG1 gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of HKNG1 gene-specific mutations or polymorphisms can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.1, above, under conditions favorable for the specific annealing of these reagents to their complementary sequences within or flanking the HKNG1 gene. The diagnostic methods of the present invention further encompass contacting and incubating nucleic acids for the detection of single nucleotide mutations or polymorphisms of the HKNG1 gene. Preferably, these nucleic acid reagent sequences within the HKNG1 gene, or chromosome 18p nucleotide sequences flanking the HKNG1 gene are 15 to 30 nucleotides in length.

After incubation, all non-annealed nucleic acids are removed from the nucleic acid:HKNG1 molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled HKNG1 nucleic acid reagents is accomplished using standard techniques well-known to those in the art. The HKNG1 gene sequences to which the nucleic acid reagents have annealed can be compared to the annealing pattern expected from a normal HKNG1 gene sequence in order to determine whether a HKNG1 gene mutation is present.

In a preferred embodiment, HKNG1 mutations or polymorphisms can be detected by using a microassay of HKNG1 nucleic acid sequences immobilized to a substrate or "gene chip" (see, e.g. Cronin, et al., 1996, Human Mutation 7:244–255).

Alternative diagnostic methods for the detection of HKNG1 gene-specific nucleic acid molecules (or HKNG1 flanking sequences), in patient samples or other appropriate cell sources, may involve their amplification, e.g., by PCR useful for amplification of HKNG1 exons are preferably derived from adjacent introns. Appropriate primer pairs can be chosen such that each of the eleven HKNG1 exons are amplified. Primers for the amplification of HKNG1 exons can be routinely designed by one of ordinary skill in the art by utilizing the exon and intron sequences of HKNG1 shown in FIGS. 3A–3CC.

As an example, and not by way of limitation, Table 1, below, lists primers and primer pairs which can be utilized for the amplification of each of the human HKNG1 exons one through eleven. In this table, a primer pair is listed for each exon which consists of a forward primer derived from intron sequence upstream of the exon to be amplified, and a reverse primer derived from intron sequence downstream of the exon to be amplified. For exons greater than about 300 base pairs in length, i.e., exons 4 and 7, two primer pairs are listed (marked 4a, 4b, 7a and 7b). Each of the primer pairs can be utilized, therefore, as part of a standard PCR reaction to amplify an individual HKNG1 exon (or portion thereof). Primer sequences are depicted in a 5' to 3' orientation.

TABLE 1

|   | Primer Sequence | | |
|---|---|---|---|
| 1 | cggggttggtttccacc | (SEQ ID NO:8) | forward |
|   | gcgaggagagaaatctggg | (SEQ ID NO:9) | reverse |
| 2 | tgctcactactttgcagtgttc | (SEQ ID NO:10) | forward |
|   | tgagatcgtgtcactgcattct | (SEQ ID NO:11) | reverse |
| 3 | gtaaatctcaaaatgttgggttaatag | (SEQ ID NO:12) | forward |
|   | ctaactcttcttctatcattactc | (SEQ ID NO:13) | reverse |
| 4A | tgtttattgtgtgtctgctgtg | (SEQ ID NO:14) | forward |
|   | ggacaaccaacatgcaaacag | (SEQ ID NO:15) | reverse |
| 4B | cccaggtgttttcaattgatgc | (SEQ ID NO:16) | foward |
|   | agcagttttgtccttccaagtg | (SEQ ID NO:17) | reverse |
| 5 | gtgttttgtaatctgatcagatctc | (SEQ ID NO:18) | forward |
|   | gcagtatttctggtccagatc | (SEQ ID NO:19) | reverse |
| 6 | ggtgcacatagatcatgaaatgg | (SEQ ID NO:20) | forward |
|   | taagctgaaataggtgccttaag | (SEQ ID NO:21) | reverse |
| 7A | tttattccatttctgtccctac | (SEQ ID NO:22) | forward |
|   | aaggctcagttaggtctgtatc | (SEQ ID NO:23) | reverse |
| 7B | caggagttttaacgtcttcagac | (SEQ ID NO:24) | forward |
|   | gactcagaaatgtctaccatttc | (SEQ ID NO:25) | reverse |
| 8 | tgtctccacttcttcaaagtgc | (SEQ ID NO:26) | forward |
|   | caaaatgtacctgagaacttaaag | (SEQ ID NO:27) | reverse |
| 9 | cacctccaagtttcatggac | (SEQ ID NO:28) | forward |
|   | caaggtatgcacgtgtcatttc | (SEQ ID NO:29) | reverse |
| 10 | gaatgtgtattgggatttagtaaac | (SEQ ID NO:30) | forward |
|   | ttgagaattaactattcctgtcaac | (SEQ ID NO:31) | reverse |
| 11 | ccatcctggacttttactcc | (SEQ ID NO:32) | forward |
|   | ctttcctgcaactgtgtttattg | (SEQ ID NO:33) | reverse |

(the experimental embodiment set forth in Mullis, 1987, U.S. Pat. No. 4,683,202), followed by the analysis of the amplified molecules using techniques well known to those of skill in the art, such as, for example, those listed above. The resulting amplified sequences can be compared to those that would be expected if the nucleic acid being amplified contained only normal copies of the HKNG1 gene in order to determine whether a HKNG1 gene mutation or polymorphism in linkage disequilibrium with a disease-causing HKNG1 allele exists.

Among those HKNG1 nucleic acid sequences which are preferred for such amplification-related diagnostic screening analyses are oligonucleotide primers which amplify HKNG1 exon sequences. The sequences of such oligonucleotide primers are, therefore, preferably derived from HKNG1 intron sequences so that the entire exon, or coding region, can be analyzed as discussed below. Primer pairs Each primer pair above can be used to generate an amplified sequence of about 300 base pairs. This is especially desirable in instances in which sequence analysis is performed using SSCP gel electrophoretic procedures, in that such procedures work optimally using sequences of about 300 base pairs or less.

Additional HKNG1 nucleic acid sequences which are preferred for such amplification-related analyses are those which will detect the presence of an HKNG1 polymorphism which differs from the HKNG1 sequence depicted in FIGS. 3A–3CC. Such polymorphisms include ones which represent mutations associated with an HKNG1-mediated neuropsychiatric disorder, such as BAD or schizophrenia. For example, a single base mutation identified in the Example presented in Section 8, below, results in a mutant HKNG1 gene product comprising substitution of a lysine residue for the wild-type glutamic acid residue at amino acid position 202 of the HKNG1 amino acid sequence shown in FIGS. 1A–1C (SEQ ID NO:2) or amino acid position 184 of the HKNG1 amino acid sequence shown in FIGS. 2A–2C (SEQ ID NO:4). Such polymorphisms also include ones that correlate with the presence of a HKNG1-mediated neuropsychiatric disorder, e.g., polymorphisms that are in linkage disequilibrium with disorder-causing HKNG1 alleles.

Amplification techniques are well known to those of skill in the art and can routinely be utilized in connection with primers such as those listed in Table 1 above. In general, hybridization conditions can be as follows. In general, for probes between 14 and 70 nucleotides in length the melting temperature TM is calculated using the formula: Tm(°C.)=81.5+16.6(log[monovalent cations])+0.41(% G+C)–(500/N) where N is the length of the probe. If the hybridization is carried out in a solution containing formamide, the melting temperature is calculated using the equation Tm(°C.)=81.5+16.6(log[monovalent cations])+0.41(% G+C)–(0.61% formamide)–(500/N) where N is the length of the probe.

Additionally, well-known genotyping techniques can be performed to identify individuals carrying HKNG1 gene mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of HKNG1 gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the HKNG1 gene, and the diagnosis of diseases and disorders related to HKNG1 mutations.

Also, Caskey et al. (U.S. Pat. No. 5,364,759) describe a DNA profiling assay for detecting short tri and tetra nucleotide repeat sequences. The process includes extracting the DNA of interest, such as the HKNG1 gene, amplifying the extracted DNA, and labelling the repeat sequences to form a genotypic map of the individual's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, single stranded conformational polymorphism (SSCP) analysis (see, e.g., Orita et al., 1989, *Proc. Natl. Acad. Sci. USA* 86:2766–2770), denaturing gradient gel electrophoresis (DGGE), heterodulex analysis, mismatch cleavage detection, and other routine techniques well known in the art (see, e.g., Sheffield et al., 1989, *Proc. Natl. Acad. Sci.* 86:5855–5892; Grompe, 1993, *Nature Genetics* 5:111–117). Alternative, preferred methods of detecting and mapping SNPs involve microsequencing techniques wherein an SNP site in a target DNA is detecting by a single nucleotide primer extension reaction (see, e.g., Goelet et al., PCT Publication No. WO92/15712; Mundy, U.S. Pat. No. 4,656,127; Vary and Diamond, U.S. Pat. No. 4,851,331; Cohen et al., PCT Publication No. WO91/02087; Chee et al., PCT Publication No. WO95/11995; Landegren et al., 1988, *Science* 241:1077–1080; Nicerson et al., 1990, *Proc. Natl. Acad. Sci. U.S.A.* 87:8923–8927; Pastinen et al.,1997, *Genome Res.* 7:606–614; Pastinen et al., 1996, *Clin. Chem.* 42:1391–1397; Jalanko et al., 1992, *Clin. Chem.* 38:39–43; Shumaker et al., 1996, *Hum. Mutation* 7:346–354; Caskey et al., PCT Publication No. WO 95/00669).

The level of HKNG1 gene expression can also be assayed. For example, RNA from a cell type or tissue known, or suspected, to express the HKNG1 gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the HKNG1 gene. Such analyses may reveal both quantitative and qualitative aspects of the expression pattern of the HKNG1 gene, including activation or inactivation of HKNG1 gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the HKNG1 gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such HKNG1 gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the HKNG1 gene.

5.7. Detection of HKNG1 Gene Products

Antibodies directed against unimpaired or mutant HKNG1 gene products or conserved variants or peptide fragments thereof, which are discussed, above, in Section 5.3, may also be used as diagnostics and prognostics for a HKNG1-mediated disorder, e.g., a neuropsychiatric disorder such as BAD or schizophrenia. Such methods may be used to detect abnormalities in the level of HKNG1 gene product synthesis or expression, or abnormalities in the structure, temporal expression, and/or physical location of HKNG1 gene product. The antibodies and immunoassay methods described herein have, for example, important in vitro applications in assessing the efficacy of treatments for HKNG1-mediated disorders. Antibodies, or fragments of antibodies, such as those described below, may be used to screen potentially therapeutic compounds in vitro to determine their effects on HKNG1 gene expression and HKNG1 gene product production. The compounds that have beneficial effects on a HKNG1-mediated disorder, such as BAD or schizophrenia.

In vitro immunoassays may also be used, for example, to assess the efficacy of cell-based gene therapy for a HKNG1- mediated disorder, e.g., a neuropsychiatric disorder, such as BAD schizophrenia. Antibodies directed against HKNG1 gene products may be used in vitro to determine, for example, the level of HKNG1 gene expression achieved in cells genetically engineered to produce HKNG1 gene product. In the case of intracellular HKNG1 gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the HKNG1 gene. The protein isolation methods employed herein may, for example, be such as those described in Harlow and Lane (1988, "Antibodies: A Laboratory Manual", Cold Spring Harbor Laboratory Press, Cold Spring Harbor, N.Y.). The isolated cells can be derived from cell culture or from a patient. The analysis of cells taken from culture may be a necessary step in the assessment of cells to be used as part of a cell-based gene therapy technique or, alternatively, to test the effect of compounds on the expression of the HKNG1 gene.

Preferred diagnostic methods for the detection of HKNG1 gene products, conserved variants or peptide fragments thereof, may involve, for example, immunoassays wherein the HKNG1 gene products or conserved variants or peptide fragments are detected by their interaction with an anti-HKNG1 gene product-specific antibody.

For example, antibodies, or fragments of antibodies, such as those described, above, in Section 5.3, may be used to quantitatively or qualitatively detect the presence of HKNG1 gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for HKNG1 gene products that are expressed on the cell surface.

The antibodies (or fragments thereof) useful in the present invention may, additionally, be employed histologically, as in immunofluorescence or immunoelectron microscopy, for in situ detection of HKNG1 gene products, conserved variants or peptide fragments thereof. In situ detection may be accomplished by removing a histological specimen from a patient, and applying thereto a labeled antibody that binds to an rTs polypeptide. The antibody (or fragment) is preferably applied by overlaying the labeled antibody (or fragment) onto a biological sample. Through the use of such a procedure, it is possible to determine not only the presence of the HKNG1 gene product, conserved variants or peptide fragments, but also its distribution in the examined tissue. Using the present invention, those of ordinary skill will readily recognize that any of a wide variety of histological methods (such as staining procedures) can be modified in order to achieve in situ detection of a HKNG1 gene product.

Immunoassays for HKNG1 gene products, conserved variants, or peptide fragments thereof will typically comprise incubating a sample, such as a biological fluid, a tissue extract, freshly harvested cells, or lysates of cells in the presence of a detectably labeled antibody capable of identifying HKNG1 gene product, conserved variants or peptide fragments thereof, and detecting the bound antibody by any of a number of techniques well-known in the art.

The biological sample may be brought in contact with and immobilized onto a solid phase support or carrier, such as nitrocellulose, that is capable of immobilizing cells, cell particles or soluble proteins. The support may then be washed with suitable buffers followed by treatment with the detectably labeled HKNG1 gene product specific antibody. The solid phase support may then be washed with the buffer a second time to remove unbound antibody. The amount of bound label on the solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which the HKNG1 gene product-specific antibody can be detectably labeled is by linking the same to an enzyme, such as for use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect HKNG1 gene products through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8. Screening Assays for Compounds That Modulate HKNG1 Gene Activity

The following assays are designed to identify compounds that bind to a HKNG1 gene product, compounds that bind to proteins, or portions of proteins that interact with a HKNG1 gene product, compounds that modulate, e.g., interfere with, the interaction of a HKNG1 gene product with proteins and compounds that modulate the activity of the HKNG1 gene (i.e., modulate the level of HKNG1 gene expression and/or modulate the level of HKNG1 gene product activity). Assays may additionally be utilized that identify compounds that bind to HKNG1 gene regulatory sequences (e.g., promoter sequences; see e.g., Platt, 1994, J. Biol. Chem. 269, 28558–28562), and that can modulate the level of HKNG1 gene expression. Such compounds may include, but are not limited to, small organic molecules, such as ones that are able to cross the blood-brain barrier, gain to and/or entry into an appropriate cell and affect expression of the HKNG1 gene or some other gene involved in a HKNG1 regulatory pathway.

Methods for the identification of such proteins are described, below, in Section 5.8.2. Such proteins may be involved in the control and/or regulation of mood. Further, among these compounds are compounds that affect the level of HKNG1 gene expression and/or HKNG1 gene product activity and that can be used in the therapeutic treatment of HKNG1-mediated disorders, e.g., neuropsychiatric disorders such as BAD and schizophrenia as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354:82–84; Houghten, et al., 1991, Nature 354:84–86), and combinatorial chemistry-derived molecular library made of D- and/or L-configuration amino acids, phosphopeptides (including, but not limited to members of random or partially degenerate, directed phosphopeptide libraries; see, e.g., Songyang, et al., 1993, Cell 72:767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Such compounds may further comprise compounds, in particular drugs or members of classes or families of drugs, known to ameliorate the symptoms of a HKNG1-mediated disorder, e.g., a neuropsychiatric disorder such as BAD or schizophrenia.

Such compounds include families of antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

Compounds identified via assays such as those described herein may be useful, for example, in elaborating the biological function of the HKNG1 gene product and for ameliorating HKNG1-mediated neuropsychiatric disorders, such as BAD and schizophrenia. Assays for testing the effectiveness of compounds identified by, for example, techniques such as those described in Sections 5.8.1–5.8.3, are discussed, below, in Section 5.8.4.

5.8.1. In Vitro Screening Assays for Compounds That Bind to the HKNG1 Gene Product In vitro systems may be designed to identify compounds capable of binding the HKNG1 gene products of the invention. Compounds identified may be useful, for example, in modulating the activity of unimpaired and/or mutant HKNG1 gene products, may be useful in elaborating the biological function of the HKNG1 gene product, may be utilized in screens for identifying compounds that disrupt normal HKNG1 gene product interactions, or may in themselves disrupt such interactions.

The principle of the assays used to identify compounds that bind to the HKNG1 gene product involves preparing a reaction mixture of the HKNG1 gene product and the test compound under conditions and for a time sufficient to allow the two components to interact and bind, thus forming a complex that can be removed and/or detected in the reaction mixture. These assays can be conducted in a variety of ways. For example, one method to conduct such an assay involves anchoring a HKNG1 gene product or a test substance onto a solid support and detecting HKNG1 gene product/test compound complexes formed on the solid support at the end of the reaction. In one embodiment of such a method, the HKNG1 gene product may be anchored onto a solid support, and the test compound, which is not anchored, may be labeled, either directly or indirectly.

In practice, microtiter plates are conveniently utilized as the solid support. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for HKNG1 gene product or the test compound to anchor any complexes formed in solution, and a labeled antibody specific for the other component of the possible complex to detect anchored complexes.

5.8.2. Assays for Proteins That Interact With HKNG1 Gene Products

Any method suitable for detecting protein-protein interactions may be employed for identifying HKNG1 gene product-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with HKNG1 gene products. Once isolated, such a protein can be identified and can be used in conjunction with standard techniques, to identify proteins it interacts with. For example, at least a portion of the amino acid sequence of a protein that interacts with the HKNG1 gene product can be ascertained using techniques well known to those of skill in the art, such as via the Edman degradation technique (see, e.g., Creighton, 1983, "Proteins: Structures and Molecular Principles," W. H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode a protein which interacts with a HKNG1 gene product. These methods include, for example, probing expression libraries with labeled HKNG1 gene product, using HKNG1 gene product in a manner similar to the well known technique of antibody probing of λgt11 libraries.

One method that detects protein interactions in vivo, the two-hybrid system, is described in detail for illustration only and not by way of limitation. One version of this system has been described (Chien, et al., 1991, Proc. Natl. Acad. Sci. U.S.A., 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the HKNG1 gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodologies may be used to screen activation domain libraries for proteins that interact with the "bait" gene product. By way of example, and not by way of limitation, HKNG1 gene products may be used as the bait gene product. Total genomic or cDNA sequences are fused to the DNA encoding an activation domain. This library and a plasmid encoding a hybrid of a bait HKNG1 gene product fused to the DNA-binding domain are co-transformed into a yeast reporter strain, and the resulting transformants are screened for those that express the reporter gene. For example, a bait HKNG1 gene sequence, such as the open reading frame of the HKNG1 gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait HKNG1 gene product are to be detected can be made using methods routinely practiced in the art. According to the particular system described herein, for example, the cDNA fragments can be inserted into a vector such that they are translationally fused to the transcriptional activation domain of GAL4. Such a library can be co-transformed along with the bait HKNG1 gene-GAL4 fusion plasmid into a yeast strain that contains a lacZ gene driven by a promoter that contains GAL4 activation sequence. A cDNA encoded protein, fused to a GAL4 transcriptional activation domain that interacts with bait HKNG1 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait HKNG1 gene product-interacting protein using techniques routinely practiced in the art.

5.8.3. Assays for Compounds That Interfere With or Potentiate HKNG1 Gene Product Macromolecule Interaction The HKNG1 gene products may, in vivo, interact with one or more macromolecules, including intracellular macromolecules, such as proteins. Such macromolecules may include, but are not limited to, nucleic acid molecules and those proteins identified via methods such as those described, above, in Sections 5.8.1–5.8.2. For purposes of this discussion, the macromolecules are referred to herein as "binding partners". Compounds that disrupt HKNG1 gene product binding to a binding partner may be useful in regulating the activity of the HKNG1 gene product, especially mutant HKNG1 gene products. Such compounds may include, but are not limited to molecules such as peptides, and the like, as described, for example, in Section 5.8.2 above.

The basic principle of an assay system used to identify compounds that interfere with or potentiate the interaction between the HKNG1 gene product and a binding partner or partners involves preparing a reaction mixture containing the HKNG1 gene product and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of HKNG1 gene product and its binding partner. Control reaction mixtures are incubated without the test compound or with a compound which is known not to block complex formation. The formation of any complexes between the HKNG1 gene product and the binding partner is then detected. The formation of a complex in the control reaction, but not in the reaction mixture containing the test compound, indicates that the compound interferes with the interaction of the HKNG1 gene product and the binding partner. Additionally, complex formation within reaction mixtures containing the test compound and normal HKNG1 gene product may also be compared to complex formation within reaction mixtures containing the test compound and a mutant HKNG1 gene product. This comparison may be important in those cases wherein it is desirable to identify compounds that disrupt interactions of mutant but not normal HKNG1 gene product.

In order to test a compound for potentiating activity, the reaction mixture is prepared in the presence and absence of the test compound. The test compound may be initially included in the reaction mixture, or may be added at a time subsequent to the addition of HKNG1 gene product and its binding partner. Control reaction mixtures are incubated without the test compound or with a compound which is known not to block complex formation. The formation of any complexes between the HKNG1 gene product and the binding partner is then detected. Increased formation of a complex in the reaction mixture containing the test compound, but not in the control reaction, indicates that the compound enhances and therefore potentiates the interaction of the HKNG1 gene product and the binding partner. Additionally, complex formation within reaction mixtures containing the test compound and normal HKNG1 gene product may also be compared to complex formation within reaction mixtures containing the test compound and a mutant HKNG1 gene product. This comparison may be important in those cases wherein it is desirable to identify compounds that enhance interactions of mutant but not normal HKNG1 gene product.

In alternative embodiments, the above assays may be performed using a reaction mixture containing the HKNG1 gene product, a binding partner, and a third which disrupts or enhances HKNG1 gene product binding to the binding partner. The reaction mixture is prepared and incubated in the presence and absence of the test compound, as described above, and the formation of any complexes between the HKNG1 gene product and the binding partner is detected. In this embodiment, the formation of a complex in the reaction mixture containing the test compound, but not in the control reaction, indicates that the test compound interferes with the ability of the second compound to disrupt HKNG1 gene product binding to its binding partner.

The assays for compounds that interfere with or potentiate the interaction of the HKNG1 gene products and binding partners can be conducted in a heterogeneous or homogeneous format. Heterogeneous assays involve anchoring either the HKNG1 gene product or the binding partner onto a solid support and detecting complexes formed on the solid support at the end of the reaction. In homogeneous assays, the entire reaction is carried out in a liquid phase. In either approach, the order of addition of reactants can be varied to obtain different information about the compounds being tested. For example, test compounds that interfere with or potentiate the interaction between the HKNG1 gene products and the binding partners, e.g., by competition, can be identified by conducting the reaction in the presence of the test substance; i.e., by adding the test substance to the reaction mixture prior to or simultaneously with the HKNG1 gene product and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the HKNG1 gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the HKNG1 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex formation or that disrupt preformed complexes can be identified.

In an alternate embodiment of the invention, a homogeneous assay can be used. In this approach, a preformed complex of the HKNG1 gene product and the interactive binding partner is prepared in which either the HKNG1 gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt HKNG1 gene product/binding partner interaction can be identified.

In another embodiment of the invention, these same techniques can be employed using peptide fragments that correspond to the binding domains of the HKNG1 product and/or the binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments is engineered to express peptide fragments of the protein, it can then be tested for binding activity and purified or synthesized.

For example, and not by way of limitation, a HKNG1 gene product can be anchored to a solid material as described, above, in this Section by making a GST-HKNG1 fusion protein and allowing it to bind to glutathione agarose beads. The binding partner can be labeled with a radioactive isotope, such as $^{35}S$, and cleaved with a proteolytic enzyme such as trypsin. Cleavage products can then be added to the anchored GST-HKNG1 fusion protein and allowed to bind. After washing away unbound peptides, labeled bound material, representing the binding partner binding domain, can be eluted, purified, and analyzed for amino acid sequence by well-known methods. Peptides so identified can be produced synthetically or produced using recombinant DNA technology.

5.8.4. Assays for Identification of Compounds That Ameliorate a HKNG1-Mediated Disorder Compounds, including but not limited to binding compounds identified via assay techniques such as those described, above, in Sections 5.8.1–5.8.4, can be tested for the ability to ameliorate symptoms of a HKNG1-mediated disorder, e.g., a CNS-related disorder, such as a neuropsychiatric disorder, including schizophrenia and bipolar affective (mood) disorders, including severe bipolar affective (mood) disorder (BP-I), bipolar affective (mood) disorder with hypomania and major depression (BP-II), and myopia disorders.

It should be noted that the assays described herein can identify compounds that affect HKNG1 activity by either affecting HKNG1 gene expression or by affecting the level of HKNG1 gene product activity. For example, compounds may be identified that are involved in another step in the pathway in which the HKNG1 gene and/or HKNG1 gene product is involved and, by affecting this same pathway may modulate the effect of HKNG1 on the development of a HKNG1-mediated disorder. Such compounds can be used, e.g., as part of a therapeutic method for the treatment of the disorder.

Described below are cell-based and animal model-based assays for the identification of compounds exhibiting such an ability to ameliorate symptoms of a HKNG1-mediated disorder, e.g., neuropsychiatric disorder, such as BAD or schizophrenia.

First, cell-based systems can be used to identify compounds that may act to ameliorate symptoms of a HKNG1-mediated disorder. Such cell systems can include, for example, recombinant or non-recombinant cell, such as cell lines, that express the HKNG1 gene.

In utilizing such cell systems, cells that express HKNG1 may be exposed to a compound suspected of exhibiting an ability to ameliorate symptoms of a HKNG1-mediated disorder, e.g., a neuropsychiatric disorder, such as BAD or schizophrenia, at a sufficient concentration and for a sufficient time to elicit such an amelioration of such symptoms in the exposed cells. After exposure, the cells can be assayed to measure alterations in the expression of the HKNG1 gene, e.g., by assaying cell lysates for HKNG1 mRNA transcripts (e.g., by Northern analysis) or for HKNG1 gene products expressed by the cell; compounds that modulate expression of the HKNG1 gene are good candidates as therapeutics.

In addition, animal-based systems or models for a HKNG1-mediated disorder, e.g., neuropsychiatric disorder, for example, transgenic mice containing a human or altered form of HKNG1 gene, may be used to identify compounds capable of ameliorating symptoms of the disorder. Such animal models may be used as test substrates for the identification of drugs, pharmaceuticals, therapies and interventions. For example, animal models may be exposed to a compound suspected of exhibiting an ability to ameliorate symptoms, at a sufficient concentration and for a sufficient time to elicit such an amelioration of symptoms of a HKNG1-mediated disorder. The response of the animals to the exposure may be monitored by assessing the reversal of the symptoms of the disorder.

With regard to intervention, any treatments that reverse any aspect of symptoms of a HKNG1-mediated disorder, should be considered as candidates for human therapeutic intervention in such disorders. Dosages of test agents may be determined by deriving dose-response curves, as discussed in Section 5.10.1, below.

5.9. Compounds and Methods for the Treatment of HKNG1-Mediated Disorders

Described below are methods and compositions whereby a HKNG1-mediated disorder described herein, e.g., a HKNG1-mediated neuropsychiatric disorder, such as BAD or schizophrenia, may be treated. For example, such methods can comprise administering compounds which modulate the expression of a mammalian HKNG1 gene and/or the synthesis or activity of a mammalian HKNG1 gene product (e.g., a recombinant HKNG1 gene product) so symptoms of the disorder are ameliorated.

Alternatively, in those instances whereby the HKNG1-mediated disorders result from HKNG1 gene mutations, such methods can comprise supplying the subject with a nucleic acid molecule encoding an unimpaired HKNG1 gene product such that an unimpaired HKNG1 gene product is expressed and symptoms of the disorder are ameliorated.

In another embodiment of methods for the treatment of HKNG1-mediated disorders resulting from HKNG1 gene mutations, such methods can comprise supplying the subject with a cell comprising a nucleic acid molecule that encodes an unimpaired HKNG1 gene product such that the cell expresses the unimpaired HKNG1 gene product and symptoms of the disorder are ameliorated.

In cases in which a loss of normal HKNG1 gene product function results in the development of a HKNG1-mediated disorder an increase in HKNG1 gene product activity would facilitate progress towards an asymptomatic state in individuals exhibiting a deficient level of HKNG1 gene expression and/or HKNG1 gene product activity. Methods for enhancing the expression or synthesis of HKNG1 can include, for example, methods such as those described below, in Section 5.9.2.

Alternatively, symptoms of HKNG1-mediated neuropsychiatric disorders, may be ameliorated by administering a compound that decreases the level of HKNG1 gene expression and/or HKNG1 gene product activity. Methods for inhibiting or reducing the level of HKNG1 gene product synthesis or expression can include, for example, methods such as those described in Section 5.9.1.

In one embodiment of treatment methods, the compounds administered comprise compounds, in particular drugs, which ameliorate the symptoms of a disorder described herein as a neuropsychiatric disorder, such as BAD or schizophrenia. Such compounds include drugs within the families of antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and iso-carboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

In another embodiment, symptoms of a disorder described herein, e.g., a HKNG1-mediated neuropsychiatric disorder such as BAD or schizophrenia, may be ameliorated by HKNG1 protein therapy methods, e.g., decreasing or increasing the level and/or of HKNG1-activity using the HKNG1 protein, fusion protein, and peptide sequences described in Section 5.2, above, or by the administration of proteins or protein fragments (e.g., peptides) which interact with an HKNG1 gene or gene product and thereby inhibit or potentiate its activity.

Such protein therapy may include, for example, the administration of a functional HKNG1 protein or fragments of an HKNG1 protein (e.g., peptides) which represent functional HKNG1 domains.

In one embodiment, HKNG1 fragments or peptides representing a functional HKNG1 binding domain are administered to an individual such that the peptides bind to an HKNG1 binding protein, e.g., an HKNG1 receptor. Such fragments or peptides may serve to inhibit HKNG1 activity in an individual by competing with, and thereby inhibiting, binding of HKNG1 to the binding protein, thereby ameliorating symptoms of a disorder described herein. Alternatively, such fragments or peptides may enhance HKNG1 activity in an individual by mimicking the function of HKNG1 in vivo, thereby ameliorating the symptoms of a disorder described herein.

The proteins and peptides which may be used in the methods of the invention include synthetic (e.g., recombinant or chemically synthesized) proteins and peptides, as well as naturally occurring proteins and peptides. The proteins and peptides may have both naturally occurring and non-naturally occuring amino acid residues (e.g., D-amino acid residues) and/or one or more non-peptide bonds (e.g., imino, ester, hydrazide, semicarbazide, and azo bonds). The proteins or peptides may also contain additional chemical groups (i.e., functional groups) present at the amino and/or carboxy termini, such that, for example, the stability, bioavailability, and/or inhibitory activity of the peptide is enhanced. Exemplary functional groups include hydrophobic groups (e.g. carbobenzoxyl, dansyl, and t-butyloxycarbonyl, groups), an acetyl group, a 9-fluorenylmethoxy-carbonyl group, and macromolecular carrier groups (e.g., lipid-fatty acid conjugates, polyethylene glycol, or carbohydrates) including peptide groups.

5.9.1. Inhibitory Antisense, Ribozyme and Triple Helix Approaches

In another embodiment, symptoms of HKNG1-mediated neuropsychiatric disorders may be ameliorated by decreasing the level of HKNG1 gene expression and/or HKNG1 gene product activity by using HKNG1 gene sequences in conjunction with well-known antisense, gene "knock-out," ribozyme and/or triple helix methods to decrease the level of HKNG1 gene expression. Among the compounds that may exhibit the ability to modulate the activity, expression or synthesis of the HKNG1 gene, including the ability to ameliorate the symptoms of a HKNG1-mediated neuropsychiatric disorder, such as BAD or schizophrenia, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the HKNG1 gene could be used in an antisense approach to inhibit translation of endogenous HKNG1 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86:6553–6556; Lemaitre, et al., 1987, Proc. Natl. Acad. Sci. U.S.A. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15:6625–6641). The oligonucleotide is a 2'-O-methylribonucleotide (Inoue, et al., 1987, Nucl. Acids Res. 15:6131–6148), or a chimeric RNA-DNA analogue (Inoue, et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin, et al., 1988, Proc. Natl. Acad. Sci. U.S.A. 85:7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

A preferred approach to achieve intracellular concentrations of the antisense sufficient to suppress translation of endogenous mRNAs utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner, et al., 1981, Proc. Natl. Acad. Sci. U.S.A. 78:1441–1445), the regulatory sequences of the metallothionein gene (Brinster, et al., 1982, Nature 296:39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially FIG. 4, page 833) and in Haseloff and Gerlach, 1988, Nature, 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317:230–234; Thomas and Capecchi, 1987, Cell 51:503–512; Thompson, et al., 1989, Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6):569–584; Helene, et al., 1992, Ann. N.Y. Acad. Sci., 660:27–36; and Maher, 1992, Bioassays 14(12):807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.9.2. Gene Replacement Therapy

HKNG1 gene nucleic acid sequences, described above in Section 5.1, can be utilized for transferring recombinant HKNG1 nucleic acid sequences to cells and expressing said sequences in recipient cells. Such techniques can be used, for example, in marking cells or for the treatment of a HKNG1-mediated neuropsychiatric disorder. Such treatment can be in the form of gene replacement therapy. Specifically, one or more copies of a normal HKNG1 gene or a portion of the HKNG1 gene that directs the production of a HKNG1 gene product exhibiting normal HKNG1 gene function, may be inserted into the appropriate cells within a patient, using vectors that include, but are not limited to adenovirus, adeno-associated virus, and retrovirus vectors, in addition to other particles that introduce DNA into cells, such as liposomes.

Because the HKNG1 gene is expressed in the brain, such gene replacement therapy techniques should be capable of delivering HKNG1 gene sequences to these cell types within patients. Thus, in one embodiment, techniques that are well known to those of skill in the art (see, e.g., PCT Publication No. WO89/10134, published Apr. 25, 1988) can be used to enable HKNG1 gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration, e.g., by stereotactic delivery of such HKNG1 gene sequences to the site of the cells in which the HKNG1 gene sequences are to be expressed.

Additional methods that may be utilized to increase the overall level of HKNG1 gene expression and/or HKNG1 gene product activity include using targeted homologous recombination methods, discussed in Section 5.2, above, to modify the expression characteristics of an endogenous HKNG1 gene in a cell or microorganism by inserting a heterologous DNA regulatory element such that the inserted regulatory element is operatively linked with the endogenous HKNG1 gene in question. Targeted homologous recombination can thus be used to activate transcription of an endogenous HKNG1 gene that is "transcriptionally silent", i.e., is not normally expressed or is normally expressed at very low levels, or to enhance the expression of an endogenous HKNG1 gene that is normally expressed.

Further, the overall level of HKNG1 gene expression and/or HKNG1 gene product activity may be increased by the introduction of appropriate HKNG1-expressing cells, preferably autologous cells, into a patient at positions and in numbers that are sufficient to ameliorate the symptoms of a HKNG1-mediated neuropsychiatric disorder. Such cells may be either recombinant or non-recombinant.

Among the cells that can be administered to increase the overall level of HKNG1 gene expression in a patient are normal cells, preferably brain cells, that express the HKNG1 gene. Alternatively, cells, preferably autologous cells, can be engineered to express HKNG1 gene sequences, and may then be introduced into a patient in positions appropriate for the amelioration of the symptoms of a HKNG1-mediated neuropsychiatric disorder. Alternately, cells that express an unimpaired HKNG1 gene and that are from a MHC matched individual can be utilized, and may include, for example, brain cells. The expression of the HKNG1 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.8, that are capable of modulating HKNG1 gene product activity can be administered using standard techniques that are well known to those of skill in the art. In instances in which the compounds to be administered are to involve an interaction with brain cells, the administration techniques should include well known ones that allow for a crossing of the blood-brain barrier.

5.10. Pharmaceutical Preparation and Methods of Administration

The compounds that are determined to affect HKNG1 gene expression or gene product activity can be administered to a patient at therapeutically effective doses to treat or ameliorate a HKNG1-mediated disorder or modulate a HKNG1-related process described herein. A therapeutically effective dose refers to that amount of the compound sufficient to result in amelioration of symptoms of such a disorder.

5.10.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of antibody, protein, or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

5.10.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral rectal or topical administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In certain embodiments, it may be desirable to administer the pharmaceutical compositions of the invention locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the compounds may be combined with a carrier so that an effective dosage is delivered, based on the desired activity A topical formulation for treatment of some of the eye disorders discussed infra (e.g., myopia) consists of an effective amount of the compounds in a ophthalmologically acceptable excipient such as buffered saline, mineral oil, vegetable oils such as corn or arachis oil, petroleum jelly, Miglyol 182, alcohol solutions, or liposomes or liposome-like products. Any of these compositions may also include preservatives, antioxidants, antibiotics, immunosuppressants, and other biologically or pharmaceutically effective agents which do not exert a detrimental effect on the compound.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE: THE HKNG1 GENE OF CHROMOSOME 18 IS ASSOCIATED WITH THE NEUROPSYCHIATRIC DISORDER BAD

In the Example presented in this Section, studies are described that define a narrow interval of approximately 27 kb on the short arm of human chromosome 18 which is associated with the neuropsychiatric disorder BAD. The interval is demonstrated to lie within the gene referred to herein as the HKNG1 gene.

6.1. Materials and Methods

6.1.1. Linkage Disequilibrium

Linkage disequilibrium (LD) studies were performed using DNA from a population sample of neuropsychiatric disorder (BP-I) patients. The population sample and LD techniques were as described in Escamilla et al., 1996, *Am J. Med. Genet.* 67:244–253. The present LD study took advantage of the additional population sample collection and the additional physical markers identified via the physical mapping techniques described below.

6.1.2. Yeast Artificial Chromosome (YAC) Mapping

For physical mapping, yeast artificial chromosomes (YACs) containing human sequences were mapped to the region being analyzed based on publicly available maps (Cohen et al., 1993, C.R. Acad. Sci. 316:1484–1488). The YACs were then ordered and contig reconstructed by performing standard short tag sequence (STS)-content mapping with microsatellite markers and non-polymorphic STSs available from databases that surround the genetically defined candidate region.

6.1.3. Bacterial Artificial Chromosome (BAC) Mapping

STSs from the short arm of human chromosome 18 were used to screen a human BAC library (Research Genetics, Huntsville, Ala.). The ends of the BACs were cloned or directly sequenced. The end sequences were used to amplify the next overlapping BACs. From each BAC, additional microsatellites were identified. Specifically, random sheared libraries were prepared from overlapping BACs within the defined genetic interval. BAC DNA was sheared with a nebulizer (CIS-US Inc., Bedford, Mass.). Fragments in the size range of 600 to 1,000 bp were utilized for the sublibrary production. Microsatellite sequences from the sublibraries were identified by corresponding microsatellite probes. Sequences around such repeats were obtained to enable development of PCR primers for genomic DNA.

6.1.4. Radiation Hybrid (RH) Mapping

Standard RH mapping techniques were applied to a Stanford G3 RH mapping panel (Research Genetics, Huntsville, Ala.) to order all microsatellite markers and non-polymorphic STSs in the region being analyzed.

6.1.5. Sample Sequencing

Random sheared libraries were made from all the BACs within the defined genetic region. Approximately 9,000 subclones within the approximately 340 kb region containing the BAD interval were sequenced with vector primers in order to achieve an 8-fold sequence coverage of the region. All sequences were processed through an automated sequence analysis pipeline that assessed quality, removed vector sequences and masked repetitive sequences. The resulting sequences were then compared to public DNA and protein databases using BLAST algorithms (Altschul, et al., 1990, J. Molec. Biol., 215:403–410).

All sequences were contiged using Sequencher 3.0 (Gene Code Corp.) and PHRED and PHRAP (Phill Green, Washington University) into a single DNA fragment of 340 kb.

6.2. Results

Genetic regions involved in bipolar affective disorder (BAD) human genes had previously been reported to map to portions of the long (18q) and short (18p) arms of human chromosome 18 (Freimer et al., 1996, Neuropsychiat. Genet. 67:254–263; Freimer et al., 1996, Nature Genetics 12:436–441; and McInnis et al., *Proc. Natl. Acad. Scie. U.S.A.* 93:13060–13065).

High resolution physical mapping using YAC, BAC and RH techniques. In order to provide the precise order of genetic markers necessary for linkage and LD mapping, and to guide new microsatellite marker development for finer mapping, a high resolution physical map of the 18p candidate region was developed using YAC, BAC and RH techniques.

For such physical mapping, first, YACs were mapped to the chromosome 18 region being analyzed. Using the mapped YAC contig as a framework, the region from publicly available markers spanning the 18p region were also mapped and contiged with BACs. Sublibraries from the contiged BACs were constructed, from which microsatellite marker sequences were identified and sequenced.

To ensure development of an accurate physical map, the radiation hybrid (RH) mapping technique was independently applied to the region being analyzed. RH was used to order all microsatellite markers and non-polymorphic STSs in the region. Thus, the high resolution physical map ultimately constructed was obtained using data from RH mapping and STS-content mapping.

Linkage Disequilibrium. Prior to attempting to identify gene sequences, studies were performed to further narrow the neuropsychiatric disorder region. Specifically, a linkage disequilibrium (LD) analysis was performed using population samples and techniques as described in Section 6.1, above, which took advantage of the additional physical markers identified via the physical mapping techniques described below.

Initial LD analysis narrowed the interval which associates with BAD disorders to a 340 kb region of 18p. BAC clones within this newly identified neuropsychiatric disorder region were analyzed to identify specific genes within the region. A combination of sample sequencing, cDNA selection and transcription mapping analyses were used to arrange sequences into tentative transcription units, that is, tentatively delineating the coding sequences of genes within this genomic region of interest.

Subsequent LD analyses further narrowed the BAD region of 18p to a narrow interval of approximately 27 kb. This was accomplished by identifying the maximum haplotype shared among affected individuals using additional markers. Statistical analysis of the entire 18p candidate region indicated that the 27 kb haplotype was significantly elevated in frequency among affected Costa Rican individuals (LOD=2.2; p=0.0005).

This newly identified narrow interval was found to map completely within one of the transcription units identified as described above. The gene corresponding to this transcription unit is referred to herein as the HKNG1 gene. Thus, the results of the mapping analyses presented in this Section demonstrate that the HKNG1 gene of human chromosome 18 is associated the neuropsychiatric disorder BAD.

Analysis of the BAD interval indicated that the 27 kb BAD disease-associated chromosomal interval identified in the linkage disequilibrium studies is contained within an approximately 60 kb genomic region which contains a sequence referred to as GS4642 or rod photoreceptor protein (RPP) gene (Shimizu-Matsumoto, A. et al., 1997, Invest. Ophthalmol. Vis. Sci. 38:2576–2585).

7. EXAMPLE: SEQUENCE AND CHARACTERIZATION OF THE HKNG1 GENE

As demonstrated in the Example presented in Section 6, above, the HKNG1 gene is involved in the neuropsychiatric disorder BAD. The results presented in this Section further characterize the HKNG1 gene and gene product. In particular, isolation of additional cDNA clones and analyses of genomic and cDNA sequences have revealed both the full length HKNG1 amino acid sequence and the HKNG1 genomic intron/exon structure. In particular, the nucleotide and predicted amino acid sequence of the HKNG1 gene identified by these analyses disclose new HKNG1 exon sequences, including new HKNG1 protein coding sequence, discovered herein. Further, the expression of HKNG1 in human tissue, especially neural tissue, is characterized by Northern and in situ hybridization analysis. The results presented herein are consistent with the HKNG1 gene being a gene which mediates neuropsychiatric disorders such as BAD.

7.1. Material and Methods

HKNG1 cDNA Clone Isolation: Hybridization of a human brain and kidney cDNA library was performed according to standard techniques and identified a full-length HKNG1 cDNA clone. In addition, a HKNG1 cDNA derived from a splice variant was isolated, as described in Section 7.2, below.

Northern Blot Analysis: Standard RNA isolation techniques and Northern blotting procedures were followed. The HKNG1 probe utilized corresponds to the complementary sequence of base pairs 1367 to 1578 of the full length HKNG1 cDNA sequence (SEQ ID NO. 1). Clontech multiple tissue northern blots were probed. In particular, Clontech human I, human II, human III, human fetal II, human brain II and human brain III blots were utilized for this study.

In Situ Hybridization Analysis: Standard in situ hybridization techniques were utilized. The HKNG1 probe utilized corresponds to the complementary sequence of base pairs 910 to 1422 of the full length HKNG1 cDNA sequence (SEQ ID NO. 1). Brains for in situ hybridization analysis were obtained from McLean Hospital (The Harvard Brain Tissue Resource Center, Belmont, Mass. 02178).

Other techniques: The remaining techniques described in Section 7.2, below, were performed according to standard techniques or as discussed in Section 6.1, above.

7.2. Results

7.2.1. HKNG1 Nucleotide and Amino Acid Sequence

A human brain cDNA library was screened and a full-length clone of HKNG1 was isolated from this library, as described above. By comparing the isolated cDNA sequence to sequences in the public databases, a clone was identified which had been previously identified as GS4642, or rod photoreceptor protein (RPP) gene (GenBank Accession No. D63813; Shimizu-Matsumoto, A. et al., 1997, Invest. Ophthalmol. Vis. Sci. 38:2576–2585). Although Shimizu-Matsumoto et al. refer to GS4642 as a full-length cDNA sequence, the isolated HKNG1 cDNA extends approximately 200 bp beyond the 5' end of the identified GS4642 clone.

Importantly, the HKNG1 clone isolated herein reveals that, contrary to the amino acid sequence described in Shimizu-Matsumoto et al., the full length HKNG1 amino acid sequence contains an additional 29 amino acid residues N-terminal to what had previously been identified as the full-length RPP (SEQ ID NO:64). The full-length HKNG1 nucleotide sequence (SEQ ID NO: 1) and the derived amino acid sequence of the full-length HKNG1 polypeptide (SEQ ID NO: 2) encoded by this sequence are depicted in FIGS. 1A–1C.

The full-length HKNG1 polypeptide was found to contain two clusterin similarity domains: clusterin similarity domain 1 which corresponds to amino acid residues 134 to amino acid residue 160, and clusterin similarity domain 2 which corresponds to amino acid residue 334 to amino acid residue 362. Such cluterin domains are typically characterized by five shared cysteine residues. In clusterin domain 1, these shared cysteine residues correspond to Cys134, Cys145, Cys148, Cys158, and Cys 160. The shared cysteine residues in clusterin domain 2 correspond to the residues Cys334, Cys344, Cys351, Cys354, and Cys362.

Full-length HKNG1 cDNA sequence was compared with the genomic contig completed by random sheared library sequencing. Exon-intron boundaries were identified manually by aligning the two sequences in Sequencher 3.0 and by observing the conservative splicing sites where the alignments ended. This sequence comparison revealed that the additional cDNA sequence discovered through isolation of the full-length HKNG1 cDNA clone actually belongs within three HKNG1 exons.

Prior to the isolation and analysis of HKNG1 cDNA described herein, nine exons were predicted to be present within the corresponding genomic sequence. As discovered herein, however, the HKNG1 gene, in contrast, actually contains 13 exons, with the new cDNA containing sequence which corresponds to a new exon 1, exon 2 and a 5' extension of what had previously been designated exon 1. Splice variants, discussed in Section 9 below, also exist which comprise additional exons 2' and 2". The genomic sequence and intron/exon structure of the HKNG1 gene is shown in FIGS. 3A–3CC.

The breakdown of exons was confirmed by the perfect alignment of the cDNA sequence with the genomic sequence and by observation of expected splicing sites flanking each of the additional, newly discovered exons.

HKNG1 nucleotide sequence was used to search databases of partial sequences of cDNA clones. This search identified a partial cDNA sequence derived from IMAGE clone R61493 having similarity to the human HKNG1 sequence. IMAGE clone R61493 was obtained and consists of a cDNA insert, the Lafmid BA vector backbone, and DNA originating from the oligo dT primer and Hind III adaptors used in cDNA library construction. The Lafmid BA vector nucleotide sequence is available at the URL http://image.rzpd.de/lafmida_seq.html and descriptions of the oligo dT primer and Hind III adaptors are available in the GENBANK record corresponding to accession number R61493.

The sequence of the cDNA insert revealed that the insert was derived from an alternatively spliced HKNG1 mRNA variant, referred to herein as HKNG1-V1. In particular, this HKNG1 variant is deleted for exon 3 of the full length 13 exon HKNG1 sequence. The nucleotide sequence of this HKNG1 variant (SEQ ID NO:3) is depicted in FIGS. 2A–2C. The amino acid sequence encoded by the HKNG1 variant (SEQ ID NO:3) is also shown in FIGS. 2A–2C.

Preferably therefore, the nucleic acids of the invention include nucleic acid molecules comprising the nucleotide sequence of HKNG1-V1 or encoding the polypeptide encoded by HKNG1-V1 in the absence of heterologous sequences (e.g., cloning vector sequences such as Lafmid BA; oligo dT primer, and Hind III adaptor).

7.2.2. HKNG1 Gene Expression

HKNG1 gene expression was examined by Northern blot analysis in various human tissues. A transcript of approximately 2 kb was detected in fetal brain, lung and kidney, and in adult brain, kidney, pancreas, prostate, testis, ovary, stomach, thyroid, spinal cord, lymph node and trachea. An approximately 1.5 kb transcript was also seen in trachea. In addition, a larger transcript of approximately 5 kb was detected in all adult neural regions tested (that is, cerebellum, cortex, medulla, spinal cord, occipital pole, frontal lobe, temporal, putamen, amygdala, caudatte nucleus, corpus callosum, hippocampus, whole brain, substantia nigra, subthalamic nucleus and thalamus). Once again, this is in direct contrast to previous Northern analysis of the RPP gene, which reported that expression was limited to the retina (Shimizu-Matsumoto, A. et al., 1997, Invest. Ophthalmal. Vis. Sci. 38:2576–2585).

Analysis of HKNG1 the tissue distribution was extended through an in situ hybridization analysis. In particular, the HKNG1 mRNA distribution in normal human brain tissue was analyzed. The results of this analysis are depicted in FIGS. 4A–4B. As summarized in FIGS. 4A–4B, HKNG1 is expressed throughout the brain, with transcripts being localized to neuronal and grey matter cell types.

Finally, expression of HKNG1 in recombinant cells demonstrates that the HKNG1 gene encodes a secreted polypeptide(s).

8. A MISSENSE MUTATION WITHIN HKNG1 CORRELATES WITH BAD

The Example presented in Section 6, above, shows that the BAD disorder maps to an interval completely contained within the HKNG1 gene of the short arm of human chromosome 18. The Example presented in Section 7, above, characterizes the HKNG1 gene and gene products. The results presented in this Example further these studies by identifying a mutation within the coding region of a HKNG1 allele of an individual exhibiting a BAD disorder.

Thus, the results described herein demonstrate a positive correlation between a mutation which encodes a non-wild-type HKNG1 polypeptide and the appearance of the neuropsychiatric disorder BAD. The results presented herein, coupled with the results presented in Section 6, above, identify HKNG1 as a gene which mediates neuropsychiatric disorders such as BAD.

8.1. Materials and Methods

Pairs of PCR primers that flank each exon (see TABLE 1, above) were made and used to PCR amplify genomic DNA isolated from BAD affected and normal individuals. The amplified PCR products were analyzed using SSCP gel electrophoresis or by DNA sequencing. The DNA sequences and SSCP patterns of the affected and controls were compared and variations were further analyzed.

8.2. Results

In order to more definitively show that the HKNG1 gene mediates neuropsychiatric disorders, in particular BAD, a study was conducted to explore whether a HKNG1 mutation that correlates with BAD could be identified.

First, exon scanning was performed on all eleven exons of the HKNG1 gene using chromosomes isolated from three affected and one normal individual from the Costa Rican population utilized for the LD studies discussed in Section 6, above. No obvious mutations correlating with BAD were found through this analysis.

Next, HKNG1 intron and 3'-untranslated regions within the 27 kb BAD interval were scanned by sscp and/or sequencing for all variants among three affected and one normal individual from the same population. Approximately 60 variants were identified after scanning approximately two-thirds of the 27 kb genomic interval, which can be genotyped and analyzed by haplotype sharing and LD analyses, as described above, in order to identify ones which correlate with bipolar affective disorder. FIGS. 5A–5C lists selected variants identified through this study.

Exon scanning using chromosomal DNA from the general population of Costa Rica, however, successfully identified a HKNG1 missense mutation in an individual affected with BAD who did not share the common diseased haplotype identified by the LD analysis provided above. In particular, exon scanning was done on exons 1–11 of HKNG1 nucleic acid from 129 individuals from the general population affected with BAD.

This analysis identified a point mutation in the coding region of exon 7 not seen in non-bipolar affected disorder individuals. Specifically, the guanine corresponding to nucleotide residue 604 of SEQ ID NO:1 (or nucleotide predicted amino acid sequence (SEQ ID NOS:66–82) of the HKNG1Δ7 gene product it encodes.

Two other novel splice variants, referred to herein as HKNG1-V2 and HKNG1-V3, were isolated and identified by using RT-PCR analysis to isolate additional HKNG1 sequences. The following primer sequences were used:

5'-AGTTGCGTCCCTCTCTGTTG-3' (SEQ ID NO:83)

5'-GCTTCATGTTCCCGCTGTTA-3' (SEQ ID NO:84)

These splice variants included additional exons between exons 2 and 3 of the full length HKNG1 sequence (SEQ ID NO:1).

The RT-PCR product derived from HKNG1-V2 includes a novel exon referred to as "exon 2'", whereas the RT-PCR product derived from HKNG1-V3 includes a novel exon referred to as "exon 2''". The sequence of these novel exons are provided in Table 2 below. The nucleotide sequence of the HKNG1-V2 RT-PCR product containing novel exon 2' is depicted in FIG. 6A (SEQ ID NO:36), whereas the HKNG1-V3 RT-PCR product containing novel exon 2'' is depicted in FIG. 6B (SEQ ID NO:37). Both exon 2' and 2'' are part of the 5'-untranslated region of the HKNG1 cDNA.

TABLE 2

| | | |
|---|---|---|
| Exon 2' | 5'-TTCCCTCCCTTTGGAACGCAGCGTGGGCACC TGCAACGCAGAGACCACTGTATCCCCGGTGCAGA ATGTAATGAGTGCCTGATACATTTGCCGAATAAA CTATTCCAAGGGTTGAACTTGCTGGAAGCAAGAG AAGCACTATTCTGG-3' | (SEQ ID NO:34) |
| Exon 2'' | 5'-ATGGAGTCTTGCTCTCGTTGCCCAGACTGGA GTGCACTGCTGCGATCTCAGCTCACTGCAACCTC TACCTCCCAGGTTCAAGCGATTCTCCTGCCTCAG CCTCTCGAGTGGCTGGGACTATAG-3' | (SEQ DI NO:35) | residue 550 of SEQ ID NO:3) had mutated to an adenine. HKNG1 protein expressed from this mutated HKNG1 allele comprises the substitution of a lysine residue at amino acid residue 202 of SEQ ID NO:2 (or amino acid residue 184 of SEQ ID NO:4) in place of the wild-type glutamic acid residue.

Additional HKNG1 polymorphisms relative to the HKNG1 wild-type sequence, and which, therefore, represent HKNG1 alleles, were identified through sequence analysis of the HKNG1 alleles within a collection of schizophrenic patients of mixed ethnicity from the United States and within a BAD collection from the San Francisco area. These variants are depicted in FIGS. 5A–5C, respectively. Statistical analysis indicated that there were significantly more variants in the collection of schizophrenic patients of mixed ethnicity from the United States and the San Francisco BAD and Costa Rican BAD samples than in a collection of 242 controls (p<0.05).

9. EXAMPLE: IDENTIFICATION OF ADDITIONAL HKNG1 SPLICE VARIANTS

This example describes the isolation and identification of three novel splice variants of the human gene HKNG1. First, a novel HKNG1 clone was isolated from a human retinal cDNA library. This clone, which completely lacks exon 7 of the full length HKNG1 cDNA sequence, is referred to herein as HKNG1Δ7. Because the deletion of exon 7 from the full length HKNG1 sequence leads to an immediate frameshift, the clone HKNG1Δ7 encodes a truncated form of the HKNG1 protein. The HKNG1Δ7 cDNA sequence (SEQ ID NO:65) is depicted in FIGS. 18A–18C along with the

10. EXAMPLE: IDENTIFICATION OF HKNG1 ORTHOLOGS

This example describes the isolation and characterization of genes in other mammalian species which are orthologs to human HKNG1. Specifically, both guinea pig and bovine HKNG1 sequences are described.

10.1. Guinea Pig HKNG1 Orthologs

A guinea pig HKNG1 ortholog, referred to as gphkng1815, was isolated using RT-PCR. The cDNA sequence (SEQ ID NO:38) and predicted amino acid sequence (SEQ ID NO:39) are depicted in FIGS. 7A–7C. Both the nucleotide and the predicted amino acid sequence of gphkng 1815 are similar to the human HKNG1 nucleotide and amino acid sequences. Specifically, the program ALIGNv2.0 identified a 71.5% nucleotide sequence identity and a 62.8% amino acid sequence identity using standard parameters (Scoring Matrix: PAM120; GAP penalties:–12/–4).

Like the human HKNG1 polypeptide, the predicted gph-kng 1815 polypeptide also contains two clusterin similarity domains, which correspond to amino acid residues 105 to 131 (clusterin domain 1), and amino acid residues 305–333 (clusterin domain 2), respectively. Both of these domains contain the five conserved cysteine residues typically associated with clusterin domains. Specifically, these conserved cysteines correspond to Cys105, Cys116, Cys119, Cys124 and Cys131 (clusterin similarity domain 1) and Cys305, Cys315, Cys322, Cys325, and Cys333 (clusterin similarity domain 1) of the gphkng 1815 polypeptide sequence.

Three allelic variants of gphkng 1815, referred to as gphkng 7b, gphkng 7c, and gphkng 7d, respectively, were also identified by RT-PCR. Their nucleotide [SEQ ID NO:40 (gphkng 7b), SEQ ID NO:42 (gphkng 7c), and SEQ ID NO:44 (gphkng 7d)] and amino acid [SEQ ID NO:41 (gphkng 7b), SEQ ID NO:43 (gphkng 7c), and SEQ ID NO:45 (gphkng 7d)] sequences are depicted in FIGS. 8A–8C through 10A–10C, respectively. Each of these three allelic variants contains a deletion within a region homologous to exon 7 of human HKNG1. The allelic variants retain the open reading frame of the gene, however, each allelic variant contains a deletion, relative to gphkng 1815, of 16, 92, and 93 amino acid residues, respectively.

An alignment of the predicted amino acid sequences of gphkng1815, gphkng 7b, gphkng 7c, and gphkng7d is shown in FIGS. 14A–14M. An alignment of the predicted amino acid sequences of the human HKNG1 gene product, the guinea pig HKNG1 ortholog gphkng1815, and the bovine HKNG1 ortholog described in Subsection 10.2 below are shown in FIG. 16.

10.2. Bovine HKNG1 Orthologs

Bovine orthologs of HKNG1 were also cloned by screening a cDNA library made from pooled bovine retinal tissue using a nucleotide sequence that corresponded to the complementary sequence of base pairs 910–1422 of the full length human HKNG1 cDNA sequence (SEQ ID NO:1) as a probe. Three independent bovine cDNA species, referred to as bhkng1, bhkng2, and bhkng3 (SEQ ID NOS: 46 to 48, respectively) were isolated. Each of these allelic variants contains several single nucleotide polymorphisms (SNPs). None of the SNPs results in an altered predicted amino acid sequence. Thus all three bovine cDNAs encodes the same predicted amino acid sequence (SEQ ID NO:49). These SNPs apparently reflect the natural allelic variation of the pooled cDNA library from which the sequences were isolated. Each of the three bovine HKNG1 allelic variants is depicted in FIGS. 11A–C to 13A–13C, respectively, along with the predicted amino acid sequence which they encode.

The predicted bovine HKNG1 polypeptide also contains two clusterin similarity domains, corresponding to amino acid residues 105–131 and amino acid residues 304–332, respectively, of SEQ ID NO:49. Clusterin domain 1 contains the five shared cysteine amino acid residues typically associated with this type of domain: Cys105, Cys116, Cys119, Cys124, and Cys131. Clusterin domain 2 of the bovine HKNG1 polypeptide contains four conserved cystein residues: Cys314, Cys321, Cys324, and Cys332.

11. EXPRESSION OF HUMAN HKNG1 GENE PRODUCT

Described in this example is the construction of expression vectors and the successful expression of recombinant human HKNG1 sequences. Expression vectors are described both for native HKNG1 and for various HKNG1 fusion proteins.

11.1. Expression of Human HKNG1:Flag

A human HKNG1 flag epitope-tagged protein (HKNG1:flag) vector was constructed by PCR followed by ligation into an vector for expression in HEK 293T cells. The full open-reading frame of the full length HKNG1 cDNA sequence (SEQ ID NO:5) was PCR amplified using the following primer sequences:

5' primer 5'-TTTTTCTGAATTCGCCACCATGAAAAT-TAAAGCAGAGAAAAACG-3' (SEQ ID NO:52)

3' primer 5'-TTTTTGTCGACTTATCACT-TGTCGTCGTCGTCCTTGTAGTCCCAG-GTTTTAAAATGTTCCTTAAAATGC-3' (SEQ ID NO:53)

the 5' primer incorporating a Kozak sequence upstream of and including the upstream initiator methionine and the 3' primer including the nucleotide sequence encoding the flag epitope DYKDDDDK (SEQ ID NO:50) followed by a termination codon.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-flag polyclonal antibody (1:500, Sigma) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Flag immunoreactivity appeared as a doublet of bands that migrated by SDS-PAGE between 60 and 95 kDa as determined by Multimark molecular weight markers (Novex), demonstrating secretion of the HKNG1:Flag protein. The double band indicates at least two different species with different mobilities on SDS-PAGE. Such doublets most commonly arise with posttranslational modifications to the protein, such as glycosylation and/or proteolysis. Treatment of the PNGase F (Oxford Glycosciences) according to the manufacturer's directions resulted in a single band of increased mobility, indicating that two original bands contain N-linked carbohydrate. When run in the absence of a reducing agent, the relative mobility of the immunoreactive bands was greater than 100 kDa relative to the same markers, indicating that HKNG1:flag fusion proteins may be a disulfide linked dimer or higher oligomer.

11.2. Expression of Human HKNG1-V1:Flag

A human HKNG1-V1 flag epitope-tagged protein (HKNG1-V1:flag) vector was also constructed by PCR followed by ligation into an expression vector, pMET stop. The full length open-reading frame of the HKNG1-V1 cDNA sequence (SEQ ID NO:6) was PCR amplified using the following primer sequences:

5' primer 5'-TTTTTCTGAATTCACCATGAGGACCTGG-GACTACAGTAAC-3' (SEQ ID NO:54)

3' primer 5'-TTTTTGTCGACTTATCACT-TGTCGTCGTCGTCCTTGTAGTCCCAG-GTTTTAAAATGTTCCTTAAAATGC-3' (SEQ ID NO:53)

The 5' primer incorporated a Kozak sequence upstream of and including the upstream initiator methionine. The 3' primer included the nucleotide sequence encoding the flag epitope DYKDDDDK (SEQ ID NO:50) followed by a termination codon.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-flag polyclonal antibody (1:500, Sigma) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Flag immunoreactivity appeared as a doublet of bands that migrated by SDS-PAGE between 60 and 95 kDa as determined by Multimark molecular weight markers (Novex), demonstrating secretion of the HKNG1:Flag protein. When run in the absence of reducing agent, the relative mobility of the immunoreactive bands was greater than 100 kDA relative to the same markers, suggesting that the HKNG1 -V1:flag fusion protein may be a disulfide linked dimer or higher oligomer.

11.3. Expression of Human HKNG1:Fc

A human HKNG1/hIgG1Fc fusion protein vector was constructed by PCR. The full-length open-reading frame of the full length HKNG1 cDNA (SEQ ID NO:5) was PCR amplified using the following primer sequences:

5' primer 5'-TTTTTCTCTCGAGACCATGAAAAT-
    TAAAGCAGAGAAAAACG-3' (SEQ ID NO:55)

3' primer 5'-TTTTTGGATCCGCTGCTGCCCAGGTTT-
    TAAAATGTTCCTTAAAATGC-3' (SEQ ID NO:56)

The 5' primer incorporated a Kozak sequence before the upstream methionine to the amino acid residue before the stop codon. The 3' PCR primer contained a 3 alanine linker at the junction of HKNG1 and the human IgG1 Fc domain, which starts at residues DPE. The genomic sequence of the human IgG1 Fc domain was ligated along with the PCR product into a pCDM8 vector (Invitrogen, Carlsbad Calif.) for transient expression.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-Fc polyclonal antibody (1:500, Jackson ImmunoResearch Laboratories, Inc.) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Human IgG1 Fc immunoreactivity appeared as a doublet of bands that migrated by SDS-PAGE between 148 and 60 kDa standards of the Multimark molecular weight markers (Novex), demonstrating secretion of the HKNG1:Fc fusion protein.

11.4. Expression of Human HKNG1-V1:Fc

A human HKNG1-V1/hIgG1Fc fusion protein (HKNG1-V1:Fc) vector was also constructed by PCR. The full-length open reading frame of HKNG1-V1 cDNA (SEQ ID NO:6) was PCR amplified using the following primer sequences:

5' primer 5'-TTTTTCTCTCGAGACCATGAGGACCTGG-
    GACTACAGTAAC-3' (SEQ ID NO:57)

3' primer 5'-TTTTTGGATCCGCTGCTGCCCAGGTTT-
    TAAAATGTTCCTTAAAATGC-3' (SEQ ID NO:56)

The 5' primer incorporated a Kozak sequence before the upstream methionine to the amino acid residue before the stop codon. The 3' PCR primer contained a 3 alanine linker at the junction of HKNG1-V1 and the human IgG1 Fc domain, which starts at residues DPE. The genomic sequence of the human IgG1 Fc domain was ligated along with the PCR product into a pCDM8 vector for transient expression.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an anti-human Fc polyclonal antibody (1:500, Jackson ImmunoResearch Laboratories, Inc.) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Human IgG1 Fc immunoreactivity appeared as a doublet of bands that migrated by SDS-PAGE between 148 and 60 kDa standards of the Multimark molecular weight markers (Novex) centered approximately between 125 and 150 kDa, demonstrating secretion mediated by the HKNG1 signal peptide.

11.5. Expression of Human HKNG1Δ7:Fc

A human HKNG1Δ7:hIgG1Fc fusion protein vector was also constructed by PCR. The sequence of the HKNG1Δ7 splice variant was amplified by PCR amplification using Exons 1 through 6 of the full length HKNG1 cDNA sequence (SEQ ID NO:1) as a template with the following primer sequences:

5' primer 5'-TTTTTCTGAATTCACCATGAAGCCGC-
    CACTCTTGGTG-3' (SEQ ID NO:58)

3' primer 5'-TTTTTGGATCCGCTGCGGCCTCCGTGGT-
    CAGGAGCTTATTTTTCACAGAGGACCAGCTAG-3' (SEQ ID NO:59)

The 5' primer incorporated a Kozak sequence upstream of and including the upsream initiator methionine. The 3' primer included the first17 (coding) nucleotides of exon 8 followed by nucleotides encoding a 3 alanine linker.

The genomic sequence of the human IgG1 Fc domain was ligated along with the PCR product into a pCDM8 vector for transient expression.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an anti-human Fc polyclonal antibody (1:500, Jackson ImmunoResearch Laboratories) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). Human IgG1 Fc immunoreactivity appeared as a band that migrated by SDS-PAGE between 42 and 60 kDa relative to Multimark molecular weight markers (Novex) centered approximately between 36.5 and 55.4 kDa relative to Mark 12 molecular weight markers (Novex).

11.6. Expression of Native Human HKNG1

A human HKNG1 expression vector was constructed by PCR amplification of the human HKNG1 cDNA sequence (SEQ ID NO:1) followed by ligation into an expression vector, pcDNA3.1 (Invitrogen, Carlsbad Calif.). The full open-reading frame of the HKNG1 cDNA sequence (SEQ ID NO:5) was PCR amplified using the following primer sequences:

5' primer 5'-TTTTTCTCTCGAGGACTACAGGACA-CAGCTAAATCC-3' (SEQ ID NO:60)

3' primer 5'-TTTTTGGATCCTTATCACCAGGTTT-TAAAATGTTCCTTAAAATGC-3' (SEQ ID NO:61)

The 5' primer incorporated a Kozak sequence upstream of and including the upstream initiator methionine. The 3' primer included a tandem pair of termination codons.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an anti-HKNG1 polyclonal antibody (#84, 1:500) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). HKNG1 immunoreactivity appeared as a doublet of bands that migrated by SDS-PAGE between 60 and 95 kDa as determined by Multimark molecular weight markers (Novex).

11.7. Expression of Native Human HKNG1-V1

A human HKNG1-V1 expression vector was also constructed by PCR amplification of the human HKNG1-V1 cDNA sequence (SEQ ID NO:3) followed by ligation into an expression vector, pcDNA3.1. The full open-reading frame of the HKNG1 cDNA sequence (SEQ ID NO:6) was PCR amplified using the following primer sequences:

5' primer 5'-TTTTTCTGAATTCACCATGAAGCCGC-CACTCTTGGTG-3' (SEQ ID NO:62)

5' primer 5'-TTTTTCTCTCGAGACCATGAGGACCTGG-GACTACAGTAAC-3' (SEQ ID NO:63)

3' primer 5'-TTTTTGGATCCTTATCACCAGGTTT-TAAAATGTTCCTTAAAATGC-3' (SEQ ID NO:61)

The 5' primer incorporated a Kozak sequence upstream of and including the upstream initiator methionine. The 3' primer included a tandem pair of termination codons.

The sequenced DNA construct was transiently transfected into HEK 293T cells in 150 mm plates using Lipofectamine (GIBCO/BRL) according to the manufacturer's protocol. Seventy-two hours post-transfection, the serum-free conditioned medium (OptiMEM, GIBCO/BRL) was harvested and spun and the remaining monolayer of cells was lysed using 2 mL of lysis buffer [50 mM Tris pH 8.0, 150 mM NaCl, 1% NP-40, 0.05% SDS with "Complete" protease cocktail (Boehringer Mannheim) diluted according to manufacturers instructions]. Insoluble material was pelleted before preparation of SDS-PAGE samples.

Conditioned medium was electroblotted onto a PVDF membrane (Novex) after separation by SDS-PAGE on 4–20% gradient gels and probed with an M2 anti-HKNG1 polyclonal antibody (#84, 1:500) followed by horseradish peroxidase (HRP) conjugated sheep anti-mouse antibody (1:5000, Amersham), developed using chemiluminescent reagents (Renaissance, Dupont), and exposed to autoradiography film (Biomax MR2 film, Kodak). HKNG immunoreactivity appeared as a doublet of bands that migrated by SDS-PAGE between 70 and 95 kDa as determined by Multimark molecular weight markers (Novex), demonstrating secretion mediated by the HKNG1 signal peptide.

11.8. Expression of Human HKNG:AP Fusion Proteins

Expression vectors were also constructed for human HKNG1 alkaline phosphatase C-terminal fusion protein (HKNG1:AP), human HKNG1-V1 alkaline phosphatase C-terminal fusion protein (HKNG1-V1:AP), and human HKNG1 alkaline phosphatase N-terminal fusion protein (AP:HKNG1).

The expression vector for human HKNG1:AP was constructed by PCR amplification followed by ligation into a vector for suitable for expression in HEK 293T cells. The full-length open-reading frame of human HKNG1 (SEQ ID NO:5) was PCR amplified using a 5' primer incorporating an EcoRI restriction site followed by a Kozak sequence prior to the upstream initiator methionine. The 3' primer included a XhoI restriction site immediately following the final codon of HKNG1. Thus, the open reading frame of the construct includes the HKNG1 signal peptide and the full HKNG1 sequence followed by the full sequence of human placental alkaline phosphatase.

The expression vector for human HKNG1-V1:AP was constructed by PCR amplification followed by ligation into pMEAP3 vector. The full length open reading frame of human HKNG1-V1 (SEQ ID NO:6) was PCR amplified using a 5' primer incorporating an EcoRI restriction site followed by a Kozak sequence prior to the upstream initiator methionine. The 3' primer included a XhoI restriction site immediately following the final codon of HKNG1-V1. Thus, the open reading frame of the construct includes the HKNG1-V1 signal and the full length HKNG1-V1 sequence followed by the full sequence of human placental alkaline phosphatase.

The expression vector for human AP:HKNG1 was constructed by PCR amplification followed by ligation into the AP-Tag3 vector reported by Cheng and Flanagan, 1994, *Cell* 79:157–168. The full-length open-reading frame of human HKNG1 (SEQ ID NO:5) was PCR amplified using a 5' primer incorporating a BamHI restriction site prior to the nucleotides encoding the first amino acids (i.e., APT) of the mature HKNG protein, and a 3' primer that included a XhoI restriction site immediately following the termination codon of HKNG1. Thus, the open reading frame of the complete construct includes the AP signal peptide and the full sequence of human placental alkaline phosphatase, followed by the full HKNG1 sequence.

The sequenced DNA constructs were transiently transfected in HEK 293T cells in 150 mM plates using Lipofectamine (GIBCO/BRL) according to the manufacturer's protocol. 72 hours post-transfection, the serum-free conditioned media (OptiMEM, Gibco/BRL) were harvested, spun and filtered. Alkaline phosphatase activity in the conditioned media was quantitated using an enzymatic assay kit (Phospha-Light, Tropix) according to the manufacturer's instructions. When alkaline phosphatase fusion protein concentrations below 2 nM were observed, conditioned medium was concentrated by centrifugation using a 30 kDa cut-off membrane. Conditioned medium samples before and after concentration were analyzed by SDS-PAGE followed by Western blot using anti-human alkaline phosphatase antibodies (1:250, Genzyme) and chemiluminsecent detection. A band at 140 kDa was observed in concentrated supernatant of HKNG1:AP, HKNG1-V1:AP, and AP:HKNG1 transfections. Conditioned medium samples were adjusted to 10% fetal calf serum and stored at 4° C.

11.9. Purification of Flag-Tagged HKNG1 Proteins

The secreted flag-tagged proteins described in subsections 12.1 and 12.2 above were isolated by a one step purification scheme utilizing the affinity of the flag epitope to M2 anti-flag antibodies. The conditioned media was passed over an M2-biotin (Sigma)/streptavidin Poros column (2.1×30 mm, PE Biosystems). The column was then washed with PBS, pH 7.4, and flag-tagged protein was eluted with 200 mM glycine, pH 3.0. Fraction was neutralized with 1.0 M Tris pH 8.0. Eluted fractions with 280 nm absorbance greater than background were then analyzed on SDS-PAGE gels and by Western blot. The fractions containing flag taged protein were pooled and dialyzed in 8000 MWCO dialysis tubing against 2 changes of 4 L PBS, pH 7.4 at 4° C. with constant stirring. The buffered exchanged material was then sterile filtered (0.2 μm, Millipore) and frozen at −80° C.

11.10. Purification of HKNG1 Fc Fusion Proteins

The secreted Fc fusion proteins described in Subsections 12.3–12.5 above were isolated by a one step purification scheme utilizing the affinity of the human IgG1 Fc domain to Protein A. The conditioned media was passed over a POROS A column (4.6×100 mm, PerSeptive Biosystems); the column was then washed with PBS, pH 7.4 and eluted with 200 mM glycine, pH 3.0. Fractions were neutralized with 1.0 M Tris pH 8.0. A constant flow rate of 7 ml/min was maintained throughout the procedure. Eluted fractions with 280 nm absorbance greater than background were then analyzed on SDS-PAGE gels and by Western blot. The fractions containing Fc fusion protein were pooled and dialyzed in 8000 MWCO dialysis tubing against 2 changes of 4 L PBS, pH 7.4 at 4° C. with constant stirring. The buffered exchanged material was then sterile filtered (0.2 μm, Millipore) and frozen at −80° C.

12. PRODUCTION OF ANTI-HKNG1 ANTIBODIES

Described in the example presented in this Section is the production and characterization of polyclonal and monoclonal antibodies directed against HKNG1 proteins.

12.1. Production of Polyclonal Antibodies

Polyclonal antisera were raised in rabbits against each of the three peptides listed in Table 3 below. Each of the peptides was derived from the HKNG1 amino acid sequence (SEQ ID NO:2) by standard techniques (see, in particular, Harlow&Lane, 1988, *Antibodies: A Laboratory Manual*, Cold Spring Harbor Laboratory Press, the contents of which is incorporated herein by reference in its entirety). Each of the peptides is also represented in the HKNG1-V1 polypeptide sequence (SEQ ID NO:4). Antisera was subsequently affinity purified using the peptide immunogens.

TABLE 3

| Antibody | Peptide/Immunogen | a.a. residues (SEQ ID NO:2) |
|---|---|---|
| Antibody 84 | APTWKDKTAISENLK | 50–64 |
| Antibody 85 | KAIEDLPKQDK | 304–314 |
| Antibody 86 | KALQHFKEHFKTW | 483–495 |

Monoclonal antibodies were raised in mice by standard techniques (see, Harlow & Lane, supra) against the HKNG-Fc fusion protein described in Section 11.3 above. Wells were screened by ELISA for binding to the HKNG-Fc fusion protein. Those wells reacting with the Fc protein were identified by ELISA for binding to an irrelevant Fc fusion protein and discarded. HKNG-Fc specific wells were tested for their ability to immunoprecipitate HKNG-Fc and subjected to isotype analysis by standard techniques (Harlow & Lane, supra), and eight wells were selected for subcloning. The isotype of the subcloned monoclonal antibodies was confirmed and is presented in Table 4 below.

Based on Western blotting, immunoprecipitation and immunostaining data discussed in SubSection 12.3 below, two monoclonal antibodies (3D17 and 4N6) were selected for large scale production.

TABLE 4

| Clone | Isotype |
|---|---|
| 1F24 | 2a |
| 1J18 | 2a |
| 2O20 | 1 |
| 3D17 | 1 |
| 3D24 | 2a |
| 4N6 | 1 |
| 4O16 | 2b |
| 10C6 | 2a |

12.3. Western Blotting and Immunoprecipitation of Recombinant HKNG Protein

The polyclonal antisera and all eight monoclonal antibodies described in subsection 12.1 and 12.2 above were tested for their ability to recognize recombinant HKNG1 proteins on Western blots using standard techniques (see, in particular, Harlow & Lane, 1988, *Antibodies: A Laboratory Manual*, Cold Spring Harbor Laboratory Press). Polyclonal antisera 84 and 85 and monoclonal antibodies 3D17 and 4N6 were able to recognize all forms of the mature (i.e., secreted) recombinant HKNG proteins tested (i.e., HKNG1:Fc, HKNG1:flag, AP:HKNG1, and native HKNG1) in Western blots.

Table 5 indicates the ability of each monoclonal antibody to immunoprecipitate recombinant HKNG1, as assessed by Western blotting of immunoprecipitates with the polyclonal antisera 84 and 85. None of the polyclonal antisera were able to immunoprecipitate recombinant HKNG1 proteins. All eight monoclonal antibodies immunoprecipitated HKNG1:Fc. Immunoprecipitation of the other recombinant HKNG1 proteins was variable.

TABLE 5

| Monoclonal Antibody | Protein | | | |
|---|---|---|---|---|
| | HKNG1:Fc | HKNG1:flag | AP:HKNG1 | HKNG1 (native) |
| 1F24 | + | + | + | −/+ |
| 1J18 | + | − | −/+ | +/+ |
| 2O20 | + | − | + | − |
| 3D17 | +/+ | +/+ | − | +/+ |
| 3D24 | + | − | − | − |
| 4N6 | + | + | + | + |
| 4O16 | + | − | − | +/+ |
| 10C6 | + | − | − | + |

13. CONFIRMATION OF THE HKNG N-TERMINUS AND DISULFIDE BOND STRUCTURE

The experiments described in this section provide data identifying the N-terminus of the mature secreted human HKNG protein. The experiments also provide data identifying the disulfide bond linkages between cysteine amino acid residues in the mature, secreted protein.

Specifically, mature, secreted HKNG:flag, HKNG, and HKNG:Fc recombinant proteins were produced and purified as described in Section 11 above. The mature recombinant proteins were digested with trypsin, and the tryptic fragments were identified and sequenced using reverse-phase liquid chromatography coupled with electrospray ionization tandem mass spectrometry (LC/MS/MS). The N-terminus of all mature secreted proteins tested was unambiguously identified as APTWKDKT, which corresponds to the amino acid sequence starting at alanine 50 of the HKNG1 amino acid sequence (FIGS. 1A–1C; SEQ ID NO:2) or alanine 32 of the HKNG1-V1 amino acid sequence (FIGS. 2A–2C; SEQ ID NO:4). Thus, although the cDNA sequences of HKNG1 and HKNG1-V1 encode distinct amino acid sequences, the mature secreted proteins produced by these two splice variants of the human HKNG1 gene are identical, since the alternative splicing that gives rise to HKNG1-V1 (i.e., the deletion of exon 3) affects the amino acid sequence of the proteolytically cleaved signal peptide. The amino acid sequence of the mature secreted HKNG1 protein is shown in FIGS. 17A–17B (SEQ ID NO:51).

The mature secreted HKNG protein is also distinct from the RPP amino acid sequence disclosed by Shimizu-Matsumo et al. (1997, *Invest. Ophthalmal. Vis. Sci.* 38:2576–2585). In particular, amino acid residues 1 to 20 of the RPP amino acid sequence disclosed in FIG. 3 of Shimizu-Matsumo et al., supra, correspond to the cleaved signal peptide of HKNG1-V1. The amino acid sequence of the mature secreted form of the HKNG1 gene product is depicted in FIG. 17 (SEQ ID NO:51).

Disulfide bond linkages for 8 of the 13 cysteine residues in the mature, secreted HKNG protein were also identified from LC/MS/MS of peptides recovered from tryptic digestion of the unreduced protein. In particular, the following disulfide bonded pairs of cysteines were identified numbering refers to the HKNG1 protein shown in FIGS. 1A–1C; SEQ ID NO:2):

Cys 134 to Cys 145;
Cys 148 to Cys 153;
Cys 160 to Cys 334; and
Cys 354 to Cys 362.

14. EXAMPLE: LOCALIZATION OF HKNG mRNA AND PROTEIN EXPRESSION

This example describes experiments wherein the HKNG gene product is shown to be expressed in human brain and retinal tissue. Specifically, in situ hybridization experiments performed using standard techniques with a probe that corresponded to the complementary sequence of base pairs 910–1422 of the full length HKNG1 cDNA sequence (SEQ ID NO:1) detected HKNG messenger RNA in the photoreceptor layer (outer nuclear layer) of human retina in eyes obtained from the New England Eye Bank.

The polyclonal antisera and all eight monoclonal antibodies described in Section 12 above were tested for immunostaining of human retina. Polyclonal antiserum 85 and monoclonal antibodies 1F24, 4N6 and 4O16 showed immunostaining of HKNG protein in the photoreceptor layer and adjacent layers of the retina. The immunostaining in these tissues with polyclonal antiserum was blocked by 85 peptide immunogen, but not by the other two peptide immunogens (i.e., 84 and 86), confirming that the immunostaining was due to HKNG protein expressed in the photoreceptor layer.

The same antibodies were then used to localize HKNG protein by immunostaining in sections of human and monkey brain. HKNG protein was observed in cortical neurons in the frontal cortex. The majority of pyramidal neurons in layers IV–V were immunoreactive for HKNG protein. A subpopulation of neurons was also labeled in layers I–III. HKNG immunoreactivity was also observed in the pyramidal cell layer of the hippocampus and in a small number of neurons in the striatum.

These data further support the fact that HKNG is, indeed, a gene which mediates neuropsychiatric disorders such as BAD. Furthermore, the fact that HKNG is also expressed in human retinal tissue suggests that the gene also plays a role in myopia conditions. Specifically, Young et al. (1998, *American Journal of Human Genetics* 63:109–119) report a strong linkage (LOD=9.59) for primary myopia and secondary macular degeneration and retinal detachment in the telomeric region of human chromosome 18p. Through fine mapping analysis, this candidate region has been narrowed to a 7.6 cM haplotype flanked by markers D18S59 and D18S1138 (Young et al., supra). However, the marker D18S59 lies within the HKNG1 gene. This fact, coupled with the finding the HKNG is expressed in high levels in the retina, strongly suggests that the HKNG1 gene is also responsible for human myopia conditions and/or other eye related diseases such as primary myopia, secondary macular degeneration, and retinal detachment.

15. EXAMPLE: IMMATURE PROTEIN PRODUCTS OF THE HKNG1 cDNA SEQUENCES

This section describes experiments which were performed to determine which of the two putative initiator methionines encoded by both the full length HKNG1 cDNA and the alternatively spliced HKNG1-V1 cDNA are used in the synthesis of immature HKNG1 protein. The results indicate that both initiator methionines are used at varying levels, resulting in the production of three different forms of the immature HKNG1 protein, referred to herein as immature protein form 1 (IPF1), immature protein form 2 (IPF2), and immature protein form 3 (IPF3).

Both the full length HKNG1 cDNA sequence shown in FIGS. 1A–1C (SEQ ID NO:1) and the alternatively spliced HKNG1-V1 cDNA sequence shown in FIGS. 2A–2C (SEQ ID NO:3) encode predicted proteins that have methionines in close proximity to their predicted initiator methionines. The predicted protein sequence encoded by the full length HKNG1 cDNA sequence has a second methionine at amino acid residue number 30 of the amino acid sequence depicted in FIGS. 1A–1C (SEQ ID NO:2). Thus, although FIGS. 1A–1C indicates that the full length HKNG1 cDNA encodes the first immature form of the HKNG1 protein depicted in FIGS. 1A–1C (referred to herein as IPF1), the full length HKNG1 cDNA may additionally encode a second immature protein form (referred to herein as IPF2), whose sequence (SEQ ID NO:64) is provided on the third line of the protein alignment depicted in FIGS. 17A–17B. IPF2 is initiated at methionine 30 of the IPF1 protein sequence, and is identical to the RPP polypeptide sequence taught by Shimizu-Matsumoto et al (1997, Invest. Ophthalmol. Vis. Sci. 38:2576–2585). Likewise, the alternatively spliced HKNG1-V1 cDNA sequence encodes the predicted immature protein form, referred to herein as IPF3, depicted in FIGS. 2A–2C (SEQ ID NO:4). However, the HKNG1-V1 cDNA may also encoded another immature protein form, identical to IPF 2, that is initiated at methionine 12 of the IPF3 protein sequence. FIGS. 17A–17B illustrates an alignment of the three immature HKNG1 protein sequences IPF1 (second row), IPF2 (third row), and IPF3 (bottom row). As explained is Section 13 above, the mature HKNG1 gene product secreted by cells expressing the HKNG1 constructs described in Section 11, above, is in fact the same cleaved product (SEQ ID NO:51), regardless of the immature HKNG1 protein (IPF1, IPF2, or IPF3) from which it is produced. An alignment of the mature secreted HKNG1 protein is therefore also depicted in FIGS. 17A–17B (top row).

Modified HKNG1:flag and HKNG1-V1:flag expression vectors were constructed as described in Sections 12.1 and 12.2, respectively. However, the nucleotide sequence of full length HKNG1 was modified, using standard site directed mutagenesis techniques, so as to introduce an additional base pair between the upstream methionine (i.e., met 1 in SEQ ID NO:2) and the downstream methionine (i.e., met 30 in SEQ ID NO:2). The nucleotide sequence of HKNG1-V1 was likewise modified, using standard site directed mutagenesis techniques, to introduce an additional base between its upstream methionine (i.e., met 1 in SEQ ID NO:4) and downstream methionine (i.e., met 12 in SEQ ID NO:4). Thus, in both modified constructs, the C-terminal flag epitope tag was no longer in the same reading frame as the upstream methionine but was in frame with the downstream methionine. Consequently, exclusive translation initiation at the first methionine of a construct would lead to the production of non-flag immunoreactive proteins. However, exclusive translation initiation at the second methionine of a construct would lead to the production of flag immunoreactive proteins.

Unmodified HKNG1:flag, unmodified HKNG1-V1:flag, modified HKNG1:flag, and modified HKNG1-V1:flag constructs were transfected into cells, and their resulting gene products were harvested, blotted onto a PVDF membrane, and probed with an M2 anti-flag polyclonal antibody, and developed according to the methods described in Sections 12.1 and 12.2 above.

Flag immunoreactivity was detected in all four samples. The unmodified HKNG1:flag and HKNG1-V1:flag expression vectors produced amounts of mature secreted HKNG1:flag protein consistent with the levels detected in Sections 12.1 and 12.2 above. Further, the flag immunoreactive band detected for the modified HKNG1:flag construct was indistinguishable in intensity from the band detected for the unmodified HKNG1:flag construct, indicating that the immature HKNG1 protein produced by full length HKNG1 cDNA is predominantly IPF2, while IPF1 is produced by full length HKNG1 cDNA in relatively minor amounts.

The flag immunoreactive band from the modified HKNG1-V1:flag construct had dramatically reduced intensity relative to the band from the unmodified HKNG1-V1:flag construct. Thus, HKNG1-V1 produces primarily the immature HKNG1 protein IPF3, while the immature HKNG1 protein IPF2 is produced by HKNG1-V1 in relatively minor amounts. These results are summarized below in Table 6.

TABLE 6

| Construct | Immature Protein | Prominance |
| --- | --- | --- |
| HKNG1 | IPF1 (SEQ ID NO:2) | Minor |
|  | IPF2 (SEQ ID NO:64) | Predominant |
| HKNG1-V1 | IPF2 (SEQ ID NO:64) | Minor |
|  | IPF3 (SEQ ID NO:4) | Predominant |

Thus, the HKNG1 gene products of the invention include gene products corresponding to the immature protein forms IPF1 and IPF3. However, preferably the HKNG1 gene products of the invention do not include amino acid sequences consisting of the IPF2 sequence (SEQ ID NO:64).

16. REFERENCES CITED

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings.

All publications, patents, and patent applications mentioned in this specification are herein incorporated by reference to the same extent as if each individual publication or patent application was specifically and individually indicated to be incorporated by reference.

What is claimed is:

1. A method for identifying a compound which modulates expression of a Hong Kong new gene 1 (HKNG1) gene comprising:

(a) contacting a test compound to a cell that expresses an HKNG 1 gene;

(b) measuring a level of HKNG1 gene expression in the cell;

(c) comparing the level of HKNG1 gene expression in the cell in the presence of the test compound to a level of HKNG1 gene expression in the cell in the absence of the test compound, wherein if the level of HKNG1 gene expression in the cell in the presence of the test compound differs from the level of expression of the HKNG1 gene in the cell in the absence of the test compound, a compound that modulates expression of an HKNG1 gene is identified.

2. The method of claim 1, wherein the HKNG1 gene encodes an HKNG1 gene product comprising:

(a) the amino acid sequence of SEQ ID NO:2;

(b) the amino acid sequence of SEQ ID NO:4;

(c) the amino acid sequence of SEQ ID NO:39;

(d) the amino acid sequence of SEQ ID NO:41;

(e) the amino acid sequence of SEQ ID NO:43;

(f) the amino acid sequence of SEQ ID NO:45;

(g) the amino acid sequence of SEQ ID NO:49;

(h) the amino acid sequence of SEQ ID NO:51;

(i) the amino acid sequence of SEQ ID NO:64; or (j) the amino acid sequence of SEQ ID NO:66.

3. The method of claim 2, wherein the HKNG1 gene comprises:

(a) the nucleotide sequence of SEQ ID NO:1;

(b) the nucleotide sequence of SEQ ID NO:3;

(c) the nucleotide sequence of SEQ ID NO:5;

(d) the nucleotide sequence of SEQ ID NO:6;

(e) the nucleotide sequence of SEQ ID NO:34;

(f) the nucleotide sequence of SEQ ID NO:35;

(g) the nucleotide sequence of SEQ ID NO:38;

(h) the nucleotide sequence of SEQ ID NO:40;

(i) the nucleotide sequence of SEQ ID NO:42;

(j) the nucleotide sequence of SEQ ID NO:44;

(k) the nucleotide sequence of SEQ ID NO:46;

(l) the nucleotide sequence of SEQ ID NO:47;

(m) the nucleotide sequence of SEQ ID NO:48; or (n) the nucleotide sequence of SEQ ID NO:65.

4. A method for identifying a compound which modulates expression or activity of an HKNG1 gene product comprising:

(a) contacting a test compound to a cell that expresses an HKNG1 gene product;

(b) measuring a level of HKNG1 gene product expression or activity in the cell;

(c) comparing the level of HKNG1 gene product expression or activity in the cell in the presence of the test compound to a level of HKNG1 gene product expression or activity in the cell in the absence of the test compound, wherein if the level of HKNG1 gene product expression or activity in the cell in the presence of the test compound differs from the level of HKNG1 gene product expression or activity in the cell in the absence of the test compound, a compound that modulates expression or activity of an HKNG1 gene product is identified.

5. The method of claim 4, wherein the HKNG1 gene product comprises:

(a) the amino acid sequence of SEQ ID NO:2;
(b) the amino acid sequence of SEQ ID NO:4;
(c) the amino acid sequence of SEQ ID NO:39;
(d) the amino acid sequence of SEQ ID NO:41;
(e) the amino acid sequence of SEQ ID NO:43;
(f) the amino acid sequence of SEQ ID NO:45;
(g) the amino acid sequence of SEQ ID NO:49;
(h) the amino acid sequence of SEQ ID NO:51; or
(i) the amino acid sequence of SEQ ID NO:64.

6. The method of claim 4, wherein the method further comprises the step of analyzing the sequence of the coding region of the human HKNG1 gene by preparing and sequencing cDNA comprising a sequence that hybridizes under stringent conditions to the complement of a nucleotide sequence which encodes the polypeptide sequence depicted in SEQ ID NO:2, wherein said stringent conditions comprise hybridization in 6×SSC at about 45° C. followed by one or more washes in 0.2×SSC/0.1% SDS at about 50–65° C.

7. The method of claim 1 wherein the HKNG1 gene comprises an isolated nucleic acid molecule that hybridizes under highly stringent conditions to the complement of:
(a) the nucleotide acid sequence of SEQ ID NO: 1;
(b) the nucleotide acid sequence of SEQ ID NO:3;
(c) the nucleotide acid sequence of SEQ ID NO:5;
(d) the nucleotide acid sequence of SEQ ID NO:6;
(e) the nucleotide acid sequence of SEQ ID NO:34;
(f) the nucleotide acid sequence of SEQ ID NO:35;
(g) the nucleotide acid sequence of SEQ ID NO:38;
(h) the nucleotide acid sequence of SEQ ID NO:40;
(i) the nucleotide acid sequence of SEQ ID NO:42;
(j) the nucleotide acid sequence of SEQ ID NO:44;
(k) the nucleotide acid sequence of SEQ ID NO:46;
(l) the nucleotide acid sequence of SEQ ID NO:47;
(m) the nucleotide acid sequence of SEQ ID NO:48; or
(n) the nucleotide acid sequence of SEQ ID NO:65,
wherein said stringent conditions comprise hybridization in 6×SSC at about 45° C. followed by one or more washes in 0.1×SSC/0.2% SDS at about 68° C.

8. The method of claim 1 or 7, wherein the HKNG1 gene is under-expressed relative to wild-type HKNG1 levels of expression in the presence of the test compound.

9. The method of claim 1 or 7 in which the compound is an oligonucleotide complementary to the 5' region of the gene and blocks transcription via triplex helix formation.

10. The method of claim 1 or 7 in which the compound is an antisense or ribozyme molecule that blocks translation of the gene.

11. The method of claim 1 or 7 in which the compound is a small organic or inorganic molecule that modulates the activity of the protein product by binding to the protein product.

12. The method of claim 1 or 7 in which the compound is an antibody that modulates the activity of the protein product by binding to the protein product.

13. The method of claim 1 or 7 wherein the HKNG1 gene is over-expressed relative to wild-type HKNG1 levels of expression in the presence of the test compound.

14. The method of claim 1 or 7 in which the compound is an oligonucleotide complementary to the 5' region of the gene and blocks transcription via triplex helix formation.

15. The method of claim 1 or 7 in which the compound is an antisense or ribozyme molecule that blocks translation of the gene.

16. The method of claim 1 or 7 in which the compound is a small organic or inorganic molecule that modulates the activity of the protein product by binding to the protein product.

17. The method of claim 1 or 7 in which the compound is an antibody that modulates the activity of the protein product by binding to the protein product.

* * * * *